US012752015B2

(12) United States Patent
Sun

(10) Patent No.: US 12,752,015 B2
(45) Date of Patent: Oct. 6, 2026

(54) ANTI-GALECTIN 3 ANTIBODIES AND THEIR USE IN EPILEPSY AND RELATED DISEASES

(71) Applicant: SUNMED THERAPEUTIC LIMITED, Hong Kong (CN)

(72) Inventor: Dongxu Sun, Shenzhen (CN)

(73) Assignee: SUNMED THERAPEUTIC LIMITED, Hong Kong (CN)

( * ) Notice: Subject to any disclaimer, the term of this patent is extended or adjusted under 35 U.S.C. 154(b) by 0 days.

(21) Appl. No.: 19/347,462

(22) Filed: Oct. 1, 2025

(65) Prior Publication Data

US 2026/0034233 A1 Feb. 5, 2026

Related U.S. Application Data

(63) Continuation of application No. PCT/CN2025/081169, filed on Mar. 7, 2025.

(30) Foreign Application Priority Data

Mar. 8, 2024 (WO) ................ PCT/CN2024/080726

(51) Int. Cl.

| | |
|---|---|
| ***A61K 47/68*** | (2017.01) |
| ***A61K 9/00*** | (2006.01) |
| ***A61K 39/00*** | (2006.01) |
| ***A61P 25/08*** | (2006.01) |
| ***C07K 16/28*** | (2006.01) |

(52) U.S. Cl.

CPC ........ *A61K 47/6849* (2017.08); *A61K 9/0019* (2013.01); *A61P 25/08* (2018.01); *C07K 16/2851* (2013.01); *A61K 2039/505* (2013.01); *A61K 2039/545* (2013.01); *C07K 2317/24* (2013.01); *C07K 2317/33* (2013.01); *C07K 2317/565* (2013.01)

(58) Field of Classification Search

None

See application file for complete search history.

(56) References Cited

U.S. PATENT DOCUMENTS

| | | | |
|---|---|---|---|
| 11,091,552 | B2 | 8/2021 | Fontayne et al. |
| 2024/0026009 | A1 | 1/2024 | Spriggs et al. |

FOREIGN PATENT DOCUMENTS

| | | | |
|---|---|---|---|
| WO | 2021146218 | A1 | 7/2021 |
| WO | 2022231978 | A1 | 11/2022 |
| WO | 2023180533 | A1 | 9/2023 |

OTHER PUBLICATIONS

Casset et al. Biochemical and Biophysical Research Communications, vol. 307, p. 198-205. (Year: 2003).*

Vajdos et al. Journal of Molecular Biology, vol. 320, p. 415-428. (Year: 2002).*

Chiu et al. (Antibodies 8(4);55, 1-80) Dec. 2019.*

Rentero et al., Chimia, 65: 843-845 (2011).*

Ahmed, R. et al. "Development of Galectin-3 Targeting Drugs for Therapeutic Applications in Various Diseases" Diseases. Int. J. Mo/. Sci., vol. 24, May 1, 2023 (May 1, 2023), 8116 pp. 1-24.

Tan. Y.Y. et al. "Galectin-3: a key player in microglia-mediated neuroinflammation and Alzheimer's disease" Cell Biosci, vol. 11, Apr. 27, 2021 (Apr. 27, 2021), 78 pp. 1-13.

Garcia-Revilla, J. et al. "Galectin-3, a rising star in modulating microglia activation under conditions of neurodegeneration" Cell Death and Disease, vol. 13, Jul. 20, 2022 (Jul. 20, 2022), 628 pp. 1-11.

Soares, LC. et al. "Novel Galectin-3 Roles in Neurogenesis, Inflammation and Neurological Diseases" Cells, vol. 10, Nov. 5, 2021 (Nov. 5, 2021), 3047 pp. 1-24.

Fan, Z.Y.et al. "Recent advance in role of galectin-3 in central neurodegenerative diseases" Chin J Neuromed, vol. 21, No. 2, Feb. 28, 2022 (Feb. 28, 2022), pp. 183-188 Abstract only.

Susumu Nakahara et al., Regulation of cancer-related gene expression by galectin-3 and the molecular mechanism of its nuclear import pathway, Cancer Metastasis Rev, 26(0): 605-610, 2007.

Neil C. Henderson et al., Galectin-3 regulates myofibroblast activation and hepatic fibrosis, Proceedings of the National Academy of Sciences, 103(13): 5060-5065, 2006.

V. Juniantito et al., Heterogeneity of Macrophage Populations and Expression of Galectin-3 in Cutaneous Wound Healing in Rats, Journal of Comparative Pathology, 145: 378-389, 2011.

Pingping Li et al., Hematopoietic-derived Galectin-3 Causes Cellular and Systemic Insulin Resistance, Cell, 167(4): 973-984.e12, 2016.

Nada Pejnovic, Galectin-3 In Obesity And Type 2 Diabetes, Serbian Journal of Experimental and Clinical Research, 16(4): 273-280, 2015.

Lesya Bobronnikova, Galectin-3 as a potential biomarker of metabolic disorders and cardiovascular remodeling in patients with hypertension and type 2 diabetes, Vessel Plus, 1:61-67, 2017.

M. T. Elola, Galectins: Matricellular glycan-binding proteins linking cell adhesion, migration, and survival, Cellular and Molecular Life Sciences, 64: 1679-1700, 2007.

Jerka Dumic, Galectin-3: An open-ended story, Biochimica et Biophysica Acta, 1760(4): 616-635, 2006.

Neil C. Henderson et al., The regulation of inflammation by galectin-3. Immunological Reviews, 230: 160-171, 2009.

Cheng-Feng Bian et al., Structural Basis for Distinct Binding Properties of the Human Galectins to Thomsen-Friedenreich Antigen, PLoS One, 6(9): e25007, 2011.

Mario A. Bianchet et al., soluble β-galactosyl-binding lectin (galectin) from toad ovary: Crystallographic studies of two protein-sugar complexes, Proteins: Structure, Function, and Genetics, 40: 378-388, 2000.

Yoshinobu Kariya et al., Bisecting GlcNAc Residues on Laminin-332 Down-regulate Galectin-3-dependent Keratinocyte Motility, The Journal of Biological Chemistry, 285(5): 3330-3340, 2010.

Josiah Ochieng et al., Regulation of Cellular Adhesion to Extracellular Matrix Proteins by Galectin-3, Biochemical and Biophysical Research Communications, 246(3): 788-791, 1998.

(Continued)

*Primary Examiner* — Gary B Nickol

(74) *Attorney, Agent, or Firm* — Kilpatrick Townsend & Stockton LLP; Yifan Mao

(57) ABSTRACT

Provided herein are antibodies that target Galectin-3. Such antibodies are used in methods of treating epilepsy and related neurological disorders, such as Alzheimer's disease (AD) and Parkinson's disease (PD).

20 Claims, 23 Drawing Sheets

Specification includes a Sequence Listing.

(56) References Cited

OTHER PUBLICATIONS

Tomoharu Fukumori et al., CD29 and CD7 Mediate Galectin-3-Induced Type II T-Cell Apoptosis, Cancer Research, 63: 8302-8311, 2003.

Elisabeth Feuk-Lagerstedt et al., Identification of CD66a and CD66b as the major galectin-3 receptor candidates in human neutrophils, The Journal of Immunology, 163: 5592-5598, 1999.

Ian Rosenberg et al., Mac-2-binding glycoproteins. Putative ligands for a cytosolic beta-galactoside lectin, The Journal of biological chemistry, 266(28), 18731-18736, 1991.

Jung W. Park et al., Association of galectin-1 and galectin-3 with Gemin4 in complexes containing the SMN protein, Nucleic Acids Research, 27(17): 3595-3602, 2001.

Tatsuo Shimura et al., Galectin-3, a novel binding partner of beta-catenin, Cancer Research, 64: 6363-6367, 2004.

Henrique Rocha Mendonça et al., Neuroinflammation and oxidative stress act in concert to promote neurodegeneration in the diabetic retina and optic nerve: galectin-3 participation, Neural Regeneration Research, 15(4): 625-635, 2020.

Rui Dong et al., Galectin-3 as a novel biomarker for disease diagnosis and a target for therapy (Review), International journal of molecular medicine, 41(2), 599-614, 2018.

Taekyun Shin, The pleiotropic effects of galectin-3 in neuroinflammation: a review, Acta Histochemica, 115(5): 407-411, 2013.

Reza Rahimian et al., Galectin-3: mediator of microglia responses in injured brain, Drug Discovery Today, 23(2), 375-381, 2018.

Reza Rahimian et al., Delayed galectin-3-mediated reprogramming of microglia after stroke is protective, Molecular Neurobiology, 56(9): 6371-85, 2019.

International Search report received in the counterpart international application PCT/CN2025/081169, mailed on Jun. 11, 2025.

Suhail Rasool et al., Potential Reversal of Alzheimer's Disease pathology by Antibody TB006 Targeting Galectin-3, the Root Cause of Oligomerization of Amyloid Proteins, Alzheimer's Dementia, 18(Suppl. 10): e060393, 2022.

The Invitation pursuant to Rule 63(1) EPC received in the counterpart European Application 25767464.8, mailed on Jun. 26, 2026.

Liu, Fu-Tong et al., "Modulation of Functional Properties of Galectin-3 by Monoclonal Antibodies Binding to the Non-Lectin Domains", Biochemistry, vol. 35, No. 19, 1996, pp. 6073-6079.

* cited by examiner

FIG. 4A
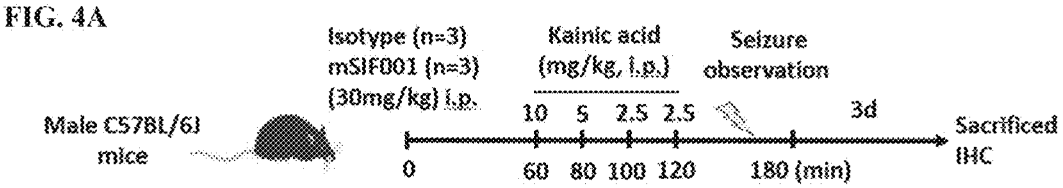
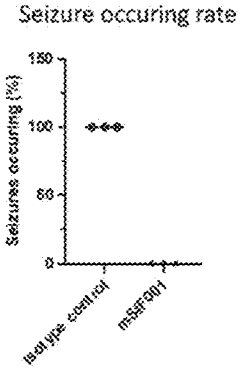
FIG. 4B
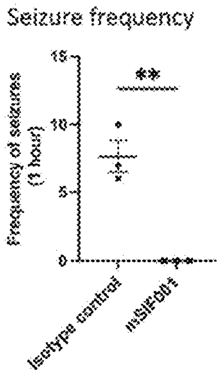
FIG. 4C
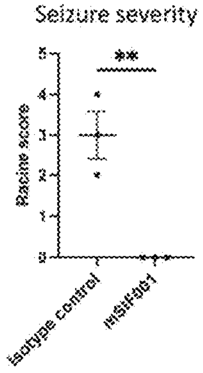
FIG. 4D
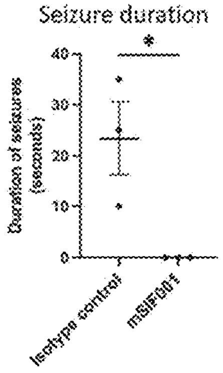
FIG. 4E SIF001 heavy chain CDR

| HCDR1 | HCDR2 | HCDR3 |
|---|---|---|
| 31NYGMN35 (SEQ ID NO: 4) | 50WINTYTGEPTYADDFKG66 (SEQ ID NO: 25) | 99YAMDY103 (SEQ ID NO: 46) |

A.

SIF001 light chain CDR

| LCDR1 | LCDR2 | LCDR3 |
|---|---|---|
| 23RSSTGAVTTSNYAN36 (SEQ ID NO: 172) | 52GTSNRAP58 (SEQ ID NO: 193) | 91ALWYSTHYV99 (SEQ ID NO: 214) |

B.

| HCDR1 | HCDR2 | HCDR3 |
|---|---|---|
| $NX_2X_3MN$ | $X_1IX_3TYTGEPTYADDFKG$ (SEQ ID NO: 358) | $X_1AMDY$ (SEQ ID NO: 359) |

A.

| LCDR1 | LCDR2 | LCDR3 |
|---|---|---|
| $RSSTGAVTTSNX_{12}AN$ (SEQ ID NO: 360) | GTSNRAP (SEQ ID NO: 361) | $ALX_3YSTHX_8V$ (SEQ ID NO: 362) |

B.

SIF002 heavy chain CDR

| HCDR1 | HCDR2 | HCDR3 |
| --- | --- | --- |
| 31RFWMS35 (SEQ ID NO: 8) | 50EISPDSNTIDLTPSLKD66 (SEQ ID NO: 29) | 99PYYGYY104 (SEQ ID NO: 50) |

A.

SIF002 light chain CDR

| LCDR1 | LCDR2 | LCDR3 |
| --- | --- | --- |
| 24RSSQSLFSSTNQKNYLT40 (SEQ ID NO: 369) | 56WASSRES62 (SEQ ID NO: 197) | 95QNDYTSPFT103 (SEQ ID NO: 218) |

B.

| HCDR1 | HCDR2 | HCDR3 |
|---|---|---|
| RF$X_3$MS (SEQ ID NO: 363) | $X_1$ISPDSNTIDLTPSLKD (SEQ ID NO: 364) | PYYG$X_5$Y (SEQ ID NO: 365) |

A.

| LCDR1 | LCDR2 | LCDR3 |
|---|---|---|
| RSSQSLFSSTNQKN$X_{15}$LT (SEQ ID NO: 366) | WASSRES (SEQ ID NO: 367) | QNDYTSPFT (SEQ ID NO: 368) |

B.

ANTI-GALECTIN 3 ANTIBODIES AND THEIR USE IN EPILEPSY AND RELATED DISEASES

CROSS REFERENCE TO RELATED APPLICATIONS

This application is a continuation of International Application No. PCT/CN2025/081169, filed Mar. 7, 2025, which claims priority to International Application No. PCT/CN2024/080726, filed Mar. 8, 2024, the disclosure of which is herein incorporated by reference in its entirety for all purposes.

SEQUENCE LISTING

The instant application contains a Sequence Listing which has been submitted via Patent Center and is hereby incorporated by reference in its entirety. Said .xml copy, created on Sep. 29, 2025, is named 112130-1526877-000100US, and is 452,679 bytes in size.

BACKGROUND

Epilepsy is a neurological disease characterized by recurrent spontaneous seizures. Despite the efficacy of current anti-epileptic drugs, almost 30% of patients with epilepsy are refractory to medical treatment, have progressive cognitive impairment, and may require neurosurgical resection of the epileptic focus to alleviate seizure recurrence. Although the exact cellular and molecular mechanisms of epileptogenesis are not clear, it is postulated that focal or systemic unregulated inflammatory processes lead to aberrant neural connectivity and the hyper-excitable neuronal network, which mediate the onset of epilepsy. Epileptogenesis is associated with an increased and persistent inflammatory state in the microenvironment of neural tissues, which can lead to the production of cytokines by glial cells and neurons. A safe and efficient treatment of epilepsy and/or related neurological disorders is highly needed.

SUMMARY

In one aspect, provided herein is an antibody or a binding fragment thereof that binds to Galectin-3, wherein the antibody comprises: a heavy chain variable ($V_H$) region comprising: a HCDR1 amino acid sequence at least 70% identical to any one of SEQ ID NOS: 1-21 and 370-389, a HCDR2 amino acid sequence at least 70% identical to any one of SEQ ID NOS: 22-42 and 390-417, and/or a HCDR3 amino acid sequence at least 70% identical to any one of SEQ ID NOS: 43-63 and 418-439, and/or a light chain variable ($V_L$) region comprising: a LCDR1 amino acid sequence at least 70% identical to any one of SEQ ID NOS: 169-189 and 440-462, a LCDR2 amino acid sequence at least 70% identical to any one of SEQ ID NOS: 190-210 and 463-480, and/or a LCDR3 amino acid sequence at least 70% identical to any one of SEQ ID NOS: 211-231 and 481-507. In some embodiments, the Galectin-3 is human Galectin-3.

In some embodiments, the antibody comprises: a heavy chain variable region comprising a HCDR1 amino acid sequence at least 70% identical to SEQ ID NO: 1, a HCDR2 amino acid sequence at least 70% identical to SEQ ID NO: 22, and a HCDR3 amino acid sequence at least 70% identical to SEQ ID NO: 43; and a light chain variable region comprising a LCDR1 amino acid sequence at least 70% identical to SEQ ID NO: 169, a LCDR2 amino acid sequence at least 70% identical to SEQ ID NO: 190, and a LCDR3 amino acid sequence at least 70% identical to SEQ ID NO: 211, or a heavy chain variable region comprising a HCDR1 amino acid sequence at least 70% identical to SEQ ID NO: 2, a HCDR2 amino acid sequence at least 70% identical to SEQ ID NO: 23, and a HCDR3 amino acid sequence at least 70% identical to SEQ ID NO: 44; and a light chain variable region comprising a LCDR1 amino acid sequence at least 70% identical to SEQ ID NO: 170, a LCDR2 amino acid sequence at least 70% identical to SEQ ID NO: 191, and a LCDR3 amino acid sequence at least 70% identical to SEQ ID NO: 212, or a heavy chain variable region comprising a HCDR1 amino acid sequence at least 70% identical to SEQ ID NO: 3, a HCDR2 amino acid sequence at least 70% identical to SEQ ID NO: 24, and a HCDR3 amino acid sequence at least 70% identical to SEQ ID NO: 45; and a light chain variable region comprising a LCDR1 amino acid sequence at least 70% identical to SEQ ID NO: 171, a LCDR2 amino acid sequence at least 70% identical to SEQ ID NO: 192, and a LCDR3 amino acid sequence at least 70% identical to SEQ ID NO: 213, or a heavy chain variable region comprising a HCDR1 amino acid sequence at least 70% identical to SEQ ID NO: 4, a HCDR2 amino acid sequence at least 70% identical to SEQ ID NO: 25, and a HCDR3 amino acid sequence at least 70% identical to SEQ ID NO: 46; and a light chain variable region comprising a LCDR1 amino acid sequence at least 70% identical to SEQ ID NO: 172, a LCDR2 amino acid sequence at least 70% identical to SEQ ID NO: 193, and a LCDR3 amino acid sequence at least 70% identical to SEQ ID NO: 214, or a heavy chain variable region comprising a HCDR1 amino acid sequence at least 70% identical to SEQ ID NO: 5, a HCDR2 amino acid sequence at least 70% identical to SEQ ID NO: 26, and a HCDR3 amino acid sequence at least 70% identical to SEQ ID NO: 47; and a light chain variable region comprising a LCDR1 amino acid sequence at least 70% identical to SEQ ID NO: 173, a LCDR2 amino acid sequence at least 70% identical to SEQ ID NO: 194, and a LCDR3 amino acid sequence at least 70% identical to SEQ ID NO: 215, or a heavy chain variable region comprising a HCDR1 amino acid sequence at least 70% identical to SEQ ID NO: 6, a HCDR2 amino acid sequence at least 70% identical to SEQ ID NO: 27, and a HCDR3 amino acid sequence at least 70% identical to SEQ ID NO: 48; and a light chain variable region comprising a LCDR1 amino acid sequence at least 70% identical to SEQ ID NO: 174, a LCDR2 amino acid sequence at least 70% identical to SEQ ID NO: 195, and a LCDR3 amino acid sequence at least 70% identical to SEQ ID NO: 216, or a heavy chain variable region comprising a HCDR1 amino acid sequence at least 70% identical to SEQ ID NO: 7, a HCDR2 amino acid sequence at least 70% identical to SEQ ID NO: 28, and a HCDR3 amino acid sequence at least 70% identical to SEQ ID NO: 49; and a light chain variable region comprising a LCDR1 amino acid sequence at least 70% identical to SEQ ID NO: 175, a LCDR2 amino acid sequence at least 70% identical to SEQ ID NO: 196, and a LCDR3 amino acid sequence at least 70% identical to SEQ ID NO: 217, or a heavy chain variable region comprising a HCDR1 amino acid sequence at least 70% identical to SEQ ID NO: 8, a HCDR2 amino acid sequence at least 70% identical to SEQ ID NO: 29, and a HCDR3 amino acid sequence at least 70% identical to SEQ ID NO: 50; and a light chain variable region comprising a LCDR1 amino acid sequence at least 70% identical to SEQ ID NO: 176, a LCDR2 amino acid sequence at least 70% identical to SEQ ID NO: 197, and a LCDR3 amino acid sequence at least 70% identical to SEQ ID NO: 218, or a heavy chain variable region comprising a HCDR1 amino acid sequence at least 70% identical to SEQ ID NO: 9, a HCDR2 amino acid sequence at least 70% identical to SEQ ID NO: 30, and a HCDR3 amino acid sequence at least 70% identical to SEQ ID NO: 51; and a light chain variable region comprising a LCDR1 amino acid sequence at least 70% identical to SEQ ID NO: 177, a LCDR2 amino acid sequence at least 70% identical to SEQ ID NO: 198, and a LCDR3 amino acid sequence at least 70% identical to SEQ ID NO: 219, or a heavy chain variable region comprising a HCDR1 amino acid sequence at least 70% identical to SEQ ID NO: 10, a HCDR2 amino acid sequence at least 70% identical to SEQ ID NO: 31, and a HCDR3 amino acid sequence at least 70% identical to SEQ ID NO: 52; and a light chain variable region comprising a LCDR1 amino acid sequence at least 70% identical to SEQ ID NO: 178, a LCDR2 amino acid sequence at least 70% identical to SEQ ID NO: 199, and a LCDR3 amino acid sequence at least 70% identical to SEQ ID NO: 220, or a heavy chain variable region comprising a HCDR1 amino acid sequence at least 70% identical to SEQ ID NO: 11, a HCDR2 amino acid sequence at least 70% identical to SEQ ID NO: 32, and a HCDR3 amino acid sequence at least 70% identical to SEQ ID NO: 53; and a light chain variable region comprising a LCDR1 amino acid sequence at least 70% identical to SEQ ID NO: 179, a LCDR2 amino acid sequence at least 70% identical to SEQ ID NO: 200, and a LCDR3 amino acid sequence at least 70% identical to SEQ ID NO: 221, or a heavy chain variable region comprising a HCDR1 amino acid sequence at least 70% identical to SEQ ID NO: 12, a HCDR2 amino acid sequence at least 70% identical to SEQ ID NO: 33, and a HCDR3 amino acid sequence at least 70% identical to SEQ ID NO: 54; and a light chain variable region comprising a LCDR1 amino acid sequence at least 70% identical to SEQ ID NO: 180, a LCDR2 amino acid sequence at least 70% identical to SEQ ID NO: 201, and a LCDR3 amino acid sequence at least 70% identical to SEQ ID NO: 222, or a heavy chain variable region comprising a HCDR1 amino acid sequence at least 70% identical to SEQ ID NO: 13, a HCDR2 amino acid sequence at least 70% identical to SEQ ID NO: 34, and a HCDR3 amino acid sequence at least 70% identical to SEQ ID NO: 55; and a light chain variable region comprising a LCDR1 amino acid sequence at least 70% identical to SEQ ID NO: 181, a LCDR2 amino acid sequence at least 70% identical to SEQ ID NO: 202, and a LCDR3 amino acid sequence at least 70% identical to SEQ ID NO: 223, or a heavy chain variable region comprising a HCDR1 amino acid sequence at least 70% identical to SEQ ID NO: 14, a HCDR2 amino acid sequence at least 70% identical to SEQ ID NO: 35, and a HCDR3 amino acid sequence at least 70% identical to SEQ ID NO: 56; and a light chain variable region comprising a LCDR1 amino acid sequence at least 70% identical to SEQ ID NO: 182, a LCDR2 amino acid sequence at least 70% identical to SEQ ID NO: 203, and a LCDR3 amino acid sequence at least 70% identical to SEQ ID NO: 224, or a heavy chain variable region comprising a HCDR1 amino acid sequence at least 70% identical to SEQ ID NO: 15, a HCDR2 amino acid sequence at least 70% identical to SEQ ID NO: 36, and a HCDR3 amino acid sequence at least 70% identical to SEQ ID NO: 57; and a light chain variable region comprising a LCDR1 amino acid sequence at least 70% identical to SEQ ID NO: 183, a LCDR2 amino acid sequence at least 70% identical to SEQ ID NO: 204, and a LCDR3 amino acid sequence at least 70% identical to SEQ ID NO: 225, or a heavy chain variable region comprising a HCDR1 amino acid sequence at least 70% identical to SEQ ID NO: 16, a HCDR2 amino acid sequence at least 70% identical to SEQ ID NO: 37, and a HCDR3 amino acid sequence at least 70% identical to SEQ ID NO: 58; and a light chain variable region comprising a LCDR1 amino acid sequence at least 70% identical to SEQ ID NO: 184, a LCDR2 amino acid sequence at least 70% identical to SEQ ID NO: 205, and a LCDR3 amino acid sequence at least 70% identical to SEQ ID NO: 226, or a heavy chain variable region comprising a HCDR1 amino acid sequence at least 70% identical to SEQ ID NO: 17, a HCDR2 amino acid sequence at least 70% identical to SEQ ID NO: 38, and a HCDR3 amino acid sequence at least 70% identical to SEQ ID NO: 59; and a light chain variable region comprising a LCDR1 amino acid sequence at least 70% identical to SEQ ID NO: 185, a LCDR2 amino acid sequence at least 70% identical to SEQ ID NO: 206, and a LCDR3 amino acid sequence at least 70% identical to SEQ ID NO: 227, or a heavy chain variable region comprising a HCDR1 amino acid sequence at least 70% identical to SEQ ID NO: 18, a HCDR2 amino acid sequence at least 70% identical to SEQ ID NO: 39, and a HCDR3 amino acid sequence at least 70% identical to SEQ ID NO: 60; and a light chain variable region comprising a LCDR1 amino acid sequence at least 70% identical to SEQ ID NO: 186, a LCDR2 amino acid sequence at least 70% identical to SEQ ID NO: 207, and a LCDR3 amino acid sequence at least 70% identical to SEQ ID NO: 228, or a heavy chain variable region comprising a HCDR1 amino acid sequence at least 70% identical to SEQ ID NO: 19, a HCDR2 amino acid sequence at least 70% identical to SEQ ID NO: 40, and a HCDR3 amino acid sequence at least 70% identical to SEQ ID NO: 61; and a light chain variable region comprising a LCDR1 amino acid sequence at least 70% identical to SEQ ID NO: 187, a LCDR2 amino acid sequence at least 70% identical to SEQ ID NO: 208, and a LCDR3 amino acid sequence at least 70% identical to SEQ ID NO: 229, or a heavy chain variable region comprising a HCDR1 amino acid sequence at least 70% identical to SEQ ID NO: 20, a HCDR2 amino acid sequence at least 70% identical to SEQ ID NO: 41, and a HCDR3 amino acid sequence at least 70% identical to SEQ ID NO: 62; and a light chain variable region comprising a LCDR1 amino acid sequence at least 70% identical to SEQ ID NO: 188, a LCDR2 amino acid sequence at least 70% identical to SEQ ID NO: 209, and a LCDR3 amino acid sequence at least 70% identical to SEQ ID NO: 230, or a heavy chain variable region comprising a HCDR1 amino acid sequence at least 70% identical to SEQ ID NO: 21, a HCDR2 amino acid sequence at least 70% identical to SEQ ID NO: 42, and a HCDR3 amino acid sequence at least 70% identical to SEQ ID NO: 63; and a light chain variable region comprising a LCDR1 amino acid sequence at least 70% identical to SEQ ID NO: 189, a LCDR2 amino acid sequence at least 70% identical to SEQ ID NO: 210, and a LCDR3 amino acid sequence at least 70% identical to SEQ ID NO: 231.

In some embodiments, the antibody comprises: a heavy chain variable region comprising a HCDR1 amino acid sequence at least 70% identical to SEQ ID NO: 370, a HCDR2 amino acid sequence at least 70% identical to SEQ ID NO: 390, and a HCDR3 amino acid sequence at least 70% identical to SEQ ID NO: 418; and a light chain variable region comprising a LCDR1 amino acid sequence at least 70% identical to SEQ ID NO: 440, a LCDR2 amino acid sequence at least 70% identical to SEQ ID NO: 463, and a LCDR3 amino acid sequence at least 70% identical to SEQ ID NO: 481, or a heavy chain variable region comprising a HCDR1 amino acid sequence at least 70% identical to SEQ ID NO: 371, a HCDR2 amino acid sequence at least 70% identical to SEQ ID NO: 391, and a HCDR3 amino acid sequence at least 70% identical to SEQ ID NO: 418; and a light chain variable region comprising a LCDR1 amino acid sequence at least 70% identical to SEQ ID NO: 441, a LCDR2 amino acid sequence at least 70% identical to SEQ ID NO: 464, and a LCDR3 amino acid sequence at least 70% identical to SEQ ID NO: 482, or a heavy chain variable region comprising a HCDR1 amino acid sequence at least 70% identical to SEQ ID NO: 372, a HCDR2 amino acid sequence at least 70% identical to SEQ ID NO: 392, and a HCDR3 amino acid sequence at least 70% identical to DNL; and a light chain variable region comprising a LCDR1 amino acid sequence at least 70% identical to SEQ ID NO: 442, a LCDR2 amino acid sequence at least 70% identical to SEQ ID NO: 465, and a LCDR3 amino acid sequence at least 70% identical to SEQ ID NO: 483, or a heavy chain variable region comprising a HCDR1 amino acid sequence at least 70% identical to SEQ ID NO: 373, a HCDR2 amino acid sequence at least 70% identical to SEQ ID NO: 393, and a HCDR3 amino acid sequence at least 70% identical to SEQ ID NO: 419; and a light chain variable region comprising a LCDR1 amino acid sequence at least 70% identical to SEQ ID NO: 443, a LCDR2 amino acid sequence at least 70% identical to SEQ ID NO: 466, and a LCDR3 amino acid sequence at least 70% identical to SEQ ID NO: 484, or a heavy chain variable region comprising a HCDR1 amino acid sequence at least 70% identical to SEQ ID NO: 374, a HCDR2 amino acid sequence at least 70% identical to SEQ ID NO: 394, and a HCDR3 amino acid sequence at least 70% identical to SEQ ID NO: 420; and a light chain variable region comprising a LCDR1 amino acid sequence at least 70% identical to SEQ ID NO: 444, a LCDR2 amino acid sequence at least 70% identical to SEQ ID NO: 467, and a LCDR3 amino acid sequence at least 70% identical to SEQ ID NO: 485, or a heavy chain variable region comprising a HCDR1 amino acid sequence at least 70% identical to SEQ ID NO: 375, a HCDR2 amino acid sequence at least 70% identical to SEQ ID NO: 395, and a HCDR3 amino acid sequence at least 70% identical to SEQ ID NO: 421; and a light chain variable region comprising a LCDR1 amino acid sequence at least 70% identical to SEQ ID NO: 445, a LCDR2 amino acid sequence at least 70% identical to SEQ ID NO: 468, and a LCDR3 amino acid sequence at least 70% identical to SEQ ID NO: 486, or a heavy chain variable region comprising a HCDR1 amino acid sequence at least 70% identical to SEQ ID NO: 376, a HCDR2 amino acid sequence at least 70% identical to SEQ ID NO: 396, and a HCDR3 amino acid sequence at least 70% identical to SEQ ID NO: 422; and a light chain variable region comprising a LCDR1 amino acid sequence at least 70% identical to SEQ ID NO: 446, a LCDR2 amino acid sequence at least 70% identical to SEQ ID NO: 469, and a LCDR3 amino acid sequence at least 70% identical to SEQ ID NO: 487, or a heavy chain variable region comprising a HCDR1 amino acid sequence at least 70% identical to SEQ ID NO: 373, a HCDR2 amino acid sequence at least 70% identical to SEQ ID NO: 393, and a HCDR3 amino acid sequence at least 70% identical to SEQ ID NO: 419; and a light chain variable region comprising a LCDR1 amino acid sequence at least 70% identical to SEQ ID NO: 447, a LCDR2 amino acid sequence at least 70% identical to SEQ ID NO: 470, and a LCDR3 amino acid sequence at least 70% identical to SEQ ID NO: 484, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 423; and a light chain variable region comprising a LCDR1 amino acid sequence at least 70% identical to SEQ ID NO: 448, a LCDR2 amino acid sequence at least 70% identical to SEQ ID NO: 471, and a LCDR3 amino acid sequence at least 70% identical to SEQ ID NO: 488, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 423; and a light chain variable region comprising a LCDR1 amino acid sequence at least 70% identical to SEQ ID NO: 449, a LCDR2 amino acid sequence at least 70% identical to SEQ ID NO: 472, and a LCDR3 amino acid sequence at least 70% identical to SEQ ID NO: 488, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 423; and a light chain variable region comprising a LCDR1 amino acid sequence at least 70% identical to SEQ ID NO: 450, a LCDR2 amino acid sequence at least 70% identical to SEQ ID NO: 471, and a LCDR3 amino acid sequence at least 70% identical to SEQ ID NO: 488, or a heavy chain variable region comprising a HCDR1 amino acid sequence at least 70% identical to SEQ ID NO: 377, a HCDR2 amino acid sequence at least 70% identical to SEQ ID NO: 398, and a HCDR3 amino acid sequence at least 70% identical to SEQ ID NO: 423; and a light chain variable region comprising a LCDR1 amino acid sequence at least 70% identical to SEQ ID NO: 448, a LCDR2 amino acid sequence at least 70% identical to SEQ ID NO: 471, and a LCDR3 amino acid sequence at least 70% identical to SEQ ID NO: 488, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 424; and a light chain variable region comprising a LCDR1 amino acid sequence at least 70% identical to SEQ ID NO: 448, a LCDR2 amino acid sequence at least 70% identical to SEQ ID NO: 472, and a LCDR3 amino acid sequence at least 70% identical to SEQ ID NO: 489, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 423; and a light chain variable region comprising a LCDR1 amino acid sequence at least 70% identical to SEQ ID NO: 448, a LCDR2 amino acid sequence at least 70% identical to SEQ ID NO: 472, and a LCDR3 amino acid sequence at least 70% identical to SEQ ID NO: 488, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 423; and a light chain variable region comprising a LCDR1 amino acid sequence at least 70% identical to SEQ ID NO: 448, a LCDR2 amino acid sequence at least 70% identical to SEQ ID NO: 471, and a LCDR3 amino acid sequence at least 70% identical to SEQ ID NO: 490, or a heavy chain variable region comprising a HCDR1 amino acid sequence at least 70% identical to SEQ ID NO: 377, a HCDR2 amino acid sequence at least 70% identical to SEQ ID NO: 398, and a HCDR3 amino acid sequence at least 70% identical to SEQ ID NO: 423; and a light chain variable region comprising a LCDR1 amino acid sequence at least 70% identical to SEQ ID NO: 448, a LCDR2 amino acid sequence at least 70% identical to SEQ ID NO: 471, and a LCDR3 amino acid sequence at least 70% identical to SEQ ID NO: 491, or a heavy chain variable region comprising a HCDR1 amino acid sequence at least 70% identical to SEQ ID NO: 377, a HCDR2 amino acid sequence at least 70% identical to SEQ ID NO: 399, and a HCDR3 amino acid sequence at least 70% identical to SEQ ID NO: 424; and a light chain variable region comprising a LCDR1 amino acid sequence at least 70% identical to SEQ ID NO: 448, a LCDR2 amino acid sequence at least 70% identical to SEQ ID NO: 472, and a LCDR3 amino acid sequence at least 70% identical to SEQ ID NO: 489, or a heavy chain variable region comprising a HCDR1 amino acid sequence at least 70% identical to SEQ ID NO: 377, a HCDR2 amino acid sequence at least 70% identical to SEQ ID NO: 397, and a HCDR3 amino acid sequence at least 70% identical to SEQ ID NO: 424; and a light chain variable region comprising a LCDR1 amino acid sequence at least 70% identical to SEQ ID NO: 448, a LCDR2 amino acid sequence at least 70% identical to SEQ ID NO: 471, and a LCDR3 amino acid sequence at least 70% identical to SEQ ID NO: 488, or a heavy chain variable region comprising a HCDR1 amino acid sequence at least 70% identical to SEQ ID NO: 378, a HCDR2 amino acid sequence at least 70% identical to SEQ ID NO: 400, and a HCDR3 amino acid sequence at least 70% identical to SEQ ID NO: 425; and a light chain variable region comprising a LCDR1 amino acid sequence at least 70% identical to SEQ ID NO: 451, a LCDR2 amino acid sequence at least 70% identical to SEQ ID NO: 473, and a LCDR3 amino acid sequence at least 70% identical to SEQ ID NO: 492, or a heavy chain variable region comprising a HCDR1 amino acid sequence at least 70% identical to SEQ ID NO: 378, a HCDR2 amino acid sequence at least 70% identical to SEQ ID NO: 401, and a HCDR3 amino acid sequence at least 70% identical to SEQ ID NO: 425; and a light chain variable region comprising a LCDR1 amino acid sequence at least 70% identical to SEQ ID NO: 452, a LCDR2 amino acid sequence at least 70% identical to SEQ ID NO: 473, and a LCDR3 amino acid sequence at least 70% identical to SEQ ID NO: 493, or a heavy chain variable region comprising a HCDR1 amino acid sequence at least 70% identical to SEQ ID NO: 378, a HCDR2 amino acid sequence at least 70% identical to SEQ ID NO: 402, and a HCDR3 amino acid sequence at least 70% identical to SEQ ID NO: 425; and a light chain variable region comprising a LCDR1 amino acid sequence at least 70% identical to SEQ ID NO: 452, a LCDR2 amino acid sequence at least 70% identical to SEQ ID NO: 473, and a LCDR3 amino acid sequence at least 70% identical to SEQ ID NO: 493, or a heavy chain variable region comprising a HCDR1 amino acid sequence at least 70% identical to SEQ ID NO: 379, a HCDR2 amino acid sequence at least 70% identical to SEQ ID NO: 403, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 470, and a LCDR3 amino acid sequence at least 70% identical to SEQ ID NO: 494, or a heavy chain variable region comprising a HCDR1 amino acid sequence at least 70% identical to SEQ ID NO: 380, a HCDR2 amino acid sequence at least 70% identical to SEQ ID NO: 403, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 470, and a LCDR3 amino acid sequence at least 70% identical to SEQ ID NO: 494, or a heavy chain variable region comprising a HCDR1 amino acid sequence at least 70% identical to SEQ ID NO: 380, a HCDR2 amino acid sequence at least 70% identical to SEQ ID NO: 403, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 474, and a LCDR3 amino acid sequence at least 70% identical to SEQ ID NO: 494, or a heavy chain variable region comprising a HCDR1 amino acid sequence at least 70% identical to SEQ ID NO: 381, a HCDR2 amino acid sequence at least 70% identical to SEQ ID NO: 404, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 470, and a LCDR3 amino acid sequence at least 70% identical to SEQ ID NO: 494, or a heavy chain variable region comprising a HCDR1 amino acid sequence at least 70% identical to SEQ ID NO: 381, a HCDR2 amino acid sequence at least 70% identical to SEQ ID NO: 404, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 470, and a LCDR3 amino acid sequence at least 70% identical to SEQ ID NO: 495, or a heavy chain variable region comprising a HCDR1 amino acid sequence at least 70% identical to SEQ ID NO: 381, a HCDR2 amino acid sequence at least 70% identical to SEQ ID NO: 405, and a HCDR3 amino acid sequence at least 70% identical to SEQ ID NO: 426; and a light chain variable region comprising a LCDR1 amino acid sequence at least 70% identical to SEQ ID NO: 453, a LCDR2 amino acid sequence at least 70% identical to SEQ ID NO: 470, and a LCDR3 amino acid sequence at least 70% identical to SEQ ID NO: 494, or a heavy chain variable region comprising a HCDR1 amino acid sequence at least 70% identical to SEQ ID NO: 378, a HCDR2 amino acid sequence at least 70% identical to SEQ ID NO: 406, and a HCDR3 amino acid sequence at least 70% identical to SEQ ID NO: 427; and a light chain variable region comprising a LCDR1 amino acid sequence at least 70% identical to SEQ ID NO: 452, a LCDR2 amino acid sequence at least 70% identical to SEQ ID NO: 470, and a LCDR3 amino acid sequence at least 70% identical to SEQ ID NO: 496, or a heavy chain variable region comprising a HCDR1 amino acid sequence at least 70% identical to SEQ ID NO: 378, a HCDR2 amino acid sequence at least 70% identical to SEQ ID NO: 407, and a HCDR3 amino acid sequence at least 70% identical to SEQ ID NO: 425; and a light chain variable region comprising a LCDR1 amino acid sequence at least 70% identical to SEQ ID NO: 452, a LCDR2 amino acid sequence at least 70% identical to SEQ ID NO: 475, and a LCDR3 amino acid sequence at least 70% identical to SEQ ID NO: 496, or a heavy chain variable region comprising a HCDR1 amino acid sequence at least 70% identical to SEQ ID NO: 382, a HCDR2 amino acid sequence at least 70% identical to SEQ ID NO: 408, and a HCDR3 amino acid sequence at least 70% identical to SEQ ID NO: 428; and a light chain variable region comprising a LCDR1 amino acid sequence at least 70% identical to SEQ ID NO: 454, a LCDR2 amino acid sequence at least 70% identical to SEQ ID NO: 471, and a LCDR3 amino acid sequence at least 70% identical to SEQ ID NO: 497, or a heavy chain variable region comprising a HCDR1 amino acid sequence at least 70% identical to SEQ ID NO: 382, a HCDR2 amino acid sequence at least 70% identical to SEQ ID NO: 408, and a HCDR3 amino acid sequence at least 70% identical to SEQ ID NO: 429; and a light chain variable region comprising a LCDR1 amino acid sequence at least 70% identical to SEQ ID NO: 455, a LCDR2 amino acid sequence at least 70% identical to SEQ ID NO: 476, and a LCDR3 amino acid sequence at least 70% identical to SEQ ID NO: 498, or a heavy chain variable region comprising a HCDR1 amino acid sequence at least 70% identical to SEQ ID NO: 382, a HCDR2 amino acid sequence at least 70% identical to SEQ ID NO: 408, and a HCDR3 amino acid sequence at least 70% identical to SEQ ID NO: 429; and a light chain variable region comprising a LCDR1 amino acid sequence at least 70% identical to SEQ ID NO: 454, a LCDR2 amino acid sequence at least 70% identical to SEQ ID NO: 468, and a LCDR3 amino acid sequence at least 70% identical to SEQ ID NO: 497, or a heavy chain variable region comprising a HCDR1 amino acid sequence at least 70% identical to SEQ ID NO: 382, a HCDR2 amino acid sequence at least 70% identical to SEQ ID NO: 408, and a HCDR3 amino acid sequence at least 70% identical to SEQ ID NO: 430; and a light chain variable region comprising a LCDR1 amino acid sequence at least 70% identical to SEQ ID NO: 454, a LCDR2 amino acid sequence at least 70% identical to SEQ ID NO: 477, and a LCDR3 amino acid sequence at least 70% identical to SEQ ID NO: 497, or a heavy chain variable region comprising a HCDR1 amino acid sequence at least 70% identical to SEQ ID NO: 383, a HCDR2 amino acid sequence at least 70% identical to SEQ ID NO: 409, and a HCDR3 amino acid sequence at least 70% identical to SEQ ID NO: 431; and a light chain variable region comprising a LCDR1 amino acid sequence at least 70% identical to SEQ ID NO: 456, a LCDR2 amino acid sequence at least 70% identical to SEQ ID NO: 474, and a LCDR3 amino acid sequence at least 70% identical to SEQ ID NO: 499, or a heavy chain variable region comprising a HCDR1 amino acid sequence at least 70% identical to SEQ ID NO: 383, a HCDR2 amino acid sequence at least 70% identical to SEQ ID NO: 409, and a HCDR3 amino acid sequence at least 70% identical to SEQ ID NO: 431; and a light chain variable region comprising a LCDR1 amino acid sequence at least 70% identical to SEQ ID NO: 456, a LCDR2 amino acid sequence at least 70% identical to SEQ ID NO: 478, and a LCDR3 amino acid sequence at least 70% identical to SEQ ID NO: 499, or a heavy chain variable region comprising a HCDR1 amino acid sequence at least 70% identical to SEQ ID NO: 384, a HCDR2 amino acid sequence at least 70% identical to SEQ ID NO: 410, and a HCDR3 amino acid sequence at least 70% identical to SEQ ID NO: 431; and a light chain variable region comprising a LCDR1 amino acid sequence at least 70% identical to SEQ ID NO: 457, a LCDR2 amino acid sequence at least 70% identical to SEQ ID NO: 474, and a LCDR3 amino acid sequence at least 70% identical to SEQ ID NO: 500, or a heavy chain variable region comprising a HCDR1 amino acid sequence at least 70% identical to SEQ ID NO: 384, a HCDR2 amino acid sequence at least 70% identical to SEQ ID NO: 410, and a HCDR3 amino acid sequence at least 70% identical to SEQ ID NO: 432; and a light chain variable region comprising a LCDR1 amino acid sequence at least 70% identical to SEQ ID NO: 458, a LCDR2 amino acid sequence at least 70% identical to SEQ ID NO: 474, and a LCDR3 amino acid sequence at least 70% identical to SEQ ID NO: 500, or a heavy chain variable region comprising a HCDR1 amino acid sequence at least 70% identical to SEQ ID NO: 385, a HCDR2 amino acid sequence at least 70% identical to SEQ ID NO: 411, and a HCDR3 amino acid sequence at least 70% identical to SEQ ID NO: 433; and a light chain variable region comprising a LCDR1 amino acid sequence at least 70% identical to SEQ ID NO: 459, a LCDR2 amino acid sequence at least 70% identical to SEQ ID NO: 470, and a LCDR3 amino acid sequence at least 70% identical to SEQ ID NO: 501.

In some embodiments, the antibody comprises: a heavy chain variable region comprising a HCDR1 amino acid sequence at least 70% identical to SEQ ID NO: 386, a HCDR2 amino acid sequence at least 70% identical to SEQ ID NO: 412, and a HCDR3 amino acid sequence at least 70% identical to SEQ ID NO: 434; and a light chain variable region comprising a LCDR1 amino acid sequence at least 70% identical to SEQ ID NO: 460, a LCDR2 amino acid sequence at least 70% identical to SEQ ID NO: 479, and a LCDR3 amino acid sequence at least 70% identical to SEQ ID NO: 502, or a heavy chain variable region comprising a HCDR1 amino acid sequence at least 70% identical to SEQ ID NO: 387, a HCDR2 amino acid sequence at least 70% identical to SEQ ID NO: 413, and a HCDR3 amino acid sequence at least 70% identical to SEQ ID NO: 435; and a light chain variable region comprising a LCDR1 amino acid sequence at least 70% identical to SEQ ID NO: 461, a LCDR2 amino acid sequence at least 70% identical to SEQ ID NO: 201, and a LCDR3 amino acid sequence at least 70% identical to SEQ ID NO: 503, or a heavy chain variable region comprising a HCDR1 amino acid sequence at least 70% identical to SEQ ID NO: 4, a HCDR2 amino acid sequence at least 70% identical to SEQ ID NO: 414, and a HCDR3 amino acid sequence at least 70% identical to SEQ ID NO: 436; and a light chain variable region comprising a LCDR1 amino acid sequence at least 70% identical to SEQ ID NO: 462, a LCDR2 amino acid sequence at least 70% identical to SEQ ID NO: 480, and a LCDR3 amino acid sequence at least 70% identical to SEQ ID NO: 504, or a heavy chain variable region comprising a HCDR1 amino acid sequence at least 70% identical to SEQ ID NO: 388, a HCDR2 amino acid sequence at least 70% identical to SEQ ID NO: 415, and a HCDR3 amino acid sequence at least 70% identical to SEQ ID NO: 437; and a light chain variable region comprising a LCDR1 amino acid sequence at least 70% identical to SEQ ID NO: 461, a LCDR2 amino acid sequence at least 70% identical to SEQ ID NO: 201, and a LCDR3 amino acid sequence at least 70% identical to SEQ ID NO: 505, or a heavy chain variable region comprising a HCDR1 amino acid sequence at least 70% identical to SEQ ID NO: 4, a HCDR2 amino acid sequence at least 70% identical to SEQ ID NO: 416, and a HCDR3 amino acid sequence at least 70% identical to SEQ ID NO: 438; and a light chain variable region comprising a LCDR1 amino acid sequence at least 70% identical to SEQ ID NO: 462, a LCDR2 amino acid sequence at least 70% identical to SEQ ID NO: 480, and a LCDR3 amino acid sequence at least 70% identical to SEQ ID NO: 506, or a heavy chain variable region comprising a HCDR1 amino acid sequence at least 70% identical to SEQ ID NO: 4, a HCDR2 amino acid sequence at least 70% identical to SEQ ID NO: 414, and a HCDR3 amino acid sequence at least 70% identical to SEQ ID NO: 436; and a light chain variable region comprising a LCDR1 amino acid sequence at least 70% identical to SEQ ID NO: 462, a LCDR2 amino acid sequence at least 70% identical to SEQ ID NO: 480, and a LCDR3 amino acid sequence at least 70% identical to SEQ ID NO: 507.

In some embodiments, the antibody comprises: a heavy chain variable region comprising a HCDR1 amino acid sequence at least 70% identical to SEQ ID NO: 389, a HCDR2 amino acid sequence at least 70% identical to SEQ ID NO: 417, and a HCDR3 amino acid sequence at least 70% identical to SEQ ID NO: 439.

In some embodiments, the antibody comprises all six CDRs of an antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274 and 1220SBC1068-281.

In some embodiments, the antibody or the binding fragment thereof comprises: a $V_H$ region comprising a $V_H$ amino acid sequence at least 70% identity to any one of SEQ ID NOS: 148-168, 353, and 355; and/or a $V_L$ region comprising a $V_L$ amino acid sequence at least 70% identity to any one of SEQ ID NOS: 316-336, 354, and 356.

In some embodiments, the antibody or the binding fragment thereof comprises: a $V_H$ region comprising a $V_H$ amino acid sequence at least 70% identity to SEQ ID NO: 148, and a $V_L$ region comprising a $V_L$ amino acid sequence at least 70% identity to SEQ ID NO: 316; or a $V_H$ region comprising a $V_H$ amino acid sequence at least 70% identity to SEQ ID NO: 149, and a $V_L$ region comprising a $V_L$ amino acid sequence at least 70% identity to SEQ ID NO: 317; or a $V_H$ region comprising a $V_H$ amino acid sequence at least 70% identity to SEQ ID NO: 150, and a $V_L$ region comprising a $V_L$ amino acid sequence at least 70% identity to SEQ ID NO: 318; or a $V_H$ region comprising a $V_H$ amino acid sequence at least 70% identity to SEQ ID NO: 151, and a $V_L$ region comprising a $V_L$ amino acid sequence at least 70% identity to SEQ ID NO: 319; or a $V_H$ region comprising a $V_H$ amino acid sequence at least 70% identity to SEQ ID NO: 152, and a $V_L$ region comprising a $V_L$ amino acid sequence at least 70% identity to SEQ ID NO: 320; or a $V_H$ region comprising a $V_H$ amino acid sequence at least 70% identity to SEQ ID NO: 153, and a $V_L$ region comprising a $V_L$ amino acid sequence at least 70% identity to SEQ ID NO: 321; or a $V_H$ region comprising a $V_H$ amino acid sequence at least 70% identity to SEQ ID NO: 154, and a $V_L$ region comprising a $V_L$ amino acid sequence at least 70% identity to SEQ ID NO: 322; or a $V_H$ region comprising a $V_H$ amino acid sequence at least 70% identity to SEQ ID NO: 155, and a $V_L$ region comprising a $V_L$ amino acid sequence at least 70% identity to SEQ ID NO: 323; or a $V_H$ region comprising a $V_H$ amino acid sequence at least 70% identity to SEQ ID NO: 156, and a $V_L$ region comprising a $V_L$ amino acid sequence at least 70% identity to SEQ ID NO: 324; or a $V_H$ region comprising a $V_H$ amino acid sequence at least 70% identity to SEQ ID NO: 157, and a $V_L$ region comprising a $V_L$ amino acid sequence at least 70% identity to SEQ ID NO: 325; or a $V_H$ region comprising a $V_H$ amino acid sequence at least 70% identity to SEQ ID NO: 158, and a $V_L$ region comprising a $V_L$ amino acid sequence at least 70% identity to SEQ ID NO: 326; or a $V_H$ region comprising a $V_H$ amino acid sequence at least 70% identity to SEQ ID NO: 159, and a $V_L$ region comprising a $V_L$ amino acid sequence at least 70% identity to SEQ ID NO: 327; or a $V_H$ region comprising a $V_H$ amino acid sequence at least 70% identity to SEQ ID NO: 160, and a $V_L$ region comprising a $V_L$ amino acid sequence at least 70% identity to SEQ ID NO: 328; or a $V_H$ region comprising a $V_H$ amino acid sequence at least 70% identity to SEQ ID NO: 161, and a $V_L$ region comprising a $V_L$ amino acid sequence at least 70% identity to SEQ ID NO: 329; or a $V_H$ region comprising a $V_H$ amino acid sequence at least 70% identity to SEQ ID NO: 162, and a $V_L$ region comprising a $V_L$ amino acid sequence at least 70% identity to SEQ ID NO: 330; or a $V_H$ region comprising a $V_H$ amino acid sequence at least 70% identity to SEQ ID NO: 163, and a $V_L$ region comprising a $V_L$ amino acid sequence at least 70% identity to SEQ ID NO: 331; or a $V_H$ region comprising a $V_H$ amino acid sequence at least 70% identity to SEQ ID NO: 164, and a $V_L$ region comprising a $V_L$ amino acid sequence at least 70% identity to SEQ ID NO: 332; or a $V_H$ region comprising a $V_H$ amino acid sequence at least 70% identity to SEQ ID NO: 165, and a $V_L$ region comprising a $V_L$ amino acid sequence at least 70% identity to SEQ ID NO: 333; or a $V_H$ region comprising a $V_H$ amino acid sequence at least 70% identity to SEQ ID NO: 166, and a $V_L$ region comprising a $V_L$ amino acid sequence at least 70% identity to SEQ ID NO: 334; or a $V_H$ region comprising a $V_H$ amino acid sequence at least 70% identity to SEQ ID NO: 167, and a $V_L$ region comprising a $V_L$ amino acid sequence at least 70% identity to SEQ ID NO: 335; or a $V_H$ region comprising a $V_H$ amino acid sequence at least 70% identity to SEQ ID NO: 168, and a $V_L$ region comprising a $V_L$ amino acid sequence at least 70% identity to SEQ ID NO: 336; or a $V_H$ region comprising a $V_H$ amino acid sequence at least 70% identity to SEQ ID NO: 353, and a $V_L$ region comprising a $V_L$ amino acid sequence at least 70% identity to SEQ ID NO: 354; or a $V_H$ region comprising a $V_H$ amino acid sequence at least 70% identity to SEQ ID NO: 355, and a $V_L$ region comprising a $V_L$ amino acid sequence at least 70% identity to SEQ ID NO: 356.

In some embodiments, the antibody or the binding fragment thereof comprises both the $V_H$ and $V_L$ of an antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274, 1220SBC1068-281, SIF-001, SIF-002, and a variant thereof.

In some embodiments, the antibody is a humanized, chimeric, or human antibody.

In yet another aspect, provided herein is a polypeptide comprising a $V_H$ sequence and/or a $V_L$ sequence of an antibody described above. In some embodiments, provided herein is a polynucleotide encoding the polypeptide. In some embodiments, provided herein is an expression vector comprising the polynucleotide. In some embodiments, provided herein is a cell that comprises the expression vector of claim 11.

In some embodiments, provided herein is a kit that comprises an antibody, a polypeptide, a polynucleotide, an expression vector, and/or a cell of described above.

In some embodiments, provided herein is a pharmaceutical composition comprising an antibody described above and a pharmaceutically acceptable carrier.

In yet another aspect, provided herein is a method of treating epilepsy or a related neurological disorder (e.g., Alzheimer's disease (AD) or Parkinson's disease (PD)) in a subject in need thereof, comprising administering the subject an effective amount of the pharmaceutical composition above. In some embodiments, the effective amount is about 5-100 mg/kg of the antibody or the immunoconjugate per the subject's body weight. In some embodiments, the effective amount is about 5, 10, 20, 30, 40, 50, 60, 70, 80, 90, and 100 mg/kg of the antibody or the immunoconjugate per the subject's body weight or an amount within a range defined by any of the two values above. In some embodiments, the pharmaceutical composition is administered intravenously into the subject. In some embodiments, the pharmaceutical composition is administered more than once, such as two, three, four, or more times. In some embodiments, each administration is at least 7 days apart. In some embodiments, each administration is at least 14 days apart. In some embodiments, each administration is at least four weeks apart.

In some embodiments, the method for treating epilepsy, an inflammatory or fibrotic disease, or a related neurological disorder (e.g., Alzheimer's disease (AD) or Parkinson's disease (PD)) in a subject in need thereof, comprising administering to the subject an antibody comprising a means for binding to Galectin-3, for example, a human Galectin-3. In some embodiments, the neurological disorder is Alzheimer's disease (AD) or Parkinson's disease (PD).

In some embodiments, the antibody is administered in combination with an additional therapeutic agent. In some embodiments, the antibody is administered intravenously into the subject. In some embodiments, the administration dosage of the antibody is between about 5-100 mg/kg per the subject's body weight. In some embodiments, the administration dosage of the antibody is about 5, 10, 20, 30, 40, 50, 60, 70, 80, 90, and 100 mg/kg of the antibody or the immunoconjugate per the subject's body weight or a dosage within a range defined by any of the two values above.

In some embodiments, provided herein is an antibody or a binding fragment thereof for use in the treatment of epilepsy or a related neurological disorder (e.g., Alzheimer's disease (AD) or Parkinson's disease (PD)) in a subject, wherein the antibody comprises: a heavy chain variable ($V_H$) region comprising:

a HCDR1 amino acid sequence at least 70% identical to any one of SEQ ID NOS: 1-21 and 481-507, a HCDR2 amino acid sequence at least 70% identical to any one of SEQ ID NOS: 22-42 and 390-417, and/or a HCDR3 amino acid sequence at least 70% identical to any one of SEQ ID NOS: 43-63 and 418-439, and/or a light chain variable ($V_L$) region comprising:

a LCDR1 amino acid sequence at least 70% identical to any one of SEQ ID NOS: 169-189 and 440-462, a LCDR2 amino acid sequence at least 70% identical to any one of SEQ ID NOS: 190-210 and 463-480, and/or a LCDR3 amino acid sequence at least 70% identical to any one of SEQ ID NOS: 211-231 and 481-507.

In some embodiments, provided herein is an antibody or a binding fragment thereof that binds to Galectin-3, wherein the antibody comprises: a heavy chain variable region comprising:

a HCDR1 comprising a sequence NYGMN (SEQ ID NO: 4), or a variant HCDR1 in which 1, 2, or 3 amino acids are substituted relative to the sequence;

a HCDR2 comprising a sequence WINTYTGEPTYADDFKG (SEQ ID NO: 25), or a variant HCDR2 in which 1, 2, or 3 amino acids are substituted relative to the sequence; and a HCDR3 comprising a sequence YAMDY (SEQ ID NO: 46), or a variant HCDR3 in which 1, 2, or 3 amino acids are substituted relative to the sequence; and a light chain variable region comprising:

a LCDR1 comprising a sequence RSSTGAVTTSNYAN (SEQ ID NO: 172), or a variant LCDR1 in which 1 amino acid is substituted relative to the sequence;

a LCDR2 comprising a sequence GTSNRAP (SEQ ID NO: 193), or variant LCDR2 in which 1 amino acid is substituted relative to the sequence; and a LCDR3 comprising a sequence ALWYSTHYV (SEQ ID NO: 214), or a variant LCDR3 in which 1 amino acid is substituted relative to the sequence, optionally, the substitution in HCDR1 is in any of the residue #1, and #3-#5, wherein the substitution in HCDR2 is in any of the residue #2, #4-#17, wherein the substitution in HCDR3 is in any of the residues #2-#4, wherein the substitution in LCDR1 is in any of the residues #1-#11 and #13-#14, and/or wherein the substitution in LCDR3 is in any of the residues #1-#2, #4-#7, and #9.

In some embodiments, the amino acid ("aa") at position #2 residue in HCDR1 of the antibody above is Y, W, or F, wherein the aa at position #1 residue in HCDR2 is W, Y, or F, and aa at position #3 residue in HCDR1 is N or Q, wherein the aa at position #1 residue in HCDR3 is Y, wherein the aa at position #12 residue in LCDR1 is Y, W, or F, wherein the aa at position #3 in LCDR3 is Y, W, or F, and aa at position #8 residue in LCDR3 is Y, W, or F.

In some embodiments, disclosed herein is an antibody or a binding fragment thereof that binds to Galectin-3, wherein the antibody comprises: a heavy chain variable region comprising:

a HCDR1 comprising a sequence RFWMS (SEQ ID NO: 8), or a variant HCDR1 in which 1, 2, or 3 amino acids are substituted relative to the sequence;

a HCDR2 comprising a sequence EISPDSNTIDLTPSLKD (SEQ ID NO: 29), or a variant HCDR2 in which 1, 2, or 3 amino acids are substituted relative to the sequence; and a HCDR3 comprising a sequence PYYGYY (SEQ ID NO: 50), or a variant HCDR3 in which 1, 2, or 3 amino acids are substituted relative to the sequence; and a light chain variable region comprising:

a LCDR1 comprising a sequence RSSQSLFNSTNQKNYLT (SEQ ID NO: 176) or RSSQSLFSSTNQKNYLT (SEQ ID NO: 369), or a variant LCDR1 in which 1 amino acid is substituted relative to the sequence;

a LCDR2 comprising a sequence WASSRES (SEQ ID NO: 197), or variant LCDR2 in which 1 amino acid is substituted relative to the sequence; and a LCDR3 comprising a sequence QNDYTSPFT (SEQ ID NO: 218), or a variant LCDR3 in which 1 amino acid is substituted relative to the sequence.

In some embodiments, the substitution in HCDR1 in the antibody above is in any of the residue #1-2, and #4-#5, the substitution in HCDR2 is in any of the residue #2-#17, the substitution in HCDR3 is in any of the residues #1-#4 and #6, the substitution in LCDR1 is in any of the residues #1-#14 and #16-#17, and the substitution in LCDR3 is in any of the residues #1-#2, #4-#9.

In some embodiments, the aa at position #3 residue in HCDR1 is Y, W, or F, the aa at position #1 residue in HCDR2 is E or D, the aa at position #5 residue in HCDR3 is Y, W, or F, the aa at position #15 residue in LCDR1 is Y, W, or F, and/or the aa at position #3 in LCDR3 is Y.

In some embodiments, provided herein is an antibody competes for binding to GAL-3 with an antibody disclosed herein.

In some embodiments, provided herein is an antibody or a binding fragment thereof that binds to Galectin-3, wherein the antibody comprises:

a HCDR1 comprising a sequence of $NX_2GMN$ (SEQ ID NO:357), wherein $X_2$ is Y, W, or F, wherein the HCDR1 has zero or one aa substitution in rest of the residues relative to the HCDR1 sequence, a HCDR2 comprising a sequence of $X_1IX_3TYTGEPTYADDFKG$ (SEQ ID NO: 358), Where $X_1$ is W, Y, or F, and wherein $X_3$ is N or Q, wherein the HCDR2 has zero, one, two, three, or four aa substitutions in rest of the residues relative to the HCDR2 sequence, a HCDR3 comprising a sequence of YAMDY (SEQ ID NO:359), wherein the HCDR3 has zero, one, or two aa substitutions relative to the HCDR3 sequence, a LCDR1 comprising a sequence of $RSSTGAVTTSNX_{12}AN$ (SEQ ID NO:360), wherein $X_{12}$ is Y, W, or F, wherein the LCDR1 has zero, one, two, three, or four aa substitutions in the rest of the residues relative to the LCDR1 sequence, a LCDR2 comprising a sequence of GTSNRAP (SEQ ID NO: 361), wherein the LCDR2 has zero, one, two, or three aa substitutions in the rest of the residues relative to the LCDR2 sequence, and a LCDR3 comprising a sequence of $ALX_3YSTHX_8V$ (SEQ ID NO: 362), wherein $X_3$ is Y, W, or F, wherein $X_8$ is Y, W, or F, wherein the LCDR3 has zero, one, two aa substitutions in the rest of the residues relative to the LCDR3 sequence.

In some embodiments, provided herein is an antibody or a binding fragment thereof that binds to Galectin-3, wherein the antibody comprises:

a HCDR1 comprising a sequence of $NX_2GMN$ (SEQ ID NO:357), wherein $X_2$ is Y, W, or F, a HCDR2 comprising a sequence of $X_1IX_3TYTGEPTYADDFKG$ (SEQ ID NO: 358), Where $X_1$ is W, Y, or F, and wherein $X_3$ is N or Q, a HCDR3 comprising a sequence of YAMDY (SEQ ID NO:359), a LCDR1 comprising a sequence of $RSSTGAVTTSNX_{12}AN$ (SEQ ID NO:360), wherein $X_{12}$ is Y, W, or F, a LCDR2 comprising a sequence of GTSNRAP (SEQ ID NO: 361), and a LCDR3 comprising a sequence of $ALX_3YSTHX_8V$ (SEQ ID NO: 362), wherein $X_3$ is Y, W, or F, wherein $X_8$ is Y, W, or F;

wherein the HCDR1 has zero or one aa substitution in rest of the residues relative to the HCDR1 sequence, the HCDR2 has zero, one, two, three, or four aa substitutions in rest of the residues relative to the HCDR2 sequence, the HCDR3 has zero, one, or two aa substitutions relative to the HCDR3 sequence, the LCDR1 has zero, one, two, three, or four aa substitutions in the rest of the residues relative to the LCDR1 sequence, the LCDR2 has zero, one, two, or three aa substitutions in the rest of the residues relative to the LCDR2 sequence, and/or the LCDR3 has zero, one, two aa substitutions in the rest of the residues relative to the LCDR3 sequence.

In some embodiments, provided herein is an antibody or a binding fragment thereof that binds to Galectin-3, wherein the antibody comprises:

a HCDR1 comprising a sequence of $RFX_3MS$ (SEQ ID NO: 363), wherein $X_3$ is Y, W, or F, and wherein the HCDR1 has zero, one, two aa substitutions in the rest of the residues relative to the HCDR1 sequence, a HCDR2 comprising $X_1ISPDSNTIDLTPSLKD$ (SEQ ID NO: 364), wherein $X_1$ is E or D, and wherein the HCDR2 has zero, one, two, three, or four aa substitutions in the rest of the residues relative to the HCDR2 sequence, a HCDR3 comprising $PYYGX_5Y$ (SEQ ID NO: 365), wherein $X_5$ is Y, W, or F, wherein the HCDR3 has zero, one, two aa substitutions in the rest of the residues relative to the HCDR3 sequence, a LCDR1 comprising RSSQSLFSSTNQKNX$_{15}$LT (SEQ ID NO: 366), wherein X$_{15}$ is Y, W, or F, wherein the LCDR1 has zero, one, two, three, or four aa substitutions in the rest of the residues relative to the LCDR1 sequence, a LCDR2 comprising WASSRES (SEQ ID NO: 367), wherein the LCDR2 has zero, one, two, or three aa substitutions relative to the LCDR2 sequence, and/or a LCDR3 comprising QNDYTSPFT (SEQ ID NO: 368), wherein the LCDR3 has zero, one, two, three, or four aa substitutions in the rest of the residues relative to the LCDR3 sequence.

In some embodiments, provided herein is an antibody or a binding fragment thereof that binds to Galectin-3, wherein the antibody comprises:

a HCDR1 comprising a sequence of RFX$_3$MS (SEQ ID NO: 363), wherein X$_3$ is Y, W, or F, a HCDR2 comprising X$_1$ISPDSNTIDLTPSLKD (SEQ ID NO: 364), wherein X$_1$ is E or D, a HCDR3 comprising PYYGX$_5$Y (SEQ ID NO: 365), wherein X$_5$ is Y, W, or F, a LCDR1 comprising RSSQSLFSSTNQKNX$_{15}$LT (SEQ ID NO: 366), wherein X$_{15}$ is Y, W, or F, a LCDR2 comprising WASSRES (SEQ ID NO: 367), and a LCDR3 comprising QNDYTSPFT (SEQ ID NO: 368); and wherein the HCDR1 has zero, one, two aa substitutions in the rest of the residues relative to the HCDR1 sequence, the HCDR2 has zero, one, two, three, or four aa substitutions in the rest of the residues relative to the HCDR2 sequence, the HCDR3 has zero, one, two aa substitutions in the rest of the residues relative to the HCDR3 sequence, the LCDR1 has zero, one, two, three, or four aa substitutions in the rest of the residues relative to the LCDR1 sequence, the LCDR2 has zero, one, two, or three aa substitutions relative to the LCDR2 sequence, and/or the LCDR3 has zero, one, two, three, or four aa substitutions in the rest of the residues relative to the LCDR3 sequence.

In some embodiments, provided herein is an antibody or a binding fragment thereof that binds to Galectin-3, wherein the antibody comprises a HCDR1 comprising a sequence of NYGMN (SEQ ID NO: 4), a HCDR2 comprising a sequence of WINTYTGEPTYADDFKG (SEQ ID NO: 25), a HCDR3 comprising a sequence of YAMDY (SEQ ID NO: 46), a LCDR1 comprising a sequence of RSSTGAVTTSNYAN (SEQ ID NO: 172), a LCDR2 comprising a sequence of GTSNRAP (SEQ ID NO: 193), and a LCDR3 comprising a sequence of ALWYSTHYV (SEQ ID NO: 214).

In some embodiments, provided herein is an antibody comprises a $V_H$ region comprising a sequence of SEQ ID NO: 353, and a $V_L$ region comprising a sequence of SEQ ID NO: 354.

In some embodiments, provided herein is an antibody or a binding fragment thereof that binds to Galectin-3, wherein the antibody comprises a HCDR1 comprising a sequence of RFWMS (SEQ ID NO: 8), a HCDR2 comprising a sequence of EISPDSNTIDLTPSLKD (SEQ ID NO: 29), a HCDR3 comprising a sequence of PYYGYY (SEQ ID NO: 50), a LCDR1 comprising a sequence of RSSQSLFNSTNQKNYLT (SEQ ID NO: 176) or RSSQSLFSSTNQKNYLT (SEQ ID NO: 369), a LCDR2 comprising a sequence of WASSRES (SEQ ID NO: 197), and a LCDR3 comprising a sequence of QNDYTSPFT (SEQ ID NO: 218).

In some embodiments, provided herein is an antibody comprises a $V_H$ region comprising a sequence of SEQ ID NO: 355, and a $V_L$ region comprising a sequence of SEQ ID NO: 356.

As disclosed herein, any of the embodiments described above can be combined with any other embodiments disclosed above, provided that the resulting combined embodiment remains operable and feasible. Such resulting combined embodiments are also within the scope of the disclosure.

BRIEF DESCRIPTION OF THE DRAWINGS

FIG. 4A depicts a study schema of the evaluation SIF001 therapeutic effects in epilepsy model in C57BL/6J mouse stimulated by KA. FIGS. 4B-4E depict the effects of SIF001 in epilepsy model in C57BL/6J mouse stimulated by KA, as evaluated in (B) seizure occurring rate, (C) seizure frequency, (D) seizure severity, and (E) seizure duration.

DETAILED DESCRIPTION

I. Introduction

Figure 1A:
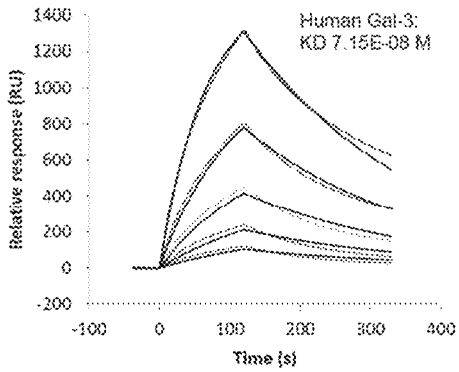
FIGS. 1A-1D depict a kinetics analysis of in vitro cross-species reactivity of SIF001 against GAL-3 in (A) human, (B) mouse, (C) rat, and (D) monkey samples.

The present disclosure provides compositions and methods for treating epilepsy and/or related diseases such as neurological disorders (e.g., AD). In particular, disclosed herein are anti-Galectin-3 antibodies and the use of these antibodies for epilepsy and/or related disease treatment.

Galectin-3 (GAL-3) plays a diverse role in biological processes including cell adhesion, proliferation, migration, apoptosis, tumor progression, and inflammation, especially in neuroinflammation. The inventor has discovered that anti-GAL-3 antibodies can significantly decrease pro-inflammatory cytokine (e.g., tumor necrosis factor-α (TNFα)), in LPS-stimulated microglia cells, and inhibit microglial activation in kainic acid (KA)-stimulated microglia BV2 cells, concluding that targeting GAL-3 with anti-GAL-3 antibodies may offer therapeutic benefits in epilepsy and related neurological disorders by suppressing neuroinflammation and reducing microglial activation.

II. Definitions

Unless specifically indicated otherwise, all technical and scientific terms used herein have the same meaning as commonly understood by those of ordinary skill in the art to which this disclosure belongs. In addition, any method or material similar or equivalent to a method or material described herein can be used in the practice of the present disclosure. For purposes of the present disclosure, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g., 1 to 5 includes 1, 1.5, 2, 2.75, 3, 3.80, 4, and 5).

Also, the words "comprise," "comprising," "contains," "containing," "include," "including," and "includes," when used in this specification and in the following claims, are intended to specify the presence of stated features, integers, components, or steps, but they do not preclude the presence or addition of one or more other features, integers, components, steps, acts, or groups.

The term "amino acid" refers to any monomeric unit that can be incorporated into a peptide, polypeptide, or protein. Amino acids include naturally occurring a-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an 1-amino acid and the corresponding d-amino acid).

The terms "identity," "substantial identity," "similarity," "substantial similarity," "homology" and the related terms and expressions used in the context of describing amino acid sequences refer to a sequence that has at least 60% sequence identity to a reference sequence. Examples include at least: 60%, 65%, 70%, 75%, 80%, 85%, 86%, 87%, 88%, 89%, 90%, 91%, 92%, 93%, 94%, 95%, 96%, 97%, 98%, or 99%, sequence identity, as compared to a reference sequence using the programs for comparison of amino acid sequences, such as BLAST using standard parameters. For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default (standard) program parameters can be used, or alternative parameters can be designated. The sequence comparison algorithm then calculates the percent sequence identities for the test sequences relative to the reference sequence, based on the program parameters. A "comparison window" includes reference to a segment of any one of the number of contiguous positions (from 20 to 600, usually about 50 to about 200, more commonly about 100 to about 150), in which a sequence may be compared to a reference sequence of the same number of contiguous positions after the two sequences are optimally aligned. Methods of alignment of sequences for comparison are well-known. Optimal alignment of sequences for comparison may be conducted, for example, by the local homology algorithm of Smith and Waterman, 1981, by the homology alignment algorithm of Needleman and Wunsch, 1970, by the search for similarity method of Pearson and Lipman, 1988, by computerized implementations of these algorithms (for example, BLAST), or by manual alignment and visual inspection.

Algorithms that are suitable for determining percent sequence identity and sequence similarity include BLAST and BLAST 2.0 algorithms, which are described in Altschul et al., 1990, and Altschul et al., 1977, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (Henikoff and Henikoff, 1989). The BLAST algorithm also performs a statistical analysis of the similarity between two sequences (Karlin and Altschul, 1993).

As disclosed herein, when referring to a range defined by "greater than a first minimum value," such range includes any subrange defined by a second minimum value that is greater than the first minimum value. This is to say, all values equal to or greater than the first minimum value are encompassed within the broader range. For example, when stating "at least 70%," this phrase inherently includes all percentages equal to or greater than 70%. It is equivalent to explicitly listing each percentage value, as follows: "at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%."

As used herein, the term "antibody" means an isolated or recombinant binding agent that comprises the necessary variable region sequences to specifically bind an antigenic epitope. Therefore, an "antibody" as used herein is any form of an antibody of any class or subclass or fragment thereof that exhibits the desired biological activity, e.g., binding a specific target antigen. Thus, it is used in the broadest sense and specifically covers a monoclonal antibody (including full-length monoclonal antibodies), human antibodies, chimeric antibodies, nanobodies, diabodies, multispecific antibodies (e.g., bispecific antibodies), antibody fragments, antigen-binding fragments including but not limited to scFv, Fab, and the like so long as they exhibit the desired biological activity.

"Antibody fragments" or "antigen-binding fragments" comprise a portion of an intact antibody, for example, the antigen-binding or variable region of the intact antibody. Examples of antibody fragments include Fab, Fab', $F(ab')_2$, and Fv fragments; diabodies; linear antibodies (e.g., Zapata et al., Protein Eng. 8 (10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab') 2 fragment with two antigen combining sites and is still capable of cross-linking antigen.

As used herein, "V-region" or "variable region" refers to an antibody variable region domain comprising the segments of Framework 1, CDR1, Framework 2, CDR2, and Framework 3, including CDR3 and Framework 4. The heavy chain V-region, $V_H$, is a consequence of the rearrangement of a V-gene (HV), a D-gene (HD), and a J-gene (HJ), in what is termed V(D)J recombination during B-cell differentiation. The light chain V-region, $V_L$, is a consequence of the rearrangement of a V-gene (LV) and a J-gene (LJ).

As used herein, "complementarity-determining region (CDR)" refers to the three hypervariable regions (HVRs) in each chain that interrupt the four "framework" regions established by the light and heavy chain variable regions. The CDRs are the primary contributors to binding to an epitope of an antigen. The CDRs of each chain are referred to as CDR1, CDR2, and CDR3, numbered sequentially starting from the N-terminus, and are also identified by the chain in which the CDR is located. Thus, a $V_H$ CDR3 (HCDR3) is in the variable domain of the heavy chain of the antibody in which it is found, whereas a $V_L$ CDR3 (LCDR3) is the CDR3 from the variable domain of the light chain of the antibody in which it is located. The term "CDR" is used interchangeably with "HVR" when referring to CDR sequences.

The amino acid sequences of the CDRs and framework regions can be determined using various well-known definitions in the art, e.g., Kabat, Chothia, international ImMunoGeneTics database (IMGT), and AbM (see, e.g., Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, Structural repertoire of the human $V_H$ segments J. Mol. Biol. 227, 799-817; Al-Lazikani et al., J. Mol. Biol. 1997, 273 (4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29 (1): 207-9 (2001); MacCallum et al., Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin et al., Methods Enzymol., 203, 121-153, (1991); Pedersen et al., Immunomethods, 1, 126, (1992); and Rees et al., In Sternberg M. J. E. (ed.), Protein Structure Prediction. Oxford University Press, Oxford, 141-172 1996). Reference to CDRs as determined by Kabat numbering is based, for example, on Kabat et al., Sequences of Proteins of Immunological Interest, 5th Ed. Public Health Service, National Institute of Health, Bethesda, MD (1991)). Chothia CDRs are determined as defined by Chothia (see, e.g., Chothia and Lesk J. Mol. Biol. 196:901-917 (1987)).

CDRs in this disclosure are defined by Kabat. As known in the art, numbering and placement of the CDRs can differ depending on the numbering system employed. It is understood that disclosure of a variable heavy and/or variable light sequence includes the disclosure of the associated CDRs, regardless of the numbering system employed.

An "Fc region" refers to the constant region of an antibody excluding the first constant region immunoglobulin domain. Thus, e.g., for human immunoglobulins, "Fc" refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cγ2 and Cγ3 and the hinge between Cγ1 and Cγ2. It is understood in the art that the boundaries of the Fc region may vary, however, the human IgG heavy chain Fc region is usually defined to comprise residues C226 or P230 to its carboxyl-terminus, using the numbering according to the EU index as in Kabat et al. (1991, NIH Publication 91-3242, National Technical Information Service, Springfield, Va.). The term "Fc region" may refer to this region in isolation or this region in the context of an antibody or antibody fragment. "Fc region" includes naturally occurring allelic variants of the Fc region as well as modified Fc regions, e.g., that are modified to modulate effector function or other properties such as pharmacokinetics, stability or production properties of an antibody. Fc regions also include variants that do not exhibit alterations in biological function. For example, one or more amino acids can be deleted from the N-terminus or C-terminus of the Fc region of an immunoglobulin without substantial loss of biological function. Such variants can be selected according to general rules known in the art to have minimal effect on activity (see, e.g., Bowie et al., Science 247:306-1310, 1990). For example, for IgG4 antibodies, a single amino acid substitution (S228P according to Kabat numbering; designated IgG4Pro) may be introduced to abolish the heterogeneity observed in recombinant IgG4 antibodies (see, e.g., Angal et al., *Mol Immunol* 30:105-108, 1993).

An "$EC_{50}$" as used herein refers to the half-maximal effective concentration, which is the concentration of an antibody that induces a response (signal generated in engagement assay) halfway between the baseline and maximum after a specified exposure time. In some embodiments, the "fold over EC50" is determined by dividing the EC50 of a reference antibody by the $EC_{50}$ of the test antibody.

The term "equilibrium dissociation constant" abbreviated ($K_D$), refers to the dissociation rate constant ($k_d$, time$^{-1}$) divided by the association rate constant ($k_a$, time$^{-1}$ M$^{-1}$). Equilibrium dissociation constants can be measured using any method. Thus, in some embodiments antibodies of the present disclosure have a $K_D$ of less than about 50 nM, typically less than about 25 nM, or less than 10 nM, e.g., less than about 5 nM or than about 1 nM and often less than about 10 nM as determined by surface plasmon resonance analysis using a biosensor system such as a Biacore® system performed at 37° C. In some embodiments, an antibody of the present disclosure has a $K_D$ of less than $5\times10^{-5}$ M, less than $10^{-5}$ M, less than $5\times10^{-6}$ M, less than $10^{-6}$M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower as measured as a bivalent antibody. In the context of the present invention, an "improved" $K_D$ refers to a lower $K_D$. In some embodiments, an antibody of the present disclosure has a $K_D$ of less than $5\times10^{-5}$ M, less than $10^{-5}$ M, less than $5\times10^{-6}$ M, less than $10^{-6}$ M, less than $5\times10^{-7}$M, less than $10^{-7}$M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$M, less than $10^{-14}$ M, less than $5\times10^{-15}$ M, or less than $10^{-15}$ M or lower as measured as a monovalent antibody, such as a monovalent Fab. In some embodiments, an anti-GAL-3 antibody of the present disclosure has $K_D$ less than 100 pM, e.g., or less than 75 pM, e.g., in the range of 1 to 100 pM, when measured by surface plasmon resonance analysis using a biosensor system such as a Biacore® system performed at 37° C. In some embodiments, an anti-GAL-3 antibody of the present disclosure has $K_D$ of greater than 100 pM, e.g., in the range of 100-1000 pM or 500-1000 pM when measured by surface plasmon resonance analysis using a biosensor system such as a Biacore® system performed at 37° C.

The terms "nucleic acid" and "polynucleotide" are used interchangeably and as used herein refer to both sense and anti-sense strands of RNA, cDNA, genomic DNA, and synthetic forms and mixed polymers of the above. In particular embodiments, a nucleotide refers to a ribonucleotide, deoxynucleotide or a modified form of either type of nucleotide, or combinations thereof. The terms also include, but is not limited to, single- and double-stranded forms of DNA. In addition, a polynucleotide, e.g., a cDNA or mRNA, may include cither or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, the substitution of one or more of the naturally occurring nucleotides with an analog, internucleotide modifications such as uncharged linkages (e.g., methyl phosphonates, phosphotriesters, phosphoramidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids that encode the same polypeptide sequence.

The terms "vector" and "expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators).

An "expression cassette" refers to a nucleic acid construct that, when introduced into a host cell, results in transcription and/or translation of an RNA or polypeptide, respectively.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "promoter," as used herein, refers to a polynucleotide sequence capable of driving transcription of a coding sequence in a cell. Thus, promoters can include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription.

The phrase "percent identical" or equivalents used in the context of two nucleic acids or polypeptides, refers to a sequence that has at least a specified level of identity, e.g., at least 50% sequence identity with a reference sequence (e.g., any SEQ ID NO included herein). Alternatively, percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein, e.g., BLAST using standard parameters, as described below.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the numbers of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215:403-410 and Altschul et al. (1977) *Nucleic Acids Res.* 25:3389-3402, respectively. Software for performing BLAST analyses is publicly available through the National Center for Biotechnology Information (NCBI) web site.

A "substitution" denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy or light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Thus, a host cell is a recombinant host cell and includes the primary transformed cell and progeny derived therefrom without regard to the number of passages.

A polypeptide "variant" is a polypeptide that typically differs from one or more polypeptide sequences specifically disclosed herein in one or more substitutions, deletions, additions, and/or insertions.

A "therapeutic agent" refers to an agent that when administered to a patient suffering from a disease, in a therapeutically effective dose, will cure, or at least partially arrest the symptoms of the disease and complications associated with the disease.

A "variant" of a reference antibody refers to an antibody that typically differs from the reference antibody in one or more substitutions, deletions, additions, and/or insertions in the amino acid sequence of the heavy and/or light chain.

As used herein, the term "internalize," or "internalization" refer to the phenomenon that an antibody molecule crosses the cell membrane and reaches the cytoplasm and/or the nucleus.

The terms "therapy," "treatment," and "amelioration" refer to any reduction in the severity of symptoms. For example, in the case of treating cancer, treatment can refer to reducing the number of cancer cells or growth rate or cell death of non-cancer cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (no detectable symptoms remaining) or partial, such that symptoms are less frequent of severe than in a patient without the treatment described herein. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, dogs, cats, and other mammalian species. The term does not necessarily indicate that the subject has been diagnosed with a particular disease but typically refers to an individual under medical supervision. A patient can be an individual that is seeking treatment, monitoring, adjustment or modification of an existing therapeutic regimen, etc.

III. Detailed Description of the Embodiments

The present disclosure is directed to compositions and methods to prevent and treat metabolic epilepsy and/or related neurological disorders through targeting Galectin-3 with anti-GAL-3 antibodies.

Galectin-3 (GAL-3)

The galectin family comprises at least fifteen β-galactoside-binding lectins, playing pivotal roles in growth and development, and contributing to the advancement of several diseases. Galectin-3 (GAL-3), a monomer but can form a multimer (dimer or pentamer) at higher concentrations[17], is one of the most studied members of the galectin family [2,18].

All galectins, including GAL-3, bind to β-galactoside, but they exhibit slight variations in their carbohydrate-binding abilities. Typically, galectins show a preference for N-acetyllactosamine, binding it significantly stronger than lactose. N-glycans rich in N-acetyllactosamine serve as effective ligands for most galectins. Notably, GAL-3's interaction with the TF-disaccharide found in O-glycans is distinct from that of galectin-1, displaying a much higher affinity in isothermal titration calorimetry (ITC) assays[22]. These differences in binding properties among galectins can be attributed to their unique three-dimensional structures. [22-24]

GAL-3 interacts with both intracellular and extracellular molecules. Unlike other galectins, GAL-3 is secreted without a conventional signal peptide[25], existing within the cytosol and the extracellular matrix (ECM)[26, 27]. Known extracellular ligands include ECM and cell surface glycoproteins like laminin[28, 29], fibronectin[30], CD29[31], CD66 [32], α1β1 integrin[30], and Mac-2 binding protein[33]. Intracellularly, GAL-3 binds to ligands such as gemin 4[34], Bcl-2[34], nucling[35], synexin[36], and β-catenin[37, 38] through various protein-carbohydrate and protein-protein interactions.

GAL-3 functions in various biological capacities, both inside cells, within the nucleus or cytoplasm, and outside, on the cell surface or in the extracellular space[3,4,17]. It connects with β-galactose-rich glycoconjugates or glycolipids on the cell membrane, influencing key cellular processes such as proliferation, apoptosis, adhesion, invasion, angiogenesis, and metastasis. These functions are critical during normal development and also play a role in the progression of diseases associated with chronic inflammation, such as cancer, fibrosis, and type 2 diabetes, etc. Studies have also shown that galectins, a family of 15 glycan-binding proteins that have been conserved throughout evolution, in modulating neuroinflammation and potentially influencing neurodegeneration[41, 42]

Galectin-3 (GAL-3) plays a diverse role in biological processes including cell adhesion, proliferation, migration, apoptosis, tumor progression, and inflammation[43-45]. It is also involved in the modulation of both the innate and adaptive immune systems. The function of GAL-3, whether pro-inflammatory or anti-inflammatory, is influenced by several factors including the specific brain region, the nature of the injury, and the stage of the disease[45].

In normal brain tissue, GAL-3 is constitutively expressed across a wide range of neuronal tissues, including neurons and glial cells in various brain regions[46]. Detailed studies, particularly those using immunohistochemistry techniques in adult rats, have mapped the presence of GAL-3 in numerous brain areas such as parts of the telencephalon (including certain areas of the cerebral cortex, olfactory region, amygdaloid nucleus, stria terminalis, and the vascular organ of the lamina terminalis), the diencephalon (encompassing the thalamus and hypothalamus), as well as in the brain stem and cerebellum (including the inferior colliculus, lateral parabrachial nucleus, pontine nucleus, cochlear nucleus, and the fibers of the cerebellar peduncles).

Under neuroinflammatory conditions within the central nervous system, GAL-3 expression is in glia, astrocytes, and oligodendrocytes. However, it is primarily expressed by microglia and astrocytes when studied in vitro[47]. This distribution and expression pattern highlight the potential roles of GAL-3 in normal brain function and its reactive upregulation in response to neuroinflammatory conditions, pointing to its significance in both the healthy and diseased states of the nervous system.

Microglia, in their activated state, undergo proliferation, morphological changes, migrate to damaged sites, and produce cytokines[48], acting as primary effectors in CNS inflammation[49]. Their functional plasticity allows them to exhibit dual phenotypes—proinflammatory M1 and anti-inflammatory M2—enabling them to adapt to various microenvironments and maintain tissue homeostasis[50].

GAL-3's involvement extends to regulating microglial polarization, influenced by the context of brain damage, through lectin-glycan interactions[42]. Its expression and activity, which can be upregulated by factors like IFN-γ, play a significant role in the proinflammatory response by activating the M1 phenotype and promoting cytokine production through pathways like JAK/STAT[51]. However, GAL-3's function in neuroinflammation is complex, displaying both protective and detrimental effects depending on the disease context, stages, and severity[52-54]. For instance, in conditions like traumatic brain injury, GAL-3 exacerbates proinflammatory responses[55], whereas in autoimmune diseases like EAE (Experimental Autoimmune Encephalomyelitis), it can contribute to neuroprotection by facilitating debris clearance and promoting regeneration and remyelination (56). This dual nature underscores the nuanced role of GAL-3 in neuroinflammatory processes, offering potential therapeutic targets for modulating microglial activity in neurological diseases.

Several GAL-3 inhibitors or antagonists, either small-molecule carbohydrates or large-molecule products, are being developed by private and public companies for therapeutic applications in various diseases.[57]

The terms "GAL-3 inhibitor" or "GAL-3 antagonist" or "GAL-3 blocker" or the like include any substance that decreases the expression, ligand binding (e.g., binding to GAL-3), or any biological activity of GAL-3 (e.g., regulating microglial polarization), that would elicit a biological or medical response of a tissue, system, subject or patient that is being sought by the administrator (such as a researcher, doctor or veterinarian) which includes any measurable alleviation of the signs, symptoms and/or clinical indicia of epilepsy and related neurological disorders, and/or the prevention, slowing or halting of progression of epilepsy and related neurological disorders. GAL-3 inhibitors include both small-molecule carbohydrates or large-molecule natural or unnatural products. Several Gal-3 inhibitors or antagonists, including small-molecule inhibitors and large molecule products, are undergoing clinical development in various diseases associated with Gal-3. A summary of the small molecule and large molecule therapies are presented in Table 1 and Table 2, respectively.

Anti-Gal-3 inhibitors that have been explored further in nonclinical and clinical development of neurological diseases include, for example, TD139, a small molecule Gal-3 inhibitor as described in Hirani, Nikhil et al. "Target inhibition of galectin-3 by inhaled TD139 in patients with idiopathic pulmonary fibrosis." The European respiratory journal vol. 57, 5 2002559. 27 May 2021, and TB006, an anti-Gal-3 antibody as described in Rasool, S., Patel, P., Johansson, J., Voloboueva, L., Lee, S., Sun, J., Lan, X., Ahmed, T. and Sun, D. (2022), Potential Reversal of Alzheimer's Disease pathology by Antibody TB006 Targeting Galectin-3, the Root Cause of Oligomerization of Amyloid Proteins. Alzheimer's Dement., 18: e060393; each of which is hereby incorporated by reference in its entirety.

Small-Molecular GAL-3 Targeted Inhibitors

Small molecule anti-GAL-3 inhibitors offer several benefits compared to the large molecule counterparts, including the ability to create a compact structure with desired traits like suitable polar surface area and biostability which enabled the oral formulation development, that can be manufactured consistently on a large scale and is straightforward to characterize, and facilitate pharmacokinetic studies. Nonetheless, synthetic molecules may pose toxicity risks at elevated dosages. Table 1 lists a summary of clinical trials of small molecule Gal-3 inhibitors.

TABLE 1

Overview of Clinical Trials of Small Molecule Gal-3 Inhibitors

| Sponsor | Compound | Indication | Phase | Trial# | Status |
|---|---|---|---|---|---|
| Galecto Bio | GB0139 | IPF | 2 | NCT03832946 | Active, not rec (n = 426) |
| | TD139 | IPF | 1/2a | NCT02257177 | Completed (n = 60) |
| | TD139 | COVID-19 | 1, 2 | NCT04473053 | Active, not rec (n = 200) |
| | GB1211 | Healthy Adults | 1 | NCT03809052 | Completed (n = 78) |
| | | NASH | 1b | NCT04607655 | Withdrawn |
| | | Hepatic Impairment | 1 | NCT05009680 | Active, not rec (n = 54) |
| | | NSCLC | 1 | NCT05009680 | Recruiting (n = 102) |

Galecto Bio, Galecto Biotech; IPF, Idiopathic pulmonary fibrosis; NASH, Nonalcoholic steatohepatitis; NSCLC, Non-small cell lung cancer; not rec, not recruiting.

Large-Molecular GAL-3 Targeted Inhibitors

Pectins, sourced or modified from plants, represent large molecule antagonists of GAL-3 that have undergone clinical examination for a range of conditions, as documented on clinicaltrials.gov (retrieved on 20 Feb. 2023). However, these pectins do not target a specific galectin and exhibit weak binding to GAL-3, with affinities ranging 2.6 to 10 μM. Table 2 lists a summary of clinical trials of large molecule Gal-3 inhibitors.

TABLE 2

Overview of Clinical Trials of Large Molecule Gal-3 Inhibitors

| Sponsor | Compound | Indication | Phase | Trial# | Status |
|---|---|---|---|---|---|
| TrueBinding | TB006 | Healthy Adults | 1 | NCT04920786 | Unknown |
| | | AD | 1b/2a | NCT05074498 | Completed (n = 154) |
| | | COVID-19 | 1 | NCT04801056 | Withdrawn |
| | | Acute ischemic stroke | 2 | NCT05156827 | Withdrawn |
| | | Autism spectrum disorder | 2 | NCT06500637 | Recruiting |
| EcoNugenics | MCP | Prostatic neoplasm | 2 | NCT01681823 | Completed (n = 60) |
| MGH | MCP | Osteoarthritis | 3 | NCT02800629 | Unknown |
| La Jolla | GCS-100 | CKD | 1 | NCT01717248 | Completed (n = 29) |
| | | CLL | 2 | NCT00514696 | Completed (n = 12) |
| | | CKD | 2a | NCT01843790 | Completed (n = 120) |
| | | | 2a | NCT02155673 | Completed (n = 92) |
| | | | 2a | NCT02333955 | Withdrawn |
| | | Multiple myeloma | 1/2 | NCT00609817 | Terminated |
| | | B cell lymphoma | 1/2 | NCT00776802 | Withdrawn |
| Gal Thera | GM-CT-01 | Solid tumors | 1 | NCT00054977 | Completed (n = 40) |
| | GM-CT-01 + 5-FU | Colorectal Cancer | 2 | NCT00110721 | Terminated |
| | GM-CT-01 in comb | Colorectal Cancer | 2 | NCT00388700 | Withdrawn |
| | GM-CT-01 | Metastatic melanoma | 2 | NCT01723813 | Terminated |
| | | Bile duct and Gall Bladder cancer | 2 | NCT00386516 | Withdrawn |
| | GR-MD-02 | NASH and fibrosis | 1 | NCT01899859 | Completed (n = 31) |
| | | NASH and fibrosis | 2 | NCT02421094 | Completed (n = 30) |
| | | NASH cirrhosis and Portal hypertension | 2 | NCT02462967 | Completed (n = 162) |
| | | NASH cirrhosis and Esophageal varices | 2b/3 | NCT04365868 | Recruiting |
| | | Psoriasis | 2 | NCT02407041 | Completed (n = 5) |
| Prov Med | GR-MD-02 + Ipilumumab | Metastatic melanoma | 1 | NCT02117362 | Completed (n = 8) |
| | GR-MD-02 + Pembrolizumab | Melanoma, NSCLC | 1 | NCT02575404 | Active, not rec |

TABLE 2-continued

Overview of Clinical Trials of Large Molecule Gal-3 Inhibitors

| Sponsor | Compound | Indication | Phase | Trial# | Status |
|---|---|---|---|---|---|
| | GR-MD-02 + Pembrolizumab | Metastatic melanoma | 2 | NCT04987996 | Suspended |
| BioXyTran | Prolectin-M | COVID-19 | N/A | NCT04512027 | Completed (n = 10) |
| | | COVID-19 | 1b/2a | NCT05733780 | Not yet recruiting |
| | | COVID-19 | 3 | NCT05096052 | Not yet recruiting |

AD, Alheimer's disease; MCP, Modified citrus pectin; MGH, Massachusetts General Hospital; CKD, Chronic Kidney disease; CLL, Chronic lymphocytic leukemia; Gal Thera, Galectin Therapeutics; GM-CT- 01 in comb, GM-CT-01 in combination with 5-flourouracil, Avastin, and Leucovorin; Prov Med, Providence Portland Medical Center; NSCLC, Non-small cell lung cancer; not rec, not recruiting; NA, Not applicable.

In some embodiments, the anti-GAL-3 antibodies disclosed herein can be used in combination with any of the aforementioned small- or large-molecule GAL-3 targeted inhibitors, for treating epilepsy or a neurological disorder in a subject in need thereof. In some embodiments, the anti-GAL-3 antibodies disclosed herein can be used to treat patients who have not responded to treatment with any of the aforementioned small- or large-molecule GAL-3 targeted inhibitors.

GAL-3 Targeted Inhibitors for Treatment of Neurological Disorders

Recently, anti-GAL-3 inhibitors for the treatment of neurological disorders such as Alzheimer's disease (AD) have been studied in clinical trials as disclosed on https://clinicaltrials.gov/(NCT05074498, NCT05476783, NCT05156827).

Anti-GAL-3 Antibodies

As disclosed herein, the GAL-3 inhibitor can be an anti-GAL-3 antibody or antigen-binding fragment thereof that binds specifically to GAL-3 (e.g., human GAL-3) or any soluble fragment thereof (e.g., monoclonal antibodies (e.g., fully human monoclonal antibodies), polyclonal antibodies, bispecific antibodies, Fab antibody fragments, F(ab)2 antibody fragments, Fv antibody fragments (e.g., $V_H$ or $V_L$), single chain Fv antibody fragments, dsFv antibody fragments, humanized antibodies or chimeric antibodies.

In some instances, the anti-GAL-3 antibody specifically binds to human Galectin-3. In other instances, the anti-GAL-3 antibody binds to both human Galectin-3 and Galectin-3 from other species such as mouse, rat, monkey, etc. As disclosed herein, the anti-GAL-3 antibody can be any humanized, chimeric, or human antibody that binds to Galectin-3. In some embodiments, the anti-GAL-3 antibody is generated from other species but humanized to bind human Galectin-3. In some embodiments, the anti-GAL-3 antibody is a chimeric antibody. In some embodiments, the anti-GAL-3 antibody is a human antibody.

In some embodiments, the anti-GAL-3 antibody comprises a heavy chain variable ($V_H$) region comprising a heavy chain CDR1 (HCDR1), HCDR2, and HCDR3 and a light chain variable ($V_L$) region comprising light chain CDR1 (LCDR1), LCDR2, and LCDR3. In some embodiments, the $V_H$ region comprises a HCDR1 amino acid sequence at least 70%, at least 75%, at least 80%, at least 85%, at least 90%, or at least 95% identical to any one of SEQ ID NOS: 1-21 and 481-507, a HCDR2 amino acid sequence at least 70%, at least 75%, at least 80%, at least 85%, at least 90%, or at least 95% identical to any one of SEQ ID NOS: 22-42 and 390-417, and/or a HCDR3 amino acid sequence at least 70%, at least 75%, at least 80%, at least 85%, at least 90%, or at least 95% identical to any one of SEQ ID NOS: 43-63 and 418-439. In some embodiments, the $V_L$ region comprises a LCDR1 amino acid sequence at least 70%, at least 75%, at least 80%, at least 85%, at least 90%, or at least 95% identical to any one of SEQ ID NOS: 169-189 and 440-462, a LCDR2 amino acid sequence at least 70%, at least 75%, at least 80%, at least 85%, at least 90%, or at least 95% identical to any one of SEQ ID NOS: 190-210 and 463-480, and/or a LCDR3 amino acid sequence at least 70%, at least 75%, at least 80%, at least 85%, at least 90%, or at least 95% identical to any one of SEQ ID NOS: 211-231 and 481-507. The exemplary heavy chain CDRs and light chain CDRs are listed in Tables 3 and 4, respectively.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 1, a HCDR2 amino acid sequence at least 70%, at least 75%, at least 80%, at least 85%, at least 90%, or at least 95% identical to SEQ ID NO: 22, and a HCDR3 amino acid sequence at least 70%, at least 75%, at least 80%, at least 85%, at least 90%, or at least 95% identical to SEQ ID NO: 43; and a light chain variable region comprising a LCDR1 amino acid sequence at least 70%, at least 75%, at least 80%, at least 85%, at least 90%, or at least 95% identical to SEQ ID NO: 169, a LCDR2 amino acid sequence at least 70%, at least 75%, at least 80%, at least 85%, at least 90%, or at least 95% identical to SEQ ID NO: 190, and a LCDR3 amino acid sequence at least 70%, at least 75%, at least 80%, at least 85%, at least 90%, or at least 95% identical to SEQ ID NO: 211. In a particular embodiment, the anti-GAL-3 antibody comprises a HCDR1 amino acid sequence of SEQ ID NO: 1, a HCDR2 amino acid sequence of SEQ ID NO: 22, a HCDR3 amino acid sequence of SEQ ID NO: 43, a LCDR1 amino acid sequence of SEQ ID NO: 169, a LCDR2 amino acid sequence of SEQ ID NO: 190, and a LCDR3 amino acid sequence of SEQ ID NO: 211.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 2, a HCDR2 amino acid sequence at least 70%, at least 75%, at least 80%, at least 85%, at least 90%, or at least 95% identical to SEQ ID NO: 23, and a HCDR3 amino acid sequence at least 70%, at least 75%, at least 80%, at least 85%, at least 90%, or at least 95% identical to SEQ ID NO: 44; and a light chain variable region comprising a LCDR1 amino acid sequence at least 70%, at least 75%, at least 80%, at least 85%, at least 90%, or at least 95% identical to SEQ ID NO: 170, a LCDR2 amino acid sequence at least 70%, at least 75%, at least 80%, at least 85%, at least 90%, or at least 95% identical to SEQ ID NO: 191, and a LCDR3 amino acid sequence at least 70%, at least 75%, at least 80%, at least 85%, at least 90%, or at least 95% identical to SEQ ID NO: 212. In a particular embodiment, the anti-GAL-3 antibody comprises a HCDR1 amino acid sequence of SEQ ID NO: 2, a HCDR2 amino acid sequence of SEQ ID NO: 23, a HCDR3 amino acid sequence of SEQ ID NO: 44, a LCDR1 amino acid sequence of SEQ ID NO: 170, a LCDR2 amino acid sequence of SEQ ID NO: 191, and a LCDR3 amino acid sequence of SEQ ID NO: 212.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 3, a HCDR2 amino acid sequence at least 70%, at least 75%, at least 80%, at least 85%, at least 90%, or at least 95% identical to SEQ ID NO: 24, and a HCDR3 amino acid sequence at least 70%, at least 75%, at least 80%, at least 85%, at least 90%, or at least 95% identical to SEQ ID NO: 45; and a light chain variable region comprising a LCDR1 amino acid sequence at least 70%, at least 75%, at least 80%, at least 85%, at least 90%, or at least 95% identical to SEQ ID NO: 171, a LCDR2 amino acid sequence at least 70%, at least 75%, at least 80%, at least 85%, at least 90%, or at least 95% identical to SEQ ID NO: 192, and a LCDR3 amino acid sequence at least 70%, at least 75%, at least 80%, at least 85%, at least 90%, or at least 95% identical to SEQ ID NO: 213. In a particular embodiment, the anti-GAL-3 antibody comprises a HCDR1 amino acid sequence of SEQ ID NO: 3, a HCDR2 amino acid sequence of SEQ ID NO: 24, a HCDR3 amino acid sequence of SEQ ID NO: 45, a LCDR1 amino acid sequence of SEQ ID NO: 171, a LCDR2 amino acid sequence of SEQ ID NO: 192, and a LCDR3 amino acid sequence of SEQ ID NO: 213.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 4, a HCDR2 amino acid sequence at least 70%, at least 75%, at least 80%, at least 85%, at least 90%, or at least 95% identical to SEQ ID NO: 25, and a HCDR3 amino acid sequence at least 70%, at least 75%, at least 80%, at least 85%, at least 90%, or at least 95% identical to SEQ ID NO: 46; and a light chain variable region comprising a LCDR1 amino acid sequence at least 70%, at least 75%, at least 80%, at least 85%, at least 90%, or at least 95% identical to SEQ ID NO: 172, a LCDR2 amino acid sequence at least 70%, at least 75%, at least 80%, at least 85%, at least 90%, or at least 95% identical to SEQ ID NO: 193, and a LCDR3 amino acid sequence at least 70%, at least 75%, at least 80%, at least 85%, at least 90%, or at least 95% identical to SEQ ID NO: 214. In a particular embodiment, the anti-GAL-3 antibody comprises a HCDR1 amino acid sequence of SEQ ID NO: 4, a HCDR2 amino acid sequence of SEQ ID NO: 25, a HCDR3 amino acid sequence of SEQ ID NO: 46, a LCDR1 amino acid sequence of SEQ ID NO: 172, a LCDR2 amino acid sequence of SEQ ID NO: 193, and a LCDR3 amino acid sequence of SEQ ID NO: 214.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 5, a HCDR2 amino acid sequence at least 70%, at least 75%, at least 80%, at least 85%, at least 90%, or at least 95% identical to SEQ ID NO: 26, and a HCDR3 amino acid sequence at least 70%, at least 75%, at least 80%, at least 85%, at least 90%, or at least 95% identical to SEQ ID NO: 47; and a light chain variable region comprising a LCDR1 amino acid sequence at least 70%, at least 75%, at least 80%, at least 85%, at least 90%, or at least 95% identical to SEQ ID NO: 173, a LCDR2 amino acid sequence at least 70%, at least 75%, at least 80%, at least 85%, at least 90%, or at least 95% identical to SEQ ID NO: 194, and a LCDR3 amino acid sequence at least 70%, at least 75%, at least 80%, at least 85%, at least 90%, or at least 95% identical to SEQ ID NO: 215. In a particular embodiment, the anti-GAL-3 antibody comprises a HCDR1 amino acid sequence of SEQ ID NO: 5, a HCDR2 amino acid sequence of SEQ ID NO: 26, a HCDR3 amino acid sequence of SEQ ID NO: 47, a LCDR1 amino acid sequence of SEQ ID NO: 173, a LCDR2 amino acid sequence of SEQ ID NO: 194, and a LCDR3 amino acid sequence of SEQ ID NO: 215.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 7, a HCDR2 amino acid sequence at least 70%, at least 75%, at least 80%, at least 85%, at least 90%, or at least 95% identical to SEQ ID NO: 28, and a HCDR3 amino acid sequence at least 70%, at least 75%, at least 80%, at least 85%, at least 90%, or at least 95% identical to SEQ ID NO: 49; and a light chain variable region comprising a LCDR1 amino acid sequence at least 70%, at least 75%, at least 80%, at least 85%, at least 90%, or at least 95% identical to SEQ ID NO: 174, a LCDR2 amino acid sequence at least 70%, at least 75%, at least 80%, at least 85%, at least 90%, or at least 95% identical to SEQ ID NO: 195, and a LCDR3 amino acid sequence at least 70%, at least 75%, at least 80%, at least 85%, at least 90%, or at least 95% identical to SEQ ID NO: 216. In a particular embodiment, the anti-GAL-3 antibody comprises a HCDR1 amino acid sequence of SEQ ID NO: 6, a HCDR2 amino acid sequence of SEQ ID NO: 27, a HCDR3 amino acid sequence of SEQ ID NO: 48, a LCDR1 amino acid sequence of SEQ ID NO: 174, a LCDR2 amino acid sequence of SEQ ID NO: 195, and a LCDR3 amino acid sequence of SEQ ID NO: 216.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 7, a HCDR2 amino acid sequence at least 70%, at least 75%, at least 80%, at least 85%, at least 90%, or at least 95% identical to SEQ ID NO: 28, and a HCDR3 amino acid sequence at least 70%, at least 75%, at least 80%, at least 85%, at least 90%, or at least 95% identical to SEQ ID NO: 49; and a light chain variable region comprising a LCDR1 amino acid sequence at least 70%, at least 75%, at least 80%, at least 85%, at least 90%, or at least 95% identical to SEQ ID NO: 175, a LCDR2 amino acid sequence at least 70%, at least 75%, at least 80%, at least 85%, at least 90%, or at least 95% identical to SEQ ID NO: 196, and a LCDR3 amino acid sequence at least 70%, at least 75%, at least 80%, at least 85%, at least 90%, or at least 95% identical to SEQ ID NO: 217. In a particular embodiment, the anti-GAL-3 antibody comprises a HCDR1 amino acid sequence of SEQ ID NO: 7, a HCDR2 amino acid sequence of SEQ ID NO: 28, a HCDR3 amino acid sequence of SEQ ID NO: 49, a LCDR1 amino acid sequence of SEQ ID NO: 175, a LCDR2 amino acid sequence of SEQ ID NO: 196, and a LCDR3 amino acid sequence of SEQ ID NO: 217.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 8, a HCDR2 amino acid sequence at least 70%, at least 75%, at least 80%, at least 85%, at least 90%, or at least 95% identical to SEQ ID NO: 29, and a HCDR3 amino acid sequence at least 70%, at least 75%, at least 80%, at least 85%, at least 90%, or at least 95% identical to SEQ ID NO: 50; and a light chain variable region comprising a LCDR1 amino acid sequence at least 70%, at least 75%, at least 80%, at least 85%, at least 90%, or at least 95% identical to SEQ ID NO: 176 or 369, a LCDR2 amino acid sequence at least 70%, at least 75%, at least 80%, at least 85%, at least 90%, or at least 95% identical to SEQ ID NO: 197, and a LCDR3 amino acid sequence at least 70%, at least 75%, at least 80%, at least 85%, at least 90%, or at least 95% identical to SEQ ID NO: 218. In a particular embodiment, the anti-GAL-3 antibody comprises a HCDR1 amino acid sequence of SEQ ID NO: 8, a HCDR2 amino acid sequence of SEQ ID NO: 29, a HCDR3 amino acid sequence of SEQ ID NO: 50, a LCDR1 amino acid sequence of SEQ ID NO: 176 or 369, a LCDR2 amino acid sequence of SEQ ID NO: 197, and a LCDR3 amino acid sequence of SEQ ID NO: 218.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 9, a HCDR2 amino acid sequence at least 70%, at least 75%, at least 80%, at least 85%, at least 90%, or at least 95% identical to SEQ ID NO: 80, and a HCDR3 amino acid sequence at least 70%, at least 75%, at least 80%, at least 85%, at least 90%, or at least 95% identical to SEQ ID NO: 51; and a light chain variable region comprising a LCDR1 amino acid sequence at least 70%, at least 75%, at least 80%, at least 85%, at least 90%, or at least 95% identical to SEQ ID NO: 177, a LCDR2 amino acid sequence at least 70%, at least 75%, at least 80%, at least 85%, at least 90%, or at least 95% identical to SEQ ID NO: 198, and a LCDR3 amino acid sequence at least 70%, at least 75%, at least 80%, at least 85%, at least 90%, or at least 95% identical to SEQ ID NO: 219. In a particular embodiment, the anti-GAL-3 antibody comprises a HCDR1 amino acid sequence of SEQ ID NO: 9, a HCDR2 amino acid sequence of SEQ ID NO: 30, a HCDR3 amino acid sequence of SEQ ID NO: 51, a LCDR1 amino acid sequence of SEQ ID NO: 177, a LCDR2 amino acid sequence of SEQ ID NO: 198, and a LCDR3 amino acid sequence of SEQ ID NO: 219.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 10, a HCDR2 amino acid sequence at least 70%, at least 75%, at least 80%, at least 85%, at least 90%, or at least 95% identical to SEQ ID NO: 31, and a HCDR3 amino acid sequence at least 70%, at least 75%, at least 80%, at least 85%, at least 90%, or at least 95% identical to SEQ ID NO: 52; and a light chain variable region comprising a LCDR1 amino acid sequence at least 70%, at least 75%, at least 80%, at least 85%, at least 90%, or at least 95% identical to SEQ ID NO: 178, a LCDR2 amino acid sequence at least 70%, at least 75%, at least 80%, at least 85%, at least 90%, or at least 95% identical to SEQ ID NO: 199, and a LCDR3 amino acid sequence at least 70%, at least 75%, at least 80%, at least 85%, at least 90%, or at least 95% identical to SEQ ID NO: 220. In a particular embodiment, the anti-GAL-3 antibody comprises a HCDR1 amino acid sequence of SEQ ID NO: 10, a HCDR2 amino acid sequence of SEQ ID NO: 31, a HCDR3 amino acid sequence of SEQ ID NO: 52, a LCDR1 amino acid sequence of SEQ ID NO: 178, a LCDR2 amino acid sequence of SEQ ID NO: 199, and a LCDR3 amino acid sequence of SEQ ID NO: 220.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 11, a HCDR2 amino acid sequence at least 70%, at least 75%, at least 80%, at least 85%, at least 90%, or at least 95% identical to SEQ ID NO: 32, and a HCDR3 amino acid sequence at least 70%, at least 75%, at least 80%, at least 85%, at least 90%, or at least 95% identical to SEQ ID NO: 53; and a light chain variable region comprising a LCDR1 amino acid sequence at least 70%, at least 75%, at least 80%, at least 85%, at least 90%, or at least 95% identical to SEQ ID NO: 179, a LCDR2 amino acid sequence at least 70%, at least 75%, at least 80%, at least 85%, at least 90%, or at least 95% identical to SEQ ID NO: 200, and a LCDR3 amino acid sequence at least 70%, at least 75%, at least 80%, at least 85%, at least 90%, or at least 95% identical to SEQ ID NO: 221. In a particular embodiment, the anti-GAL-3 antibody comprises a HCDR1 amino acid sequence of SEQ ID NO: 11, a HCDR2 amino acid sequence of SEQ ID NO: 32, a HCDR3 amino acid sequence of SEQ ID NO: 53, a LCDR1 amino acid sequence of SEQ ID NO: 179, a LCDR2 amino acid sequence of SEQ ID NO: 200, and a LCDR3 amino acid sequence of SEQ ID NO: 221.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 12, a HCDR2 amino acid sequence at least 70%, at least 75%, at least 80%, at least 85%, at least 90%, or at least 95% identical to SEQ ID NO: 33, and a HCDR3 amino acid sequence at least 70%, at least 75%, at least 80%, at least 85%, at least 90%, or at least 95% identical to SEQ ID NO: 54; and a light chain variable region comprising a LCDR1 amino acid sequence at least 70%, at least 75%, at least 80%, at least 85%, at least 90%, or at least 95% identical to SEQ ID NO: 180, a LCDR2 amino acid sequence at least 70%, at least 75%, at least 80%, at least 85%, at least 90%, or at least 95% identical to SEQ ID NO: 201, and a LCDR3 amino acid sequence at least 70%, at least 75%, at least 80%, at least 85%, at least 90%, or at least 95% identical to SEQ ID NO: 222. In a particular embodiment, the anti-GAL-3 antibody comprises a HCDR1 amino acid sequence of SEQ ID NO: 12, a HCDR2 amino acid sequence of SEQ ID NO: 33, a HCDR3 amino acid sequence of SEQ ID NO: 54, a LCDR1 amino acid sequence of SEQ ID NO: 180, a LCDR2 amino acid sequence of SEQ ID NO: 201, and a LCDR3 amino acid sequence of SEQ ID NO: 222.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 13, a HCDR2 amino acid sequence at least 70%, at least 75%, at least 80%, at least 85%, at least 90%, or at least 95% identical to SEQ ID NO: 34, and a HCDR3 amino acid sequence at least 70%, at least 75%, at least 80%, at least 85%, at least 90%, or at least 95% identical to SEQ ID NO: 55; and a light chain variable region comprising a LCDR1 amino acid sequence at least 70%, at least 75%, at least 80%, at least 85%, at least 90%, or at least 95% identical to SEQ ID NO: 181, a LCDR2 amino acid sequence at least 70%, at least 75%, at least 80%, at least 85%, at least 90%, or at least 95% identical to SEQ ID NO: 202, and a LCDR3 amino acid sequence at least 70%, at least 75%, at least 80%, at least 85%, at least 90%, or at least 95% identical to SEQ ID NO: 223. In a particular embodiment, the anti-GAL-3 antibody comprises a HCDR1 amino acid sequence of SEQ ID NO: 13, a HCDR2 amino acid sequence of SEQ ID NO: 34, a HCDR3 amino acid sequence of SEQ ID NO: 55, a LCDR1 amino acid sequence of SEQ ID NO: 181, a LCDR2 amino acid sequence of SEQ ID NO: 202, and a LCDR3 amino acid sequence of SEQ ID NO: 223.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 14, a HCDR2 amino acid sequence at least 70%, at least 75%, at least 80%, at least 85%, at least 90%, or at least 95% identical to SEQ ID NO: 35, and a HCDR3 amino acid sequence at least 70%, at least 75%, at least 80%, at least 85%, at least 90%, or at least 95% identical to SEQ ID NO: 56; and a light chain variable region comprising a LCDR1 amino acid sequence at least 70%, at least 75%, at least 80%, at least 85%, at least 90%, or at least 95% identical to SEQ ID NO: 182, a LCDR2 amino acid sequence at least 70%, at least 75%, at least 80%, at least 85%, at least 90%, or at least 95% identical to SEQ ID NO: 203, and a LCDR3 amino acid sequence at least 70%, at least 75%, at least 80%, at least 85%, at least 90%, or at least 95% identical to SEQ ID NO: 224. In a particular embodiment, the anti-GAL-3 antibody comprises a HCDR1 amino acid sequence of SEQ ID NO: 14, a HCDR2 amino acid sequence of SEQ ID NO: 35, a HCDR3 amino acid sequence of SEQ ID NO: 56, a LCDR1 amino acid sequence of SEQ ID NO: 182, a LCDR2 amino acid sequence of SEQ ID NO: 203, and a LCDR3 amino acid sequence of SEQ ID NO: 224.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 15, a HCDR2 amino acid sequence at least 70%, at least 75%, at least 80%, at least 85%, at least 90%, or at least 95% identical to SEQ ID NO: 36, and a HCDR3 amino acid sequence at least 70%, at least 75%, at least 80%, at least 85%, at least 90%, or at least 95% identical to SEQ ID NO: 57; and a light chain variable region comprising a LCDR1 amino acid sequence at least 70%, at least 75%, at least 80%, at least 85%, at least 90%, or at least 95% identical to SEQ ID NO: 183, a LCDR2 amino acid sequence at least 70%, at least 75%, at least 80%, at least 85%, at least 90%, or at least 95% identical to SEQ ID NO: 204, and a LCDR3 amino acid sequence at least 70%, at least 75%, at least 80%, at least 85%, at least 90%, or at least 95% identical to SEQ ID NO: 225. In a particular embodiment, the anti-GAL-3 antibody comprises a HCDR1 amino acid sequence of SEQ ID NO: 15, a HCDR2 amino acid sequence of SEQ ID NO: 36, a HCDR3 amino acid sequence of SEQ ID NO: 57, a LCDR1 amino acid sequence of SEQ ID NO: 183, a LCDR2 amino acid sequence of SEQ ID NO: 204, and a LCDR3 amino acid sequence of SEQ ID NO: 225.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 16, a HCDR2 amino acid sequence at least 70%, at least 75%, at least 80%, at least 85%, at least 90%, or at least 95% identical to SEQ ID NO: 37, and a HCDR3 amino acid sequence at least 70%, at least 75%, at least 80%, at least 85%, at least 90%, or at least 95% identical to SEQ ID NO: 58; and a light chain variable region comprising a LCDR1 amino acid sequence at least 70%, at least 75%, at least 80%, at least 85%, at least 90%, or at least 95% identical to SEQ ID NO: 184, a LCDR2 amino acid sequence at least 70%, at least 75%, at least 80%, at least 85%, at least 90%, or at least 95% identical to SEQ ID NO: 205, and a LCDR3 amino acid sequence at least 70%, at least 75%, at least 80%, at least 85%, at least 90%, or at least 95% identical to SEQ ID NO: 226. In a particular embodiment, the anti-GAL-3 antibody comprises a HCDR1 amino acid sequence of SEQ ID NO: 16, a HCDR2 amino acid sequence of SEQ ID NO: 37, a HCDR3 amino acid sequence of SEQ ID NO: 58, a LCDR1 amino acid sequence of SEQ ID NO: 184, a LCDR2 amino acid sequence of SEQ ID NO: 205, and a LCDR3 amino acid sequence of SEQ ID NO: 226.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 17, a HCDR2 amino acid sequence at least 70%, at least 75%, at least 80%, at least 85%, at least 90%, or at least 95% identical to SEQ ID NO: 38, and a HCDR3 amino acid sequence at least 70%, at least 75%, at least 80%, at least 85%, at least 90%, or at least 95% identical to SEQ ID NO: 59; and a light chain variable region comprising a LCDR1 amino acid sequence at least 70%, at least 75%, at least 80%, at least 85%, at least 90%, or at least 95% identical to SEQ ID NO: 185, a LCDR2 amino acid sequence at least 70%, at least 75%, at least 80%, at least 85%, at least 90%, or at least 95% identical to SEQ ID NO: 206, and a LCDR3 amino acid sequence at least 70%, at least 75%, at least 80%, at least 85%, at least 90%, or at least 95% identical to SEQ ID NO: 227. In a particular embodiment, the anti-GAL-3 antibody comprises a HCDR1 amino acid sequence of SEQ ID NO: 17, a HCDR2 amino acid sequence of SEQ ID NO: 38, a HCDR3 amino acid sequence of SEQ ID NO: 59, a LCDR1 amino acid sequence of SEQ ID NO: 185, a LCDR2 amino acid sequence of SEQ ID NO: 206, and a LCDR3 amino acid sequence of SEQ ID NO: 227.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 18, a HCDR2 amino acid sequence at least 70%, at least 75%, at least 80%, at least 85%, at least 90%, or at least 95% identical to SEQ ID NO: 39, and a HCDR3 amino acid sequence at least 70%, at least 75%, at least 80%, at least 85%, at least 90%, or at least 95% identical to SEQ ID NO: 60; and a light chain variable region comprising a LCDR1 amino acid sequence at least 70%, at least 75%, at least 80%, at least 85%, at least 90%, or at least 95% identical to SEQ ID NO: 186, a LCDR2 amino acid sequence at least 70%, at least 75%, at least 80%, at least 85%, at least 90%, or at least 95% identical to SEQ ID NO: 207, and a LCDR3 amino acid sequence at least 70%, at least 75%, at least 80%, at least 85%, at least 90%, or at least 95% identical to SEQ ID NO: 228. In a particular embodiment, the anti-GAL-3 antibody comprises a HCDR1 amino acid sequence of SEQ ID NO: 18, a HCDR2 amino acid sequence of SEQ ID NO: 39, a HCDR3 amino acid sequence of SEQ ID NO: 60, a LCDR1 amino acid sequence of SEQ ID NO: 186, a LCDR2 amino acid sequence of SEQ ID NO: 207, and a LCDR3 amino acid sequence of SEQ ID NO: 228.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 19, a HCDR2 amino acid sequence at least 70%, at least 75%, at least 80%, at least 85%, at least 90%, or at least 95% identical to SEQ ID NO: 40, and a HCDR3 amino acid sequence at least 70%, at least 75%, at least 80%, at least 85%, at least 90%, or at least 95% identical to SEQ ID NO: 61; and a light chain variable region comprising a LCDR1 amino acid sequence at least 70%, at least 75%, at least 80%, at least 85%, at least 90%, or at least 95% identical to SEQ ID NO: 187, a LCDR2 amino acid sequence at least 70%, at least 75%, at least 80%, at least 85%, at least 90%, or at least 95% identical to SEQ ID NO: 208, and a LCDR3 amino acid sequence at least 70%, at least 75%, at least 80%, at least 85%, at least 90%, or at least 95% identical to SEQ ID NO: 229. In a particular embodiment, the anti-GAL-3 antibody comprises a HCDR1 amino acid sequence of SEQ ID NO: 19, a HCDR2 amino acid sequence of SEQ ID NO: 40, a HCDR3 amino acid sequence of SEQ ID NO: 61, a LCDR1 amino acid sequence of SEQ ID NO: 187, a LCDR2 amino acid sequence of SEQ ID NO: 208, and a LCDR3 amino acid sequence of SEQ ID NO: 229.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 20, a HCDR2 amino acid sequence at least 70%, at least 75%, at least 80%, at least 85%, at least 90%, or at least 95% identical to SEQ ID NO: 41, and a HCDR3 amino acid sequence at least 70%, at least 75%, at least 80%, at least 85%, at least 90%, or at least 95% identical to SEQ ID NO: 62; and a light chain variable region comprising a LCDR1 amino acid sequence at least 70%, at least 75%, at least 80%, at least 85%, at least 90%, or at least 95% identical to SEQ ID NO: 188, a LCDR2 amino acid sequence at least 70%, at least 75%, at least 80%, at least 85%, at least 90%, or at least 95% identical to SEQ ID NO: 209, and a LCDR3 amino acid sequence at least 70%, at least 75%, at least 80%, at least 85%, at least 90%, or at least 95% identical to SEQ ID NO: 230. In a particular embodiment, the anti-GAL-3 antibody comprises a HCDR1 amino acid sequence of SEQ ID NO: 20, a HCDR2 amino acid sequence of SEQ ID NO: 41, a HCDR3 amino acid sequence of SEQ ID NO: 64, a LCDR1 amino acid sequence of SEQ ID NO: 188, a LCDR2 amino acid sequence of SEQ ID NO: 209, and a LCDR3 amino acid sequence of SEQ ID NO: 230.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 21, a HCDR2 amino acid sequence at least 70%, at least 75%, at least 80%, at least 85%, at least 90%, or at least 95% identical to SEQ ID NO: 42, and a HCDR3 amino acid sequence at least 70%, at least 75%, at least 80%, at least 85%, at least 90%, or at least 95% identical to SEQ ID NO: 63; and a light chain variable region comprising a LCDR1 amino acid sequence at least 70%, at least 75%, at least 80%, at least 85%, at least 90%, or at least 95% identical to SEQ ID NO: 189, a LCDR2 amino acid sequence at least 70%, at least 75%, at least 80%, at least 85%, at least 90%, or at least 95% identical to SEQ ID NO: 220, and a LCDR3 amino acid sequence at least 70%, at least 75%, at least 80%, at least 85%, at least 90%, or at least 95% identical to SEQ ID NO: 231. In a particular embodiment, the anti-GAL-3 antibody comprises a HCDR1 amino acid sequence of SEQ ID NO: 21, a HCDR2 amino acid sequence of SEQ ID NO: 42, a HCDR3 amino acid sequence of SEQ ID NO: 63, a LCDR1 amino acid sequence of SEQ ID NO: 189, a LCDR2 amino acid sequence of SEQ ID NO: 210, and a LCDR3 amino acid sequence of SEQ ID NO: 231.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 370, a HCDR2 amino acid sequence at least 70%, at least 75%, at least 80%, at least 85%, at least 90%, or at least 95% identical to SEQ ID NO: 390, and a HCDR3 amino acid sequence at least 70%, at least 75%, at least 80%, at least 85%, at least 90%, or at least 95% identical to SEQ ID NO: 418; and a light chain variable region comprising a LCDR1 amino acid sequence at least 70%, at least 75%, at least 80%, at least 85%, at least 90%, or at least 95% identical to SEQ ID NO: 440, a LCDR2 amino acid sequence at least 70%, at least 75%, at least 80%, at least 85%, at least 90%, or at least 95% identical to SEQ ID NO: 463, and a LCDR3 amino acid sequence at least 70%, at least 75%, at least 80%, at least 85%, at least 90%, or at least 95% identical to SEQ ID NO: 481. In a particular embodiment, the anti-GAL-3 antibody comprises a HCDR1 amino acid sequence of SEQ ID NO: 370, a HCDR2 amino acid sequence of SEQ ID NO: 390, a HCDR3 amino acid sequence of SEQ ID NO: 418, a LCDR1 amino acid sequence of SEQ ID NO: 440, a LCDR2 amino acid sequence of SEQ ID NO: 463, and a LCDR3 amino acid sequence of SEQ ID NO: 481.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 370, a HCDR2 amino acid sequence at least 70%, at least 75%, at least 80%, at least 85%, at least 90%, or at least 95% identical to SEQ ID NO: 390, and a HCDR3 amino acid sequence at least 70%, at least 75%, at least 80%, at least 85%, at least 90%, or at least 95% identical to SEQ ID NO: 418; and a light chain variable region comprising a LCDR1 amino acid sequence at least 70%, at least 75%, at least 80%, at least 85%, at least 90%, or at least 95% identical to SEQ ID NO: 440, a LCDR2 amino acid sequence at least 70%, at least 75%, at least 80%, at least 85%, at least 90%, or at least 95% identical to SEQ ID NO: 463, and a LCDR3 amino acid sequence at least 70%, at least 75%, at least 80%, at least 85%, at least 90%, or at least 95% identical to SEQ ID NO: 481. In a particular embodiment, the anti-GAL-3 antibody comprises a HCDR1 amino acid sequence of SEQ ID NO: 370, a HCDR2 amino acid sequence of SEQ ID NO: 390, a HCDR3 amino acid sequence of SEQ ID NO: 418, a LCDR1 amino acid sequence of SEQ ID NO: 440, a LCDR2 amino acid sequence of SEQ ID NO: 463, and a LCDR3 amino acid sequence of SEQ ID NO: 481.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 371, a HCDR2 amino acid sequence at least 70%, at least 75%, at least 80%, at least 85%, at least 90%, or at least 95% identical to SEQ ID NO: 391, and a HCDR3 amino acid sequence at least 70%, at least 75%, at least 80%, at least 85%, at least 90%, or at least 95% identical to SEQ ID NO: 418; and a light chain variable region comprising a LCDR1 amino acid sequence at least 70%, at least 75%, at least 80%, at least 85%, at least 90%, or at least 95% identical to SEQ ID NO: 441, a LCDR2 amino acid sequence at least 70%, at least 75%, at least 80%, at least 85%, at least 90%, or at least 95% identical to SEQ ID NO: 464, and a LCDR3 amino acid sequence at least 70%, at least 75%, at least 80%, at least 85%, at least 90%, or at least 95% identical to SEQ ID NO: 482. In a particular embodiment, the anti-GAL-3 antibody comprises a HCDR1 amino acid sequence of SEQ ID NO: 371, a HCDR2 amino acid sequence of SEQ ID NO: 391, a HCDR3 amino acid sequence of SEQ ID NO: 418, a LCDR1 amino acid sequence of SEQ ID NO: 441, a LCDR2 amino acid sequence of SEQ ID NO: 464, and a LCDR3 amino acid sequence of SEQ ID NO: 482.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 372, a HCDR2 amino acid sequence at least 70%, at least 75%, at least 80%, at least 85%, at least 90%, or at least 95% identical to SEQ ID NO: 392, and a HCDR3 amino acid sequence at least 70%, at least 75%, at least 80%, at least 85%, at least 90%, or at least 95% identical to DNL; and a light chain variable region comprising a LCDR1 amino acid sequence at least 70%, at least 75%, at least 80%, at least 85%, at least 90%, or at least 95% identical to SEQ ID NO: 442, a LCDR2 amino acid sequence at least 70%, at least 75%, at least 80%, at least 85%, at least 90%, or at least 95% identical to SEQ ID NO: 465, and a LCDR3 amino acid sequence at least 70%, at least 75%, at least 80%, at least 85%, at least 90%, or at least 95% identical to SEQ ID NO: 483. In a particular embodiment, the anti-GAL-3 antibody comprises a HCDR1 amino acid sequence of SEQ ID NO: 372, a HCDR2 amino acid sequence of SEQ ID NO: 392, a HCDR3 amino acid sequence of DNL, a LCDR1 amino acid sequence of SEQ ID NO: 442, a LCDR2 amino acid sequence of SEQ ID NO: 465, and a LCDR3 amino acid sequence of SEQ ID NO: 483.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 373, a HCDR2 amino acid sequence at least 70%, at least 75%, at least 80%, at least 85%, at least 90%, or at least 95% identical to SEQ ID NO: 393, and a HCDR3 amino acid sequence at least 70%, at least 75%, at least 80%, at least 85%, at least 90%, or at least 95% identical to SEQ ID NO: 419; and a light chain variable region comprising a LCDR1 amino acid sequence at least 70%, at least 75%, at least 80%, at least 85%, at least 90%, or at least 95% identical to SEQ ID NO: 443, a LCDR2 amino acid sequence at least 70%, at least 75%, at least 80%, at least 85%, at least 90%, or at least 95% identical to SEQ ID NO: 466, and a LCDR3 amino acid sequence at least 70%, at least 75%, at least 80%, at least 85%, at least 90%, or at least 95% identical to SEQ ID NO: 484. In a particular embodiment, the anti-GAL-3 antibody comprises a HCDR1 amino acid sequence of SEQ ID NO: 373, a HCDR2 amino acid sequence of SEQ ID NO: 393, a HCDR3 amino acid sequence of SEQ ID NO: 419, a LCDR1 amino acid sequence of SEQ ID NO: 443, a LCDR2 amino acid sequence of SEQ ID NO: 466, and a LCDR3 amino acid sequence of SEQ ID NO: 484.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 374, a HCDR2 amino acid sequence at least 70%, at least 75%, at least 80%, at least 85%, at least 90%, or at least 95% identical to SEQ ID NO: 394, and a HCDR3 amino acid sequence at least 70%, at least 75%, at least 80%, at least 85%, at least 90%, or at least 95% identical to SEQ ID NO: 420; and a light chain variable region comprising a LCDR1 amino acid sequence at least 70%, at least 75%, at least 80%, at least 85%, at least 90%, or at least 95% identical to SEQ ID NO: 444, a LCDR2 amino acid sequence at least 70%, at least 75%, at least 80%, at least 85%, at least 90%, or at least 95% identical to SEQ ID NO: 467, and a LCDR3 amino acid sequence at least 70%, at least 75%, at least 80%, at least 85%, at least 90%, or at least 95% identical to SEQ ID NO: 485. In a particular embodiment, the anti-GAL-3 antibody comprises a HCDR1 amino acid sequence of SEQ ID NO: 374, a HCDR2 amino acid sequence of SEQ ID NO: 394, a HCDR3 amino acid sequence of SEQ ID NO: 420, a LCDR1 amino acid sequence of SEQ ID NO: 444, a LCDR2 amino acid sequence of SEQ ID NO: 467, and a LCDR3 amino acid sequence of SEQ ID NO: 485.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 375, a HCDR2 amino acid sequence at least 70%, at least 75%, at least 80%, at least 85%, at least 90%, or at least 95% identical to SEQ ID NO: 395, and a HCDR3 amino acid sequence at least 70%, at least 75%, at least 80%, at least 85%, at least 90%, or at least 95% identical to SEQ ID NO: 421; and a light chain variable region comprising a LCDR1 amino acid sequence at least 70%, at least 75%, at least 80%, at least 85%, at least 90%, or at least 95% identical to SEQ ID NO: 445, a LCDR2 amino acid sequence at least 70%, at least 75%, at least 80%, at least 85%, at least 90%, or at least 95% identical to SEQ ID NO: 468, and a LCDR3 amino acid sequence at least 70%, at least 75%, at least 80%, at least 85%, at least 90%, or at least 95% identical to SEQ ID NO: 486. In a particular embodiment, the anti-GAL-3 antibody comprises a HCDR1 amino acid sequence of SEQ ID NO: 375, a HCDR2 amino acid sequence of SEQ ID NO: 395, a HCDR3 amino acid sequence of SEQ ID NO: 421, a LCDR1 amino acid sequence of SEQ ID NO: 445, a LCDR2 amino acid sequence of SEQ ID NO: 468, and a LCDR3 amino acid sequence of SEQ ID NO: 486.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 376, a HCDR2 amino acid sequence at least 70%, at least 75%, at least 80%, at least 85%, at least 90%, or at least 95% identical to SEQ ID NO: 396, and a HCDR3 amino acid sequence at least 70%, at least 75%, at least 80%, at least 85%, at least 90%, or at least 95% identical to SEQ ID NO: 422; and a light chain variable region comprising a LCDR1 amino acid sequence at least 70%, at least 75%, at least 80%, at least 85%, at least 90%, or at least 95% identical to SEQ ID NO: 446, a LCDR2 amino acid sequence at least 70%, at least 75%, at least 80%, at least 85%, at least 90%, or at least 95% identical to SEQ ID NO: 469, and a LCDR3 amino acid sequence at least 70%, at least 75%, at least 80%, at least 85%, at least 90%, or at least 95% identical to SEQ ID NO: 487. In a particular embodiment, the anti-GAL-3 antibody comprises a HCDR1 amino acid sequence of SEQ ID NO: 376, a HCDR2 amino acid sequence of SEQ ID NO: 396, a HCDR3 amino acid sequence of SEQ ID NO: 422, a LCDR1 amino acid sequence of SEQ ID NO: 446, a LCDR2 amino acid sequence of SEQ ID NO: 469, and a LCDR3 amino acid sequence of SEQ ID NO: 487.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 373, a HCDR2 amino acid sequence at least 70%, at least 75%, at least 80%, at least 85%, at least 90%, or at least 95% identical to SEQ ID NO: 393, and a HCDR3 amino acid sequence at least 70%, at least 75%, at least 80%, at least 85%, at least 90%, or at least 95% identical to SEQ ID NO: 419; and a light chain variable region comprising a LCDR1 amino acid sequence at least 70%, at least 75%, at least 80%, at least 85%, at least 90%, or at least 95% identical to SEQ ID NO: 447, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, at least 90%, or at least 95% identical to SEQ ID NO: 484. In a particular embodiment, the anti-GAL-3 antibody comprises a HCDR1 amino acid sequence of SEQ ID NO: 373, a HCDR2 amino acid sequence of SEQ ID NO: 393, a HCDR3 amino acid sequence of SEQ ID NO: 419, a LCDR1 amino acid sequence of SEQ ID NO: 447, a LCDR2 amino acid sequence of SEQ ID NO: 470, and a LCDR3 amino acid sequence of SEQ ID NO: 484.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 488. In a particular embodiment, the anti-amino acid sequence of SEQ ID NO: 448, a LCDR2 amino acid sequence of SEQ ID NO: 471, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 449, a LCDR2 amino acid sequence at least 70%, at least 75%, at least 80%, at least 85%, at least 90%, or at least 95% identical to SEQ ID NO: 472, and a LCDR3 amino acid sequence at least 70%, at least 75%, at least 80%, at least 85%, at least 90%, or at least 95% identical to SEQ ID NO: 488. In a particular embodiment, the anti-GAL-3 antibody comprises a HCDR1 amino acid sequence of SEQ ID NO: 377, a HCDR2 amino acid sequence of SEQ ID NO: 397, a HCDR3 amino acid sequence of SEQ ID NO: 423, a LCDR1 amino acid sequence of SEQ ID NO: 449, a LCDR2 amino acid sequence of SEQ ID NO: 472, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 450, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 488. In a particular embodiment, the anti-amino acid sequence of SEQ ID NO: 450, a LCDR2 amino acid sequence of SEQ ID NO: 471, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 398, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 488. In a particular embodiment, the anti-GAL-3 antibody comprises a HCDR1 amino acid sequence of SEQ ID NO: 377, a HCDR2 amino acid sequence of SEQ ID NO: 398, a HCDR3 amino acid sequence of SEQ ID NO: 423, a LCDR1 amino acid sequence of SEQ ID NO: 448, a LCDR2 amino acid sequence of SEQ ID NO: 471, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 424; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 472, and a LCDR3 amino acid sequence at least 70%, at least 75%, at least 80%, at least 85%, at least 90%, or at least 95% identical to SEQ ID NO: 489. In a particular embodiment, the anti-acid sequence of SEQ ID NO: 397, a HCDR3 amino acid sequence of SEQ ID NO: 424, a LCDR1 amino acid sequence of SEQ ID NO: 448, a LCDR2 amino acid sequence of SEQ ID NO: 472, and a LCDR3 amino acid sequence of SEQ ID NO: 489.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 472, and a LCDR3 amino acid sequence at least 70%, at least 75%, at least 80%, at least 85%, at least 90%, or at least 95% identical to SEQ ID NO: 488. In a particular embodiment, the anti-GAL-3 antibody comprises a HCDR1 amino acid sequence of SEQ ID NO: 377, a HCDR2 amino acid sequence of SEQ ID NO: 397, a HCDR3 amino acid sequence of SEQ ID NO: 423, a LCDR1 amino acid sequence of SEQ ID NO: 448, a LCDR2 amino acid sequence of SEQ ID NO: 472, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 490. In a particular embodiment, the anti-acid sequence of SEQ ID NO: 397, a HCDR3 amino acid sequence of SEQ ID NO: 423, a LCDR1 amino acid sequence of SEQ ID NO: 448, a LCDR2 amino acid sequence of SEQ ID NO: 471, and a LCDR3 amino acid sequence of SEQ ID NO: 490.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 398, and a HCDR3 amino acid sequence at least 70%, at least 75%, at least 80%, at least 85%, at least 90%, or at least 95% identical to SEQ ID NO: 423; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 491. In a particular embodiment, the anti-GAL-3 antibody comprises a HCDR1 amino acid sequence of SEQ ID NO: 377, a HCDR2 amino acid sequence of SEQ ID NO: 398, a HCDR3 amino acid sequence of SEQ ID NO: 423, a LCDR1 amino acid sequence of SEQ ID NO: 448, a LCDR2 amino acid sequence of SEQ ID NO: 471, and a LCDR3 amino acid sequence of SEQ ID NO: 491.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 399, and a HCDR3 amino acid sequence at least 70%, at least 75%, at least 80%, at least 85%, at least 90%, or at least 95% identical to SEQ ID NO: 424; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 472, and a LCDR3 amino acid sequence at least 70%, at least 75%, at least 80%, at least 85%, at least 90%, or at least 95% identical to SEQ ID NO: 489. In a particular embodiment, the anti-acid sequence of SEQ ID NO: 399, a HCDR3 amino acid sequence of SEQ ID NO: 424, a LCDR1 amino acid sequence of SEQ ID NO: 448, a LCDR2 amino acid sequence of SEQ ID NO: 472, and a LCDR3 amino acid sequence of SEQ ID NO: 489.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 377, a HCDR2 amino acid sequence at least 70%, at least 75%, at least 80%, at least 85%, at least 90%, or at least 95% identical to SEQ ID NO: 397, and a HCDR3 amino acid sequence at least 70%, at least 75%, at least 80%, at least 85%, at least 90%, or at least 95% identical to SEQ ID NO: 424; and a light chain variable region comprising a LCDR1 amino acid sequence at least 70%, at least 75%, at least 80%, at least 85%, at least 90%, or at least 95% identical to SEQ ID NO: 448, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 488. In a particular embodiment, the anti-GAL-3 antibody comprises a HCDR1 amino acid sequence of SEQ ID NO: 377, a HCDR2 amino acid sequence of SEQ ID NO: 397, a HCDR3 amino acid sequence of SEQ ID NO: 424, a LCDR1 amino acid sequence of SEQ ID NO: 448, a LCDR2 amino acid sequence of SEQ ID NO: 471, and a LCDR3 amino acid sequence of SEQ ID NO: 488.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 378, a HCDR2 amino acid sequence at least 70%, at least 75%, at least 80%, at least 85%, at least 90%, or at least 95% identical to SEQ ID NO: 400, and a HCDR3 amino acid sequence at least 70%, at least 75%, at least 80%, at least 85%, at least 90%, or at least 95% identical to SEQ ID NO: 425; and a light chain variable region comprising a LCDR1 amino acid sequence at least 70%, at least 75%, at least 80%, at least 85%, at least 90%, or at least 95% identical to SEQ ID NO: 451, a LCDR2 amino acid sequence at least 70%, at least 75%, at least 80%, at least 85%, at least 90%, or at least 95% identical to SEQ ID NO:

473, and a LCDR3 amino acid sequence at least 70%, at least 75%, at least 80%, at least 85%, at least 90%, or at least 95% identical to SEQ ID NO: 492. In a particular embodiment, the anti-acid sequence of SEQ ID NO: 400, a HCDR3 amino acid sequence of SEQ ID NO: 425, a LCDR1 amino acid sequence of SEQ ID NO: 451, a LCDR2 amino acid sequence of SEQ ID NO: 473, and a LCDR3 amino acid sequence of SEQ ID NO: 492.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 378, a HCDR2 amino acid sequence at least 70%, at least 75%, at least 80%, at least 85%, at least 90%, or at least 95% identical to SEQ ID NO: 401, and a HCDR3 amino acid sequence at least 70%, at least 75%, at least 80%, at least 85%, at least 90%, or at least 95% identical to SEQ ID NO: 425; and a light chain variable region comprising a LCDR1 amino acid sequence at least 70%, at least 75%, at least 80%, at least 85%, at least 90%, or at least 95% identical to SEQ ID NO: 452, a LCDR2 amino acid sequence at least 70%, at least 75%, at least 80%, at least 85%, at least 90%, or at least 95% identical to SEQ ID NO: 473, and a LCDR3 amino acid sequence at least 70%, at least 75%, at least 80%, at least 85%, at least 90%, or at least 95% identical to SEQ ID NO: 493. In a particular embodiment, the anti-GAL-3 antibody comprises a HCDR1 amino acid sequence of SEQ ID NO: 378, a HCDR2 amino acid sequence of SEQ ID NO: 401, a HCDR3 amino acid sequence of SEQ ID NO: 425, a LCDR1 amino acid sequence of SEQ ID NO: 452, a LCDR2 amino acid sequence of SEQ ID NO: 473, and a LCDR3 amino acid sequence of SEQ ID NO: 493.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 378, a HCDR2 amino acid sequence at least 70%, at least 75%, at least 80%, at least 85%, at least 90%, or at least 95% identical to SEQ ID NO: 402, and a HCDR3 amino acid sequence at least 70%, at least 75%, at least 80%, at least 85%, at least 90%, or at least 95% identical to SEQ ID NO: 425; and a light chain variable region comprising a LCDR1 amino acid sequence at least 70%, at least 75%, at least 80%, at least 85%, at least 90%, or at least 95% identical to SEQ ID NO: 452, a LCDR2 amino acid sequence at least 70%, at least 75%, at least 80%, at least 85%, at least 90%, or at least 95% identical to SEQ ID NO: 473, and a LCDR3 amino acid sequence at least 70%, at least 75%, at least 80%, at least 85%, at least 90%, or at least 95% identical to SEQ ID NO: 493. In a particular embodiment, the anti-acid sequence of SEQ ID NO: 402, a HCDR3 amino acid sequence of SEQ ID NO: 425, a LCDR1 amino acid sequence of SEQ ID NO: 452, a LCDR2 amino acid sequence of SEQ ID NO: 473, and a LCDR3 amino acid sequence of SEQ ID NO: 493.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 379, a HCDR2 amino acid sequence at least 70%, at least 75%, at least 80%, at least 85%, at least 90%, or at least 95% identical to SEQ ID NO: 403, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, at least 90%, or at least 95% identical to SEQ ID NO: 494. In a particular embodiment, the anti-GAL-3 antibody comprises a HCDR1 amino acid sequence of SEQ ID NO: 379, a HCDR2 amino acid sequence of SEQ ID NO: 403, a HCDR3 amino acid sequence of SEQ ID NO: 426, a LCDR1 amino acid sequence of SEQ ID NO: 453, a LCDR2 amino acid sequence of SEQ ID NO: 470, and a LCDR3 amino acid sequence of SEQ ID NO: 494.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 380, a HCDR2 amino acid sequence at least 70%, at least 75%, at least 80%, at least 85%, at least 90%, or at least 95% identical to SEQ ID NO: 403, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, GAL-3 antibody comprises a HCDR1 amino acid sequence of SEQ ID NO: 380, a HCDR2 amino acid sequence of SEQ ID NO: 403, a HCDR3 amino acid sequence of SEQ ID NO: 426, a LCDR1 and a LCDR3 amino acid sequence of SEQ ID NO: 494.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 380, a HCDR2 amino acid sequence at least 70%, at least 75%, at least 80%, at least 85%, at least 90%, or at least 95% identical to SEQ ID NO: 403, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 474, and a LCDR3 amino acid sequence at least 70%, at least 75%, at least 80%, at least 85%, at least 90%, or at least 95% identical to SEQ ID NO: 494. In a particular embodiment, the anti-GAL-3 antibody comprises a HCDR1 amino acid sequence of SEQ ID NO: 380, a HCDR2 amino acid sequence of SEQ ID NO: 403, a HCDR3 amino acid sequence of SEQ ID NO: 426, a LCDR1 amino acid sequence of SEQ ID NO: 453, a LCDR2 amino acid sequence of SEQ ID NO: 474, and a LCDR3 amino acid sequence of SEQ ID NO: 494.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 381, a HCDR2 amino acid sequence at least 70%, at least 75%, at least 80%, at least 85%, at least 90%, or at least 95% identical to SEQ ID NO: 404, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, acid sequence of SEQ ID NO: 404, a HCDR3 amino acid sequence of SEQ ID NO: 426, a LCDR1 and a LCDR3 amino acid sequence of SEQ ID NO: 494.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 381, a HCDR2 amino acid sequence at least 70%, at least 75%, at least 80%, at least 85%, at least 90%, or at least 95% identical to SEQ ID NO: 404, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, at least 90%, or at least 95% identical to SEQ ID NO: 495. In a particular embodiment, the anti-GAL-3 antibody comprises a HCDR1 amino acid sequence of SEQ ID NO: 381, a HCDR2 amino acid sequence of SEQ ID NO: 404, a HCDR3 amino acid sequence of SEQ ID NO: 426, a LCDR1 amino acid sequence of SEQ ID NO: 453, a LCDR2 amino acid sequence of SEQ ID NO: 470, and a LCDR3 amino acid sequence of SEQ ID NO: 495.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 381, a HCDR2 amino acid sequence at least 70%, at least 75%, at least 80%, at least 85%, at least 90%, or at least 95% identical to SEQ ID NO: 405, and a HCDR3 amino acid sequence at least 70%, at least 75%, at least 80%, at least 85%, at least 90%, or at least 95% identical to SEQ ID NO: 426; and a light chain variable region comprising a LCDR1 amino acid sequence at least 70%, at least 75%, at least 80%, at least 85%, at least 90%, or at least 95% identical to SEQ ID NO: 453, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, acid sequence of SEQ ID NO: 405, a HCDR3 amino acid sequence of SEQ ID NO: 426, a LCDR1 and a LCDR3 amino acid sequence of SEQ ID NO: 494.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 378, a HCDR2 amino acid sequence at least 70%, at least 75%, at least 80%, at least 85%, at least 90%, or at least 95% identical to SEQ ID NO: 406, and a HCDR3 amino acid sequence at least 70%, at least 75%, at least 80%, at least 85%, at least 90%, or at least 95% identical to SEQ ID NO: 427; and a light chain variable region comprising a LCDR1 amino acid sequence at least 70%, at least 75%, at least 80%, at least 85%, at least 90%, or at least 95% identical to SEQ ID NO: 452, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, at least 90%, or at least 95% identical to SEQ ID NO: 496. In a particular embodiment, the anti-GAL-3 antibody comprises a HCDR1 amino acid sequence of SEQ ID NO: 378, a HCDR2 amino acid sequence of SEQ ID NO: 406, a HCDR3 amino acid sequence of SEQ ID NO: 427, a LCDR1 amino acid sequence of SEQ ID NO: 452, a LCDR2 amino acid sequence of SEQ ID NO: 470, and a LCDR3 amino acid sequence of SEQ ID NO: 496.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 378, a HCDR2 amino acid sequence at least 70%, at least 75%, at least 80%, at least 85%, at least 90%, or at least 95% identical to SEQ ID NO: 407, and a HCDR3 amino acid sequence at least 70%, at least 75%, at least 80%, at least 85%, at least 90%, or at least 95% identical to SEQ ID NO: 425; and a light chain variable region comprising a LCDR1 amino acid sequence at least 70%, at least 75%, at least 80%, at least 85%, at least 90%, or at least 95% identical to SEQ ID NO: 452, a LCDR2 amino acid sequence at least 70%, at least 75%, at least 80%, at least 85%, at least 90%, or at least 95% identical to SEQ ID NO: 475, and a LCDR3 amino acid sequence at least 70%, at least 75%, at least 80%, at least 85%, at least 90%, or at least 95% identical to SEQ ID NO: 496. In a particular embodiment, the anti-acid sequence of SEQ ID NO: 407, a HCDR3 amino acid sequence of SEQ ID NO: 425, a LCDR1 amino acid sequence of SEQ ID NO: 452, a LCDR2 amino acid sequence of SEQ ID NO: 475, and a LCDR3 amino acid sequence of SEQ ID NO: 496.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 382, a HCDR2 amino acid sequence at least 70%, at least 75%, at least 80%, at least 85%, at least 90%, or at least 95% identical to SEQ ID NO: 408, and a HCDR3 amino acid sequence at least 70%, at least 75%, at least 80%, at least 85%, at least 90%, or at least 95% identical to SEQ ID NO: 428; and a light chain variable region comprising a LCDR1 amino acid sequence at least 70%, at least 75%, at least 80%, at least 85%, at least 90%, or at least 95% identical to SEQ ID NO: 454, a LCDR2 amino acid sequence at least 70%, at least 75%, at least 80%, at least 85%, at least 90%, or at least 95% identical to SEQ ID NO: 471, and a LCDR3 amino acid sequence at least 70%, at least 75%, at least 80%, at least 85%, at least 90%, or at least 95% identical to SEQ ID NO: 497. In a particular embodiment, the anti-GAL-3 antibody comprises a HCDR1 amino acid sequence of SEQ ID NO: 382, a HCDR2 amino acid sequence of SEQ ID NO: 408, a HCDR3 amino acid sequence of SEQ ID NO: 428, a LCDR1 amino acid sequence of SEQ ID NO: 454, a LCDR2 amino acid sequence of SEQ ID NO: 471, and a LCDR3 amino acid sequence of SEQ ID NO: 497.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 382, a HCDR2 amino acid sequence at least 70%, at least 75%, at least 80%, at least 85%, at least 90%, or at least 95% identical to SEQ ID NO: 408, and a HCDR3 amino acid sequence at least 70%, at least 75%, at least 80%, at least 85%, at least 90%, or at least 95% identical to SEQ ID NO: 429; and a light chain variable region comprising a LCDR1 amino acid sequence at least 70%, at least 75%, at least 80%, at least 85%, at least 90%, or at least 95% identical to SEQ ID NO: 455, a LCDR2 amino acid sequence at least 70%, at least 75%, at least 80%, at least 85%, at least 90%, or at least 95% identical to SEQ ID NO: 476, and a LCDR3 amino acid sequence at least 70%, at least 75%, at least 80%, at least 85%, at least 90%, or at least 95% identical to SEQ ID NO: 498. In a particular embodiment, the anti-acid sequence of SEQ ID NO: 408, a HCDR3 amino acid sequence of SEQ ID NO: 429, a LCDR1 amino acid sequence of SEQ ID NO: 455, a LCDR2 amino acid sequence of SEQ ID NO: 476, and a LCDR3 amino acid sequence of SEQ ID NO: 498.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 382, a HCDR2 amino acid sequence at least 70%, at least 75%, at least 80%, at least 85%, at least 90%, or at least 95% identical to SEQ ID NO: 408, and a HCDR3 amino acid sequence at least 70%, at least 75%, at least 80%, at least 85%, at least 90%, or at least 95% identical to SEQ ID NO: 429; and a light chain variable region comprising a LCDR1 amino acid sequence at least 70%, at least 75%, at least 80%, at least 85%, at least 90%, or at least 95% identical to SEQ ID NO: 454, a LCDR2 amino acid sequence at least 70%, at least 75%, at least 80%, at least 85%, at least 90%, or at least 95% identical to SEQ ID NO: 468, and a LCDR3 amino acid sequence at least 70%, at least 75%, at least 80%, at least 85%, at least 90%, or at least 95% identical to SEQ ID NO: 497. In a particular embodiment, the anti-GAL-3 antibody comprises a HCDR1 amino acid sequence of SEQ ID NO: 382, a HCDR2 amino acid sequence of SEQ ID NO: 408, a HCDR3 amino acid sequence of SEQ ID NO: 429, a LCDR1 amino acid sequence of SEQ ID NO: 454, a LCDR2 amino acid sequence of SEQ ID NO: 468, and a LCDR3 amino acid sequence of SEQ ID NO: 497.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 382, a HCDR2 amino acid sequence at least 70%, at least 75%, at least 80%, at least 85%, at least 90%, or at least 95% identical to SEQ ID NO: 408, and a HCDR3 amino acid sequence at least 70%, at least 75%, at least 80%, at least 85%, at least 90%, or at least 95% identical to SEQ ID NO: 430; and a light chain variable region comprising a LCDR1 amino acid sequence at least 70%, at least 75%, at least 80%, at least 85%, at least 90%, or at least 95% identical to SEQ ID NO: 454, a LCDR2 amino acid sequence at least 70%, at least 75%, at least 80%, at least 85%, at least 90%, or at least 95% identical to SEQ ID NO: 477, and a LCDR3 amino acid sequence at least 70%, at least 75%, at least 80%, at least 85%, at least 90%, or at least 95% identical to SEQ ID NO: 497. In a particular embodiment, the anti-acid sequence of SEQ ID NO: 408, a HCDR3 amino acid sequence of SEQ ID NO: 430, a LCDR1 amino acid sequence of SEQ ID NO: 454, a LCDR2 amino acid sequence of SEQ ID NO: 477, and a LCDR3 amino acid sequence of SEQ ID NO: 497.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 383, a HCDR2 amino acid sequence at least 70%, at least 75%, at least 80%, at least 85%, at least 90%, or at least 95% identical to SEQ ID NO: 409, and a HCDR3 amino acid sequence at least 70%, at least 75%, at least 80%, at least 85%, at least 90%, or at least 95% identical to SEQ ID NO: 431; and a light chain variable region comprising a LCDR1 amino acid sequence at least 70%, at least 75%, at least 80%, at least 85%, at least 90%, or at least 95% identical to SEQ ID NO: 456, a LCDR2 amino acid sequence at least 70%, at least 75%, at least 80%, at least 85%, at least 90%, or at least 95% identical to SEQ ID NO: 474, and a LCDR3 amino acid sequence at least 70%, at least 75%, at least 80%, at least 85%, at least 90%, or at least 95% identical to SEQ ID NO: 499. In a particular embodiment, the anti-GAL-3 antibody comprises a HCDR1 amino acid sequence of SEQ ID NO: 383, a HCDR2 amino acid sequence of SEQ ID NO: 409, a HCDR3 amino acid sequence of SEQ ID NO: 431, a LCDR1 amino acid sequence of SEQ ID NO: 456, a LCDR2 amino acid sequence of SEQ ID NO: 474, and a LCDR3 amino acid sequence of SEQ ID NO: 499.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 383, a HCDR2 amino acid sequence at least 70%, at least 75%, at least 80%, at least 85%, at least 90%, or at least 95% identical to SEQ ID NO: 409, and a HCDR3 amino acid sequence at least 70%, at least 75%, at least 80%, at least 85%, at least 90%, or at least 95% identical to SEQ ID NO: 431; and a light chain variable region comprising a LCDR1 amino acid sequence at least 70%, at least 75%, at least 80%, at least 85%, at least 90%, or at least 95% identical to SEQ ID NO: 456, a LCDR2 amino acid sequence at least 70%, at least 75%, at least 80%, at least 85%, at least 90%, or at least 95% identical to SEQ ID NO: 478, and a LCDR3 amino acid sequence at least 70%, at least 75%, at least 80%, at least 85%, at least 90%, or at least 95% identical to SEQ ID NO: 499. In a particular embodiment, the anti-GAL-3 antibody comprises a HCDR1 amino acid sequence of SEQ ID NO: 383, a HCDR2 amino acid sequence of SEQ ID NO: 409, a HCDR3 amino acid sequence of SEQ ID NO: 431, a LCDR1 amino acid sequence of SEQ ID NO: 456, a LCDR2 amino acid sequence of SEQ ID NO: 478, and a LCDR3 amino acid sequence of SEQ ID NO: 499.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 384, a HCDR2 amino acid sequence at least 70%, at least 75%, at least 80%, at least 85%, at least 90%, or at least 95% identical to SEQ ID NO: 410, and a HCDR3 amino acid sequence at least 70%, at least 75%, at least 80%, at least 85%, at least 90%, or at least 95% identical to SEQ ID NO: 431; and a light chain variable region comprising a LCDR1 amino acid sequence at least 70%, at least 75%, at least 80%, at least 85%, at least 90%, or at least 95% identical to SEQ ID NO: 457, a LCDR2 amino acid sequence at least 70%, at least 75%, at least 80%, at least 85%, at least 90%, or at least 95% identical to SEQ ID NO:

474, and a LCDR3 amino acid sequence at least 70%, at least 75%, at least 80%, at least 85%, at least 90%, or at least 95% identical to SEQ ID NO: 500. In a particular embodiment, the anti-GAL-3 antibody comprises a HCDR1 amino acid sequence of SEQ ID NO: 384, a HCDR2 amino acid sequence of SEQ ID NO: 410, a HCDR3 amino acid sequence of SEQ ID NO: 431, a LCDR1 amino acid sequence of SEQ ID NO: 457, a LCDR2 amino acid sequence of SEQ ID NO: 474, and a LCDR3 amino acid sequence of SEQ ID NO: 500.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 384, a HCDR2 amino acid sequence at least 70%, at least 75%, at least 80%, at least 85%, at least 90%, or at least 95% identical to SEQ ID NO: 410, and a HCDR3 amino acid sequence at least 70%, at least 75%, at least 80%, at least 85%, at least 90%, or at least 95% identical to SEQ ID NO: 432; and a light chain variable region comprising a LCDR1 amino acid sequence at least 70%, at least 75%, at least 80%, at least 85%, at least 90%, or at least 95% identical to SEQ ID NO: 458, a LCDR2 amino acid sequence at least 70%, at least 75%, at least 80%, at least 85%, at least 90%, or at least 95% identical to SEQ ID NO: 474, and a LCDR3 amino acid sequence at least 70%, at least 75%, at least 80%, at least 85%, at least 90%, or at least 95% identical to SEQ ID NO: 500. In a particular embodiment, the anti-GAL-3 antibody comprises a HCDR1 amino acid sequence of SEQ ID NO: 384, a HCDR2 amino acid sequence of SEQ ID NO: 410, a HCDR3 amino acid sequence of SEQ ID NO: 432, a LCDR1 amino acid sequence of SEQ ID NO: 458, a LCDR2 amino acid sequence of SEQ ID NO: 474, and a LCDR3 amino acid sequence of SEQ ID NO: 500.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 385, a HCDR2 amino acid sequence at least 70%, at least 75%, at least 80%, at least 85%, at least 90%, or at least 95% identical to SEQ ID NO: 411, and a HCDR3 amino acid sequence at least 70%, at least 75%, at least 80%, at least 85%, at least 90%, or at least 95% identical to SEQ ID NO: 433; and a light chain variable region comprising a LCDR1 amino acid sequence at least 70%, at least 75%, at least 80%, at least 85%, at least 90%, or at least 95% identical to SEQ ID NO: 459, a LCDR2 amino acid sequence at least 70%, at least 75%, at least 80%, at least 85%, at least 90%, or at least 95% identical to SEQ ID NO: 470, and a LCDR3 amino acid sequence at least 70%, at least 75%, at least 80%, at least 85%, at least 90%, or at least 95% identical to SEQ ID NO: 501. In a particular embodiment, the anti-GAL-3 antibody comprises a HCDR1 amino acid sequence of SEQ ID NO: 385, a HCDR2 amino acid sequence of SEQ ID NO: 411, a HCDR3 amino acid sequence of SEQ ID NO: 433, a LCDR1 amino acid sequence of SEQ ID NO: 459, a LCDR2 amino acid sequence of SEQ ID NO: 470, and a LCDR3 amino acid sequence of SEQ ID NO: 501.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 386, a HCDR2 amino acid sequence at least 70%, at least 75%, at least 80%, at least 85%, at least 90%, or at least 95% identical to SEQ ID NO: 412, and a HCDR3 amino acid sequence at least 70%, at least 75%, at least 80%, at least 85%, at least 90%, or at least 95% identical to SEQ ID NO: 434; and a light chain variable region comprising a LCDR1 amino acid sequence at least 70%, at least 75%, at least 80%, at least 85%, at least 90%, or at least 95% identical to SEQ ID NO: 460, a LCDR2 amino acid sequence at least 70%, at least 75%, at least 80%, at least 85%, at least 90%, or at least 95% identical to SEQ ID NO: 479, and a LCDR3 amino acid sequence at least 70%, at least 75%, at least 80%, at least 85%, at least 90%, or at least 95% identical to SEQ ID NO: 502. In a particular embodiment, the anti-GAL-3 antibody comprises a HCDR1 amino acid sequence of SEQ ID NO: 386, a HCDR2 amino acid sequence of SEQ ID NO: 412, a HCDR3 amino acid sequence of SEQ ID NO: 434, a LCDR1 amino acid sequence of SEQ ID NO: 460, a LCDR2 amino acid sequence of SEQ ID NO: 479, and a LCDR3 amino acid sequence of SEQ ID NO: 502.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 387, a HCDR2 amino acid sequence at least 70%, at least 75%, at least 80%, at least 85%, at least 90%, or at least 95% identical to SEQ ID NO: 413, and a HCDR3 amino acid sequence at least 70%, at least 75%, at least 80%, at least 85%, at least 90%, or at least 95% identical to SEQ ID NO: 435; and a light chain variable region comprising a LCDR1 amino acid sequence at least 70%, at least 75%, at least 80%, at least 85%, at least 90%, or at least 95% identical to SEQ ID NO: 461, a LCDR2 amino acid sequence at least 70%, at least 75%, at least 80%, at least 85%, at least 90%, or at least 95% identical to SEQ ID NO: 201, and a LCDR3 amino acid sequence at least 70%, at least 75%, at least 80%, at least 85%, at least 90%, or at least 95% identical to SEQ ID NO: 503. In a particular embodiment, the anti-GAL-3 antibody comprises a HCDR1 amino acid sequence of SEQ ID NO: 387, a HCDR2 amino acid sequence of SEQ ID NO: 413, a HCDR3 amino acid sequence of SEQ ID NO: 435, a LCDR1 amino acid sequence of SEQ ID NO: 461, a LCDR2 amino acid sequence of SEQ ID NO: 201, and a LCDR3 amino acid sequence of SEQ ID NO: 503.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 4, a HCDR2 amino acid sequence at least 70%, at least 75%, at least 80%, at least 85%, at least 90%, or at least 95% identical to SEQ ID NO: 414, and a HCDR3 amino acid sequence at least 70%, at least 75%, at least 80%, at least 85%, at least 90%, or at least 95% identical to SEQ ID NO: 436; and a light chain variable region comprising a LCDR1 amino acid sequence at least 70%, at least 75%, at least 80%, at least 85%, at least 90%, or at least 95% identical to SEQ ID NO: 462, a LCDR2 amino acid sequence at least 70%, at least 75%, at least 80%, at least 85%, at least 90%, or at least 95% identical to SEQ ID NO: 480, and a LCDR3 amino acid sequence at least 70%, at least 75%, at least 80%, at least 85%, at least 90%, or at least 95% identical to SEQ ID NO: 504. In a particular embodiment, the anti-acid sequence of SEQ ID NO: 414, a HCDR3 amino acid sequence of SEQ ID NO: 436, a LCDR1 amino acid sequence of SEQ ID NO: 462, a LCDR2 amino acid sequence of SEQ ID NO: 480, and a LCDR3 amino acid sequence of SEQ ID NO: 504.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 388, a HCDR2 amino acid sequence at least 70%, at least 75%, at least 80%, at least 85%, at least 90%, or at least 95% identical to SEQ ID NO: 415, and a HCDR3 amino acid sequence at least 70%, at least 75%, at least 80%, at least 85%, at least 90%, or at least 95% identical to SEQ ID NO: 437; and a light chain variable region comprising a LCDR1 amino acid sequence at least 70%, at least 75%, at least 80%, at least 85%, at least 90%, or at least 95% identical to SEQ ID NO: 461, a LCDR2 amino acid sequence at least 70%, at least 75%, at least 80%, at least 85%, at least 90%, or at least 95% identical to SEQ ID NO: 201, and a LCDR3 amino acid sequence at least 70%, at least 75%, at least 80%, at least 85%, at least 90%, or at least 95% identical to SEQ ID NO: 505. In a particular embodiment, the anti-GAL-3 antibody comprises a HCDR1 amino acid sequence of SEQ ID NO: 388, a HCDR2 amino acid sequence of SEQ ID NO: 415, a HCDR3 amino acid sequence of SEQ ID NO: 437, a LCDR1 amino acid sequence of SEQ ID NO: 461, a LCDR2 amino acid sequence of SEQ ID NO: 201, and a LCDR3 amino acid sequence of SEQ ID NO: 505.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 4, a HCDR2 amino acid sequence at least 70%, at least 75%, at least 80%, at least 85%, at least 90%, or at least 95% identical to SEQ ID NO: 416, and a HCDR3 amino acid sequence at least 70%, at least 75%, at least 80%, at least 85%, at least 90%, or at least 95% identical to SEQ ID NO: 438; and a light chain variable region comprising a LCDR1 amino acid sequence at least 70%, at least 75%, at least 80%, at least 85%, at least 90%, or at least 95% identical to SEQ ID NO: 462, a LCDR2 amino acid sequence at least 70%, at least 75%, at least 80%, at least 85%, at least 90%, or at least 95% identical to SEQ ID NO: 480, and a LCDR3 amino acid sequence at least 70%, at least 75%, at least 80%, at least 85%, at least 90%, or at least 95% identical to SEQ ID NO: 506. In a particular embodiment, the anti-acid sequence of SEQ ID NO: 416, a HCDR3 amino acid sequence of SEQ ID NO: 438, a LCDR1 amino acid sequence of SEQ ID NO: 462, a LCDR2 amino acid sequence of SEQ ID NO: 480, and a LCDR3 amino acid sequence of SEQ ID NO: 506.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 4, a HCDR2 amino acid sequence at least 70%, at least 75%, at least 80%, at least 85%, at least 90%, or at least 95% identical to SEQ ID NO: 414, and a HCDR3 amino acid sequence at least 70%, at least 75%, at least 80%, at least 85%, at least 90%, or at least 95% identical to SEQ ID NO: 436; and a light chain variable region comprising a LCDR1 amino acid sequence at least 70%, at least 75%, at least 80%, at least 85%, at least 90%, or at least 95% identical to SEQ ID NO: 462, a LCDR2 amino acid sequence at least 70%, at least 75%, at least 80%, at least 85%, at least 90%, or at least 95% identical to SEQ ID NO: 480, and a LCDR3 amino acid sequence at least 70%, at least 75%, at least 80%, at least 85%, at least 90%, or at least 95% identical to SEQ ID NO: 507. In a particular embodiment, the anti-GAL-3 antibody comprises a HCDR1 amino acid sequence of SEQ ID NO: 4, a HCDR2 amino acid sequence of SEQ ID NO: 414, a HCDR3 amino acid sequence of SEQ ID NO: 436, a LCDR1 amino acid sequence of SEQ ID NO: 462, a LCDR2 amino acid sequence of SEQ ID NO: 480, and a LCDR3 amino acid sequence of SEQ ID NO: 507.

In some embodiments, the anti-GAL-3 antibody comprises a heavy chain variable region comprising a HCDR1 amino acid sequence at least 70%, at least 75%, at least 80%, at least 85%, at least 90%, or at least 95% identical to SEQ ID NO: 389, a HCDR2 amino acid sequence at least 70%, at least 75%, at least 80%, at least 85%, at least 90%, or at least 95% identical to SEQ ID NO: 417, and a HCDR3 amino acid sequence at least 70%, at least 75%, at least 80%, at least 85%, at least 90%, or at least 95% identical to SEQ ID NO: 439. In a particular embodiment, the anti-GAL-3 antibody comprises a HCDR1 amino acid sequence of SEQ ID NO: 389, a HCDR2 amino acid sequence of SEQ ID NO: 417, a HCDR3 amino acid sequence of SEQ ID NO: 439.

In some embodiments, the anti-GAL-3 antibody comprises all six CDRs of an antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274, 1220SBC1068-281, 20240628SBC1080-002, 20240628SBC1080-003, 20240628SBC1080-004, 20240628SBC1080-005, 20240628SBC1080-006, 20240628SBC1080-007, 20240628SBC1080-008, 20240628SBC1080-009, 20240903SBC1093-015, 20240903SBC1093-020, 20240903SBC1093-021, 20240903SBC1093-025, 20240903SBC1093-030, 20240903SBC1093-182, 20240903SBC1093-183, 20240903SBC1093-184, 20240903SBC1093-185, 20240903SBC1093-230, 20240903SBC1093-033, 20240903SBC1093-034, 20240903SBC1093-035, 20240903SBC1093-044, 20240903SBC1093-054, 20240903SBC1093-055, 20240903SBC1093-056, 20240903SBC1093-057, 20240903SBC1093-059, 20240903SBC1093-219, 20240903SBC1093-228, 20240903SBC1093-023, 20240903SBC1093-036, 20240903SBC1093-037, 20240903SBC1093-220, 20240903SBC1093-074, 20240903SBC1093-075, 20240903SBC1093-193, 20240903SBC1093-194, 20240903SBC1093-099, 20240929SBC1205-022, 20241223SBC1205-061, 20241223SBC1205-063, 20241223SBC1205-119, 20241223SBC1205-130, 20241223SBC1205-131, and ANb1361-hGal-3-LP3R3 P2-69, as the $H_V$ and $H_L$ CDR amino acid sequences of the antibodies listed in Tables 3 and 4, respectively.

TABLE 3

| Heavy chain CDR sequences | | | |
|---|---|---|---|
| Antibody ID | HCDR1 | HCDR2 | HCDR3 |
| 1104SBC1068-033 | SDYAWN (SEQ ID NO: 1) | YISYSGSTSYNPSLKS (SEQ ID NO: 22) | EGGRGGTEGYYFDY (SEQ ID NO: 43) |

TABLE 3-continued

| Heavy chain CDR sequences | | | |
|---|---|---|---|
| Antibody ID | HCDR1 | HCDR2 | HCDR3 |
| 1104SBC1068-335 | NYGMN (SEQ ID NO: 2) | WINTYSGEPTYVDDFKG (SEQ ID NO: 23) | GTVVGFDY (SEQ ID NO: 44) |
| 1104SBC1068-365 | NYGMN (SEQ ID NO: 3) | WINTNTGEPTYSEEFKG (SEQ ID NO: 24) | SSYYAMDY (SEQ ID NO: 45) |
| 1104SBC1068-374 | NYGMN (SEQ ID NO: 4) | WINTYTGEPTYADDFKG (SEQ ID NO: 25) | YAMDY (SEQ ID NO: 46) |
| SIF001 | NYGMN (SEQ ID NO: 4) | WINTYTGEPTYADDFKG (SEQ ID NO: 25) | YAMDY (SEQ ID NO: 46) |
| 1104SBC1068-378 | NYGMN (SEQ ID NO: 5) | WINTYTGEPTYADDFKG (SEQ ID NO: 26) | WDDYDGFAY (SEQ ID NO: 47) |
| 1220SBC1068-022 | DYGMA (SEQ ID NO: 6) | FISNLAYSVYYADTVTG (SEQ ID NO: 27) | DRGLRESMDY (SEQ ID NO: 48) |
| 1220SBC1068-035 | GYTMN (SEQ ID NO: 7) | LISPYSGGTNYNQRFKG (SEQ ID NO: 28) | SGFITTGVPTNFDV (SEQ ID NO: 49) |
| 1220SBC1068-041 | RFWMS (SEQ ID NO: 8) | EISPDSNTIDLTPSLKD (SEQ ID NO: 29) | PYYGYY (SEQ ID NO: 50) |
| SIF002 | RFWMS (SEQ ID NO: 8) | EISPDSNTIDLTPSLKD (SEQ ID NO: 29) | PYYGYY (SEQ ID NO: 50) |
| 1220SBC1068-056 | DYGMA (SEQ ID NO: 9) | FISNLAYSVYYADTVTG (SEQ ID NO: 30) | DRGLRESMDY (SEQ ID NO: 51) |
| 1220SBC1068-058 | DYGMA (SEQ ID NO: 10) | FISNLAYSVYYADTVTG (SEQ ID NO: 31) | DRGLRETMDY (SEQ ID NO: 52) |
| 1220SBC1068-063 | RFWMS (SEQ ID NO: 11) | EISPNSSTIHQTPSLKD (SEQ ID NO: 32) | PYYGYY (SEQ ID NO: 53) |
| 1220SBC1068-097 | RYWMS (SEQ ID NO: 12) | EINPDSSTIDLTPSLKD (SEQ ID NO: 33) | PYHGYY (SEQ ID NO: 54) |
| 1220SBC1068-098 | RYWMS (SEQ ID NO: 13) | EISPDSSTIDLTPSLKD (SEQ ID NO: 34) | PYHGYY (SEQ ID NO: 55) |
| 1220SBC1068-099 | RYWMT (SEQ ID NO: 14) | EINPHSSTITYTPSLKD (SEQ ID NO: 35) | PYYGYY (SEQ ID NO: 56) |
| 1220SBC1068-129 | RFWMS (SEQ ID NO: 15) | EINPDSSTITYTPSLKD (SEQ ID NO: 36) | PYYGYY (SEQ ID NO: 57) |
| 1220SBC1068-164 | RYWMS (SEQ ID NO: 16) | EISPDSSTINYTASLKD (SEQ ID NO: 37) | PYYGYY (SEQ ID NO: 58) |
| 1220SBC1068-186 | GYTMN (SEQ ID NO: 17) | LISPYSGGTNYNQKFKG (SEQ ID NO: 38) | SGFITTGVATNFDV (SEQ ID NO: 59) |
| 1220SBC1068-197 | RFWMS (SEQ ID NO: 18) | EISPNSSTIHQTPSLKD (SEQ ID NO: 39) | PYYGYY (SEQ ID NO: 60) |
| 1220SBC1068-210 | RYWMS (SEQ ID NO: 19) | EINPDSSTIDLTPSLKD (SEQ ID NO: 40) | PYYGYY (SEQ ID NO: 61) |
| 1220SBC1068-274 | RYWMS (SEQ ID NO: 20) | EISPDSNTIDLTPSLKD (SEQ ID NO: 41) | PYYGYY (SEQ ID NO: 62) |
| 1220SBC1068-281 | DFGMA (SEQ ID NO: 21) | FISNLAYNIYYSDTVTG (SEQ ID NO: 42) | DRGLRETMDY (SEQ ID NO: 63) |
| 20240628SBC1080-002 | NHHIN (SEQ ID NO: 370) | IISASGSAYYANWAKG (SEQ ID NO: 390) | ESWMDL(SEQ ID NO: 418) |
| 20240628SBC1080-003 | NHHIN (SEQ ID NO: 371) | IISNGGSAYYANWAKG (SEQ ID NO: 391) | ESWMDL(SEQ ID NO: 418) |
| 20240628SBC1080-004 | NNAMT(SEQ ID NO: 372 | YIWRGGETYYASWAKG (SEQ ID NO: 392) | DNL |

TABLE 3-continued

| Heavy chain CDR sequences | | | |
|---|---|---|---|
| Antibody ID | HCDR1 | HCDR2 | HCDR3 |
| 20240628SBC1080-005 | RYGVS(SEQ ID NO: 373) | YIYIGDGSTYYASWVNG (SEQ ID NO: 393) | SYLSSGWGVDL(SEQ ID NO: 419) |
| 20240628SBC1080-006 | YYAMG(SEQ ID NO: 374) | IIDTNNVTYYASWAKG (SEQ ID NO: 394) | GGLDL(SEQ ID NO: 420) |
| 20240628SBC1080-007 | HYAMG(SEQ ID NO: 375) | YITFGGIAYYANWAKG (SEQ ID NO: 395) | YADFAYNL(SEQ ID NO: 421) |
| 20240628SBC1080-008 | NNHMG(SEQ ID NO: 376) | FINGNGVGSAFYANWAKG (SEQ ID NO: 396) | GPGYGCFDL(SEQ ID NO: 422) |
| 20240628SBC1080-009 | RYGVS(SEQ ID NO: 373) | YIYIGDGSTYYASWVNG (SEQ ID NO: 393) | SYLSSGWGVDL(SEQ ID NO: 419) |
| 20240903SBC1093-015 | SYWMI(SEQ ID NO: 377) | GISTIDNTYYASWAKG (SEQ ID NO: 397) | NFDT(SEQ ID NO: 423) |
| 20240903SBC1093-020 | SYWMI(SEQ ID NO: 377) | GISTIDNTYYASWAKG (SEQ ID NO: 397) | NFDT(SEQ ID NO: 423) |
| 20240903SBC1093-021 | SYWMI(SEQ ID NO: 377) | GISTIDNTYYASWAKG (SEQ ID NO: 397) | NFDT(SEQ ID NO: 423) |
| 20240903SBC1093-025 | SYWMI(SEQ ID NO: 377) | GISTIDNTYYATWAKG (SEQ ID NO: 398) | NFDT(SEQ ID NO: 423) |
| 20240903SBC1093-030 | SYWMI(SEQ ID NO: 377) | GISTIDNTYYASWAKG (SEQ ID NO: 397) | NFDI(SEQ ID NO: 424) |
| 20240903SBC1093-182 | SYWMI(SEQ ID NO: 377) | GISTIDNTYYASWAKG (SEQ ID NO: 397) | NFDT(SEQ ID NO: 423) |
| 20240903SBC1093-183 | SYWMI(SEQ ID NO: 377) | GISTIDNTYYASWAKG (SEQ ID NO: 397) | NEDT(SEQ ID NO: 423) |
| 20240903SBC1093-184 | SYWMI(SEQ ID NO: 377) | GISTIDNTYYATWAKG (SEQ ID NO: 398) | NFDT(SEQ ID NO: 423) |
| 20240903SBC1093-185 | SYWMI(SEQ ID NO: 377) | GISTIDNTYYSTWAKG (SEQ ID NO: 399) | NFDI(SEQ ID NO: 424) |
| 20240903SBC1093-230 | SYWMI(SEQ ID NO: 377) | GISTIDNTYYASWAKG (SEQ ID NO: 397) | NFDI(SEQ ID NO: 424) |
| 20240903SBC1093-033 | DYAVF(SEQ ID NO: 378) | FISSIGSTYYASWAKG (SEQ ID NO: 400) | WNLDI(SEQ ID NO: 425) |
| 20240903SBC1093-034 | DYAVF(SEQ ID NO: 378) | FISSVGTTFYASWAKG (SEQ ID NO: 401) | WNLDI(SEQ ID NO: 425) |
| 20240903SBC1093-035 | DYAVF(SEQ ID NO: 378) | FISSVGTTFYATWAKG (SEQ ID NO: 402) | WNLDI(SEQ ID NO: 425) |
| 20240903SBC1093-044 | KYAVN(SEQ ID NO: 379) | FIDAVGDTYYARWAKG (SEQ ID NO: 403) | WNTDI(SEQ ID NO: 426) |
| 20240903SBC1093-054 | NYAVN(SEQ ID NO: 380) | FIDAVGDTYYARWAKG (SEQ ID NO: 403) | WNTDI(SEQ ID NO: 426) |
| 20240903SBC1093-055 | NYAVN(SEQ ID NO: 380) | FIDAVGDTYYARWAKG (SEQ ID NO: 403) | WNTDI(SEQ ID NO: 426) |
| 20240903SBC1093-056 | NYAVY(SEQ ID NO: 381) | FIDAVGNTYYARWAKG (SEQ ID NO: 404) | WNTDI(SEQ ID NO: 426) |
| 20240903SBC1093-057 | NYAVY(SEQ ID NO: 381) | FIDAVGNTYYARWAKG (SEQ ID NO: 404) | WNTDI(SEQ ID NO: 426) |
| 20240903SBC1093-059 | NYAVY(SEQ ID NO: 381) | FIDA VGSTYYARWAKG (SEQ ID NO: 405) | WNTDI(SEQ ID NO: 426) |
| 20240903SBC1093-219 | DYAVF(SEQ ID NO: 378) | FISSVGTKFYASWAKG (SEQ ID NO: 406) | WNMDI(SEQ ID NO: 427) |

TABLE 3-continued

| Heavy chain CDR sequences | | | |
|---|---|---|---|
| Antibody ID | HCDR1 | HCDR2 | HCDR3 |
| 20240903SBC1093-228 | DYAVF(SEQ ID NO: 378) | FISSVGTTYYAPWAKG (SEQ ID NO: 407) | WNLDI(SEQ ID NO: 425) |
| 20240903SBC1093-023 | DYNFQ(SEQ ID NO: 382) | TIGIGTDTYYATWAIG(SEQ ID NO: 408) | DLYGGDSV(SEQ ID NO: 428) |
| 20240903SBC1093-036 | DYNFQ(SEQ ID NO: 382) | TIGIGTDTYYATWAIG SEQ ID NO: 408) | DLYGGDSI(SEQ ID NO: 429) |
| 20240903SBC1093-037 | DYNFQ(SEQ ID NO: 382) | TIGIGTDTYYATWAIG SEQ ID NO: 408) | DLYGGDSI(SEQ ID NO: 429) |
| 20240903SBC1093-220 | DYNFQ(SEQ ID NO: 382) | TIGIGTDTYYATWAIG SEQ ID NO: 408) | DLYGGDNI(SEQ ID NO: 430) |
| 20240903SBC1093-074 | NYYMN(SEQ ID NO: 383) | FINTGGSAYYASWAKG (SEQ ID NO: 409) | FAVVAGLNI(SEQ ID NO: 431) |
| 20240903SBC1093-075 | NYYMN(SEQ ID NO: 383) | FINTGGSAYYASWAKG (SEQ ID NO: 409) | FAVVAGLNI(SEQ ID NO: 431) |
| 20240903SBC1093-193 | SYYMN(SEQ ID NO: 384) | FIDTGGSAYFASWAKG (SEQ ID NO: 410) | FAVVAGLNI(SEQ ID NO: 431) |
| 20240903SBC1093-194 | SYYMN(SEQ ID NO: 384) | FIDTGGSAYFASWAK (SEQ ID NO: 410) | FAVVGGLNI(SEQ ID NO: 432) |
| 20240903SBC1093-099 | RYYMS(SEQ ID NO: 385) | SITTGGKGYYASWAKG (SEQ ID NO: 411) | WDYLTDFDI(SEQ ID NO: 433) |
| 20240929SBC1205-022 | RYVMH(SEQ ID NO: 386) | YINPYNHDTKYNEKFKG (SEQ ID NO: 412) | LDGYYAMDY(SEQ ID NO: 434) |
| 20241223SBC1205-061 | DYIML(SEQ ID NO: 387) | NINPYYGSTSYNLKFKG (SEQ ID NO: 413) | DGNEKYGRFAY(SEQ ID NO: 435) |
| 20241223SBC1205-063 | NYGMN(SEQ ID NO: 4) | WINTYTGEPTYVDDFKG (SEQ ID NO: 414) | YGDYYGNSYRGFDY (SEQ ID NO: 436) |
| 20241223SBC1205-119 | GYFMN(SEQ ID NO: 388) | RINHYNGDTFYNQKFKG (SEQ ID NO: 415) | AEIHYDYDDAMDY (SEQ ID NO: 437) |
| 20241223SBC1205-130 | NYGMN(SEQ ID NO: 4) | WINTYTGEPTYSDDFKG (SEQ ID NO: 416) | YGDYYGSSYRGFDY (SEQ ID NO: 438) |
| 20241223SBC1205-131 | NYGMN(SEQ ID NO: 4) | WINTYTGEPTYVDDFKG (SEQ ID NO: 414) | YGDYYGNSYRGFDY (SEQ ID NO: 436) |
| ANb1361-hGal-3-LP3R3 P2-69 | HYSIG(SEQ ID NO: 389) | CISTSDGSTYYADSVKG (SEQ ID NO: 417) | GKGSRCHGDLDA(SEQ ID NO: 439) |

TABLE 4

| Light chain CDR sequences | | | |
|---|---|---|---|
| Antibody ID | LCDR1 | LCDR2 | LCDR3 |
| 1104SBC1068-033 | RASESVDSYGNSFMH (SEQ ID NO: 169) | LASNLES (SEQ ID NO: 190) | QQNNEDPLT (SEQ ID NO: 211) |
| 1104SBC1068-335 | KSSQSLLDSDGKTYLN (SEQ ID NO: 170) | LVSKLDS (SEQ ID NO: 191) | WQGTHFPQT (SEQ ID NO: 212) |
| 1104SBC1068-365 | KSSQSLLDSDGKTYLN (SEQ ID NO: 171) | LVSKLDS (SEQ ID NO: 192) | WQATHFPQT (SEQ ID NO: 213) |
| 1104SBC1068-374 | RSSTGAVTTSNYAN (SEQ ID NO: 172) | GTSNRAP (SEQ ID NO: 193) | ALWYSTHYV (SEQ ID NO: 214) |
| SIF001 | RSSTGAVTTSNYAN (SEQ ID NO: 172) | GTSNRAP (SEQ ID NO: 193) | ALWYSTHYV (SEQ ID NO: 214) |

TABLE 4-continued

| Light chain CDR sequences | | | |
|---|---|---|---|
| Antibody ID | LCDR1 | LCDR2 | LCDR3 |
| 1104SBC1068-378 | RASQSISNNLH (SEQ ID NO: 173) | YASQSIS (SEQ ID NO: 194) | QQSNSWPLT (SEQ ID NO: 215) |
| 1220SBC1068-022 | RSSKSLLHNNGNTYLC (SEQ ID NO: 174) | RMSDLAS (SEQ ID NO: 195) | MQHLEYPYT (SEQ ID NO: 216) |
| 1220SBC1068-035 | KASQDVSTAVA (SEQ ID NO: 175) | SASYRYT (SEQ ID NO: 196) | QQHYTTPRT (SEQ ID NO: 217) |
| 1220SBC1068-041 | RSSQSLFNSTNQKNYLT (SEQ ID NO: 176) | WASSRES (SEQ ID NO: 197) | QNDYTSPFT (SEQ ID NO: 218) |
| SIF002 | RSSQSLFSSTNQKNYLT (SEQ ID NO: 369) | WASSRES (SEQ ID NO: 197) | QNDYTSPFT (SEQ ID NO: 218) |
| 1220SBC1068-056 | GSSKSLLHKNGNTYLC (SEQ ID NO: 177) | RMSNLAS (SEQ ID NO: 198) | MQHLEYPYT (SEQ ID NO: 219) |
| 1220SBC1068-058 | RSSKSLLHNNGNTYLC (SEQ ID NO: 178) | RMSNLAS (SEQ ID NO: 199) | MQHLEYPYT (SEQ ID NO: 220) |
| 1220SBC1068-063 | KSSQSLLSSINQKNYLT (SEQ ID NO: 179) | WATSRES (SEQ ID NO: 200) | HNDYSYPFT (SEQ ID NO: 221) |
| 1220SBC1068-097 | RSSQSLLNSTNQKNYLT (SEQ ID NO: 180) | WASTRES (SEQ ID NO: 201) | QNDYTSPFT (SEQ ID NO: 222) |
| 1220SBC1068-098 | RSSQSLLNSTNQKNYLT (SEQ ID NO: 181) | WASTKES (SEQ ID NO: 202) | QNDYTSPFT (SEQ ID NO: 223) |
| 1220SBC1068-099 | KSSQSLLNSGNQKIYLT (SEQ ID NO: 182) | WASIRES (SEQ ID NO: 203) | QNDYSSPFT (SEQ ID NO: 224) |
| 1220SBC1068-129 | KSSQSLLNSTNQKNYLT (SEQ ID NO: 183) | WASTRDS (SEQ ID NO: 204) | HNDYISPFT (SEQ ID NO: 225) |
| 1220SBC1068-164 | KSSQSLFNSGNQKNYLT (SEQ ID NO: 184) | WAYTRES (SEQ ID NO: 205) | HNDYTSPFT (SEQ ID NO: 226) |
| 1220SBC1068-186 | KASQDVSTAVA (SEQ ID NO: 185) | SASNRYT (SEQ ID NO: 206) | QQHYSTPRT (SEQ ID NO: 227) |
| 1220SBC1068-197 | KSSQSLLNSINQKNYLT (SEQ ID NO: 186) | WATFRES (SEQ ID NO: 207) | HNDYSYPFT (SEQ ID NO: 228) |
| 1220SBC1068-210 | RSSQSLLNSTNQKNYLT (SEQ ID NO: 187) | WASTRES (SEQ ID NO: 208) | QNDYTSPFT (SEQ ID NO: 229) |
| 1220SBC1068-274 | RSSQSLLNSTNQKNYLT (SEQ ID NO: 188) | WASTRES (SEQ ID NO: 209) | QNDYTSPFT (SEQ ID NO: 230) |
| 1220SBC1068-281 | RSNKSLLHSNGNAYLS (SEQ ID NO: 189) | RVSDLAS (SEQ ID NO: 210) | MQHLEFPYT (SEQ ID NO: 231) |
| 20240628SBC1080-002 | QASQSVGGNNDLA (SEQ ID NO: 440) | KASNLAS(SEQ ID NO: 463) | QGYYPGWIRA(SEQ ID NO: 481) |
| 20240628SBC1080-003 | QSSQSVGNNNDLA (SEQ ID NO: 441) | RTSNLAP(SEQ ID NO: 464) | LAYYPDWIRG(SEQ ID NO: 482) |
| 20240628SBC1080-004 | QSSQRVYNNNWLS(SEQ ID NO: 442) | EASKLAS(SEQ ID NO: 465) | LGTYDCSSADCGA (SEQ ID NO: 483) |
| 20240628SBC1080-005 | QASESIDNALA(SEQ ID NO: 443) | LASTLVP(SEQ ID NO: 466) | QQGYSISNVDNV(SEQ ID NO: 484) |
| 20240628SBC1080-006 | QSSQSVYNYNWLS (SEQ ID NO: 444) | SVSTLAS(SEQ ID NO: 467) | LGIYDCVSADCYG(SEQ ID NO: 485) |
| 20240628SBC1080-007 | QASQSVYSDNRLA (SEQ ID NO: 445) | RASTLAS(SEQ ID NO: 468) | LGEYSDSGEDT(SEQ ID NO: 486) |
| 20240628SBC1080-008 | QSSQSVYNNNLLA (SEQ ID NO: 446) | STSTLAS(SEQ ID NO: 469) | QAFYNDDMWV(SEQ ID NO: 487) |

TABLE 4-continued

| Light chain CDR sequences | | | |
|---|---|---|---|
| Antibody ID | LCDR1 | LCDR2 | LCDR3 |
| 20240628SBC1080-009 | QANETIGNALA(SEQ ID NO: 447) | LASTLAS(SEQ ID NO: 470) | QQGYSISNVDNV(SEQ ID NO: 484) |
| 20240903SBC1093-015 | QSSQSVGSNNRLS(SEQ ID NO: 448) | GASNLAS(SEQ ID NO: 471) | LGSYNCADGDCNA (SEQ ID NO: 488) |
| 20240903SBC1093-020 | QSSHSVGSNNRLS(SEQ ID NO: 449) | GAFNLAS(SEQ ID NO: 472) | LGSYNCADGDCNA (SEQ ID NO: 488) |
| 20240903SBC1093-021 | QSSQSVGNNKRLS(SEQ ID NO: 450) | GASNLAS(SEQ ID NO: 471) | LGSYNCADGDCNA (SEQ ID NO: 488) |
| 20240903SBC1093-025 | QSSQSVGSNNRLS(SEQ ID NO: 448) | GASNLAS(SEQ ID NO: 471) | LGSYNCADGDCNA (SEQ ID NO: 488) |
| 20240903SBC1093-030 | QSSQSVGSNNRLS(SEQ ID NO: 448) | GAFNLAS(SEQ ID NO: 472) | LGSYNCANGDCNA (SEQ ID NO: 489) |
| 20240903SBC1093-182 | QSSQSVGSNNRLS(SEQ ID NO: 448) | GAFNLAS(SEQ ID NO: 472) | LGSYNCADGDCNA (SEQ ID NO: 488) |
| 20240903SBC1093-183 | QSSQSVGSNNRLS(SEQ ID NO: 448) | GASNLAS(SEQ ID NO: 471) | LGSYNCADGDCNT (SEQ ID NO: 490) |
| 20240903SBC1093-184 | QSSQSVGSNNRLS(SEQ ID NO: 448) | GASNLAS(SEQ ID NO: 471) | LGSYNCAEGDCNA (SEQ ID NO: 491) |
| 20240903SBC1093-185 | QSSQSVGSNNRLS(SEQ ID NO: 448) | GAFNLAS(SEQ ID NO: 472) | LGSYNCANGDCNA (SEQ ID NO: 489) |
| 20240903SBC1093-230 | QSSQSVGSNNRLS(SEQ ID NO: 448) | GASNLAS(SEQ ID NO: 471) | ID LGSYNCADGDCNA (SEQ ID NO: 488) |
| 20240903SBC1093-033 | QSSQTIWDNNWLA (SEQ ID NO: 451) | LASKLAS(SEQ ID NO: 473) | AGTYSDNIYS(SEQ ID NO: 492) |
| 20240903SBC1093-034 | QSSQSIWDNNWLA (SEQ ID NO: 452) | LASKLAS(SEQ ID NO: 473) | AGTYSDNVYT(SEQ ID NO: 493) |
| 20240903SBC1093-035 | QSSQSIWDNNWLA (SEQ ID NO: 452) | LASKLAS(SEQ ID NO: 473) | AGTYSDNVYT(SEQ ID NO: 493) |
| 20240903SBC1093-044 | HSSHSIYDNNWLS(SEQ ID NO: 453) | LASTLAS(SEQ ID NO: 470) | AGTYSYNIYT(SEQ ID NO: 494) |
| 20240903SBC1093-054 | HSSHSIYDNNWLS(SEQ ID NO: 453) | LASTLAS(SEQ ID NO: 470) | AGTYSYNIYT(SEQ ID NO: 494) |
| 20240903SBC1093-055 | HSSHSIYDNNWLS(SEQ ID NO: 453) | SASTLAS(SEQ ID NO: 474) | AGTYSYNIYT(SEQ ID NO: 494) |
| 20240903SBC1093-056 | HSSHSIYDNNWLS(SEQ ID NO: 453) | LASTLAS(SEQ ID NO: 470) | AGTYSYNIYT(SEQ ID NO: 494) |
| 20240903SBC1093-057 | HSSHSIYDNNWLS(SEQ ID NO: 453) | LASTLAS(SEQ ID NO: 470) | AGTYTYNIYT(SEQ ID NO: 495) |
| 20240903SBC1093-059 | HSSHSIYDNNWLS(SEQ ID NO: 453) | LASTLAS(SEQ ID NO: 470) | AGTYSYNIYT(SEQ ID NO: 494) |
| 20240903SBC1093-219 | QSSQSIWDNNWLA (SEQ ID NO: 452) | LASTLAS(SEQ ID NO: 470) | AGTYSDNIYT(SEQ ID NO: 496) |
| 20240903SBC1093-228 | QSSQSIWDNNWLA (SEQ ID NO: 452) | LASKLAT(SEQ ID NO: 475) | AGTYSDNIYT(SEQ ID NO: 496) |
| 20240903SBC1093-023 | QSSESVWQNNRLS (SEQ ID NO: 454) | GASNLAS(SEQ ID NO: 471) | AGLKAWNDDDDG (SEQ ID NO: 497) |
| 20240903SBC1093-036 | QASQSVWQNNRLS (SEQ ID NO: 455) | TASTLAS(SEQ ID NO: 476) | AGLRAWNDDDDG (SEQ ID NO: 498) |
| 20240903SBC1093-037 | QSSESVWQNNRLS (SEQ ID NO: 454) | RASTLAS(SEQ ID NO: 468) | AGLKAWNDDDDG (SEQ ID NO: 497) |

TABLE 4-continued

| Light chain CDR sequences | | | |
|---|---|---|---|
| Antibody ID | LCDR1 | LCDR2 | LCDR3 |
| 20240903SBC1093-220 | QSSESVWQNNRLS (SEQ ID NO: 454) | QASKLAS(SEQ ID NO: 477) | AGLKAWNDDDDG (SEQ ID NO: 497) |
| 20240903SBC1093-093-074 | QSSQSVYNNNWLS (SEQ ID NO: 456) | SASTLAS(SEQ ID NO: 474) | AGDYSVGIYT(SEQ ID NO: 499) |
| 20240903SBC1093-075 | QSSQSVYNNNWLS (SEQ ID NO: 456) | YASTLAS(SEQ ID NO: 478) | AGDYSVGIYT(SEQ ID NO: 499) |
| 20240903SBC1093-193 | QSSESVYSDWLS(SEQ ID NO: 457) | SASTLAS(SEQ ID NO: 474) | AGDYSVGIYA(SEQ ID NO: 500) |
| 20240903SBC1093-194 | QSSQSVYSDWLS(SEQ ID NO: 458) | SASTLAS(SEQ ID NO: 474) | AGDYSVGIYA(SEQ ID NO: 500) |
| 20240903SBC1093-099 | QASESVYNNNFLS(SEQ ID NO: 459) | LASTLAS(SEQ ID NO: 470) | AGVKSDSTDGIA(SEQ ID NO: 501) |
| 20240929SBC1205-022 | SASQAISNYLN(SEQ ID NO: 460) | YTSSLYS(SEQ ID NO: 479) | QQYIKLPRT(SEQ ID NO: 502) |
| 20241223SBC1205-061 | KSSQSLLYSSNQKNYLA(SEQ ID NO: 461) | WASTRES(SEQ ID NO: 201) | QQYYSYPT(SEQ ID NO: 503) |
| 20241223SBC1205-063 | KASQDVGTVVA(SEQ ID NO: 462) | WASTRHT(SEQ ID NO: 480) | QQYSSYPLT(SEQ ID NO: 504) |
| 20241223SBC1205-119 | KSSQSLLYSSNQKNYLA(SEQ ID NO: 461) | WASTRES(SEQ ID NO: 201) | QQYYNYPLT(SEQ ID NO: 505) |
| 20241223SBC1205-130 | KASQDVGTVVA(SEQ ID NO: 462) | WASTRHT(SEQ ID NO: 480) | QQYSRYPLT(SEQ ID NO: 506) |
| 20241223SBC1205-131 | KASQDVGTVVA(SEQ ID NO: 462) | WASTRHT(SEQ ID NO: 480) | QQYSSFPLT(SEQ ID NO: 507) |

In some embodiments, the anti-GAL-3 antibody comprises a heavy chain variable ($V_H$) region further comprising a heavy chain framework 1 (HFR1), HFR2, HFR3, and HFR4 and a light chain variable ($V_L$) region comprising light chain FR 1 (LFR1), LFR2, LFR3, and LFR4. In some embodiments, the $V_H$ region comprises a HFR1 amino acid sequence at least 70%, at least 75%, at least 80%, at least 85%, at least 90%, or at least 95% identical to any one of SEQ ID NOS: 64-84, 337, and 341, a HFR2 amino acid sequence at least 70%, at least 75%, at least 80%, at least 85%, at least 90%, or at least 95% identical to any one of SEQ ID NOS: 85-105, 338, and 342, a HFR3 amino acid sequence at least 70%, at least 75%, at least 80%, at least 85%, at least 90%, or at least 95% identical to any one of SEQ ID NOS: 106-126, 339, and 343, and/or a HFR4 amino acid sequence at least 70%, at least 75%, at least 80%, at least 85%, at least 90%, or at least 95% identical to any one of SEQ ID NOS: 137-157, 340, and 344. In some embodiments, the $V_L$ region comprises a LFR1 amino acid sequence at least 70%, at least 75%, at least 80%, at least 85%, at least 90%, or at least 95% identical to any one of SEQ ID NOS: 232-252, 345, and 349, a LFR2 amino acid sequence at least 70%, at least 75%, at least 80%, at least 85%, at least 90%, or at least 95% identical to any one of SEQ ID NOS: 253-273, 346, and 350, a LFR3 amino acid sequence at least 70%, at least 75%, at least 80%, at least 85%, at least 90%, or at least 95% identical to any one of SEQ ID NOS: 274-294, 347, and 351, and/or a LFR4 amino acid sequence at least 70%, at least 75%, at least 80%, at least 85%, at least 90%, or at least 95% identical to any one of SEQ ID NOS: 295-315, 348, and 352. The exemplary heavy chain FR and light chain FR amino acid sequences are listed in Tables 5 and 6, respectively.

In some embodiments, the anti-GAL-3 antibody comprises all CDRs and FRs of an antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274, 1220SBC1068-281, SIF-001, and SIF-002. The $H_V$ CDR, $H_L$ CDR, $H_V$ FR, and $H_L$ FR amino acid sequences of the antibodies are listed in Tables 3-6, respectively.

TABLE 5

| Heavy chain framework sequences | | | | |
|---|---|---|---|---|
| Antibody ID | HFR1 | HFR2 | HFR3 | HFR4 |
| 1104SBC1068-033 | DVQLQESGPGLVKPS QSLSLTCTVTGYSIT (SEQ ID NO: 64) | WIRQFPGNKLE WMG (SEQ ID NO: 85) | RISITRDASKNQFFLQL NSVTTEDTATYYCAR (SEQ ID NO: 106) | WGQGTTLTV SS (SEQ ID NO: 127) |
| 1104SBC1068-335 | QIQLVQSGPELKKPG ETVKISCKASGYIFT (SEQ ID NO: 65) | WVKQAPGKGL KWMG (SEQ ID NO: 86) | RFVFSLETSASTAYLQI NNLKNEDMATYFCAR (SEQ ID NO: 107) | WGQGTTLTV SS (SEQ ID NO: 128) |
| 1104SBC1068-365 | QIQLVQSGPELKKPG ETVKISCKASGYTFT (SEQ ID NO: 66) | WVKQAPGKGL KWMG (SEQ ID NO: 87) | RFAFSLETSASTAYLQI NNLKNEDTATYFCGR (SEQ ID NO: 108) | WGQGTSVTV SS (SEQ ID NO: 129) |
| 1104SBC1068-374 | QIQLVQSGPELKKPG ETVKISCKASGYTFT (SEQ ID NO: 67) | WVKQAPGKGL KWMG (SEQ ID NO: 88) | RFAFSLETSASTAYLQI NNLKNEDMATYFCAR (SEQ ID NO: 109) | WGQGTSVTV SS (SEQ ID NO: 130) |
| 1104SBC1068-378 | QIQLVQSGPELKKPG ETVKISCKASGYTFT (SEQ ID NO: 68) | WVKQAPGKGL KWMG (SEQ ID NO: 89) | RFAFSLETSASTAYLQI NNLKNEDTATYFCAR (SEQ ID NO: 110) | WGQGTLVT VSA (SEQ ID NO: 131) |
| 1220SBC1068-022 | EVKLVESGGGLVQP GGSRKLSCAASGFTF S (SEQ ID NO: 69) | WFRQAPGKGP EWVA (SEQ ID NO: 90) | RFTISRENAKNTLFLEM SSLRSEDTAIYYCTR (SEQ ID NO: 111) | WGQGTSVTV SS (SEQ ID NO: 132) |
| 1220SBC1068-035 | EVQLQQSGPELVKPG ASMKISCKASGYAFT (SEQ ID NO: 70) | WVKQSHGKNL EWIG (SEQ ID NO: 91) | KATFTVDKSSSTAYME LLSLTSEDSGVYYCAR (SEQ ID NO: 112) | WGAGTTVT VSS (SEQ ID NO: 133) |
| 1220SBC1068-041 | EVKLLESGGGLVQPG GSLKLSCAASGFDFS (SEQ ID NO: 71) | WVRQAPGKGL EWIG (SEQ ID NO: 92) | NFIISRDNAKNALFLQ MSKVRSEDTALYYCTR (SEQ ID NO: 113) | WGQGTLVT VSA (SEQ ID NO: 134) |
| 1220SBC1068-056 | EVKLVESGGGLVQP GGSRKLSCAASGFTF S (SEQ ID NO: 72) | WFRQAPGKGP EWVA (SEQ ID NO: 93) | RFTISRENAKNTLYLE MSSLRSEDTAIYYCTR (SEQ ID NO: 114) | WGQGTSVTV SS (SEQ ID NO: 135) |
| 1220SBC1068-058 | EVKLVESGGGLVQP GGSRKLSCAASGFTF S (SEQ ID NO: 73) | WFRQAPGKGP EWVA (SEQ ID NO: 94) | RFTISRENAKNTLYLE MNSLRSEDTAIYYCTR (SEQ ID NO: 115) | WGQGTSVTV SS (SEQ ID NO: 136) |
| 1220SBC1068-063 | EVNLLESGGGLVQPG GSLKLSCEASGFDFS (SEQ ID NO: 74) | WVRQTPGEGL EWIG (SEQ ID NO: 95) | RFIISRDNAKNTLFLQM TKVTSDDSALYYCAR (SEQ ID NO: 116) | WGHGTLVT VSA (SEQ ID NO: 137) |
| 1220SBC1068-097 | EVKLLESGGGLVQPG GSLKLSCAASGFDFS (SEQ ID NO: 75) | WVRQAPGKGL EWIG (SEQ ID NO: 96) | NFIISRDNAKNALYLQ MSKVKSEDTALYYCTR (SEQ ID NO: 117) | WGQGTLVT VSA (SEQ ID NO: 138) |
| 1220SBC1068-098 | EVKLLESGGGLVQPG GSLKLSCAASGFDFS (SEQ ID NO: 76) | WVRQAPGKGL EWIG (SEQ ID NO: 97) | NFIISRDNAKNALYLQ MSKVKSEDTALYYCTR (SEQ ID NO: 118) | WGQGTLVT VSA (SEQ ID NO: 139) |
| 1220SBC1068-099 | EVKLLESGGGLVQPG GSLKLSCAASGFDFS (SEQ ID NO: 77) | WVRQAPGKGL EWIG (SEQ ID NO: 98) | KFIISRDNAKNTLYLQ MSKVSSEDTALYYCAR (SEQ ID NO: 119) | WGQGTLVT VSA (SEQ ID NO: 140) |
| 1220SBC1068-129 | EVKLLESGGDLVQPG GSLKLSCAASGFDFS (SEQ ID NO: 78) | WVRQAPGKGL EWIG (SEQ ID NO: 99) | KFIISRDNAKSSLYLQM SKVTSEDTALYYCAR (SEQ ID NO: 120) | WGQGTLVT VSA (SEQ ID NO: 141) |
| 1220SBC1068-164 | EVKLLESGGGLVQPG GSLKLSCAASGFDFS (SEQ ID NO: 79) | WVRQAPGKGL EWIG (SEQ ID NO: 100) | KFNISRDNAKNTLYLQ MSKVRSEDTALYYCA R (SEQ ID NO: 121) | WGQGTLVT VSE (SEQ ID NO: 142) |
| 1220SBC1068-186 | EVQLQQSGPELVKPG ASMKMSCKASGYSF T (SEQ ID NO: 80) | WVKQSHGKNL EWIG (SEQ ID NO: 101) | KATLTVDKSSSTAYME VFSLTSEDSGVYYCAR (SEQ ID NO: 122) | WGAGTTVT VSS (SEQ ID NO: 143) |
| 1220SBC1068-197 | EVNLLESGGGLVQPG GSLKLSCEASGFDFS (SEQ ID NO: 81) | WVRQTPGEGL EWIG (SEQ ID NO: 102) | KFFISRDNAKSTLFLQM TNVTSEDSALYYCAR (SEQ ID NO: 123) | WGHGTLVT VSA (SEQ ID NO: 144) |
| 1220SBC1068-210 | EVKLLESGGGLVQPG GSLKLSCAASGFDFS (SEQ ID NO: 82) | WVRQAPGKGL EWIG (SEQ ID NO: 103) | NFIISRDNAKNALYLQ MSKVRSEDTALYYCTR (SEQ ID NO: 124) | WGQGTLVT VSA (SEQ ID NO: 145) |

TABLE 5-continued

| Heavy chain framework sequences | | | | |
|---|---|---|---|---|
| Antibody ID | HFR1 | HFR2 | HFR3 | HFR4 |
| 1220SBC1068-274 | EVKLLESGGGLVQPG GSLKLSCAASGFDFS (SEQ ID NO: 83) | WVRQAPGKGL EWIG (SEQ ID NO: 104) | NFIISRDNAKNALYLQ MSKLRSEDTALYYCTR (SEQ ID NO: 125) | WGQGTLVT VSA (SEQ ID NO: 146) |
| 1220SBC1068-281 | EVKLVESGGGLVQS GGSRKLSCAASGFTF S (SEQ ID NO: 84) | WVRQAPGKGP EWVA (SEQ ID NO: 105) | RFTISRENAKNTLYLE MSSLRSEDTAVYYCTR (SEQ ID NO: 126) | WGQGTSVTV SS (SEQ ID NO: 147) |
| SIF001 | QVQLVQSGSELKKP GASVKVSCKASGYT FT (SEQ ID NO: 337) | WVRQAPGQGL EWMG (SEQ ID NO: 338) | RFVFSLDTSVSTAYLQI SSLKNEDMAVYFCAR (SEQ ID NO: 339) | WGQGTLVT VSS (SEQ ID NO: 340) |
| SIF002 | EVQLLESGGGLVQPG GSLRLSCAASGFTFS (SEQ ID NO: 341) | WVRQAPGKGL EWVS (SEQ ID NO: 342) | RFTISRDNSKNTLYLQ MNSLRAEDTAVYYCA K (SEQ ID NO: 343) | WGQGTLVT VSS (SEQ ID NO: 344) |

TABLE 6

| Light chain framework sequences | | | | |
|---|---|---|---|---|
| Antibody ID | LFR1 | LFR2 | LFR3 | LFR4 |
| 1104SBC1068-033 | NIVLTQSPASLAV SLGQRATISC (SEQ ID NO: 232) | WYQQKPGQPP KLLIY (SEQ ID NO: 253) | GVPARFSGSGSRTDFTL TIDPVEADDAATYYC (SEQ ID NO: 274) | FGAGTKLEL K (SEQ ID NO: 295) |
| 1104SBC1068-335 | DVVMTQTPLTLS VTIGQPASISC (SEQ ID NO: 233) | WLLQRPGQSPK RLIY (SEQ ID NO: 254) | GVPDRFTGSGSGTDFTL KISRVEAEDLGVYYC (SEQ ID NO: 275) | FGGGTKLEIK (SEQ ID NO: 296) |
| 1104SBC1068-365 | DVVMTQTPLTLS VTIGQPASISC (SEQ ID NO: 234) | WLLQRPGQSPK RLIY (SEQ ID NO: 255) | GVPDRFTGSGSGTDFTL KISRVEAEDLGVYYC (SEQ ID NO: 276) | FGGGTKLEIK (SEQ ID NO: 297) |
| 1104SBC1068-374 | QAVVTQESALTT SPGGTVILTC (SEQ ID NO: 235) | WVQEKPDHLFT GLIG (SEQ ID NO: 256) | GVPVRFSGSLIGDKAAL TITGAQTEDDAMYFC (SEQ ID NO: 277) | FGGGTKVTV L (SEQ ID NO: 298) |
| 1104SBC1068-378 | DIVLTQSPATLSV TPGDSVSLSC (SEQ ID NO: 236) | WYQQKSHESPR LLIK (SEQ ID NO: 257) | GIPSRFSGSGSGTDFTLSI NSVETEDFGMYFC (SEQ ID NO: 278) | FGAGTKLEL K (SEQ ID NO: 299) |
| 1220SBC1068-022 | DIVMTQAAPSVP VTPGESVSISC (SEQ ID NO: 237) | WFLQRPGQSPQ LLIY (SEQ ID NO: 258) | GVPDRFSGSGSGTAFTL RISRVEAEDVGVYYC (SEQ ID NO: 279) | FGGGTKLEIK (SEQ ID NO: 300) |
| 1220SBC1068-035 | DIVMTQSHKFMS TSVGDGVNITC (SEQ ID NO: 238) | WYQQKPGQSP RLLIY (SEQ ID NO: 259) | GVPDRFTGSGSGTDFTF TISSMQAEDLAVYYC (SEQ ID NO: 280) | FGGGTKLEIK (SEQ ID NO: 301) |
| 1220SBC1068-041 | DIVMTQSPSSLTV TAGEKVTMNC (SEQ ID NO: 239) | WYQQKPGQPP KLLIY (SEQ ID NO: 260) | GVPDRFTGSGSGTDFTL TISTVQTEDLAVYYC (SEQ ID NO: 281) | FGSGTRLEIK (SEQ ID NO: 302) |
| 1220SBC1068-056 | DIVMTQAAPSVP VTPGESVSISC (SEQ ID NO: 240) | WFLQRPGQSPQ LLIY (SEQ ID NO: 261) | GVPDRFSGSGSGTAFTL RISSVEAEDVGIYYC (SEQ ID NO: 282) | FGGGTKLEIK (SEQ ID NO: 303) |
| 1220SBC1068-058 | DIVMTQAAPSVP VTPGESVSISC (SEQ ID NO: 241) | WFLQRPGQSPQ LLIY (SEQ ID NO: 262) | GVPDRFSGSGSGTAFTL RISRVEAEDVGVYYC (SEQ ID NO: 283) | FGGGTKLEIK (SEQ ID NO: 304) |
| 1220SBC1068-063 | DIVMTQSPSSLTV TAGEKVTMSC (SEQ ID NO: 242) | WYQQKPGQPP KLLIY (SEQ ID NO: 263) | GVPDRFTGSGSGTDFTL TISSLQAEDLAVYYC (SEQ ID NO: 284) | FGSGTRLEIK (SEQ ID NO: 305) |
| 1220SBC1068-097 | DIVMTQSPSSLTV TAGEKVTMNC (SEQ ID NO: 243) | WYQQKPGQPP KLLIY (SEQ ID NO: 264) | GVPDRFTGSGSGTDFTL TINTVQAEDLAIYYC (SEQ ID NO: 285) | FGSGTKLEIK (SEQ ID NO: 306) |

TABLE 6-continued

Light chain framework sequences

| Antibody ID | LFR1 | LFR2 | LFR3 | LFR4 |
|---|---|---|---|---|
| 1220SBC1068-098 | DIVMTQSPSSLTV TAGEKVTMNC (SEQ ID NO: 244) | WYQQKPGQPP KLLIY (SEQ ID NO: 265) | GVPDRFTGSGSGTDFTL TINTVQAEDLAVYYC (SEQ ID NO: 286) | FGSGTKLEIK (SEQ ID NO: 307) |
| 1220SBC1068-099 | DIVMTQSPSSLTV TAGEKVTMSC (SEQ ID NO: 245) | WYQQKPGQPP KLLIY (SEQ ID NO: 266) | GVPDRFTGSGSGTDFTL TISSVQAEDLAVYYC (SEQ ID NO: 287) | FGSGTKLEIK (SEQ ID NO: 308) |
| 1220SBC1068-129 | DIVMTQSPSSLTV TAGKEVTMSC (SEQ ID NO: 246) | WYQQKPGQSP KLLIY (SEQ ID NO: 267) | GVPDRFTGSGSGTDFTL TISSVQAEDLAIYYC (SEQ ID NO: 288) | FGSGTKLEIK (SEQ ID NO: 309) |
| 1220SBC1068-164 | DIVMTQSPSSLTV TAGEKVTMSC (SEQ ID NO: 247) | WYQQKPGQPP KLLIY (SEQ ID NO: 268) | GVPDRFTGSGSGTDFTL TIHGVQAEDLAVYYC (SEQ ID NO: 289) | FGSGTKLEM K (SEQ ID NO: 310) |
| 1220SBC1068-186 | DIVMTQSHKFMS TSVGDRVSITC (SEQ ID NO: 248) | WYQQRPGQSP KLLIY (SEQ ID NO: 269) | GVPDRFTGSGSGTDFTF TISSMQAEDLAIYYC (SEQ ID NO: 290) | FGGGTKLEIK (SEQ ID NO: 311) |
| 1220SBC1068-197 | DIVMTQSPSSLTV TAGEKVTMSC (SEQ ID NO: 249) | WYQQKPGQPP KLLIY (SEQ ID NO: 270) | GVPDRFTGSGSGTDFTL TISGLQAEDLAVYYC (SEQ ID NO: 291) | FGSGTRLEIK (SEQ ID NO: 312) |
| 1220SBC1068-210 | DIVMTQSPSSLTV TAGEKVTMNC (SEQ ID NO: 250) | WYQQRPGQPP KLLIY (SEQ ID NO: 271) | GVPDRFTGSGSGTDFTL TISTVQAEDLAVYYC (SEQ ID NO: 292) | FGSGTKLEIK (SEQ ID NO: 313) |
| 1220SBC1068-274 | DIVMTQSPSSLTV TAGEKVTMNC (SEQ ID NO: 251) | WYQQKPGQPP KLLIY (SEQ ID NO: 272) | GVPDRFTGSGSGSDFTL TISTVQAEDLAVYYC (SEQ ID NO: 293) | FGSGTKLEIK (SEQ ID NO: 314) |
| 1220SBC1068-281 | DIVMTQAAPSVP VTPGESVSISC (SEQ ID NO: 252) | WFLQRPGQSPQ LLIY (SEQ ID NO: 273) | GVPDRFSGSGSGTAFTL RISRVEAEDVGIYYC (SEQ ID NO: 294) | FGGGTKLEIK (SEQ ID NO: 315) |
| SIF001 | EAVVTQEPSLTVS PGGTVTLTC (SEQ ID NO: 345) | WVQQKPGQAF TGLIG (SEQ ID NO: 346) | GTPARFSGSLLGDKAAL TLLGAQPEDEAEYFC (SEQ ID NO: 347) | FGGGTKLTV L (SEQ ID NO: 348) |
| SIF002 | DIVMTQSPDSLA VSLGERATMNC (SEQ ID NO: 349) | WYQQKPGQPP KLLIY (SEQ ID NO: 350) | GVPDRFSGSGSGTDFTL TISSLQAEDVAVYYC (SEQ ID NO: 351) | FGQGTRLEIK (SEQ ID NO: 352) |

In some embodiments, the anti-GAL-3 antibody comprises a heavy chain variable ($V_H$) region comprising a $V_H$ amino acid sequence at least 70%, at least 75%, at least 80%, at least 85%, at least 90%, or at least 95% identical to any one of SEQ ID NOS: 148-168, 353, and 355, and a $V_L$ region comprising a $V_L$ amino acid sequence at least 70%, at least 75%, at least 80%, at least 85%, at least 90%, or at least 95% identical to any one of SEQ ID NOS: 316-336, 354, and 356.

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 148, and a $V_L$ amino acid sequence at least 70%, at least 75%, at least 80%, at least 85%, at least 90%, or at least 95% identity to any one of SEQ ID NO: 316. In a particular embodiment, the anti-GAL-3 antibody comprises a $V_H$ amino acid sequence of SEQ ID NO: 148 and a $V_L$ amino acid sequence of SEQ ID NO: 316 (e.g., the antibody 1104SBC1068-033).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 149, and a $V_L$ amino acid sequence at least 70%, at least 75%, at least 80%, at least 85%, at least 90%, or at least 95% identity to any one of SEQ ID NO: 317. In a particular embodiment, the anti-GAL-3 antibody comprises a $V_H$ amino acid sequence of SEQ ID NO: 149 and a $V_L$ amino acid sequence of SEQ ID NO: 317 (e.g., the antibody 1104SBC1068-035).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 150, and a $V_L$ amino acid sequence at least 70%, at least 75%, at least 80%, at least 85%, at least 90%, or at least 95% identity to any one of SEQ ID NO: 318. In a particular embodiment, the anti-GAL-3 antibody comprises a $V_H$ amino acid sequence of SEQ ID NO: 150 and a $V_L$ amino acid sequence of SEQ ID NO: 318 (e.g., the antibody 1104SBC1068-065).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 151, and a $V_L$ amino acid sequence at least 70%, at least 75%, at least 80%, at least 85%, at least 90%, or at least 95% identity to any one of SEQ ID NO: 319. In a particular embodiment, the anti-GAL-3 antibody comprises a $V_H$ amino acid sequence of SEQ ID NO: 151 and a $V_L$ amino acid sequence of SEQ ID NO: 319 (e.g., the antibody 1104SBC1068-074).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 152, and a $V_L$ amino acid sequence at least 70%, at least 75%, at least 80%, at least 85%, at least 90%, or at least 95% identity to any one of SEQ ID NO: 320. In a particular embodiment, the anti-GAL-3 antibody comprises a $V_H$ amino acid sequence of SEQ ID NO: 152 and a $V_L$ amino acid sequence of SEQ ID NO: 320 (e.g., the antibody 1104SBC1068-078).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 153, and a $V_L$ amino acid sequence at least 70%, at least 75%, at least 80%, at least 85%, at least 90%, or at least 95% identity to any one of SEQ ID NO: 321. In a particular embodiment, the anti-GAL-3 antibody comprises a $V_H$ amino acid sequence of SEQ ID NO: 153 and a $V_L$ amino acid sequence of SEQ ID NO: 321 (e.g., the antibody 1220SBC1068-022).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 154, and a $V_L$ amino acid sequence at least 70%, at least 75%, at least 80%, at least 85%, at least 90%, or at least 95% identity to any one of SEQ ID NO: 322. In a particular embodiment, the anti-GAL-3 antibody comprises a $V_H$ amino acid sequence of SEQ ID NO: 154 and a $V_L$ amino acid sequence of SEQ ID NO: 322 (e.g., the antibody 1220SBC1068-035).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 155, and a $V_L$ amino acid sequence at least 70%, at least 75%, at least 80%, at least 85%, at least 90%, or at least 95% identity to any one of SEQ ID NO: 323. In a particular embodiment, the anti-GAL-3 antibody comprises a $V_H$ amino acid sequence of SEQ ID NO: 155 and a $V_L$ amino acid sequence of SEQ ID NO: 323 (e.g., the antibody 1220SBC1068-041).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 156, and a $V_L$ amino acid sequence at least 70%, at least 75%, at least 80%, at least 85%, at least 90%, or at least 95% identity to any one of SEQ ID NO: 324. In a particular embodiment, the anti-GAL-3 antibody comprises a $V_H$ amino acid sequence of SEQ ID NO: 156 and a $V_L$ amino acid sequence of SEQ ID NO: 324 (e.g., the antibody 1220SBC1068-056).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 157, and a $V_L$ amino acid sequence at least 70%, at least 75%, at least 80%, at least 85%, at least 90%, or at least 95% identity to any one of SEQ ID NO: 325. In a particular embodiment, the anti-GAL-3 antibody comprises a $V_H$ amino acid sequence of SEQ ID NO: 157 and a $V_L$ amino acid sequence of SEQ ID NO: 325 (e.g., the antibody 1220SBC1068-058).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 158, and a $V_L$ amino acid sequence at least 70%, at least 75%, at least 80%, at least 85%, at least 90%, or at least 95% identity to any one of SEQ ID NO: 326. In a particular embodiment, the anti-GAL-3 antibody comprises a $V_H$ amino acid sequence of SEQ ID NO: 158 and a $V_L$ amino acid sequence of SEQ ID NO: 326 (e.g., the antibody 1220SBC1068-063).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 159, and a $V_L$ amino acid sequence at least 70%, at least 75%, at least 80%, at least 85%, at least 90%, or at least 95% identity to any one of SEQ ID NO: 327. In a particular embodiment, the anti-GAL-3 antibody comprises a $V_H$ amino acid sequence of SEQ ID NO: 159 and a $V_L$ amino acid sequence of SEQ ID NO: 327 (e.g., the antibody 1220SBC1068-097).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 160, and a $V_L$ amino acid sequence at least 70%, at least 75%, at least 80%, at least 85%, at least 90%, or at least 95% identity to any one of SEQ ID NO: 328. In a particular embodiment, the anti-GAL-3 antibody comprises a $V_H$ amino acid sequence of SEQ ID NO: 160 and a $V_L$ amino acid sequence of SEQ ID NO: 328 (e.g., the antibody 1220SBC1068-098).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 161, and a $V_L$ amino acid sequence at least 70%, at least 75%, at least 80%, at least 85%, at least 90%, or at least 95% identity to any one of SEQ ID NO: 329. In a particular embodiment, the anti-GAL-3 antibody comprises a $V_H$ amino acid sequence of SEQ ID NO: 161 and a $V_L$ amino acid sequence of SEQ ID NO: 329 (e.g., the antibody 1220SBC1068-099).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 162, and a $V_L$ amino acid sequence at least 70%, at least 75%, at least 80%, at least 85%, at least 90%, or at least 95% identity to any one of SEQ ID NO: 330. In a particular embodiment, the anti-GAL-3 antibody comprises a $V_H$ amino acid sequence of SEQ ID NO: 162 and a $V_L$ amino acid sequence of SEQ ID NO: 330 (e.g., the antibody 1220SBC1068-129).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 163, and a $V_L$ amino acid sequence at least 70%, at least 75%, at least 80%, at least 85%, at least 90%, or at least 95% identity to any one of SEQ ID NO: 331. In a particular embodiment, the anti-GAL-3 antibody comprises a $V_H$ amino acid sequence of SEQ ID NO: 163 and a $V_L$ amino acid sequence of SEQ ID NO: 331 (e.g., the antibody 1220SBC1068-164).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 164, and a $V_L$ amino acid sequence at least 70%, at least 75%, at least 80%, at least 85%, at least 90%, or at least 95% identity to any one of SEQ ID NO: 332. In a particular embodiment, the anti-GAL-3 antibody comprises a $V_H$ amino acid sequence of SEQ ID NO: 164 and a $V_L$ amino acid sequence of SEQ ID NO: 332 (e.g., the antibody 1220SBC1068-186).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 165, and a $V_L$ amino acid sequence at least 70%, at least 75%, at least 80%, at least 85%, at least 90%, or at least 95% identity to any one of SEQ ID NO: 333. In a particular embodiment, the anti-GAL-3 antibody comprises a $V_H$ amino acid sequence of SEQ ID NO: 165 and a $V_L$ amino acid sequence of SEQ ID NO: 333 (e.g., the antibody 1220SBC1068-197).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 166, and a $V_L$ amino acid sequence at least 70%, at least 75%, at least 80%, at least 85%, at least 90%, or at least 95% identity to any one of SEQ ID NO: 334. In a particular embodiment, the anti-GAL-3 antibody comprises a $V_H$ amino acid sequence of SEQ ID NO: 166 and a $V_L$ amino acid sequence of SEQ ID NO: 334 (e.g., the antibody 1220SBC1068-210).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 167, and a $V_L$ amino acid sequence at least 70%, at least 75%, at least 80%, at least 85%, at least 90%, or at least 95% identity to any one of SEQ ID NO: 335. In a particular embodiment, the anti-GAL-3 antibody comprises a $V_H$ amino acid sequence of SEQ ID NO: 167 and a $V_L$ amino acid sequence of SEQ ID NO: 335 (e.g., the antibody 1220SBC1068-274).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 168, and a $V_L$ amino acid sequence at least 70%, at least 75%, at least 80%, at least 85%, at least 90%, or at least 95% identity to any one of SEQ ID NO: 336. In a particular embodiment, the anti-GAL-3 antibody comprises a $V_H$ amino acid sequence of SEQ ID NO: 168 and a $V_L$ amino acid sequence of SEQ ID NO: 336 (e.g., the antibody 1220SBC1068-281).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 353, and a $V_L$ amino acid sequence at least 70%, at least 75%, at least 80%, at least 85%, at least 90%, or at least 95% identity to any one of SEQ ID NO: 354. In a particular embodiment, the anti-GAL-3 antibody comprises a $V_H$ amino acid sequence of SEQ ID NO: 353 and a $V_L$ amino acid sequence of SEQ ID NO: 354 (e.g., the antibody SIF-001).

In some embodiments, the anti-GAL-3 antibody comprises a $V_H$ amino acid sequence at least 70%, at least 75%, at least 80%, at least 85%, at least 90%, or at least 95% identity to any one of SEQ ID NO: 355, and a $V_L$ amino acid sequence at least 70%, at least 75%, at least 80%, at least 85%, at least 90%, or at least 95% identity to any one of SEQ ID NO: 356. In a particular embodiment, the anti-GAL-3 antibody comprises a $V_H$ amino acid sequence of SEQ ID NO: 355 and a $V_L$ amino acid sequence of SEQ ID NO: 356 (e.g., the antibody SIF-002).

In some embodiments, the anti-GAL-3 antibody comprises a $H_V$ and $H_L$ amino acid sequence of an antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274, 1220SBC1068-281, SIF-001, and SIF002. The $H_V$ and $H_L$ amino acid sequence of the antibodies are listed in Table 7.

TABLE 7

Heavy and Light variable region sequences

| Antibody ID | HV | LV |
|---|---|---|
| 1104SBC1068-033 | DVQLQESGPGLVKPSQSLSLTCTVTGYSITS DYAWNWIRQFPGNKLEWMGYISYSGSTSY NPSLKSRISITRDASKNQFFLQLNSVTTEDT ATYYCAREGGRGGTEGYYFDYWGQGTTLT VSS (SEQ ID NO: 148) | NIVLTQSPASLAVSLGQRATISCRASES VDSYGNSFMHWYQQKPGQPPKLLIYL ASNLESGVPARFSGSGSRTDFTLTIDPV EADDAATYYCQQNNEDPLTFGAGTKL ELK (SEQ ID NO: 316) |
| 1104SBC1068-335 | QIQLVQSGPELKKPGETVKISCKASGYIFTN YGMNWVKQAPGKGLKWMGWINTYSGEPT YVDDFKGRFVFSLETSASTAYLQINNLKNE DMATYFCARGTVVGFDYWGQGTTLTVSS (SEQ ID NO: 149) | DVVMTQTPLTLSVTIGQPASISCKSSQS LLDSDGKTYLNWLLQRPGQSPKRLIYL VSKLDSGVPDRFTGSGSGTDFTLKISRV EAEDLGVYYCWQGTHFPQTFGGGTKL EIK (SEQ ID NO: 317) |
| 1104SBC1068-365 | QIQLVQSGPELKKPGETVKISCKASGYTFTN YGMNWVKQAPGKGLKWMGWINTNTGEPT YSEEFKGRFAFSLETSASTAYLQINNLKNED TATYFCGRSSYYAMDYWGQGTSVTVSS (SEQ ID NO: 150) | DVVMTQTPLTLSVTIGQPASISCKSSQS LLDSDGKTYLNWLLQRPGQSPKRLIYL VSKLDSGVPDRFTGSGSGTDFTLKISRV EAEDLGVYYCWQATHFPQTFGGGTKL EIK (SEQ ID NO: 318) |
| 1104SBC1068-374 | QIQLVQSGPELKKPGETVKISCKASGYTFTN YGMNWVKQAPGKGLKWMGWINTYTGEPT YADDFKGRFAFSLETSASTAYLQINNLKNE DMATYFCARYAMDYWGQGTSVTVSS (SEQ ID NO: 151) | QAVVTQESALTTSPGGTVILTCRSSTGA VTTSNYANWVQEKPDHLFTGLIGGTSN RAPGVPVRESGSLIGDKAALTITGAQTE DDAMYFCALWYSTHYVFGGGTKVTVL (SEQ ID NO: 319) |
| 1104SBC1068-378 | QIQLVQSGPELKKPGETVKISCKASGYTFTN YGMNWVKQAPGKGLKWMGWINTYTGEPT YADDFKGRFAFSLETSASTAYLQINNLKNE DTATYFCARWDDYDGFAYWGQGTLVTVS A (SEQ ID NO: 152) | DIVLTQSPATLSVTPGDSVSLSCRASQSI SNNLHWYQQKSHESPRLLIKYASQSISG IPSRFSGSGSGTDFTLSINSVETEDFGMY FCQQSNSWPLTFGAGTKLELK (SEQ ID NO: 320) |

TABLE 7-continued

Heavy and Light variable region sequences

| Antibody ID | HV | LV |
|---|---|---|
| 1220SBC1068-022 | EVKLVESGGGLVQPGGSRKLSCAASGFTFS DYGMAWFRQAPGKGPEWVAFISNLAYSVY YADTVTGRFTISRENAKNTLFLEMSSLRSED TAIYYCTRDRGLRESMDYWGQGTSVTVSS (SEQ ID NO: 153) | DIVMTQAAPSVPVTPGESVSISCRSSKS LLHNNGNTYLCWFLQRPGQSPQLLIYR MSDLASGVPDRFSGSGSGTAFTLRISRV EAEDVGVYYCMQHLEYPYTFGGGTKL EIK (SEQ ID NO: 321) |
| 1220SBC1068-035 | EVQLQQSGPELVKPGASMKISCKASGYAFT GYTMNWVKQSHGKNLEWIGLISPYSGGTN YNQRFKGKATFTVDKSSSTAYMELLSLTSE DSGVYYCARSGFITTGVPTNFDVWGAGTT VTVSS (SEQ ID NO: 154) | DIVMTQSHKFMSTSVGDGVNITCKASQ DVSTAVAWYQQKPGQSPRLLIYSASYR YTGVPDRFTGSGSGTDFTFTISSMQAED LAVYYCQQHYTTPRTFGGGTKLEIK (SEQ ID NO: 322) |
| 1220SBC1068-041 | EVKLLESGGGLVQPGGSLKLSCAASGFDFS RFWMSWVRQAPGKGLEWIGEISPDSNTIDL TPSLKDNFIISRDNAKNALFLQMSKVRSEDT ALYYCTRPYYGYYWGQGTLVTVSA (SEQ ID NO: 155) | DIVMTQSPSSLTVTAGEKVTMNCRSSQ SLFNSTNQKNYLTWYQQKPGQPPKLLI YWASSRESGVPDRFTGSGSGTDFTLTIS TVQTEDLAVYYCONDYTSPFTFGSGTR LEIK (SEQ ID NO: 323) |
| 1220SBC1068-056 | EVKLVESGGGLVQPGGSRKLSCAASGFTFS DYGMAWFRQAPGKGPEWVAFISNLAYSVY YADTVTGRFTISRENAKNTLYLEMSSLRSE DTAIYYCTRDRGLRESMDYWGQGTSVTVS S (SEQ ID NO: 156) | DIVMTQAAPSVPVTPGESVSISCGSSKS LLHKNGNTYLCWFLQRPGQSPQLLIYR MSNLASGVPDRFSGSGSGTAFTLRISSV EAEDVGIYYCMQHLEYPYTFGGGTKLE IK (SEQ ID NO: 324) |
| 1220SBC1068-058 | EVKLVESGGGLVQPGGSRKLSCAASGFTFS DYGMAWFRQAPGKGPEWVAFISNLAYSVY YADTVTGRFTISRENAKNTLYLEMNSLRSE DTAIYYCTRDRGLRETMDYWGQGTSVTVS S (SEQ ID NO: 157) | DIVMTQAAPSVPVTPGESVSISCRSSKS LLHNNGNTYLCWFLQRPGQSPQLLIYR MSNLASGVPDRFSGSGSGTAFTLRISRV EAEDVGVYYCMQHLEYPYTFGGGTKL EIK (SEQ ID NO: 325) |
| 1220SBC1068-063 | EVNLLESGGGLVQPGGSLKLSCEASGFDFS RFWMSWVRQTPGEGLEWIGEISPNSSTIHQ TPSLKDRFIISRDNAKNTLFLQMTKVTSDDS ALYYCARPYYGYYWGHGTLVTVSA (SEQ ID NO: 158) | DIVMTQSPSSLTVTAGEKVTMSCKSSQ SLLSSINQKNYLTWYQQKPGQPPKLLIY WATSRESGVPDRFTGSGSGTDFTLTISS LQAEDLAVYYCHNDYSYPFTFGSGTRL EIK (SEQ ID NO: 326) |
| 1220SBC1068-097 | EVKLLESGGGLVQPGGSLKLSCAASGFDFS RYWMSWVRQAPGKGLEWIGEINPDSSTIDL TPSLKDNFIISRDNAKNALYLQMSKVKSED TALYYCTRPYHGYYWGQGTLVTVSA (SEQ ID NO: 159) | DIVMTQSPSSLTVTAGEKVTMNCRSSQ SLLNSTNQKNYLTWYQQKPGQPPKLLI YWASTRESGVPDRFTGSGSGTDFTLTIN TVQAEDLAIYYCONDYTSPFTFGSGTK LEIK (SEQ ID NO: 327) |
| 1220SBC1068-098 | EVKLLESGGGLVQPGGSLKLSCAASGFDFS RYWMSWVRQAPGKGLEWIGEISPDSSTIDL TPSLKDNFIISRDNAKNALYLQMSKVKSED TALYYCTRPYHGYYWGQGTLVTVSA (SEQ ID NO: 160) | DIVMTQSPSSLTVTAGEKVTMNCRSSQ SLLNSTNQKNYLTWYQQKPGQPPKLLI YWASTKESGVPDRFTGSGSGTDFTLTIN TVQAEDLAVYYCONDYTSPFTFGSGTK LEIK (SEQ ID NO: 328) |
| 1220SBC1068-099 | EVKLLESGGGLVQPGGSLKLSCAASGFDFS RYWMTWVRQAPGKGLEWIGEINPHSSTITY TPSLKDKFIISRDNAKNTLYLQMSKVSSEDT ALYYCARPYYGYYWGQGTLVTVSA (SEQ ID NO: 161) | DIVMTQSPSSLTVTAGEKVTMSCKSSQ SLLNSGNQKIYLTWYQQKPGQPPKLLI YWASIRESGVPDRFTGSGSGTDFTLTIS SVQAEDLAVYYCONDYSSPFTFGSGTK LEIK (SEQ ID NO: 329) |
| 1220SBC1068-129 | EVKLLESGGDLVQPGGSLKLSCAASGFDFS RFWMSWVRQAPGKGLEWIGEINPDSSTITY TPSLKDKFIISRDNAKSSLYLQMSKVTSEDT ALYYCARPYYGYYWGQGTLVTVSA (SEQ ID NO: 162) | DIVMTQSPSSLTVTAGKEVTMSCKSSQ SLLNSTNQKNYLTWYQQKPGQSPKLLI YWASTRDSGVPDRFTGSGSGTDFTLTIS SVQAEDLAIYYCHNDYISPFTFGSGTKL EIK (SEQ ID NO: 330) |
| 1220SBC1068-164 | EVKLLESGGGLVQPGGSLKLSCAASGFDFS RYWMSWVRQAPGKGLEWIGEISPDSSTINY TASLKDKFNISRDNAKNTLYLQMSKVRSED TALYYCARPYYGYYWGQGTLVTVSE (SEQ ID NO: 163) | DIVMTQSPSSLTVTAGEKVTMSCKSSQ SLFNSGNQKNYLTWYQQKPGQPPKLLI YWAYTRESGVPDRFTGSGSGTDFTLTI HGVQAEDLAVYYCHNDYTSPFTFGSGT KLEMK (SEQ ID NO: 331) |
| 1220SBC1068-186 | EVQLQQSGPELVKPGASMKMSCKASGYSF TGYTMNWVKQSHGKNLEWIGLISPYSGGT NYNQKFKGKATLTVDKSSSTAYMEVESLTS EDSGVYYCARSGFITTGVATNFDVWGAGT TVTVSS (SEQ ID NO: 164) | DIVMTQSHKFMSTSVGDRVSITCKASQ DVSTAVAWYQQRPGQSPKLLIYSASNR YTGVPDRFTGSGSGTDFTFTISSMQAED LAIYYCQQHYSTPRTFGGGTKLEIK (SEQ ID NO: 332) |
| 1220SBC1068-197 | EVNLLESGGGLVQPGGSLKLSCEASGFDFS RFWMSWVRQTPGEGLEWIGEISPNSSTIHQ | DIVMTQSPSSLTVTAGEKVTMSCKSSQ SLLNSINQKNYLTWYQQKPGQPPKLLI |

TABLE 7-continued

Heavy and Light variable region sequences

| Antibody ID | HV | LV |
|---|---|---|
| | TPSLKDKFFISRDNAKSTLFLQMTNVTSEDS ALYYCARPYYGYYWGHGTLVTVSA (SEQ ID NO: 165) | YWATFRESGVPDRFTGSGSGTDFTLTIS GLQAEDLAVYYCHNDYSYPFTFGSGTR LEIK (SEQ ID NO: 333) |
| 1220SBC1068-210 | EVKLLESGGGLVQPGGSLKLSCAASGFDFS RYWMSWVRQAPGKGLEWIGEINPDSSTIDL TPSLKDNFIISRDNAKNALYLQMSKVRSED TALYYCTRPYYGYYWGQGTLVTVSA (SEQ ID NO: 166) | DIVMTQSPSSLTVTAGEKVTMNCRSSQ SLLNSTNQKNYLTWYQQRPGQPPKLLI YWASTRESGVPDRFTGSGSGTDFTLTIS TVQAEDLAVYYCONDYTSPFTFGSGTK LEIK (SEQ ID NO: 334) |
| 1220SBC1068-274 | EVKLLESGGGLVQPGGSLKLSCAASGFDFS RYWMSWVRQAPGKGLEWIGEISPDSNTIDL TPSLKDNFIISRDNAKNALYLQMSKLRSEDT ALYYCTRPYYGYYWGQGTLVTVSA (SEQ ID NO: 167) | DIVMTQSPSSLTVTAGEKVTMNCRSSQ SLLNSTNQKNYLTWYQQKPGQPPKLLI YWASTRESGVPDRFTGSGSGSDFTLTIS TVQAEDLAVYYCONDYTSPFTFGSGTK LEIK (SEQ ID NO: 335) |
| 1220SBC1068-281 | EVKLVESGGGLVQSGGSRKLSCAASGFTFS DFGMAWVRQAPGKGPEWVAFISNLAYNIY YSDTVTGRFTISRENAKNTLYLEMSSLRSED TAVYYCTRDRGLRETMDYWGQGTSVTVSS (SEQ ID NO: 168) | DIVMTQAAPSVPVTPGESVSISCRSNKS LLHSNGNAYLSWFLQRPGQSPQLLIYR VSDLASGVPDRFSGSGSGTAFTLRISRV EAEDVGIYYCMQHLEFPYTFGGGTKLE IK (SEQ ID NO: 336) |
| SIF001 | QVQLVQSGSELKKPGASVKVSCKASGYTFT NYGMNWVRQAPGQGLEWMGWINTYTGEP TYADDFKGRFVFSLDTSVSTAYLQISSLKNE DMAVYFCARYAMDYWGQGTLVTVSS (SEQ ID NO: 353) | EAVVTQEPSLTVSPGGTVTLTCRSSTGA VTTSNYANWVQQKPGQAFTGLIGGTS NRAPGTPARFSGSLLGDKAALTLLGAQ PEDEAEYFCALWYSTHYVFGGGTKLT VL (SEQ ID NO: 354) |
| SIF002 | EVQLLESGGGLVQPGGSLRLSCAASGFTFS RFWMSWVRQAPGKGLEWVSEISPDSNTIDL TPSLKDRFTISRDNSKNTLYLQMNSLRAED TAVYYCAKPYYGYYWGQGTLVTVSS (SEQ ID NO: 355) | DIVMTQSPDSLAVSLGERATMNCRSSQ SLFSSTNQKNYLTWYQQKPGQPPKLLI YWASSRESGVPDRFSGSGSGTDFTLTIS SLQAEDVAVYYCONDYTSPFTFGQGTR LEIK (SEQ ID NO: 356) |

In some embodiments, the anti-GAL-3 antibody comprises a heavy chain variable region comprising a HCDR1 comprising a sequence NYGMN (SEQ ID NO: 4), or a variant HCDR1 in which 1, 2, or 3 amino acids are substituted relative to the sequence; a HCDR2 comprising a sequence WINTYTGEPTYADDFKG (SEQ ID NO: 25), or a variant HCDR2 in which 1, 2, or 3 amino acids are substituted relative to the sequence; and a HCDR3 comprising a sequence YAMDY (SEQ ID NO: 46), or a variant HCDR3 in which 1, 2, or 3 amino acids are substituted relative to the sequence. In some embodiments, the anti-GAL-3 antibody further comprises a light chain variable region comprising a LCDR1 comprising a sequence RSSTGAVTTSNYAN (SEQ ID NO: 172), or a variant LCDR1 in which 1 amino acid is substituted relative to the sequence; a LCDR2 comprising a sequence GTSNRAP (SEQ ID NO: 193), or variant LCDR2 in which 1 amino acid is substituted relative to the sequence; and a LCDR3 comprising a sequence ALWYSTHYV (SEQ ID NO: 214), or a variant LCDR3 in which 1 amino acid is substituted relative to the sequence.

In some embodiments, the antibody or the binding fragment thereof that binds to Galectin-3 comprises a heavy chain variable region comprising a HCDR1 comprising a sequence RFWMS (SEQ ID NO: 8), or a variant HCDR1 in which 1, 2, or 3 amino acids are substituted relative to the sequence; a HCDR2 comprising a sequence EISPDSNTIDLTPSLKD (SEQ ID NO: 29), or a variant HCDR2 in which 1, 2, or 3 amino acids are substituted relative to the sequence; and a HCDR3 comprising a sequence PYYGYY (SEQ ID NO: 50), or a variant HCDR3 in which 1, 2, or 3 amino acids are substituted relative to the sequence. In some embodiments, the anti-GAL-3 antibody further comprises a light chain variable region comprising a LCDR1 comprising a sequence RSSQSLFNSTNQKNYLT (SEQ ID NO: 176) or RSSQSLFSSTNQKNYLT (SEQ ID NO: 369), or a variant LCDR1 in which 1 amino acid is substituted relative to the sequence; a LCDR2 comprising a sequence WASSRES (SEQ ID NO: 197), or variant LCDR2 in which 1 amino acid is substituted relative to the sequence; and a LCDR3 comprising a sequence QNDYTSPFT (SEQ ID NO: 218), or a variant LCDR3 in which I amino acid is substituted relative to the sequence.

In some embodiments, the antibody or the binding fragment thereof that binds to Galectin-3 comprises a HCDR1 comprising a sequence of $NX_2GMN$ (SEQ ID NO:357), wherein $X_2$ is Y, W, or F, wherein the HCDR1 has zero or one aa substitution in rest of the residues relative to the HCDR1 sequence, a HCDR2 comprising a sequence of $X_1IX_3TYTGEPTYADDFKG$ (SEQ ID NO: 358), Where $X_1$ is W, Y, or F, and wherein $X_3$ is N or Q, wherein the HCDR2 has zero, one, two, three, or four aa substitutions in rest of the residues relative to the HCDR2 sequence, a HCDR3 comprising a sequence of YAMDY (SEQ ID NO:359), wherein the HCDR3 has zero, one, or two aa substitutions relative to the HCDR3 sequence, a LCDR1 comprising a sequence of $RSSTGAVTTSNX_{12}AN$ (SEQ ID NO:360), wherein $X_{12}$ is Y, W, or F, wherein the LCDR1 has zero, one, two, three, or four aa substitutions in the rest of the residues relative to the LCDR1 sequence, a LCDR2 comprising a sequence of GTSNRAP (SEQ ID NO: 361), wherein the LCDR2 has zero, one, two, or three aa substitutions in the rest of the residues relative to the LCDR2 sequence, and a LCDR3 comprising a sequence of $ALX_3YSTHX_8V$ (SEQ ID NO: 362), wherein $X_3$ is Y, W, or F, wherein $X_8$ is Y, W, or F, wherein the LCDR3 has zero, one, two aa substitutions in the rest of the residues relative to the LCDR3 sequence.

In some embodiments, the antibody or the binding fragment thereof that binds to Galectin-3, wherein the antibody comprises: a HCDR1 comprising a sequence of $NX_2GMN$ (SEQ ID NO: 357), wherein $X_2$ is Y, W, or F, a HCDR2 comprising a sequence of $X_1IX_3TYTGEPTYADDFKG$ (SEQ ID NO:358), Where $X_1$ is W, Y, or F, and wherein $X_3$ is N or Q, a HCDR3 comprising a sequence of YAMDY (SEQ ID NO:359), a LCDR1 comprising a sequence of $RSSTGAVTTSNX_{12}AN$ (SEQ ID NO:360), wherein $X_{12}$ is Y, W, or F, a LCDR2 comprising a sequence of GTSNRAP (SEQ ID NO: 361), and a LCDR3 comprising a sequence of $ALX_3YSTHX_8V$ (SEQ ID NO: 362), wherein $X_3$ is Y, W, or F, wherein $X_8$ is Y, W, or F; wherein the HCDR1 has zero or one aa substitution in rest of the residues relative to the HCDR1 sequence, the HCDR2 has zero, one, two, three, or four aa substitutions in rest of the residues relative to the HCDR2 sequence, the HCDR3 has zero, one, or two aa substitutions relative to the HCDR3 sequence, the LCDR1 has zero, one, two, three, or four aa substitutions in the rest of the residues relative to the LCDR1 sequence, the LCDR2 has zero, one, two, or three aa substitutions in the rest of the residues relative to the LCDR2 sequence, or the LCDR3 has zero, one, two aa substitutions in the rest of the residues relative to the LCDR3 sequence.

In some embodiments, the antibody or the binding fragment thereof that binds to Galectin-3, wherein the antibody comprises: a HCDR1 comprising a sequence of RFX 3 MS (SEQ ID NO: 363), wherein $X_3$ is Y, W, or F, and wherein the HCDR1 has zero, one, two aa substitutions in the rest of the residues relative to the HCDR1 sequence, a HCDR2 comprising $X_1ISPDSNTIDLTPSLKD$ (SEQ ID NO: 364), wherein $X_1$ is E or D, and wherein the HCDR2 has zero, one, two, three, or four aa substitutions in the rest of the residues relative to the HCDR2 sequence, a HCDR3 comprising $PYYGX_5Y$ (SEQ ID NO: 365), wherein $X_5$ is Y, W, or F, wherein the HCDR3 has zero, one, two aa substitutions in the rest of the residues relative to the HCDR3 sequence, a LCDR1 comprising $RSSQSLFSSTNQKNX_{15}LT$ (SEQ ID NO: 366), wherein $X_{15}$ is Y, W, or F, wherein the LCDR1 has zero, one, two, three, or four aa substitutions in the rest of the residues relative to the LCDR1 sequence, a LCDR2 comprising WASSRES (SEQ ID NO: 367), wherein the LCDR2 has zero, one, two, or three aa substitutions relative to the LCDR2 sequence, and a LCDR3 comprising QNDYTSPFT (SEQ ID NO: 368), wherein the LCDR3 has zero, one, two, three, or four aa substitutions in the rest of the residues relative to the LCDR3 sequence.

In some embodiments, the antibody or the binding fragment thereof that binds to Galectin-3, wherein the antibody comprises: a HCDR1 comprising a sequence of RFX 3 MS (SEQ ID NO: 363), wherein $X_3$ is Y, W, or F, a HCDR2 comprising $X_1ISPDSNTIDLTPSLKD$ (SEQ ID NO: 364), wherein $X_1$ is E or D, a HCDR3 comprising $PYYGX_5Y$ (SEQ ID NO: 365), wherein $X_5$ is Y, W, or F, a LCDR1 comprising $RSSQSLFSSTNQKNX_{15}LT$ (SEQ ID NO: 366), wherein $X_{15}$ is Y, W, or F, a LCDR2 comprising WASSRES (SEQ ID NO: 367), and a LCDR3 comprising QNDYTSPFT (SEQ ID NO: 368); and wherein the HCDR1 has zero, one, two aa substitutions in the rest of the residues relative to the HCDR1 sequence, the HCDR2 has zero, one, two, three, or four aa substitutions in the rest of the residues relative to the HCDR2 sequence, the HCDR3 has zero, one, two aa substitutions in the rest of the residues relative to the HCDR3 sequence, the LCDR1 has zero, one, two, three, or four aa substitutions in the rest of the residues relative to the LCDR1 sequence, the LCDR2 has zero, one, two, or three aa substitutions relative to the LCDR2 sequence, or the LCDR3 has zero, one, two, three, or four aa substitutions in the rest of the residues relative to the LCDR3 sequence.

In some embodiments, the antibody or the binding fragment thereof that binds to Galectin-3, wherein the antibody comprises a HCDR1 comprising a sequence of NYGMN (SEQ ID NO: 4), a HCDR2 comprising a sequence of WINTYTGEPTYADDFKG (SEQ ID NO: 25), a HCDR3 comprising a sequence of YAMDY (SEQ ID NO: 46), a LCDR1 comprising a sequence of RSSTGAVTTSNYAN (SEQ ID NO: 172), a LCDR2 comprising a sequence of GTSNRAP (SEQ ID NO: 193), and a LCDR3 comprising a sequence of ALWYSTHYV (SEQ ID NO: 214). In some embodiments, the antibody comprises a $V_H$ region comprising a sequence of SEQ ID NO: 353, and a $V_L$ region comprising a sequence of SEQ ID NO: 354.

In some embodiments, the antibody or the binding fragment thereof that binds to Galectin-3, wherein the antibody comprises a HCDR1 comprising a sequence of RFWMS (SEQ ID NO: 8), a HCDR2 comprising a sequence of EISPDSNTIDLTPSLKD (SEQ ID NO: 29), a HCDR3 comprising a sequence of PYYGYY (SEQ ID NO: 50), a LCDR1 comprising a sequence of RSSQSLFNSTNQKNYLT (SEQ ID NO: 176) or RSSQSLFSSTNQKNYLT (SEQ ID NO: 369), a LCDR2 comprising a sequence of WASSRES (SEQ ID NO: 197), and a LCDR3 comprising a sequence of QNDYTSPFT (SEQ ID NO: 218). In some embodiments, the antibody comprises a $V_H$ region comprising a sequence of SEQ ID NO: 355, and a $V_L$ region comprising a sequence of SEQ ID NO: 356.

In some embodiments, an anti-GAL-3 antibody disclosed herein comprises i) a $V_H$ amino acid sequence and a $V_L$ amino acid sequence listed in Table 7, or ii) a $V_H$ amino acid sequence with at least 70%, at least 80%, at least 85%, at least 90%, at least 95% identity to the $V_H$ amino acid sequence in Table 7 and a $V_L$ amino acid sequence with at least 70% identity to the $V_L$ amino acid sequence in Table 7, wherein variations as compared to the $V_H$ amino acid sequence or the $V_L$ amino acid sequence in Table 7 are in the framework regions only.

In some embodiments, an anti-GAL-3 antibody disclosed herein comprises all three heavy chain CDRs of an antibody in Table 3, and the antibody comprises heavy chain framework regions having at least 70%, at least 80%, at least 85%, at least 90%, at least 95% sequence identity to the combined heavy chain framework regions in the same antibody in Table 3. In some embodiments, at least one of the antibodies comprises all three light chain CDRs of an antibody in Table 4, and the antibody comprises light chain framework regions having at least 70%, at least 80%, at least 85%, at least 90%, at least 95% sequence identity to the combined light chain framework regions of the same antibody in Table 4.

The present disclosure also provides an antibody competes for binding to GAL-3 with any one of the antibodies described herein. In some embodiments, the antibody is capable of competing for binding to GAL-3 with an antibody from a community cluster listed in Table 10. In some embodiments, the antibody competes for binding to GAL-3 with antibody 1104SBC1068-033. In some embodiments, the antibody competes for binding to GAL-3 with any one of the antibodies in community cluster 2, including 1220SBC1068-186, 1220SBC1068-205, 1220SBC1068-022, 1220SBC1068-058, 1220SBC1068-056, 20241223SBC1205-119, and 1104SBC1068-160. In some embodiments, the antibody competes for binding to GAL-3 with any one of the antibodies in community cluster 3, including 20240628SBC1080-009, 20240628SBC1080-002, 1104SBC1068-374, 20240929SBC1205-022, 1104SBC1068-335, 20040628SBC1080-006, 20240628SBC1080-008, 1104SBC1068-378, 1104SBC1068-365, ANb1361-G119-5M-LP2R2-58-higg4P, and 20240628SBC1080-007. In some embodiments, the antibody competes for binding to GAL-3 with an antibody in community cluster 4, including the antibody 1220SBC1068-035. In some embodiments, the antibody competes for binding to GAL-3 with any one of the antibodies in community cluster 5, including 1220SBC1068-098, 1220SBC1068-210, 1220SBC1068-041, 1220SBC1068-063, 1220SBC1068-274, 1220SBC1068-129, 1220SBC1068-099, 1220SBC1068-164, and 1220SBC1068-197. In some embodiments, the antibody competes for binding to GAL-3 with an antibody in community cluster 6, including the antibody 1220SBC1068-097. In some embodiments, the antibody competes for binding to GAL-3 with an antibody in community cluster 7, including the antibody 20240628SBC1080-003. In some embodiments, the antibody competes for binding to GAL-3 with the antibody 20240628SBC1080-004. In some embodiments, the antibody competes for binding to GAL-3 with an antibody in community cluster 8, including the antibody 1104SBC1068-033. In some embodiments, the antibody competes for binding to GAL-3 with any one of the antibodies, in community cluster 9, including 20240903SBC1093-015, 20240903SBC1093-020, 20240903SBC1093-023, 20240903SBC1093-030, 20240628SBC1080-005, 20240903SBC1093-183, 20240903SBC1093-220, 20240903SBC1093-230, 20240903SBC1093-185, 20240903SBC1093-021, 20240903SBC1093-037, 20240903SBC1093-036, 20240903SBC1093-099, 20240903SBC1093-025, 20240903SBC1093-182, and 20240903SBC1093-184. In some embodiments, the antibody competes for binding to GAL-3 with an antibody in community cluster 10, including the antibody 20240903SBC1093-033. In some embodiments, the antibody competes for binding to GAL-3 with an antibody in community cluster 11, including the antibody 20240903SBC1093-034. In some embodiments, the antibody competes for binding to GAL-3 with any one of the antibodies, in community cluster 12, including 20240903SBC1093-228, 20240903SBC1093-074, 20240903SBC1093-193, 20240903SBC1093-044, 20240903SBC1093-059, 20240903SBC1093-056, 20240903SBC1093-057, 20240903SBC1093-219, 20240903SBC1093-194, and 20240903SBC1093-035. In some embodiments, the antibody competes for binding to GAL-3 with an antibody in community cluster 13, including antibody 20240903SBC1093-055. In some embodiments, the antibody competes for binding to GAL-3 with an antibody in community cluster 14, including the antibody 20240903SBC1093-075. In some embodiments, the antibody competes for binding to GAL-3 with an antibody in community cluster 15, including the antibody 20241223SBC1205-061. In some embodiments, the antibody competes for binding to GAL-3 with an antibody in community cluster 16, including the antibody 20241223SBC1205-063. In some embodiments, the antibody competes for binding to GAL-3 with an antibody in community cluster 17, including the antibody 20241223SBC1205-130. In some embodiments, the antibody competes for binding to GAL-3 with an antibody in community cluster 18, including the antibody 20241223SBC1205-131.

Based on the differential binding profiles, it is predicted that combinations of the antibodies from the different community clusters described above (for example, any combination of 2 antibodies between Community cluster 1 & Bin 2 would have an improved beneficial therapeutic profile as compared to the therapeutic profile of the individual antibodies. Thus, in some embodiments, the method provides a combination of two or more antibodies from two or more different community clusters for use to treat patients in need. The two or more antibodies may be administered sequentially or simultaneously, for example, as an antibody cocktail.

Generation of Antibodies

The anti-GAL-3 antibodies can be produced using vectors and recombinant methodology well known in the art (see, e.g., Sambrook & Russell, Molecular Cloning: A Laboratory Manual, Cold Spring Harbor Laboratory Press; Ausubel, Current Protocols in Molecular Biology). Reagents, cloning vectors, and kits for genetic manipulation are available from commercial vendors.

Accordingly, in a further aspect of the disclosure, provided herein are isolated nucleic acids encoding a $V_H$ and/or $V_L$ region, or fragment thereof, of any of the GAL-3 antibodies as described herein; vectors comprising such nucleic acids and host cells into which the nucleic acids are introduced that are used to replicate the antibody-encoding nucleic acids and/or to express the antibodies. Such nucleic acids may encode an amino acid sequence containing the $V_L$ and/or an amino acid sequence containing the $V_H$ of the GAL-3 antibody (e.g., the light and/or heavy chains of the antibody).

The present disclosure further provides a polypeptide comprising a $V_H$ sequence and/or a $V_L$ amino acid sequence of the anti-GAL-3 antibody described herein. In some embodiments, the polypeptide comprises a heavy chain variable ($V_H$) region comprising a $V_H$ amino acid sequence at least 70%, at least 75%, at least 80%, at least 85%, at least 90%, or at least 95% identical to any one of SEQ ID NOS: 148-168, 353, and 355. In some embodiments, the polypeptide comprises a $V_L$ region comprising a $V_L$ amino acid sequence at least 70%, at least 75%, at least 80%, at least 85%, at least 90%, or at least 95% identical to any one of SEQ ID NOS: 316-336, 354, and 356. In some embodiments, the polypeptide comprises a $V_H$ amino acid sequence at least 70%, at least 75%, at least 80%, at least 85%, at least 90%, or at least 95% identical to any one of SEQ ID NOS: 148-168, 353, and 355, and a $V_L$ amino acid sequence at least 70%, at least 75%, at least 80%, at least 85%, at least 90%, or at least 95% identical to any one of SEQ ID NOS: 316-336, 354, and 356.

In some embodiments, the polypeptide comprising a $V_H$ sequence selected from the group consisting of SEQ ID NOS: 148-168, 353, and 355. In some embodiments, the polypeptide comprising a $V_L$ sequence selected from the group consisting of SEQ ID NOS: 316-336, 354, and 356. In some embodiments, the polypeptide comprising a $V_H$ sequence selected from the group consisting of SEQ ID NOS: 148-168, 353, and 355, and a $V_L$ sequence selected from the group consisting of SEQ ID NOS: 316-336, 354, and 356.

In some embodiments, the polypeptide comprising the $V_H$ sequence and/or the $V_L$ amino acid sequence of the anti-GAL-3 antibody selected from the group consisting of 1104SBC1068-033, 1104SBC1068-335, 1104SBC1068-365, 1104SBC1068-374, 1104SBC1068-378, 1220SBC1068-022, 1220SBC1068-035, 1220SBC1068-041, 1220SBC1068-056, 1220SBC1068-058, 1220SBC1068-063, 1220SBC1068-097, 1220SBC1068-098, 1220SBC1068-099, 1220SBC1068-129, 1220SBC1068-164, 1220SBC1068-186, 1220SBC1068-197, 1220SBC1068-210, 1220SBC1068-274, 1220SBC1068-281, SIF-001, and SIF-002.

The present disclosure further provides a polynucleotide encoding the polypeptide described herein. In some embodiments, the polynucleotide comprising one or more expression cassettes encoding the polypeptide. In some embodiments, the polynucleotide comprising one expression cassettes encoding both $V_H$ and $V_L$ amino acid sequences of the antibody. Optionally the $V_H$ and $V_L$ amino acid sequences are linked through a linker. In some embodiments, the polynucleotide comprising one expression cassettes encoding a $V_H$ amino acid sequence of the antibody and the other expression cassettes encoding a $V_L$ amino acid sequence of the antibody. In some embodiments, the expression cassette comprising a promoter operably linked to a nucleic acid encoding the $V_H$ and/or $V_L$ amino acid sequences of the antibody.

The present disclosure further provides an expression vector comprising the polynucleotide(s) described herein and a host cell which the polynucleotide(s) are introduced into for antibody expression. In some embodiments, the host cell contains (1) a vector containing a polynucleotide that encodes the $V_L$ amino acid sequence and a polynucleotide that encodes the $V_H$ amino acid sequence, or (2) a first vector containing a polynucleotide that encodes the $V_L$ amino acid sequence and a second vector containing a polynucleotide that encodes the $V_H$ amino acid sequence.

The present disclosure further provides a method of making an anti-GAL-3 antibody as described herein. In some embodiments, the method includes culturing a host cell as described in the preceding paragraph under conditions suitable for expression of the antibody. In some embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected may vary according to the host cell intended to be used, useful cloning vectors generally can self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mp18, mp19, pBR322, pMB9, ColE1 plasmids, pCR1, RP4, phage DNAs, and shuttle vectors. These and many other cloning vectors are available from commercial vendors.

Expression vectors generally are replicable polynucleotide constructs that contain a nucleic acid of the present disclosure. The expression vector can be replicable in the host cells either as episomes or as an integral part of the chromosomal DNA. Suitable expression vectors include but are not limited to plasmids and viral vectors, including adenoviruses, adeno-associated viruses, retroviruses, and any other vector.

Suitable host cells for expressing an anti-GAL-3 antibody as described herein include both prokaryotic and eukaryotic cells. For example, an anti-GAL-3 antibody may be produced in bacteria when glycosylation and Fc effector function are not needed. After expression, the antibody may be isolated from the bacterial cell paste in a soluble fraction and can be further purified. Alternatively, the host cell may be a eukaryotic host cell, including eukaryotic microorganisms, such as filamentous fungi or yeast, including fungi and yeast strains whose glycosylation pathways have been "humanized," resulting in the production of an antibody with a partially or fully human glycosylation pattern, vertebrate, invertebrate, and plant cells. Examples of invertebrate cells include insect cells. Numerous baculoviral strains have been identified which may be used in conjunction with insect cells. Plant cell cultures can also be utilized as host cells.

In some embodiments, vertebrate host cells are used for producing an anti-GAL-3 antibody of the present disclosure. For example, mammalian cell lines such as a monkey kidney CV1 line transformed by SV40 (COS-7); human embryonic kidney line (293 or 293 cells as described, e.g., in Graham et al., *J. Gen Virol.* 36:59,1977; baby hamster kidney cells (BHK); mouse sertoli cells (TM4 cells as described, e.g., in Mather, *Biol. Reprod.* 23:243-251, 1980 monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68, 1982; MRC 5 cells; and FS4 cells may be used to express an anti-GAL-3 antibody antibodies. Other useful mammalian host cell lines include Chinese hamster ovary (CHO) cells, including DHFR-CHO cells (Urlaub et al., *Proc. Natl. Acad. Sci. USA* 77:4216, 1980); and myeloma cell lines such as Y0, NS0 and Sp2/0. Host cells of the present disclosure also include, without limitation, isolated cells, in vitro cultured cells, and ex vivo cultured cells. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268, 2003.

In some embodiments, an anti-GAL-3 antibody of the present invention is produced by a CHO cell line, e.g., the CHO-K1 cell line. One or more expression plasmids can be introduced that encode heavy and light chain sequences. For example, in one embodiment, an expression plasmid encoding a heavy chain disclosed herein, and an expression plasmid encoding a light chain disclosed herein are transfected into host cells. The expression plasmids can be introduced as linearized plasmids at a ratio of 1:1 in the CHO-K1 host cell line using reagents such as Freestyle Max reagent. Fluorescence-activated cell sorting (FACS) coupled with single cell imaging can be used as a cloning method to obtain a production cell line.

A host cell transfected with an expression vector encoding an anti-GAL-3 antibody of the present disclosure, or fragment thereof, can be cultured under appropriate conditions to allow expression of the polypeptide to occur. The polypeptides may be secreted and isolated from a mixture of cells and medium containing the polypeptides. Alternatively, the polypeptide may be retained in the cytoplasm or in a membrane fraction and the cells harvested, lysed, and the polypeptide isolated using a desired method.

In some embodiments, an anti-GAL-3 antibody of the present disclosure can be produced by in vitro synthesis (see, e.g., Sutro Biopharma biochemical protein synthesis platform).

The present disclosure further provides a kit that comprises the antibody, the polypeptide, the polynucleotide, the expression vector, and/or the cell described herein.

Compositions

In one aspect, the present disclosure provides a composition comprising the antibody described herein. For examples, the composition comprises an anti-GAL-3 antibody comprising a heavy chain variable ($V_H$) region comprising a HCDR1 amino acid sequence at least 70% identical to any one of SEQ ID NOS: 1-21 and 481-507, a HCDR2 amino acid sequence at least 70% identical to any one of SEQ ID NOS: 22-42 and 390-417, and/or a HCDR3 amino acid sequence at least 70% identical to any one of SEQ ID NOS: 43-63 and 418-439, and/or a light chain variable ($V_L$) region comprising: a LCDR1 amino acid sequence at least 70% identical to any one of SEQ ID NOS: 169-189 and 440-462, a LCDR2 amino acid sequence at least 70% identical to any one of SEQ ID NOS: 190-210 and 463-480, and/or a LCDR3 amino acid sequence at least 70% identical to any one of SEQ ID NOS: 211-231 and 481-507. The compositions can additionally contain other therapeutic agents that are suitable for treating or preventing a given disorder.

In another aspect, the present disclosure provides a composition comprising the immunoconjugate described herein, wherein the immunoconjugate comprises an anti-anti-GAL-3 antibody conjugated or linked to therapeutic, imaging/detectable moieties, or enzymes.

In another aspect, the present disclosure provides a pharmaceutical composition. In some embodiments, the pharmaceutical composition comprises any of the compositions described herein and a pharmaceutically acceptable carrier. For example, the pharmaceutical composition may comprise an anti-GAL-3 antibody comprising a heavy chain variable ($V_H$) region comprising a HCDR1 amino acid sequence at least 70% identical to any one of SEQ ID NOS: 1-21 and 481-507, a HCDR2 amino acid sequence at least 70% identical to any one of SEQ ID NOS: 22-42 and 390-417, and/or a HCDR3 amino acid sequence at least 70% identical to any one of SEQ ID NOS: 43-63 and 418-439, and/or a light chain variable ($V_L$) region comprising: a LCDR1 amino acid sequence at least 70% identical to any one of SEQ ID NOS: 169-189 and 440-462, a LCDR2 amino acid sequence at least 70% identical to any one of SEQ ID NOS: 190-210 and 463-480, and/or a LCDR3 amino acid sequence at least 70% identical to any one of SEQ ID NOS: 211-231 and 481-507. The pharmaceutically acceptable carrier can enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition as described herein can be administered by a variety of methods known in the art. The route and/or mode of administration vary depending upon the desired results. In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohol such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions described herein can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions. Applicable methods for formulating the compositions and determining appropriate dosing and scheduling can be found, for example, in *Remington: The Science and Practice of Pharmacy,* 21st Ed., University of the Sciences in Philadelphia, Eds., Lippincott Williams & Wilkins (2005); and in *Martindale: The Complete Drug Reference, Sweetman,* 2005, London: Pharmaceutical Press., and in Martindale, *Martindale: The Extra Pharmacopoeia,* 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose is employed in the pharmaceutical compositions described herein. The compositions can be formulated into pharmaceutically acceptable dosage forms. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for case of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Method of Treatment

In one aspect, the present disclosure provides a method for preventing or treating epilepsy and/or a neurological disorder in a subject in need thereof, the method comprising administering to the subject an antibody comprising a means for binding to Galectin-3. In some embodiments, the Galectin-3 is human Galectin-3. In some embodiments, the method comprising administering to the subject an anti-GAL-3 antibody, wherein the antibody binds to GAL-3 in the subject thereby preventing or treating epilepsy and/or a neurological disorder. In some embodiments, the neurological disorder is Alzheimer's disease (AD) or Parkinson's disease (PD). In some embodiments, the antibody is administered in combination with an additional therapeutic agent.

In certain embodiments, an antibody described herein is administered to the subject in combination with one or more additional therapeutic agents used to treat epilepsy and/or a neurological disorder, or the side effects or associated symptoms thereof. In certain embodiments, the method comprises administering to a subject a therapeutically effective amount of an antibody as disclosed herein, or a pharmaceutical composition comprising the antibody, in combination with a therapeutically effective amount of one or more additional therapeutic agents. In one embodiment, a method for treating epilepsy and/or a neurological disorder in a subject, the method comprising administering to the subject a therapeutically effective amount of an antibody as disclosed herein, or a pharmaceutical composition comprising the antibody, in combination with a therapeutically effective amount of one or more additional therapeutic agents.

In some embodiments, the antibody or pharmaceutical composition is administered to the subject in combination with one or more additional therapeutic agents that are effective at preventing or treating epilepsy and/or a neurological disorder. In some embodiments, the one or more additional therapeutic agents comprise another anti-Gal-3 antibody that does not compete with the antibody or pharmaceutical composition for binding to Gal-3. In some embodiments, the co-administration includes two or more anti-Gal-3 antibodies disclosed herein, with each antibody selected from a different community cluster listed in Table 10. For example, the antibodies may be selected from any two or more community clusters, including community 1 (Com 1), Com 2, Com 3, Com 4, Com 5, Com 6, Com 7, Com 8, Com 9, Com 10, Com 11, Com 12, Com 13, Com 14, Com 15, Com 16, Com 17, and Com 18 in Table 10. Since each antibody is selected from a different community cluster and binds to a distinct Gal-3 epitope, they do not compete with one another.

Diseases

The anti-GAL-3 antibodies disclosed herein can be used to prevent or treat epilepsy or neurological disorders. In some embodiments, the neurological disorder is Alzheimer's disease (AD) or Parkinson's disease (PD).

Epilepsy and Drug-Resistant Epilepsy

In some embodiments, the anti-GAL-3 antibodies disclosed herein can be used to prevent or treat Epilepsy. Epilepsy is a neurological disorder characterized by recurrent unprovoked seizures. It affects approximately 1% of the global population and presents a significant burden of disease worldwide. For about 30-40% of patients, seizures cannot be effectively managed with current drug therapies, leading to a condition known as drug-resistant epilepsy (DRE). Surgical interventions offer relief to some patients, but a substantial number continue to experience seizures even after surgery.

Epileptogenesis is associated with an increased and persistent inflammatory state in the microenvironment of neural tissues, which can lead to the production of cytokines by glial cells and neurons. The anti-Gal-3 antibodies disclosed herein, by inhibiting Gal-3 activity or expression, can mitigate neuroinflammatory responses, potentially alleviating the pathological processes that contribute to epilepsy development and drug resistance. In some embodiments, the anti-Gal-3 antibodies can be used to treat drug-resistant epilepsy.

Parkinson's Disease

In some embodiments, the anti-GAL-3 antibodies disclosed herein can be used to prevent or treat Parkinson's disease (PD). Parkinson's disease (PD) is the second most prevalent neurodegenerative disease in the world. It is characterized by intense neurodegeneration in the basal ganglia area leading to severe and progressive motor impairment. The presence of Lewy bodies (LBs), described as neuronal intracytoplasmic deposits of α-synuclein (αSYN), is the second hallmark of the disease. While dopaminergic neurons from the substantia nigra (SN) are frequently the most affected cells, neurodegeneration and LB formation commonly appear in other central and enteric nervous system locations even years before than in the SN.

Disease modifying therapies are being developed that work either through targeting αSYN, inflammation, metabolism, vasculature and/or neuroplasticity. Galectin-3 (GAL3) is associated with LB formation and toxicity. As such, an anti-GAL-3 antibody disclosed herein can be used for therapeutical treatment to prevent or slow down PD progression.

Alzheimer's Disease

In some embodiments, the anti-GAL-3 antibodies disclosed herein can be used to prevent or treat Alzheimer's disease (AD). Alzheimer's disease (AD) is a chronic progressive neurodegenerative disorder that is the leading cause of dementia among older adults. There are two major pathological hallmark proteins associated with toxic changes in the brain that may lead to AD: AB and tau. The disease is characterized by accumulation of extracellular amyloid plaques, intracellular neurofibrillary tangles, and extensive synaptic loss leading to progressive cognitive impairment and eventually dementia. Abnormal tau (hyperphosphorylated tau) accumulates to form neurofibrillary tangles, while Aβ plaques accumulate both extracellular and intracellular. Amyloid plaques and hyperphosphorylated tau in the brain are therefore the major hallmarks of AD.

Gal-3 is highly upregulated in the brains of AD patients. As such, an anti-GAL-3 antibody disclosed herein can be used for therapeutical treatment to prevent or slow down AD progression. In some embodiments, the anti-GAL-3 antibody disclosed herein enhances Aβ oligomerization. In some embodiments, the anti-GAL-3 antibody disclosed herein reduces and/or degrades the formation of neurotoxic conformational oligomers, such as $A\beta_{42}$ oligomers. In some embodiments, the anti-GAL-3 antibody disclosed herein reduces neuroinflammation and/or AD-related pathology in a subject. In some embodiments, the anti-GAL-3 antibody disclosed herein enhances cognitive memory function in a subject.

In particular embodiments, the method for preventing or treating epilepsy and/or a neurological disorder in a subject, comprises administering to the subject an effective amount of the pharmaceutical composition comprising an antibody which comprises a heavy chain variable ($V_H$) region comprising a HCDR1 amino acid sequence at least 70% identical to any one of SEQ ID NOS: 1-21 and 481-507, a HCDR2 amino acid sequence at least 70% identical to any one of SEQ ID NOS: 22-42 and 390-417, and/or a HCDR3 amino acid sequence at least 70% identical to any one of SEQ ID NOS: 43-63 and 418-439, and/or a light chain variable ($V_L$) region comprising: a LCDR1 amino acid sequence at least 70% identical to any one of SEQ ID NOS: 169-189 and 440-462, a LCDR2 amino acid sequence at least 70% identical to any one of SEQ ID NOS: 190-210 and 463-480, and/or a LCDR3 amino acid sequence at least 70% identical to any one of SEQ ID NOS: 211-231 and 481-507. In some embodiments, the pharmaceutical composition further comprises one or more therapeutic agent(s), wherein the therapeutic agent(s) can be either conjugated to the antibody or in a separate form apart from the antibody.

In another aspect, the disclosure additionally provides methods of identifying subjects who are candidates for treatment with an anti-GAL-3 antibody. Thus, in one embodiment, the disclosure provides a method of identifying a subject who can benefit from treatment with the anti-GAL-3 antibody disclosed herein. In one embodiment, the subject has epilepsy and/or a neurological disorder that overexpresses Galectin-3. Binding of the antibody to Galectin-3 can be measured using any assay, such as immunohistochemistry or flow cytometry. In some embodiments, binding of the antibody to at least 0.2%, 0.5%, or 1%, or at least 5% or 10%, or at least 20%, 30%, or 50%, of Galectin-3 in a sample may be used as a selection criterion for determining a patient to be treated with the anti-GAL-3 antibody as described herein.

In one aspect, methods of the disclosure comprise administering an anti-GAL-3 antibody disclosed herein, or a variant thereof, as a pharmaceutical composition to a patient in a therapeutically effective amount using a dosing regimen suitable for treatment of the epilepsy, the neurological disorder or the cancer. The composition can be formulated for use in a variety of drug delivery systems. One or more physiologically acceptable excipients or carriers can also be included in the compositions for proper formulation. Suitable formulations for use in the present invention are found, e.g., in Remington: The Science and Practice of Pharmacy, 21$^{st}$ Edition, Philadelphia, PA. Lippincott Williams & Wilkins, 2005.

The anti-GAL-3 antibody is provided in a solution suitable for administration to the patient, such as a sterile isotonic aqueous solution for injection. The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

Administration

The pharmaceutical compositions are administered to a patient in an amount sufficient to cure or at least partially arrest the disease or symptoms of the disease and its complications. An amount adequate to accomplish this is defined as a "therapeutically effective dose." A therapeutically effective dose is determined by monitoring a patient's response to therapy. Typical benchmarks indicative of a therapeutically effective dose includes the amelioration of symptoms of the disease in the patient. Amounts effective for this use will depend upon the severity of the disease and the general state of the patient's health, including other factors such as age, weight, gender, administration route, and the like Single or multiple administrations of the antibody may be administered depending on the dosage and frequency as required and tolerated by the patient. In any event, the methods provide a sufficient quantity of anti-GAL-3 antibody to effectively treat the patient.

An anti-GAL-3 antibody or the antibody immunoconjugate (e.g., an anti-GAL-3 antibody-drug conjugate) can be administered by any suitable means, including, for example, parenteral, intrapulmonary, and intranasal, administration, as well as local administration, such as intratumor administration. Parenteral infusions include intramuscular, intravenous, intraarterial, intraperitoneal, or subcutaneous administration. In some embodiments, the antibody may be administered by insufflation. In an illustrative embodiment, the antibody or the antibody immunoconjugate (e.g., an anti-GAL-3 antibody-drug conjugate) may be stored at 10 mg/ml in sterile isotonic aqueous saline solution for injection at 4° C. and is diluted in either 100 ml or 200 ml 0.9% sodium chloride for injection prior to administration to the patient. In some embodiments, the antibody or the antibody immunoconjugate (e.g., an anti-GAL-3 antibody-drug conjugate) is administered by intravenous infusion over the course of 1 or 2 hours at a dose of between 0.01 and 100 mg/kg per the subject's body weight. In some embodiments, the antibody or the antibody immunoconjugate (e.g., an anti-GAL-3 antibody-drug conjugate) is administered at a dose range between 0.01-1 mg/kg, between 1-10 mg/kg, between $10^{-50}$ mg/kg, or between 50-100 mg/kg per the subject's body weight. In some embodiments, the antibody or the antibody immunoconjugate (e.g., an anti-GAL-3 antibody-drug conjugate) is administered at a dose of about 10, 20, 30, 40, 50, 60, 70 mg/kg or a dose in a range defined by any two of the aforementioned values per the subject's body weight. In some embodiments, the antibody or the antibody immunoconjugate (e.g., an anti-GAL-3 antibody-drug conjugate) is administered at a dose of about 10, 20, 40, and 70 mg/kg or a dose in a range defined by any two of the aforementioned values per the subject's body weight. In other embodiments, the antibody or the antibody immunoconjugate (e.g., an anti-GAL-3 antibody-drug conjugate) is administered by intravenous infusion over a period of between 15 minutes and 2 hours. In still other embodiments, the administration procedure is via subcutaneous bolus injection.

The dose of antibody is chosen to provide effective therapy for the patient and is in the range of less than 0.01 mg/kg body weight to about 100 mg/kg body weight or in the range 1 mg-8 g per patient. Preferably the dose is in the range 0.1-50 mg/kg or approximately 50 mg-5000 mg/patient. The dose may be repeated at an appropriate frequency which may be in the range once per day to once every three months, or every six months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months or once every 6 months. In other embodiments, the antibody is administered approximately once per month.

In some embodiments, the antibody is administered more than once, such as two, three, four, or more times. In some embodiments, each administration is at least 7 days apart. In some embodiments, each administration is at least 14 days apart. In some embodiments, each administration is at least four weeks apart.

In an illustrative embodiment, the antibody may be stored at 10 mg/ml or 20 mg/ml in a sterile isotonic aqueous solution. The solution can comprise agents such as buffering agents and stabilizing agents. For example, in some embodiments, a buffering agent such as histidine is included to maintain a formulation pH of about 5.5. Additional reagents such as sucrose or alternatives can be added to prevent aggregation and fragmentation in solution and during freezing and thawing. Agents such as polysorbate 80 or an alternative can be included to lower surface tension and stabilizes the antibody against agitation-induced denaturation and air-liquid and ice-liquid surface denaturation. In some embodiments, the solution for injection is stored at 2-8° C. and is diluted in either 100 ml or 200 ml 0.9% sodium chloride for injection prior to administration to the patient. In some embodiments, the antibody is administered as a one to two-hour IV infusion from a diluted saline bag with a total volume of 100, 250, or 500 mL, depending on dose level.

IV. Examples

The present disclosure will be described in greater detail by way of specific examples. The following examples are offered for illustrative purposes only and are not intended to limit the invention in any manner. Those of skill in the art will readily recognize a variety of noncritical parameters which can be changed or modified to yield essentially the same results.

Example 1. Cross Species Reactivity of SIF001 Binding with Galectin-3 (GAL-3)

This example illustrates that the in vitro cross-species reactivity of SIF001 against GAL-3 from different species.

SIF001 is a humanized monoclonal antibody raised against the human GAL-3 protein. It has the HCDR sequences of SEQ ID Nos: 4, 25, and 46, and the LCDR sequences of SEQ ID Nos: 172, 193, and 214. The cross-species reactivity of SIF001 against GAL-3 from different species: human, mouse, rat, and cynomolgus monkey (cyno) samples was evaluated in vitro, and the affinity of GAL-3 binding to SIF001 was measured by Surface Plasmon Resonance (SPR). The binding affinity of SIF001 to human, mouse, and rat GAL-3, measured by dissociation constant (KD), is presented in Table 8 below.

TABLE 8

Binding Affinity of SIF001 to GAL-3

| | Human GAL-3 | Mouse GAL-3 | Rat GAL-3 |
|---|---|---|---|
| KD | $7.15 \times 10^{-8}$M | $1.09 \times 10^{-8}$M | $1.17 \times 10^{-8}$M |

Figure 1B:
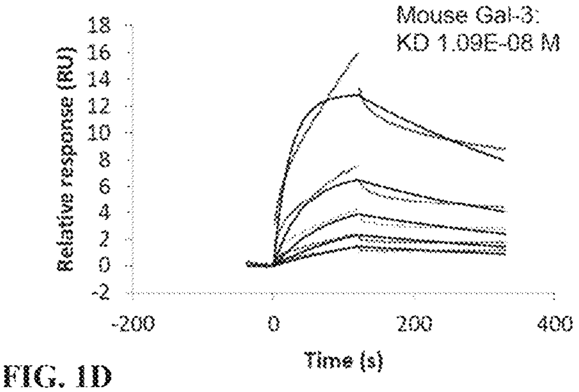
Figure 1C:
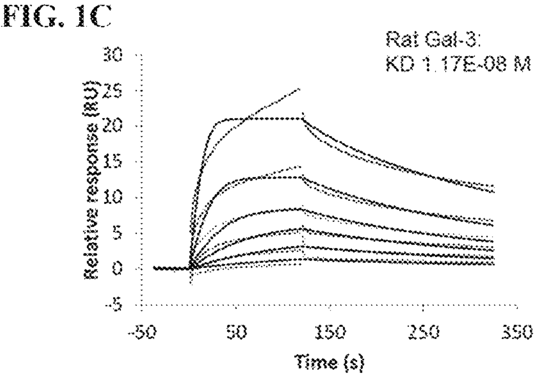
Figure 1D:
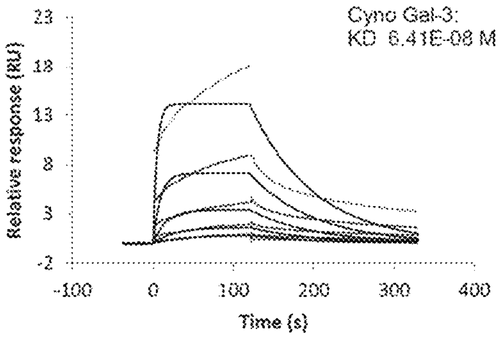

The curve fitting analysis demonstrated strong binding affinity in human, mouse, and rat samples, as evidenced by well-fitted curves (FIGS. 1A-1C). However, the curve fitting did not perform as well in monkey samples (FIG. 1D), suggesting a lack of binding affinity or potential species-specific differences in GAL-3 recognition by SIF001. These results indicate that while the SIF001 effectively binds to GAL-3 in human, mouse, and rat samples, its binding affinity may not extend to monkey GAL-3 or may be reduced in monkeys compared to other species.

Example 2. SIF001 Reduced Inflammatory Cytokine TNFα Release in LPS-Stimulated Microglia BV2 Cells This example illustrates the in vitro effect of SIF001 on inflammatory cytokine TNFα release in microglia BV2 cells when stimulated by lipopolysaccharide (LPS).

The inhibitory effects of SIF001 on the release of the inflammatory cytokine TNFα were evaluated in vitro in microglia BV2 cells stimulated by lipopolysaccharide (LPS) to mimic neuroinflammatory processes that are implicated in epileptogenesis and seizure activity. An ELISA assay was performed with the protocol shown below.

1. On the first day, seed BV2 cells into a 96-well plate, with 5,000 cells per well. Incubate at 37° C. with 5% CO2 overnight to allow the cells to adhere to the well.
2. On the second day, use a new 96-well plate with LPS concentration at 30 ug/ml. The 8th row of the 96-well plate serves as the control and contains only complete culture medium without LPS. All other wells contain 30 ug/ml LPS with a volume of 200 ul each.
3. Take two antibodies labeled as Isotype control, mSIF001. Set up 3 replicates for each antibody. The concentration for the first row of antibodies is 100 nM with a volume of 300 ul. Thoroughly mix the replicates containing the antibody, take 100 ul from it and add to the second row, mix well, and then take 100 ul from the second row to the third, continuing this process down to the seventh row, thus performing a 3-fold dilution.
4. After mixing, remove the complete culture medium from the original 96-well plate containing BV2 cells, wash 2-3 times with complete culture medium, 100 ul each time, and transfer all the liquid from step "3" into the BV2 cell plate. Incubate for 14-15 hours in the incubator.
5. After incubation, take 20 ul of culture medium from each well and dilute it 5 times with the sample diluent from a mouse TNF-α ELISA Kit (High-sensitive) (Beyotime, China). Store the remainder at 4° C.
6. Bring the reagents from the kit to room temperature to equilibrate for 20-30 minutes before use. Prepare the wash buffer by diluting the 20× wash buffer with sterile water to 1×.
7. Add 100 μl of the sample to the respective wells, seal the reaction wells with sealing film, and incubate at room temperature for 120 minutes. After incubation, manually wash the plate, adding 200 ul of wash buffer to each well, for a total of 5 washes. Tap dry on thick absorbent paper after the last wash.
8. Add 100 ul of biotinylated antibody to each well, seal the reaction wells with sealing film, and incubate at room temperature for 60 minutes. Repeat the washing step as in step 7.
9. Add 100 ul of Streptavidin-HRP to each well, seal the reaction wells with sealing film, and incubate at room temperature in the dark for 20 minutes. If the room temperature is low (below 25° C.), extend the incubation time as needed. Repeat the washing step as in step 7.
10. Add 100 μl of TMB substrate solution to each well, seal the reaction wells with sealing film, and incubate in the dark at room temperature for 5-10 minutes until a significant color change is observed in the samples. Add 50 ul of stop solution to each well, mix well, and immediately measure the absorbance at 450 nm.

Figure 2:
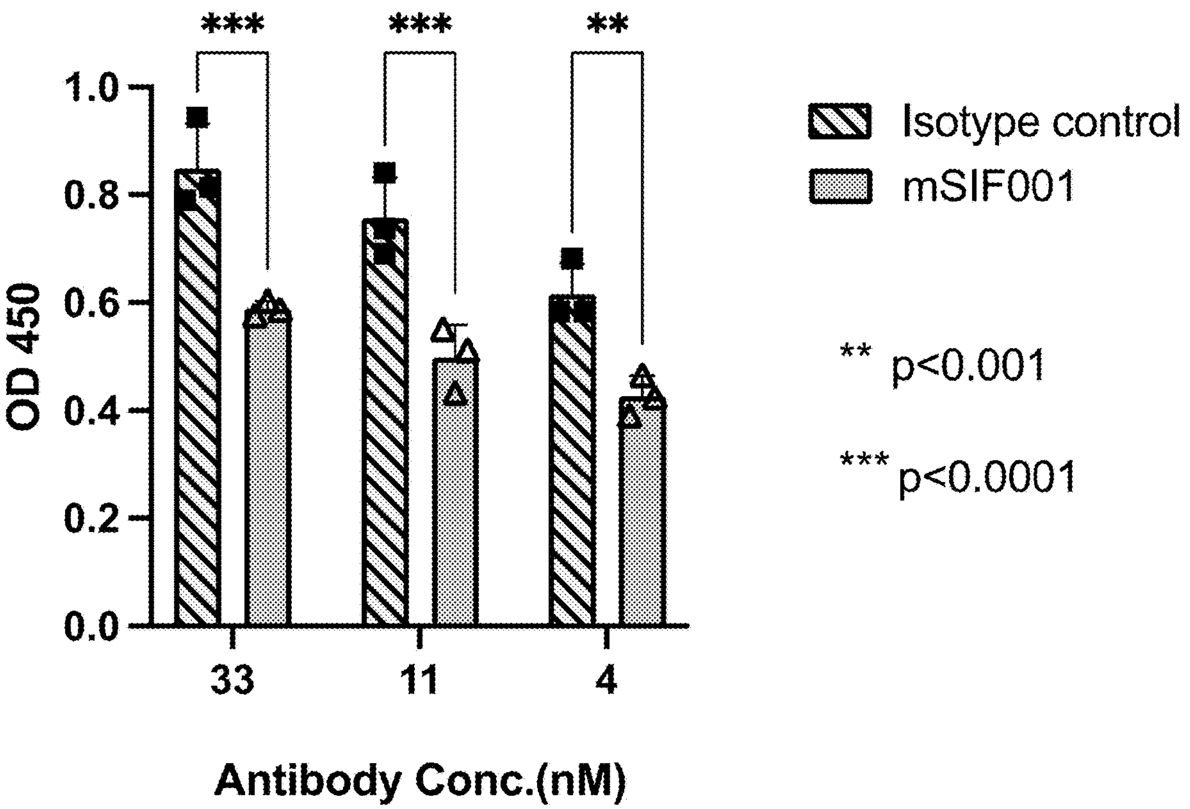
FIG. 2 depicts the effect of SIF001 on TNFα release in microglia BV2 cells stimulated with LPS.

Results demonstrated that SIF001 led to a significant decrease in TNF-α release from LPS-stimulated microglia BV2 cells (FIG. 2). Given the proposed role of neuroinflammation in epilepsy, these findings suggest the potential therapeutic efficacy of SIF001 in mitigating inflammatory responses associated with epileptic pathogenesis, thus highlighting its promise as a treatment for epilepsy.

Example 3. SIF001 Reduced Inflammation in Kainic Acid (KA)-Stimulated Microglia BV2 Cells This example illustrates the in vitro effect of SIF001 on inflammation in microglia BV2 cells stimulated by kainic acid (KA).

In this study, the effect of SIF001 on kainic acid (KA)-stimulated microglia BV2 cells was investigated using cell immunofluorescence assays, as the protocol shown below.

1. On the first day, BV2 cells were first planted in three 35 mm glass bottom dishes with 10,000 cells seeded in each dish. The incubator was incubated at 37° C. and cultured overnight with 5% carbon dioxide to make the cells stick to the wall.
2. On the second day, anti-HEL Mouse IgG2A isotype control antibody and SIF001 were taken for 100 nM each, and each antibody was added to a petri dish and incubated at 37° C. in a carbon dioxide incubator for 1 h. The control group was replaced with 1 ml complete medium. After incubation, 200 ug/ml Kainic acid (KA)

solution was added to the two treatment group petri dishes. After incubation for 24 h, the cells in 3 glass dishes were stained by immunofluorescence.

3. In a fuming cupboard, brain tissue was fixed at room temperature for 15 min with 4% PFA thawed at room temperature.
4. Transfer the PFA to the special waste liquid bucket, and wash the section tissue with PBS three times, 10 min each time.
5. A blocking solution was prepared and diluted in PBS with 5% goat serum (NGS)+0.5% Triton X-100. After removing PBS, add blocking solution and incubate at room temperature for 1 h.
6. The primary antibody was prepared, diluted in PBS with 5% goat serum+0.1% Triton X-100, added with 1:250 Iba1 primary antibody, and incubated at 4° C. overnight.
7. Wash with PBS three times in the morning of the next day, 10 min each time.
8. The secondary antibody was prepared, diluted in PBS with 5% goat serum+0.1% Triton X-100, added with 1:250 secondary antibody, and incubated at room temperature away from light for 2 h.
9. Discard the secondary antibodies, prepare 5 ug/mL DAPI on PBS for nuclear staining, and incubate at room temperature for 15 min away from light.
10. Dry in a dark place and then add antifade mounting medium with DAPI. Add about 150 uL of the sealing liquid to each slide and cover it with a cover glass to avoid bubbles. After drying in the dark, Liquid blocker super PAP pen can be sealed on all sides and stored at 4° C. in a cassette.

Figure 3:
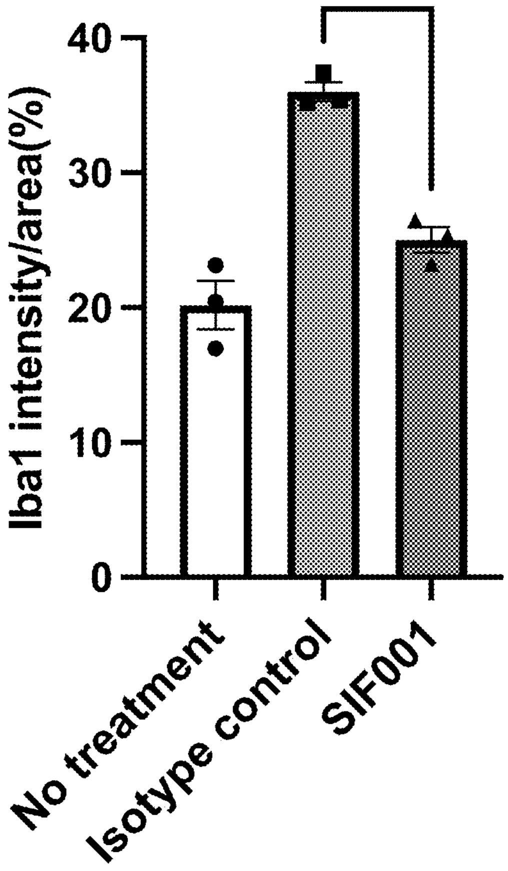
FIG. 3 depicts the effect of SIF001 on epilepsy model in microglia BV2 cells stimulated by KA via cell immunofluorescence assay.

The results from cell immunofluorescence assay (FIG. 3) confirmed that, compared to the vehicle group of microglia BV2 cells without receiving stimulation (no treatment), the proportion of IBA1-stained cells in the KA stimulated microglia cells treated with human HEL (isotype control) significantly increased and the cell morphology enlarged, while the proportion of IBA1-stained cells significantly reduced in the KA stimulated microglia BV2 cells treated with SIF001 (SIF001). These data indicate that SIF001 significantly reduced expression of activation marker IBA1 in in vitro epilepsy model of microglia BV2 cells stimulated by kainic acid (KA). While KA stimulation significantly increased the proportion of IBA1-stained cells and induced morphological changes, indicative of microglial activation, the treatment with SIF001 resulted in a significant reduction in the proportion of IBA1-stained cells in KA-stimulated microglia BV2 cells, suggesting a potential inhibitory effect of SIF001 on microglial activation induced by KA. These findings highlight the therapeutic potential of SIF001 in modulating microglial activation and neuroinflammation, which are implicated in the pathophysiology of conditions such as epilepsy.

Example 4. SIF001 Reduced Epilepsy in Mouse Model Induced by Kainic Acid (KA)

This example illustrates the effect of SIF001 on epilepsy induced by kainic acid (KA) in C57BL/6J mice.

The effect of SIF001 on the reduction of epilepsy symptoms was evaluated in 8-12 weeks male C57BL/6J mice. As illustrated in FIG. 4A, epilepsy was induced in C57BL/6 mice by administering 10 mg/kg, 5 mg/kg, 2.5 mg/kg, and 2.5 mg/kg kainic acid (KA) via i.p. injection at 60 min, 80 min, 100 min, 120 min, respectively. Before KA injection, mice were randomized into two groups to receive 30 mg/kg anti-HEL mouse IgG2A (control group) or receive 30 mg/kg mSIF001 i.p. injection at 0 min (active group). All mice were observed for 72 hours prior to the sacrifice.

Brain tissue processing for staining: Briefly, animals were deeply anesthetized with 50 mg/kg Zoletil (i.p.) and transcardially perfused with phosphate buffered saline (PBS) followed by 4% paraformaldehyde (PFA) in PBS. Whole brains were removed and allowed to post-fix in 4% PFA for 6-8 h at 4° C. before being transferred to a 30% sucrose solution for overnight cryoprotection. Coronal sections containing the medial and ventral hippocampus were sliced on a freezing stage microtome and stored at 4° C. in 0.1M PBS for staining.

Iba1 and GFAP staining was performed as the protocol shown below.

1. In a fuming cupboard, brain tissue was fixed at room temperature for 15 min with 4% PFA thawed at room temperature.
2. Transfer the PFA to the special waste liquid bucket, and wash the section tissue with PBS three times, 10 min each time.
3. A blocking solution was prepared and diluted in PBS with 5% goat serum (NGS)+0.5% Triton X-100. After removing PBS, add blocking solution and incubate at room temperature for 1 h.
4. The primary antibody was prepared, diluted in PBS with 5% goat serum+0.1% Triton X-100, added with 1:250 Iba1 primary antibody, and incubated at 4° C. overnight.
5. Wash with PBS three times in the morning of the next day, 10 min each time.
6. The secondary antibody was prepared, diluted in PBS with 5% goat serum+0.1% Triton X-100, added with 1:250 secondary antibody, and incubated at room temperature away from light for 2 h.
7. Discard the secondary antibodies, prepare 5 ug/mL DAPI in PBS for nuclear staining, and incubate at room temperature for 15 min away from light.
8. Dry in a dark place and then add antifade mounting medium with DAPI. Add about 150 uL of the sealing liquid to each slide and cover it with a cover glass to avoid bubbles. After drying in the dark, Liquid blocker super PAP pen can be sealed on all sides and stored at 4° C. in a cassette.

Bioanalysis: Three brain tissue sections were taken from each sample for staining, and the hippocampus region was selected for 10× photography with Olympus FV3000. For analyses of microglia and astrogliosis, Iba1 and GFAP staining intensities, a one-way ANOVA design was utilized with a Dunnett's multiple comparison to controls. A p-value below 0.05 was considered significant in post-hoc testing. All statistical analyses were performed using Prism 9 (GraphPad, La Jolla, CA).

Therapeutic effects of SIF001 on the epilepsy model were evaluated in terms of seizure occurring rate (FIG. 4B) among the test animals in each group, seizure frequency (FIG. 4C) in individual mouse in each group, seizure severity (FIG. 4D) per Racine score and seizure duration (FIG. 4E) in individual mouse in each group. As shown in FIGS. 4A-4D, significant inhibition of epilepsy occurrence has been observed in the active group, in which no mice treated with SIF001 showed seizure symptoms, while all mice in the control group suffered frequently occurred seizures, an average severity Racine score as of 3, and commonly with more than 20 seconds seizure duration.

Figure 5:
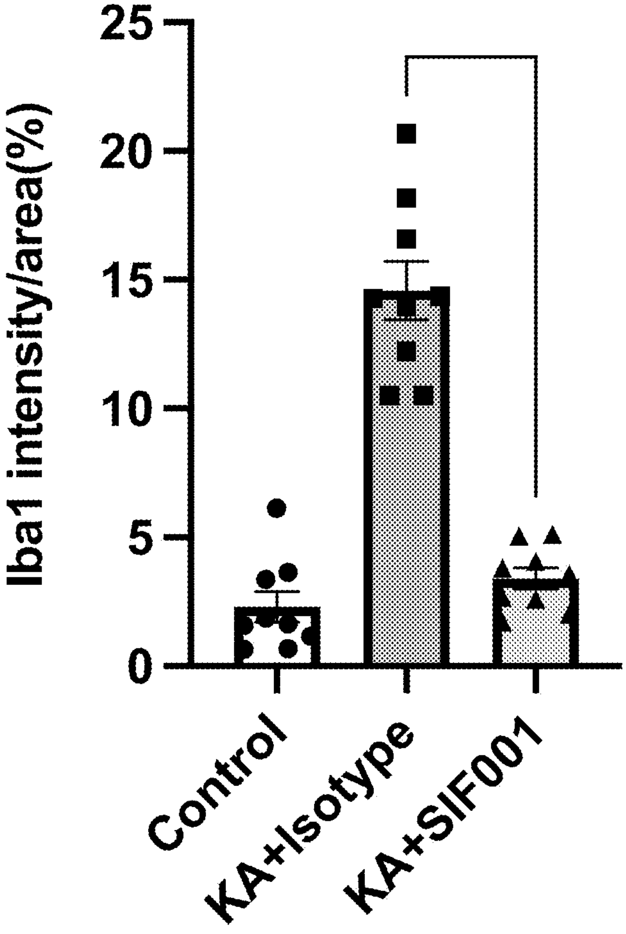
FIG. 5 depicts the effects of SIF001 on the ionized calcium-binding adaptor molecule 1 (Iba1) in hippocampus in epilepsy model of C57BL/6J mouse stimulated by KA.
Figure 6:
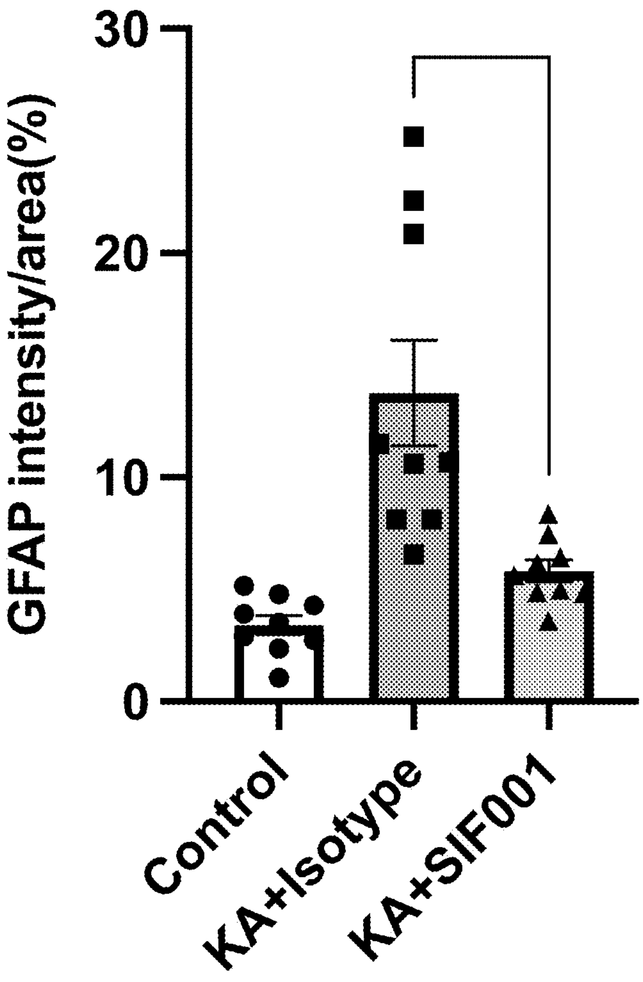
FIG. 6 depicts the effects of SIF001 on the Glial fibrillary acidic protein (GFAP) in hippocampus in epilepsy model of C57BL/6J mouse stimulated by KA.

To further explore any pathological changes underlying epilepsy, brain tissues from isotype control and active groups, and a group without any treatment, were immunefluorescent stained with IBA1 (ionized calcium-binding adapter molecule 1) and GFAP (glial fibrillary acidic protein), biomarkers for activation of microglia and astrocytes, respectively. As shown in FIGS. 5 and 6, SIF001 significantly reduced activation of microglia (FIG. 5), and astrocytes (FIG. 6), indicating that SIF001 inhibits epilepsy through disease modification. The results suggest that treatment with SIF001 led to a potential modulation of glial activation and neuroinflammation, which may contribute to the regulation of epileptic activity and neuroprotection in the hippocampus.

The results showed that, in KA-induced epilepsy model, treatment with SIF001 was able to significantly inhibit the occurrence of seizure in terms of Racine Score, frequency of seizures, duration of seizures, and significantly reduced neuroinflammatory activation of microglia and astrocytes.

Example 5. SIF001 and SIF002 Sequence Analysis

This example illustrates alanine scanning and mutagenesis assays to evaluate essential amino acid residues of the anti-GAL-3 antibodies SIF001 and SIF002 for antigen binding affinity.

Figure 7:
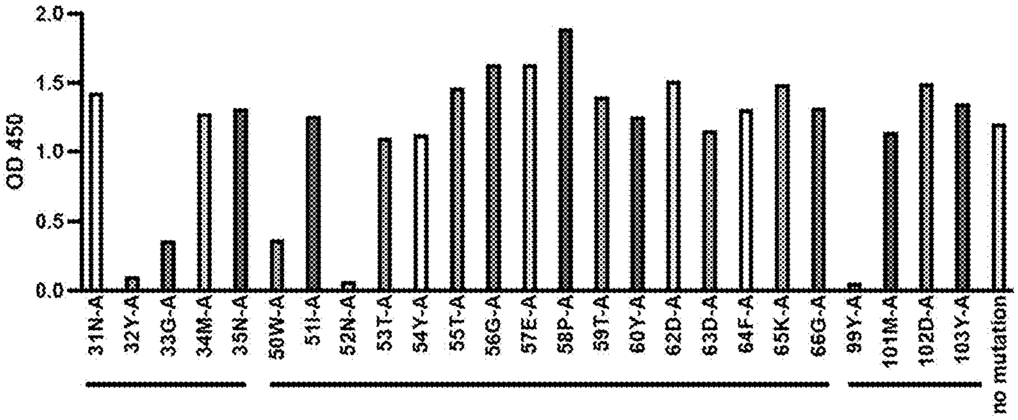
FIG. 7 depicts the alanine scanning of SIF001 CDRs. (A) Alanine scanning of SIF001 heavy chain CDRs (SEQ ID Nos: 4, 25, and 46) indicates that the amino acid residues: Y32 and G33 in HCDR1, W50 and N52 in HCDR2; and Y99 in HCDR3 (respectively underlined in the CDR sequences in the table) are essential to the antibody SIF001 binding to the antigen GAL-3. (B) Alanine scanning of SIF001 light chain CDRs (SEQ ID Nos: 172, 193, and 214) indicates that the amino acid residues: Y34 in LCDR1, and W93 and Y98 in LCDR3 (respectively underlined in the CDR sequences in the table) are essential to the antibody SIF001 binding to the antigen GAL-3.
Figure 7:
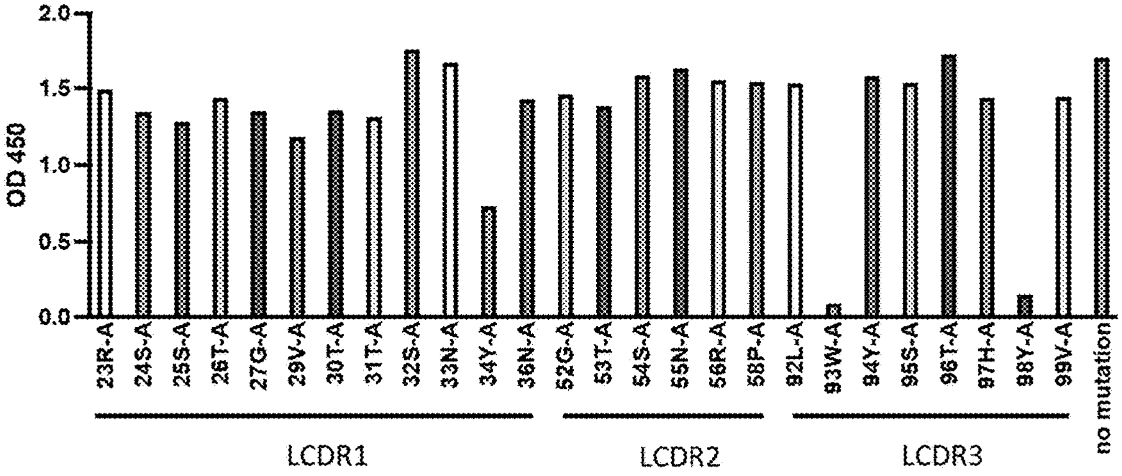

First, we utilized the Kabat numbering system to annotate the heavy chain CDRs of SIF001. As indicated in FIG. 7A, the HCDR1 (SEQ ID NO: 4) of SIF001 starts at position 31 and ends at position 35, the HCDR2 (SEQ ID NO: 25) starts at position 50 and ends at position 66, and the HCDR3 (SEQ ID NO: 46) starts at position 99 and ends at position 103. As indicated in FIG. 7B, the LCDR1 (SEQ ID NO: 172) of SIF001 starts at position 23 and ends at position 36, the LCDR2 (SEQ ID NO: 193) starts at position 52 and ends at position 58, and the LCDR3 (SEQ ID NO: 214) starts at position 91 and ends at position 99.

To determine which amino acids of the antibody are critical for antigen binding, we performed an alanine scanning assay in which each amino acid within the heavy and light chain CDR regions was individually replaced with an alanine and antigen binding affinity of each antibody variants were tested. We introduced an alanine mutation individually to each amino acid within both the heavy and light chain CDRs of SIF001, and then spliced the complete sequence of the human IgG4P subtype. We inserted the designed sequence into the pcDNA3.4 vector (Amp), extracted an ample amount of plasmid, and used an appropriate quantity of plasmid (concentration 500 ng/ul) for electroporation transfection into CHOK1 cells. The transfected cells were incubated at 37° C., 270 rpm, in an 8% CO2 environment, ensuring timely addition of supplements during the 4-day culture period. Subsequently, the cell supernatant was collected for protein expression assessment using Gator.

We evaluated the binding affinity of the SIF001 variants with an alanine mutation to human Galectin-3 through ELISA. As shown in FIG. 7A, a replacement of any one of the following amino acid residues of SIF001: Y32 and G33 in HCDR1, W50 and N52 in HCDR2; and Y99 in HCDR3 to an alanine resulted in a significant reduction of the antigen binding affinity, indicating that these amino acid residues are essential to the antibody SIF001 binding to the antigen GAL-3. As showed in FIG. 7B, a replacement of any one of the following amino acid residues of SIF001: Y34 in LCDR1, W93 and Y98 in LCDR3 to an alanine resulted in a significant reduction of the antigen binding affinity, indicating that these amino acid residues are essential to the antibody SIF001 binding to the antigen GAL-3.

Figure 8:
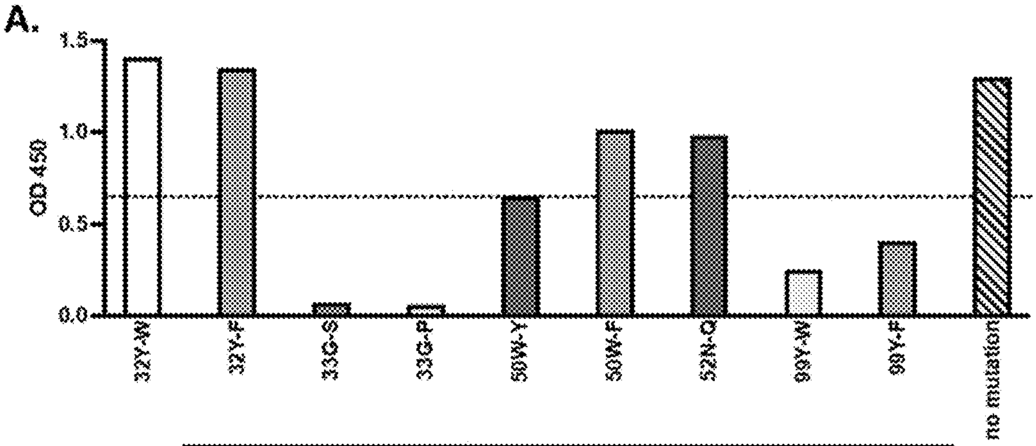
FIG. 8 depicts the antigen binding effects of anti-GAL-3 antibodies derived from SIF001 with one amino acid substitution in the CDR regions. (A) indicates that a Y32W, Y32F, W50T, W50F, or N53Q mutation in the HCDR regions (SEQ ID Nos: 358-359) of SIF001 heavy chain does not impact antibody binding to the antigen GAL-3. (B) indicates that a Y34W, Y34F, W93Y, W93F, Y98W, or Y98F mutation in the LCDR regions (SEQ ID Nos: 360-362) of SIF001 light chain does not impact antibody binding to the antigen GAL-3.
Figure 8:
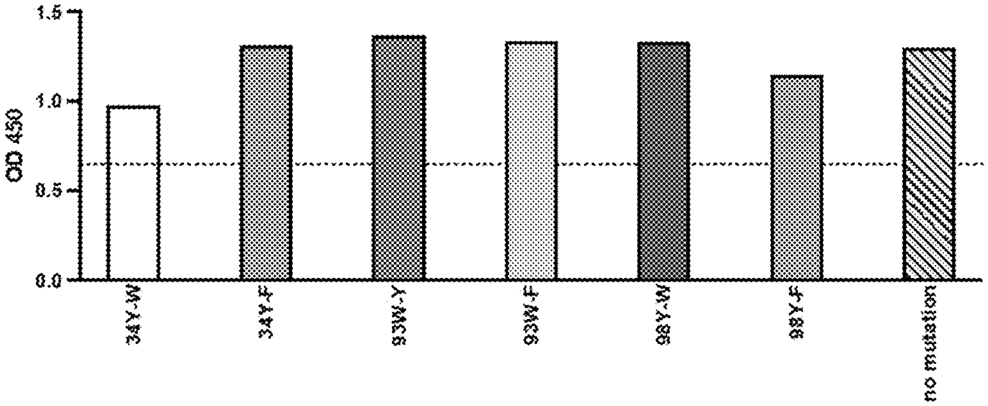

We further mutated these essential amino acids: Y32, G33, W50, N52, Y99 in the HCDR regions of SIF001 and Y34, W93, and Y98 in the LCDR regions of SIF001 to different amino acid residues, and concluded that a mutation of Y32W, Y32F, W50Y, W50F, or N52Q in the HCDR regions of SIF001 (FIG. 8A), or a mutation of Y34W, Y34F, W93Y, W93F, Y98W, or Y98F in the LCDR regions of SIF001 (FIG. 8B) did not impact antibody binding to the antigen GAL-3.

Figure 9:
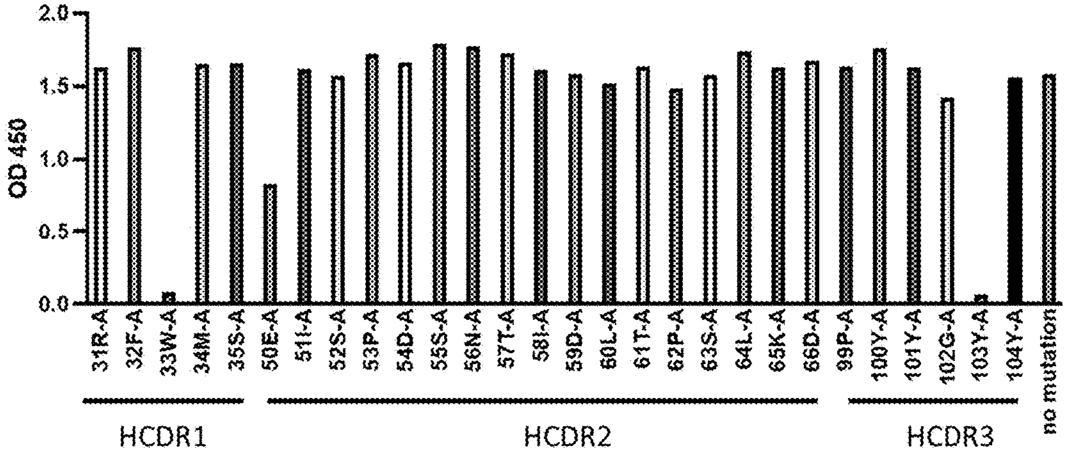
FIG. 9 depicts the alanine scanning of SIF002 CDRs. (A) Alanine scanning of SIF002 heavy chain CDRs (SEQ ID Nos: 8, 29, and 50) indicates that the amino acid residues: W33 in HCDR1, E50 in HCDR2; and Y103 in HCDR3 (respectively underlined in the CDR sequences in the table) are essential to the antibody SIF002 binding to the antigen GAL-3. (B) Alanine scanning of SIF002 light chain CDRs (SEQ ID Nos: 369, 197, and 218) indicates that the amino acid residues: Y38 in LCDR1, and D97 in LCDR3 (respectively underlined in the CDR sequences in the table) are essential to the antibody SIF002 binding to the antigen GAL-3.
Figure 9:
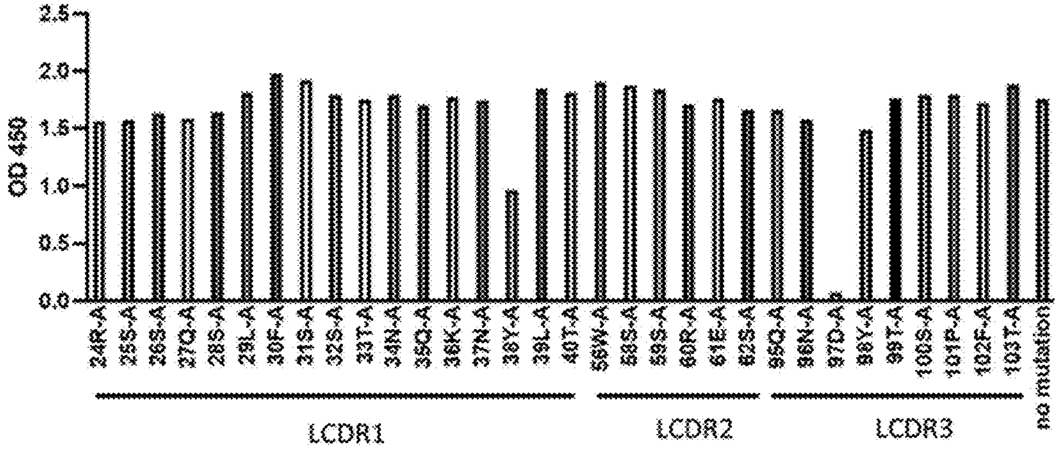

Similarly, we utilized the Kabat numbering system to annotate the heavy chain CDRs of SIF002. As indicated in the top table of FIG. 9, the HCDR1 (SEQ ID NO: 8) of SIF002 starts at position 31 and ends at position 35, the HCDR2 (SEQ ID NO: 29) starts at position 50 and ends at position 66, and the HCDR3 (SEQ ID NO: 50) starts at position 99 and ends at position 104. As indicated in the lower table of FIG. 9, the LCDR1 (SEQ ID NO: 369) of SIF002 starts at position 24 and ends at position 40, the LCDR2 (SEQ ID NO: 197) starts at position 56 and ends at position 62, and the LCDR3 (SEQ ID NO: 218) starts at position 95 and ends at position 103.

We evaluated the binding affinity of the SIF002 variants with an alanine mutation to human Galectin-3 through ELISA. As shown in FIG. 9A, a replacement of any one of the following amino acid residues of SIF002: Y33 in HCDR1, E50 in HCDR2; and Y103 in HCDR3 to an alanine resulted in a significant reduction of the antigen binding affinity, indicating that these amino acid residues are essential to the antibody SIF002's binding to the antigen GAL-3. As showed in FIG. 9B, a replacement of any one of the following amino acid residues of SIF002: Y38 in LCDR1 and D97 in LCDR3 to an alanine resulted in a significant reduction of the antigen binding affinity, indicating that these amino acid residues are essential to the antibody SIF002 binding to the antigen GAL-3.

Figure 10:
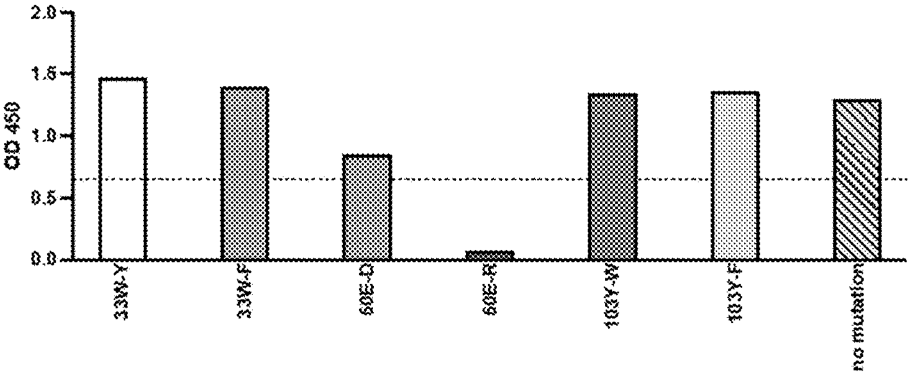
FIG. 10 depicts the antigen binding effects of anti-GAL-3 antibodies derived from SIF002 with one amino acid substitution in the CDR regions. (A) indicates that a W33Y, W33F, E50D, Y103W, or Y103F mutation in the HCDR regions (SEQ ID Nos: 363-365) of SIF002 heavy chain does not impact antibody binding to the antigen GAL-3. (B) indicates that a Y38W, or Y38F mutation in the LCDR regions (SEQ ID Nos: 366-368) of SIF002 light chain does not impact antibody binding to the antigen GAL-3.
Figure 10:
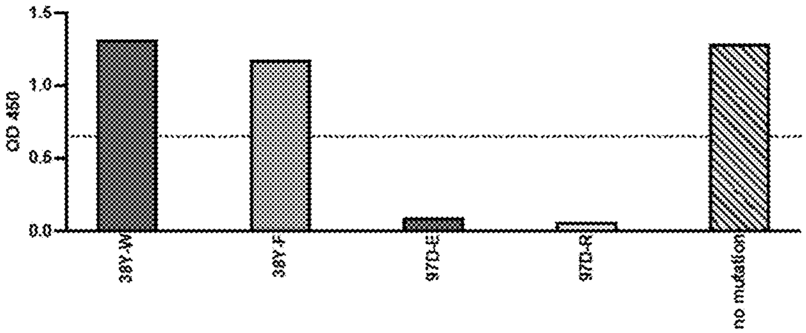

We further mutated these essential amino acids: Y33, E50, Y103 in the HCDR regions of SIF002 and Y38 and D97 in the LCDR regions of SIF002 to different amino acid residues, and concluded that a mutation of W33Y, W33F, E50D, Y103W, or Y103F in the HCDR regions of SIF002 (FIG. 10A), or a mutation of Y38W or Y38F in the LCDR regions of SIF002 (FIG. 10B) did not impact antibody binding to the antigen GAL-3.

Example 6. SIF001 Prevented Seizure Occurring in a Dose-Dependent Manner

This example illustrates that the anti-GAL-3 antibody SIF001 can prevent seizure occurring in a dose-dependent manner in mice.

Figure 11:
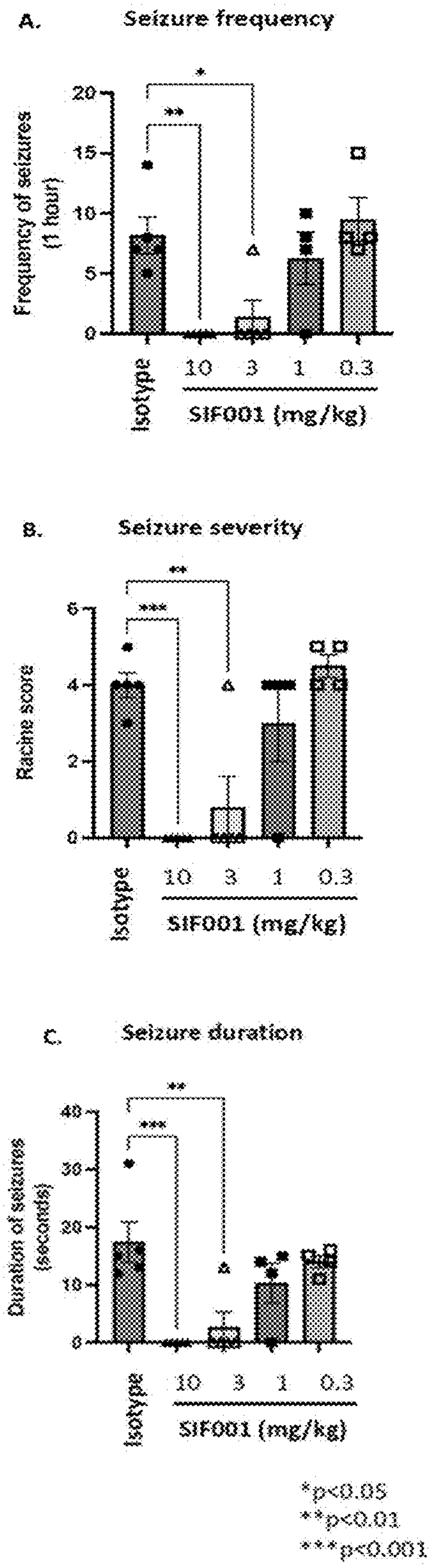
FIG. 11 depicts the antibody SIF001 prevents seizure occurring in a dose-dependent manner in mice, as measured in seizure frequency (A), seizure severity (B), and seizure duration (C).

Using the same methods described in Example 4, the effects of SIF001 on preventing seizure were evaluated in 8-12 weeks male C57BL/6J mice. As measured in seizure frequency (FIG. 11A), seizure severity (FIG. 11B), and seizure duration (FIG. 11C), 3 mg/kg of SIF001 can significantly reduce seizure occurring in mice, where 10 mg/kg of SIF001 showed even better effect, indicating that anti-GAL-3 antibody SIF001 can prevent seizure occurring in a dose-dependent manner in mice.

Example 7. Structure Determination of Galectin3-e (Gal3-e) and Fab Complex

This example illustrates utilizing cryogenic electron microscopy (Cryo-EM) to capture a high-resolution structure of a Gal3-e and Fab complex.

Summary

The objective of this research is to obtain a high-resolution structure of the Gal3-e and Fab complex. The Gal3-e is a Gal-3 peptide with an amino acid sequence of GAPGAYPGAPAPGVYPGPPSGPGAYPSSG (SEQ ID NO: 508). X-ray diffraction and Cryo-EM Single particle analysis (SPA) are the most powerful biophysical methods to build the high-resolution structure of protein or protein complex. Initially, the X-ray diffraction technique was employed to elucidate the structure. However, no diffraction patterns were observed in the optimized large crystals. Consequently, cryogenic electron microscopy (Cryo-EM) was selected as the alternative approach to determine the structure of the complex.

For X-ray diffraction, first we developed a homogeneous Gal3-e-Fab complex through Size Exclusion Chromatography (SEC) and analyzed the complex through crystallization screening and optimization. However, no diffraction patterns but only large block- and rod-shaped crystals were observed by multi-rounds of optimization. Screened commercial kits included crystal screens, structure screens, Index, JCSG plus, PEG/Ion1&2, ProPlex screens, and additive screens.

For Cryo-EM, multiple Cryo-EM sample screening experiments were conducted, employing various grids and detergents to identify optimal conditions. We obtained the optimal Cryo-EM samples by using FGG grid exhibiting particles with high contrast and diverse orientations. Next, we collected more than 5 datasets on Talos Glacios 200 kV and produced a preliminary density map with a resolution of 5.2 Å. To further enhance the resolution, we collected a dataset, including 8, 447 movies, on Titan Krios 300 kV equipped with a Falcon 4i camera and an energy filter. This dataset enabled the resolution of the Gal3-Fab complex density map to 3.17 Å. We further performed initial model building and model refinement against the 3.17 Å density map. Eventually, the 15 amino residues of the Gal3-e peptide were traced within the density map, and 9 of them were identified.

Methods

Assembly of Gal3-e and Fab

Excess Gal3-e were incubated with the Fab on ice for 30 minutes. After the incubation, Gal3-e-Fab complex was isolated from the mixture using SEC (Column: Superdex 75 increase 10/300).

Co-Crystallization

For the production of crystals, a solution of purified Gal3-e-Fab complex (15-30 mg/mL) in buffer containing 20 mM Tris pH7.5 and 150 mM NaCl was used. Crystals of the complex were grown at 18° C. using the sitting drop vapor diffusion technique by mixing equal amounts of protein solution and reservoir buffer containing the precipitating agents.

Cryo-EM

1. Cryo-EM Sample Preparation

Apply 3 μL protein sample on the grid treated with Pelco EasiGlow discharge, with subsequent blotting leaving only a thin liquid film on the grid by using Vitrobot. The thin film is then vitrified, typically by plunging into liquid ethane.

2. Cryo-EM Sample Screening & Optimization

Proceed to load the Cryo-EM samples onto the Talos Glacios 200 kV and assess the sample behavior, specifically focusing on the contrast and orientations of particle. Typically, it is anticipated that several iterations of optimization will be requisite to obtain optimal Cryo-EM samples.

3. Data Collection on Talos Glacios 200 kV

Acquire datasets on optimal Cryo-EM samples, followed by image processing. Further evaluate the quality of datasets. If possible, obtaining a density map at medium resolution.

4. Data Collection on Titan Krios 300 kV

To increase the resolution of structure by using a 300 kV TEM with higher performance.

5. Image Processing & Model Building

Image processing is a multi-stage processing workflow, which encompassed initial pre-processing, followed by particle selection, 2D classification (two-dimensional classification), 3D classification (three-dimensional classification), 3D refinement (three-dimensional refinement), and subsequent local refinement. Multiple iterations of model construction and refinement were executed in against the acquired density map.

Results

Protein Assembly

Figure 12:
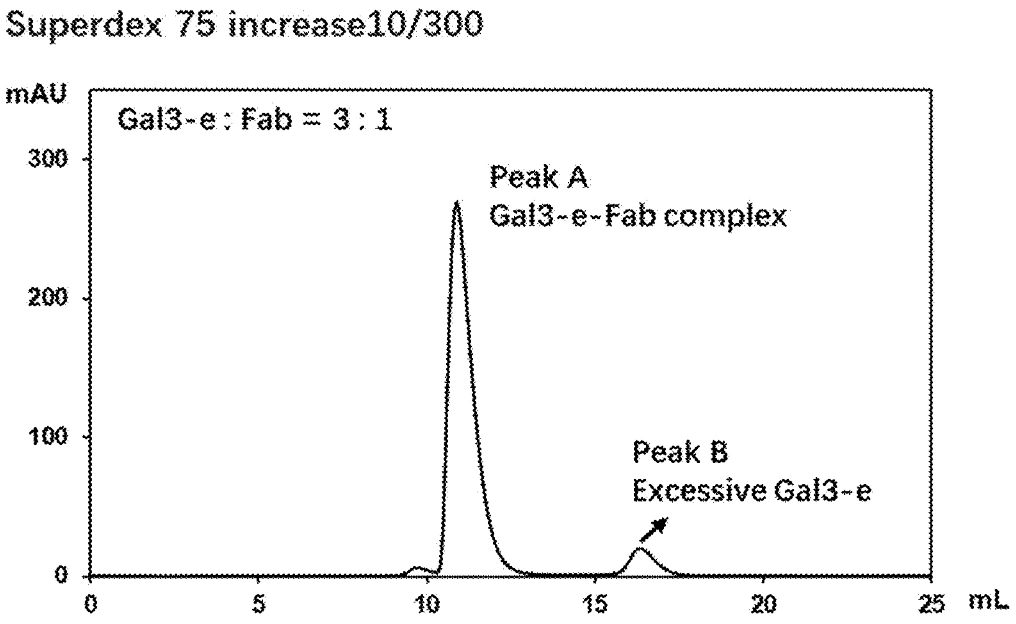
FIG. 12 depicts SEC of the Gal3-e-Fab complex.
Figure 13:
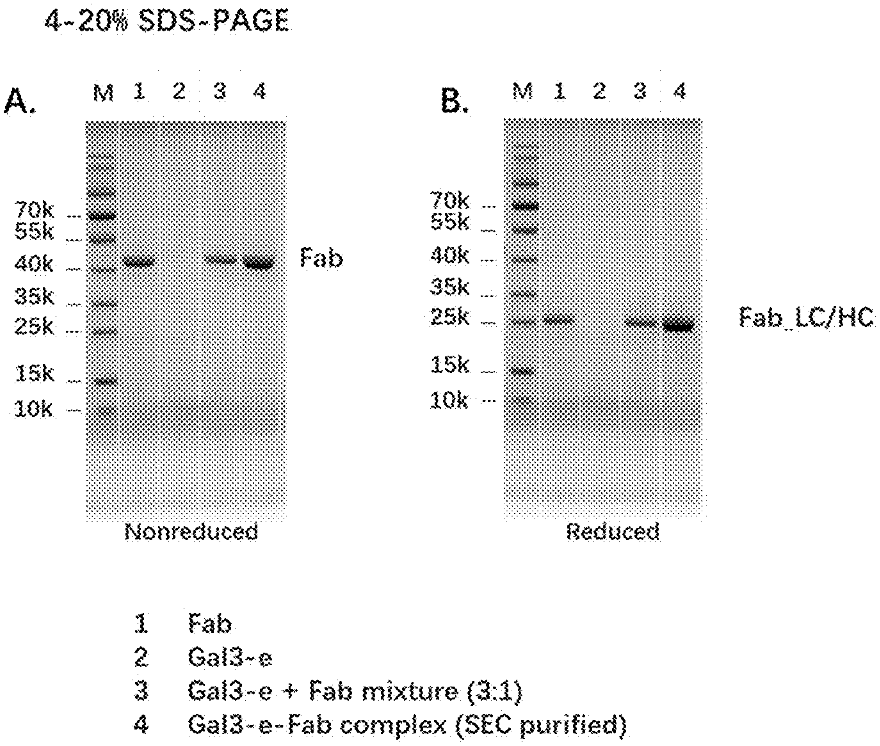
FIG. 13 depicts SDS-PAGE of Gal3-e-Fab complex.

The results of SEC demonstrated that Gal3-e and Fab were successfully assembled into homogeneous binary complex (FIG. 12). It is hard to detect the Gal3-e peptide by using regular SDS-PAGE due to its small molecular weight (3 kDa) (FIGS. 13A and 13B).

We have performed multi-rounds of co-crystallization screening and optimization of Gal3-e-Fab complex, including co-crystallized with different concentrations of samples, screening about 700 conditions (Kits). The large block-shaped and rod-shaped crystals were observed by multi-rounds of optimization, but no diffraction was detected by using internal XRD or at SSRF (Shanghai Synchrotron Radiation Facility).

Cryo-EM

To obtain optimal Cryo-EM samples, we have undertaken multi-rounds of sample screening and optimization, including adding types of detergent to increase diversity of particle orientation and using types of grids. Finally, we found that utilization of FGG grid (treated with Graphene) for sample preparation exhibits the best behaviors of particle with high contrast and diverse orientations. Then we collected 5 datasets of optimal Cryo-EM samples on Talos Glacios 200 kV. Obtained a density map of 5.7 Å (angstroms). The local density map of Gal3-e still could not be well identified due to the low resolution.

To further increase resolution, we prepared another batch of Cryo-EM samples and collected a dataset (8, 447 images) on Titan Krios 300 kV equipped with Falcon 4i and energy filter. Finally, we obtained a 3.17 Å map through delicate image processing.

Model Building

Figure 14:
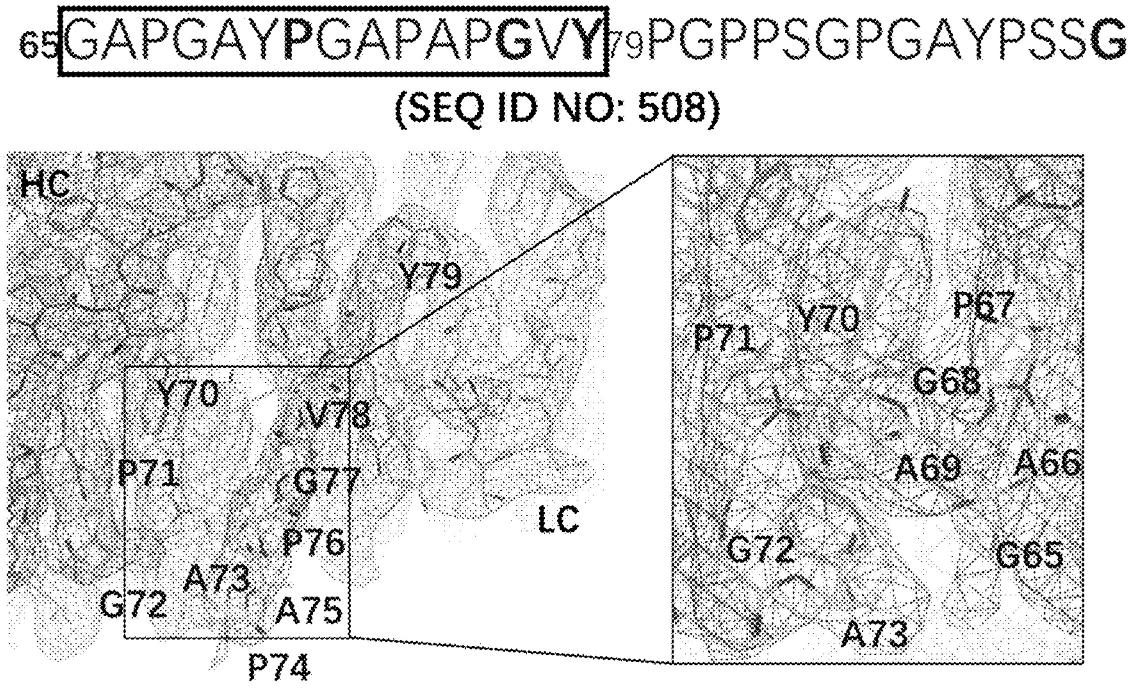
FIG. 14 depicts local density map of Gal3-e, a Galectin-3 epitope sequence (SEQ ID NO: 508).
Figure 15:
FIG. 15 depicts interface between Gal3-e and Fab.
Figure 16:
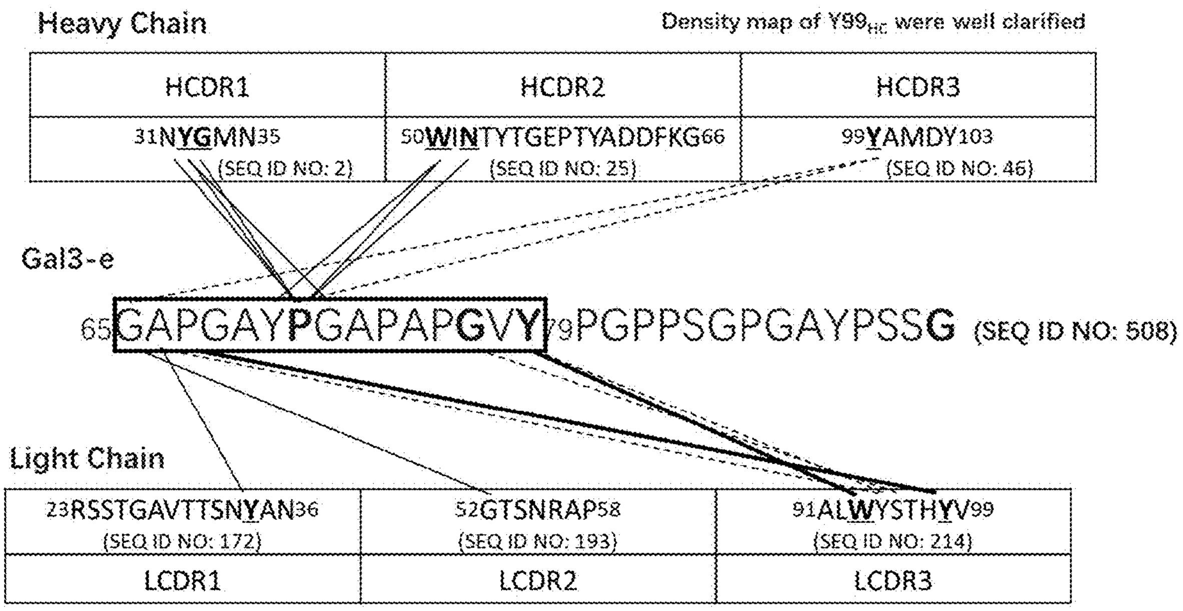
FIG. 16 depicts interactions between Gal3-e (SEQ ID NO: 508) and Fab of the SIF001 antibody with HCDR1 (SEQ ID NO: 2), HCDR2 (SEQ ID NO: 25), HCDR3 (SEQ ID NO: 46), LCDR1 (SEQ ID NO: 172), LCDR2 (SEQ ID NO: 193), and LCDR3 (SEQ ID NO: 214). Bold amino acids of the Gal3-e sequence indicate these residues are essential for Fab binding. The boxed sequence of the Gal3-e sequence indicates these residues are traced in the density map. The trace lines represent weak interactions; the bolded trace lines represent stronger interactions, and the dashed trace lines represent potential interactions.

Two preliminary structural models of the Fab fragment were constructed utilizing the Swiss-Model (https://swiss-model.expasy.org) and Alphafold3 (https://alphafoldserver-.com), respectively. Subsequently, these models were fitted into the electron density map at a resolution of 3.17 Å. Comparative analysis revealed that the model generated by Swiss-Model exhibited markedly higher precision. To enhance the accuracy of the model, iterative rounds of refinement were conducted against the density map employing the software tools Coot and Phenix. Within the density map, 15 amino residues of Gal3-e could be traced in the density map, 9 of these could be identified (FIG. 14). The interface and interactions between Gal3-e and Fab are shown in FIGS. 15 and 16.

Example 8. SIF001 for Parkinson's Disease Treatment

This example illustrates therapeutic effects of SIF001 in a Parkinson's disease mimic mice model.

Summary

The primary objective of this in vivo study is to assess the therapeutic effect of anti-Galectin-3 antibody (mSIF001) in reducing neuroinflammation and PD pathology in 10-week-old C57BL/6 male mice injected with αSYN oligomers. Amyloid protein conformational oligomers are neurotoxic in PD. In vitro, we found that Gal-3 intrinsically promotes oligomerization and that SF001 reduced or degraded αSYN oligomer formation. In order to mimic the PD pathology, αSYN oligomers intrinsically promoted by Galectin-3 was injected into the parenchyma of one hemisphere under stereotactic control. In order to investigate the effect of αSYN oligomers, mice under went the locomotor function test using rotarod. After 3 months, mice produced a statistically significant dysfunction as compared to age match control mice which is one of the phenotypic feature in PD. Mice were dosed with 30 mg/kg anti-HEL mouse IgG2A (isotype control group) or received 30 mg/kg mSIF001 (active group) via i.p. injection four weeks (2 doses/week). Treatment with anti-Galectin-3 antibody showed improvement in locomotor function and was statistically significant as compared to mice treated with Isotype control Ab. Mice were sacrificed for brain neuroinflammation analysis by immunohistochemistry (IHC) immunofluorescence (IF) staining. Results showed that, compared to the isotype antibody treatment, mSIF001 treatment significantly reduced underlying neuroinflammatory activation of microglia. In addition, mice dosed with mSF001 shows significant decrease in αSYN aggregates as compared to mice dosed with Isotype-control.

Parkinson's disease (PD) is the second most prevalent neurodegenerative disease in the world. It is characterized by intense neurodegeneration in the basal ganglia area leading to severe and progressive motor impairment. The presence of Lewy bodies (LBs), described as neuronal intracytoplasmic deposits of α-synuclein (αSYN), is the second hallmark of the disease. While dopaminergic neurons from the substantia nigra (SN) are frequently the most affected cells, neurodegeneration and LB formation commonly appear in other central and enteric nervous system locations even years before than in the SN. Disease modifying therapies are being developed that work either through targeting αSYN, inflammation, metabolism, vasculature and/or neuroplasticity. Of all the clinical trials conducted to date, none of these treatments have met clinical efficacy endpoints for PD. Thus, there is an urgent unmet medical need for treatments that can either stop or reverse the progression of PD. It has been observed prominent endogenous role for galectin-3 (GAL3) in pathological αSYN strains associated with LB formation and toxicity, thus pointing to GAL3 inhibition as a potential future therapeutical strategy to prevent or slow down PD progression Galectin-3 (Gal-3) plays a pivotal role in microglia-mediated neuroinflammation causing many neurological disorders. A mouse model of PD showing an increase in αSYN aggregates and neuroinflammation was used to assess the effect of mSIF001, an anti-Gal-3 monoclonal antibody, on the severity of neuroinflammation and the pathological changes underlying the PD pathology.

Methods and Experiments

Figure 17:
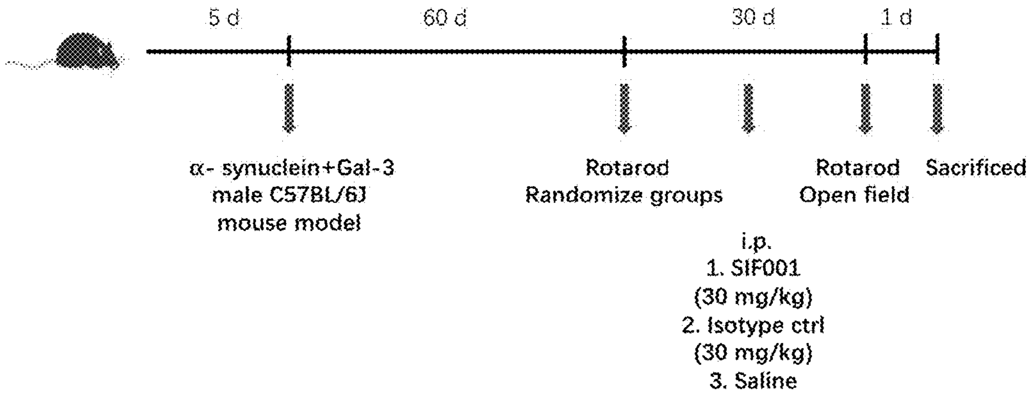
FIG. 17 depicts study design and dosing regimen of the mouse study to evaluate the therapeutic effects of mSIF001 in the Parkinson's disease mimic mouse model.

Study Design. Study design is outlined in FIG. 17.

Preparation of Alpha synuclein oligomers. It has been observed Galectin-3 intrinsically promotes oligomers of amyloid proteins. Alpha synuclein oligomers were prepared by incubating monomeric α-synuclein (300 μM) with and without Galectin-3 (100 ug/ml) in phosphate buffer pH 7.4 under stirring condition with a stir bar for 0-5 hrs. Alpha synuclein oligomers were characterized by dot blot and western blot using conformational oligomer specific antibody A11 and Alpha synuclein Ab Syn1.

Intrastriatal injection of recombinant human α-synuclein oligomers. At 10 weeks of age, male mice were deeply anesthetized with vaporized isoflurane on a stereotactic frame. Animals were bilaterally injected with 2 μL (per side) of 300 μM oligomeric α-synuclein intrinsically promoted by Galectin-3, or phosphate-buffered saline (PBS) as controls. Solutions were injected at a constant rate of 0.5 L/min and the needle left in place for 5 min followed by slowly with—drawing the needle. Coordinates for the striatum were +0.2 mm AP, ±2.0 mm ML, −2.6 mm DV. Two separate cohorts were utilized in this study. The first cohort had an experimental group injected with Alpha synuclein+Galectin-3 and a control group with bur hole only.

Behavior testing. Locomotor function test was conducted before and every month after injection of oligomers. Mice were handled for 3 days before testing began and habituated to testing room for 1 h at the start of each testing day. The order of test will be designed to minimize stress to the animals, such that low-stress tasks will be completed before high-stress tasks. Additionally, mice received at least one day rest between each test.

To further test motor activity, mice were placed on an accelerating rotarod apparatus, and time taken to fall was measured. Mice were trained on the apparatus over 2 days, with the rotarod speed increasing from 4 rpm to 40 rpm over 300 s. If mice had not fallen by 120 s on the testing trial, the rotation was halted, the mouse was removed, and the time was recorded as 120 s. Mice underwent three trials per day, with an inter-trial rest time of at least 30 min.

Animals and Husbandry. 10 weeks old C57BL/6J male mice (n=30) were used for experiments. Mice were on a 12-h light/dark cycle and had ad libitum access to food and water. Animals were housed in pairs in a controlled temperature environment under a 12-h light/dark cycle, with access to chow and water ad libitum. All animals were provided at least 72 h to acclimate following arrival at the facility, with periodic cage changes, before surgery.

Administration and Sample Collection. 10-week old C57BL/6J male mice mimicking PD pathology after stereotactic injection of αSYN oligomers were first administered with antibody treatments via intraperitoneal (i.p.) injection. Mice were dosed with 30 mg/kg anti-HEL mouse IgG2A (isotype control group) or received 30 mg/kg mSIF001 (active group) via i.p. injection four weeks (2 doses/week). After four weeks, locomotor function test was conducted to evaluate the efficacy of mSIF001Ab. Mice were sacrificed, and brain tissues were processed for histological staining.

Brain tissue processing. Briefly, animals were deeply anesthetized with 50 mg/kg Zoletil (i.p.) and transcardially perfused with phosphate buffered saline (PBS) followed by 4% paraformaldehyde (PFA) in PBS. Brain was then post-fix in 4% PFA for 24 hrs at 4° C. before being transferred to a 30% sucrose solution for overnight cryoprotection. Coronal sections containing the medial and ventral hippocampus were sliced into 25 μm thick slices on a freezing stage cryostat and stored at 4° C. in 0.1M PBS for staining.

Iba1 and αSYN Immunofluorescence staining. Brain sections were washed with PBS for 3 times, 10 min each time. Sections were then incubated with a blocking solution (PBS with 5% goat serum, 0.5% Triton X-100) at room temperature for 1 h. Tissues were incubated overnight with, IBA-1, and αSYN antibodies (1:250 diluted with the blocking solution) overnight at 4° C. After being washing with PBS three times in the morning of the next day, sections were incubated with the blocking solution containing 1:250 diluted secondary antibody for 2h. Brain sections were incubated with 5 μg/mL DAPI in PBS for nuclear staining for 15 minutes and mounted on to microscope slides to dry in a dark place and then were added with antifade mounting medium with DAPI for further analysis Bioanalysis. Five brain tissue slices were taken from each mouse for staining, and the hippocampus region was selected for Nikon ECLIPSE Ti2-U. To analyze the staining intensities of Iba1, the biomarkers of microglia, and αSYN, the antibody for αSYN aggregates, respectively, ordinary one-way ANOVA was used to compare active antibody group with isotype control antibody group. A p-value below 0.05 was considered significant in post-hoc testing (*p<0.05; *p<0.01; p<0.001). A p≥0.05 was considered not significant (ns). All statistical analyses were performed using Prism 9 macbook (GraphPad, La Jolla, CA).

Figure 18:
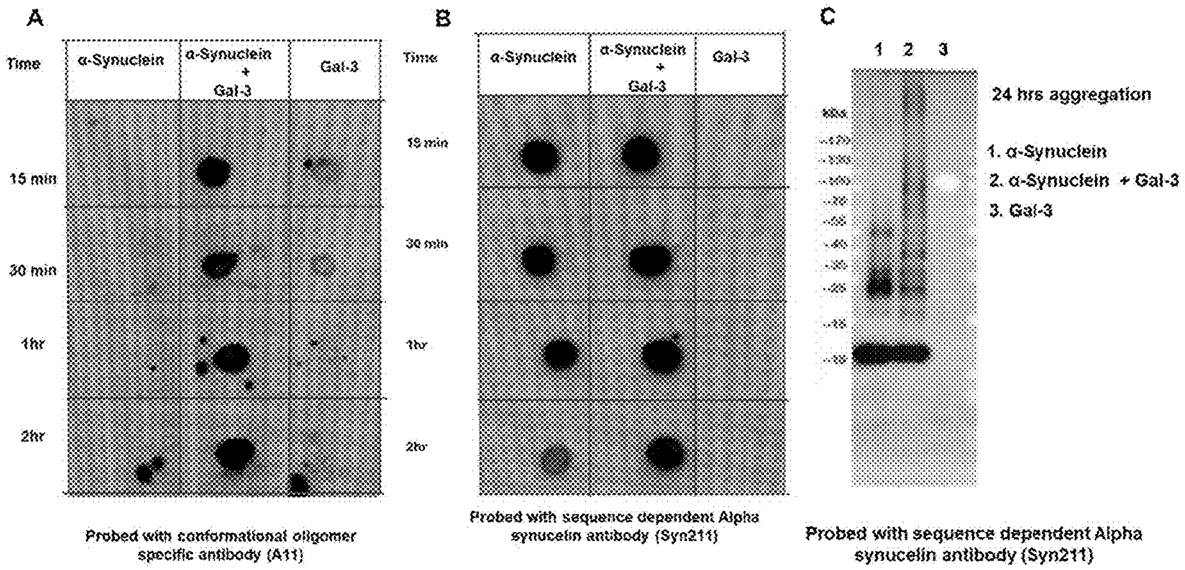
FIG. 18 depicts Galectin-3 intrinsically promotes oligomerization of Alpha synuclein (a-Synuclein).

Results. It has been observed Galectin-3 intrinsically promotes oligomers of amyloid proteins. αSYN oligomers will be prepared by incubating monomeric α-synuclein (300 μM) with and without Galectin-3 (100 ug/ml) in phosphate buffer pH 7.4 under stirring condition with a stir bar for 0-5 hrs. Alpha synuclein oligomers were characterized by western blot using conformational oligomer specific antibody A11 and αSYN Ab Syn1. As shown in FIGS. 18A and 18B, the first two lanes were loaded with equal amounts of αSYN, as confirmed by the anti-αSYN antibody Syn211 (FIG. 18B), only αSYN loaded with Gal-3 formed oligomers that were detected using the conformational oligomer specific antibody A11 (FIG. 18A). There finding indicates that Galectin-3 intrinsically promotes αSYN oligomers. After 4 hrs of incubation with Galectin-3, αSYN form LMW and HMW oligomers characterized by Western blot as shown in FIG. 18C.

Figure 19:
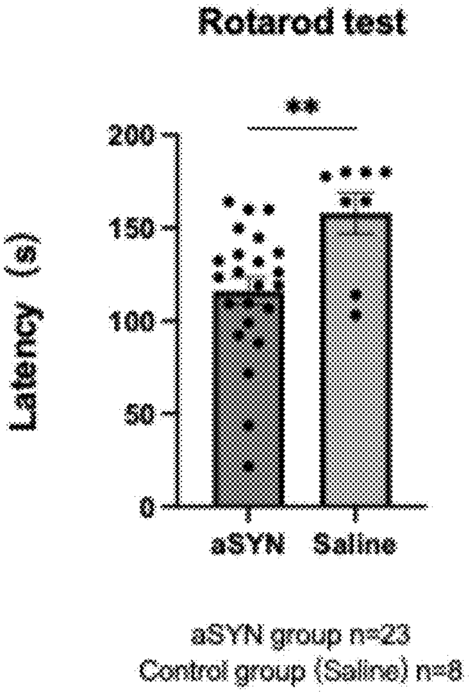
FIG. 19 depicts stereotactic injection of a-Synuclein oligomers leads to locomotor dysfunction.

Animals will be bilaterally injected with 2 μL (per side) of 300 μM oligomeric α-synuclein intrinsically promoted by Galectin-3, or phosphate-buffered saline (Saline) as controls. Solutions will be injected at a constant rate of 0.5 L/min and the needle left in place for 5 min followed by slowly with—drawing the needle. Coordinates for the striatum were +0.2 mm AP, ±2.0 mm ML, −2.6 mm DV. After 2 months, animals under locomotor function test by rotarod and it was observed animals stereotactically injected with α-synuclein oligomer shows statistically significant deficit in locomotor function test in terms of latency as compared to age matched saline treated controls as shown in FIG. 19.

Figure 20:
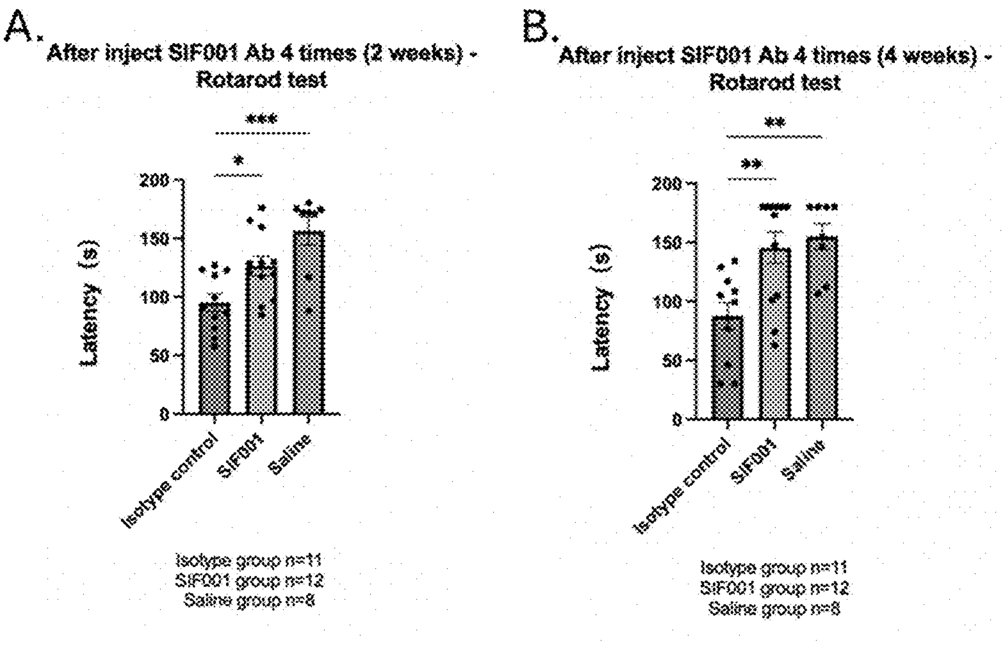
FIG. 20 depicts treatment with mSIF001 significantly improved locomotor function as compared to the isotype control antibody treatment using rotarod.

We investigated the effect of mSIF001 on the reduction of neuroinflammation and α-Synuclein pathology induced by toxic α-Synuclein oligomers. After Induction of locomotor dysfunction by α-Synuclein oligomers, mice were dosed with 30 mg/kg anti-HEL mouse IgG2A (isotype control group) or received 30 mg/kg mSIF001 (active group) via i.p. injection for four weeks (2 doses/week). In order to investigate the effect of antibodies, mice underwent the locomotor function test using rotarod. It was observed that, treatment with anti-Galectin-3 antibody shows improvement in locomotor function and the latency time was statistically significant as compared to mice treated with isotype control Ab. As shown in FIGS. 20A and 20B, significant improvement in locomotor function in terms in increase in latency time was statistically significant in mice dosed with mSIF001 Ab as compared to age matched isotype-control treated mice both after 2 and 4 weeks of treatment.

Figure 21:
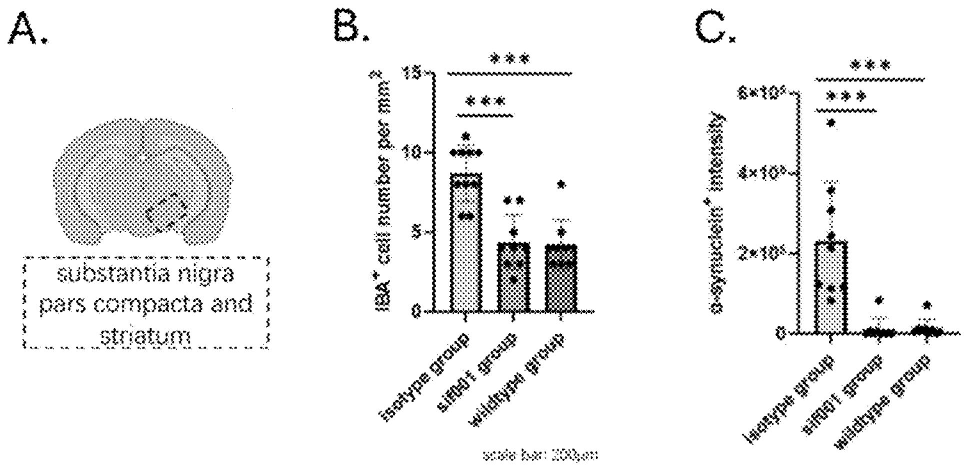
FIG. 21 depicts treatment with SF001 Ab significantly reduced activated microglia probed with IBA-1 Ab (B) and aggregated α-Synuclein (C) in the PD mimic model in the selected region of substantia nigra in mouse brains (A).

To further explore any pathological changes underlying neuroinflammation, brain tissues from isotype control and active groups, and a group without any treatment, were immuno histologically stained with IBA1 biomarkers for activation of microglia. FIG. 21A indicates the region to be chosen for analysis and it is within pars *compacta* of the substantia nigra and striatum. As shown in FIG. 21B, mSIF001 significantly reduced activation of microglia indicating that mSIF001 significantly reduced the activated microglia in PD mimic model through disease modification.

In Parkinson's disease, alpha-synuclein mis-folds and aggregates into clumps called Lewy Bodies. It is hypothesized that these may be toxic and the clumps of α-Synuclein get passed from one neuron to another, possibly causing the spread of the disease through the brain. In order to investigate the toxic α-Synuclein aggregates underlying the PD pathology brain sections were stained with α-Synuclein antibody Syn211. By immunofluorescence, it was observed that mSIF001 significantly reduced α-Synuclein aggregated as compared to Isotype control mice indicating that mSIF001 significantly reduced the aggregated α-Synuclein in PD mimic model through disease modification, as shown in FIG. 21C.

Conclusions

In Parkinson's disease mice model, treatment with mSIF001 was able to significantly improves locomotor function test and significantly reduced neuroinflammation and reduced the aggregated α-Synuclein.

Example 9. SIF001 for Alzheimer's Disease Treatment

This example illustrates therapeutic effects of SIF001 in a Alzheimer's disease mimic mice model.

Summary

Alzheimer's disease (AD) is a chronic progressive neurodegenerative disorder that is the leading cause of dementia among older adults. In the United States, AD is one of the leading causes of death, ranking 6th among US adults and 5th among adults aged 65 years or older (CDC, 2020). AD is hypothesized to be caused by toxic changes in the brain involving 2 major pathological hallmark proteins, Aβ and tau. The disease is characterized by accumulation of extracellular amyloid plaques, intracellular neurofibrillary tangles, and extensive synaptic loss leading to progressive cognitive impairment and eventually dementia. Abnormal tau (hyperphosphorylated tau) accumulates to form neurofibrillary tangles, while Aβ plaques accumulate both extracellular and intracellular. Amyloid plaques and hyperphosphorylated tau in the brain are therefore the major hallmarks of AD. Gal3 is highly upregulated in the brains of AD patients and transgenic mouse models of AD (Alzheimer's Association. 2018 Alzheimer's disease facts and figures. Alzheimer's Dement. 201814:367-429). It has been associated with aggregation of Aβ plaques in AD mouse models. Injection of Aβ in Gal3 knockout mice demonstrated reduction in AB oligomerization, whereas injection of Aβ in mice overexpressing Gal3 demonstrated enhanced AB oligomerization (Tao, C, Cheng, K, Ma, Y, et al. Galectin-3 promotes Aβ oligomerization and Aβ toxicity in a mouse model of Alzheimer's disease. Cell Death Differ. 2020; 27:192-209). The primary objective of this in vivo study is to assess the dose range therapeutic effect of anti-Galectin-3 antibody (mSIF001) on hippocampal dependent spatial memory test and reducing neuroinflammation as well as AD pathology in APP/PS1 mice (transgenic mouse model of AD). Based on different conformational states as monomers, oligomers and fibril of amyloid protein, conformational oligomers are neurotoxic in AD. In vitro, we found that Gal-3 intrinsically promotes Aβ oligomerization and that SF001 reduced or degraded Aβ42 oligomer formation. APP/PS1 mice were dosed with 30 mg/kg anti-HEL mouse IgG2A (isotype control group) or received dose range of 3, 10 and 30 mg/kg mSIF001 (active group) via intraperitoneal (i.p.) injection four weeks (2 doses/week). Treatment with anti-Galectin-3 antibody of 30 mg/Kg shows improvement in hippocampal dependent memory test (Morris water maze) and was statistically significant as compared to mice treated with Isotype control Ab.

Alzheimer's disease (AD) is one of the most common devastating, irreversible, neurodegenerative disorders related to age, that eventually result in death. Amyloid beta (Aβ) plaque and neurofibrillary tangles deposition are two pathological indicators of AD. So far, there are seven FDA approved prescription drugs to treat AD. However, these drugs can only relieve symptoms of the disease temporarily and none one of them has proven the ability to cure or stop the progression of the disease. The newest FDA-approved drug lecanemab only works in the stage of mild cognitive impairment (MCI) or very early AD (Redzic, Z. Molecular biology of the blood-brain and the bloodcerebrospinal fluid barriers: Similarities and differences. Fluids Barriers CNS. 2011, 8:3). Galectin-3 (Gal-3) plays a pivotal role in microglia-mediated neuroinflammation causing many neurological disorders. In vitro, we found that Gal-3 intrinsically promotes oligomerization and that SF001 reduced or degraded Aβ42 oligomer formation. A transgenic mouse model of AD shows increasing in Aβ aggregates and neuroinflammation and it was used to assess the dose range effect of mSIF001, an anti-Gal-3 monoclonal antibody on the spatial memory hippocampal dependent function test.

Methods and Experiments

Figure 22:
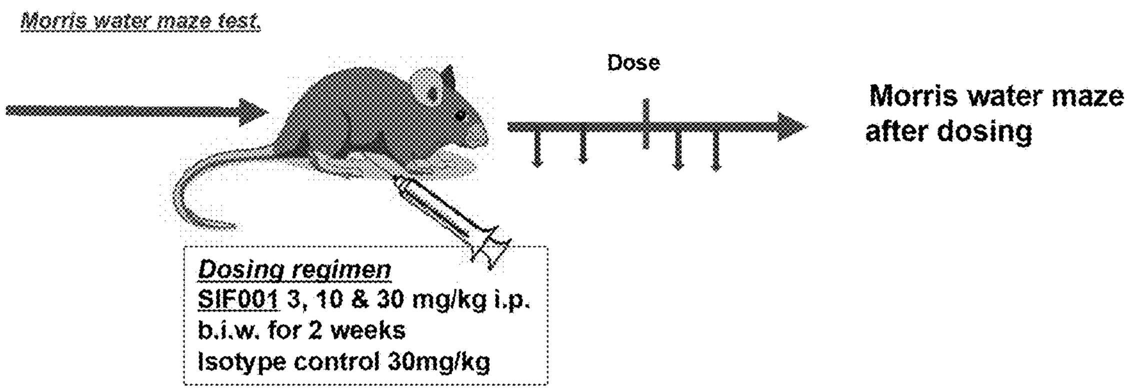
FIG. 22 depicts study design and dosing regimen of the mouse study to evaluate the therapeutic effects of mSIF001 in the Alzheimer's disease mimic mouse model.

Study Design. Study design is outlined in FIG. 22.

Preparation of Aβ42 Oligomers.

It has been observed Galectin-3 intrinsically promotes oligomers of amyloid proteins. $A\beta_{42}$ oligomers were prepared by incubating monomeric $A\beta_{42}$ (100 ug) with and without Galectin-3 (100 μg/ml) in phosphate buffer pH 7.4 under stirring condition with a stir bar for 0-3 hrs. The solution was continuously stirred using a stir bar while incubating at room temperature. At various time points after mixing, samples were taken and probed on a Whatman nitrocellulose membrane for dot blotting. Different concentrations of SIF001 and isotype control (1-100 μg/ml) antibodies were added to Gal-3-induced $A\beta_{42}$ oligomers. After 1 hour of incubation, 2 μl of each sample was pipetted onto a dot blot. $A\beta_{42}$ oligomers were characterized by dot blotting and western blotting using conformational oligomer specific antibody A11 and Aβ sequence-dependent antibody 6E10. Similar procedure was used for the aggregation of Tau, Phospho-Tau, APOE3 & APOE4.

Dot Blotting

Dot blot membrane was incubated in 10% nonfat dried milk in TBS-T for 1 hour at room temperature to block nonspecific binding. The blot was then incubated with A11 conformational oligomer-specific antibody (Invitrogen) and Aβ sequence dependent antibody 6E10 (BioLegend) overnight at 4° C. After three washes in TBS-T, the membrane was incubated with the appropriate secondary antibody (goat anti-rabbit IgG H&L [HRP] or goat anti-mouse IgG H&L [HRP], Abcam) for 1 hour at room temperature. Following three washes in TBS-T, the membrane was incubated by mixing equal amounts of chemiluminescent detection reagents (Advansta) for 1-5 sec. The dot blot images of the results were obtained using imager (Bio-Rad Chemi doc).

5.2.2 Western Blotting

Fifteen μl of each sample were mixed with 4× loading buffer, and the resulting 20-ul mixtures were loaded onto a 4-12% Criterion™ XT Bis-Tris Protein Gel (Bio-Rad). The gel was run at 100 V in sodium dodecyl sulfate-polyacrylamide gel electrophoresis (SDS-PAGE) apparatus (Bio-Rad), and the resolved proteins were transferred onto a nitrocellulose membrane at 300 mA for 60 min. The membrane was thereafter processed as described above. Blots were incubated with 6E10 antibody.

Animals

APPPS1 mice contain human transgenes for both APP bearing the Swedish mutation and PSEN1 containing an L166P mutation, both under the control of the Thy1 promoter. In these mice, expression of the human APP transgene is approximately 3-fold higher than endogenous murine APP. Human $A\beta_{42}$ is preferentially generated over $A\beta_{40}$, but levels of both increase with age. AB deposition begins at 6 weeks of age in the cortex and 3-4 months of age in the hippocampus. Six months old APPSwe mice were purchased from Huachuang Sino, Ltd. For SIF001 and Iso-control treatment, mice were administered intraperitoneally (IP) with doses of 3, 10 and 30 mg/kg of SIF001 and isotype control antibody of 30 mg/kg.

Hippocampal Dependent Spatial Memory Test

Morris water maze test was conducted before and after receiving the different doses of SIF001 antibody. Mice were handled for 3 days before testing and were habituated to testing room for 1 h at the start of each testing day. The order of test will be designed to minimize stress to the animals, such that low-stress tasks will be completed before high-stress tasks. Additionally, mice received at least one day rest between each test.

Morris water maze is a special memory task related to hippocampus. The apparatus used for all water maze tasks was a circular aluminum tank (1.5 m diameter) painted white and filled with water maintained at 26° C.-29° C. The maze was located in a room containing simple visual, extra-maze cues. To reduce stress, mice were placed on the platform in both the hidden and cued versions of the task for 15 sec. prior to the first training trial. Mice were trained to swim to a circular clear Plexiglas platform (14 cm diameter) submerged 1.5 cm beneath the surface of the water and invisible to the mice while swimming. The platform location was selected randomly, but was kept the same for each individual mouse throughout training. On each trial, the mouse was placed into the tank at one of four designated start points in a pseudorandom order. Mice were allowed 60 sec to find the submerged platform. If a mouse failed to find the platform at 60 sec, it was manually guided to the platform and allowed to remain there for 15 sec. After this, each mouse was placed into a holding cage under a warming lamp for 30 s before beginning the next trial. To ensure that memory differences were not due to lack of task learning, mice were given four trials a day for as many days as required to train the APP/PS1 mice to reach the criterion (<20 sec.). To control for overtraining, probe trials were run for each group, both as soon as they reached group criterion and after all groups had reached criterion. We trained the APP/PS1 mice for 8 days. Retention of the spatial training was tested 1.5 hr and again 24 hr after the last training trial. Both probe trials consisted of a 60s free swim in the pool without the platform. Mice were monitored by a camera mounted in the ceiling directly above the pool to record the 1.5 hr and 24 hr test. The parameters measured during the probe trial included initial latency to cross the platform location, number of platform location crosses, and time spent in the quadrant opposite to the one containing the platform during training Animals and Treatment Groups 6 months old APP/PS1 (n=30) and age matched wild type C57BL/6J mice (n=8) were used for experiments. Animals were housed in pairs in a controlled temperature environment under a 12-h light/dark cycle, with access to chow and water ad libitum. All animals were provided at least 72 h to acclimate following arrival at the facility, with periodic cage changes, before surgery. All mice were divided to three treatment groups as shown in Table 9.

TABLE 9

| Treatment groups | | | | |
|---|---|---|---|---|
| Treatment Group | Animal | Dose | Animal No. | Route |
| Isotype control antibody (Anti-HEL antibody) | APP/PS1 | 30 mg/kg | 4 | Intraperitoneal |
| Active (mSIF001 in mouse IgG2A backbone) | APP/PS1 | 3, 10 and 30 mg/kg | 5 per dose | Intraperitoneal |
| Wild type C57BL/6J mice | C57BL/6J | No dose | 10 | |

Bioanalysis

To analyze the behavior memory data, ordinary one-way ANOVA was used to compare active antibody group with isotype control antibody group. A p-value below 0.05 was considered significant in post-hoc testing (*$p<0.05$; $p<0.01$; *$p<0.001$). A $p\geq 0.05$ was considered not significant (ns). All statistical analyses were performed using Prism 9 (GraphPad, La Jolla, CA).

Results

Figure 23:
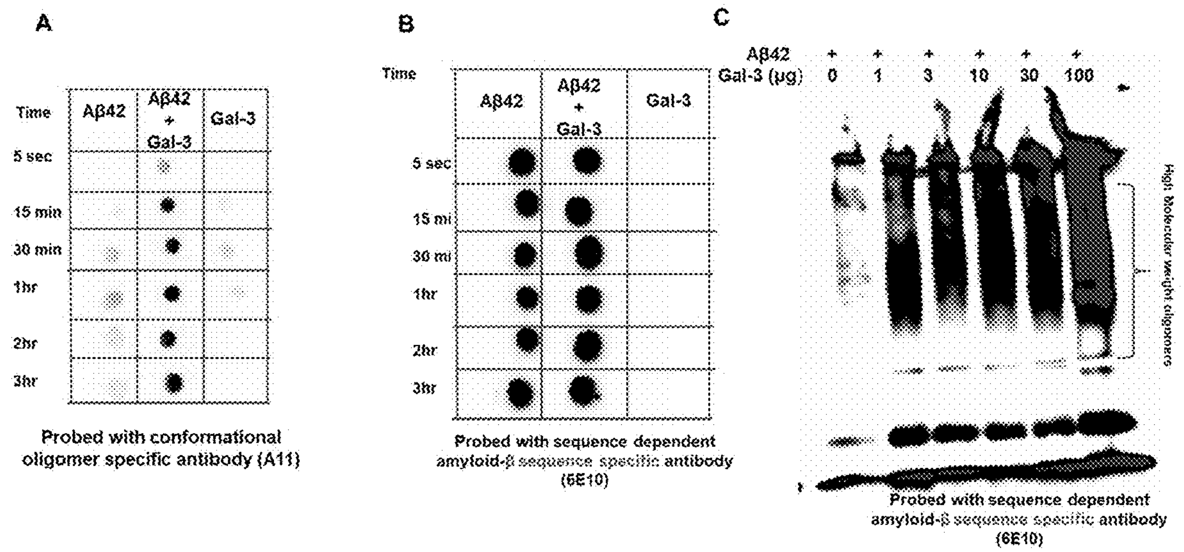
FIG. 23 depicts Galectin-3 intrinsically promotes oligomerization of $A\beta_{42}$, as characterized by dot blot using a conformational oligomer specific antibody A11 (A) and an $A\beta_{42}$ sequence-dependent antibody 6E10 (B). Gal-3 oligomerized $A\beta_{42}$ peptide into high molecular weight oligomers in a dose dependent manner as characterized by Western blot probed with an Aβ sequence-dependent antibody 6E10 (C).

It is widely accepted that Aβ oligomers rather than monomers and fibrils play a critical role in AD progression. $A\beta_{42}$ oligomers can trigger a series of toxic reactions in neurons, such as receptor disability, mitochondrial damage, $Ca^{2+}$ homeostasis dysregulation and abnormal Tau phosphorylation. Targeting the most toxic oligomers may be an effective treatment for AD by preventing aggregation of $A\beta_{42}$. Gal-3 was reported to be involved directly or indirectly in the oligomerization of AB in in-vivo studies. It has been observed Galectin-3 intrinsically promotes oligomers of amyloid proteins. $A\beta_{42}$ oligomers were prepared by incubating monomeric $A\beta_{42}$ (100 μg) with and without Galectin-3 (100 ug/ml) in 100 mM phosphate buffer pH 7.4 under stirring condition with a stir bar for 0-3 hrs. $A\beta_{42}$ oligomers were characterized by dot blotting using conformational oligomer specific antibody A11 (FIG. 23A) and total $A\beta_{42}$ was demonstrated by $A\beta_{42}$ sequence-dependent antibody 6E10 (FIG. 23B). Gal-3 oligomerized $A\beta_{42}$ peptide into high molecular weight oligomers in a dose dependent manner as shown in Western blot probed with Aβ sequence dependent antibody 6E10 (FIG. 23C). As shown in FIG. 23C, the sample without Gal-3 exhibits significantly fewer high molecular weight oligomers, while with the increasing amount of Gal-3, the intensity of high molecular weight oligomers also increases, indicating that Gal-3 dose-dependently enhances the oligomerization.

Figure 24:
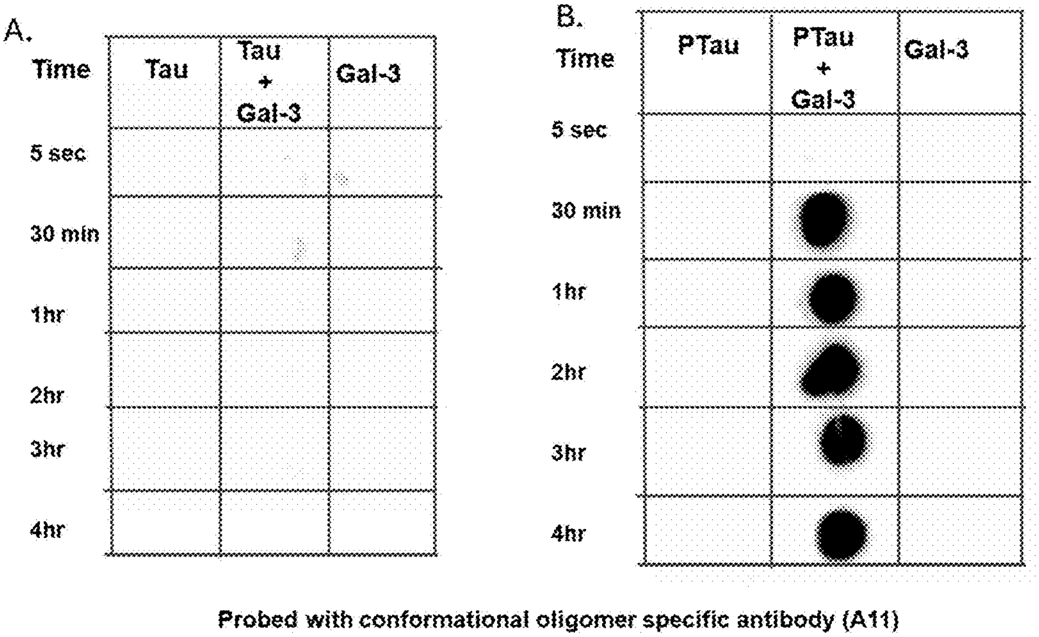
FIG. 24 depicts Galectin-3 intrinsically promotes oligomerization of Phospho Tau (396) (B) but not normal Tau (A).

Abnormal tau (hyperphosphorylated tau) is another pathological hallmark of AD. In addition to Aβ, Gal-3 intrinsically promotes aggregation of phosphorylated tau (FIG. 24B), but not normal tau (FIG. 24A), probed with conformational oligomer antibody A11.

Figure 25:
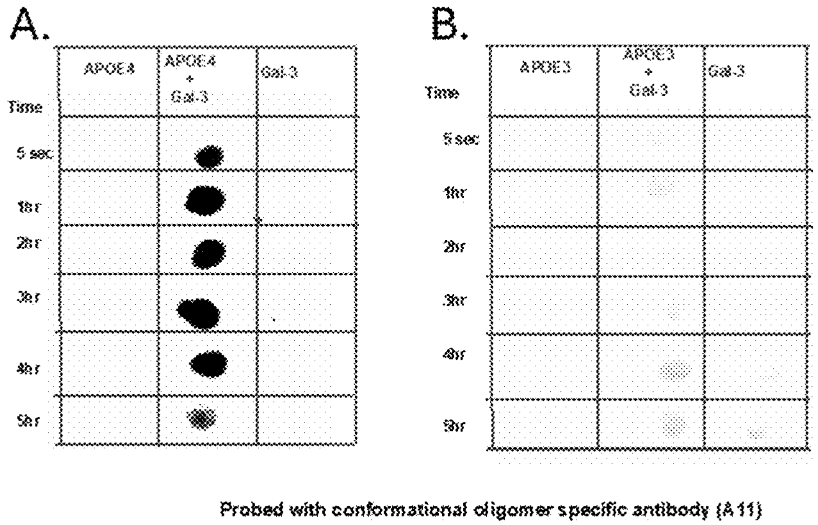
FIG. 25 depicts Galectin-3 intrinsically promotes oligomerization of APOE4 (A) but not APOE3 (B).

AD is the most common cause of dementia worldwide, and its prevalence is rapidly increasing due to extended lifespans. Among the increasing number of genetic risk factors identified, the apolipoprotein E (APOE) gene remains the strongest and most prevalent, impacting more than half of all AD cases. While the ε4 allele of the APOE gene significantly increases AD risk. Genome-wide association studies revealed that the ε4 allele, but not the ε3 allele, of the apolipoprotein E (APOE4) gene, is the strongest genetic risk factor for AD and Lewy body dementia (LBD), signifying an important role of APOE4 in both amyloid-β (Aβ) and α-Synuclein pathogenesis. Here we showed Gal-3 intrinsically promotes APOE4 but not APOE3 as shown in FIGS. 25A and 25B.

Figure 26:
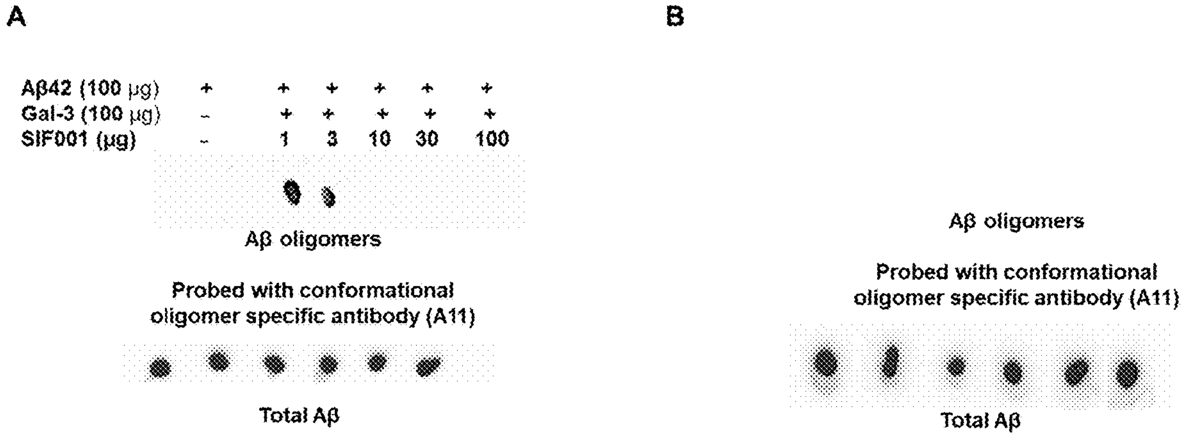
FIG. 26 depicts SIF001Ab dose-dependently dissolves Aβ42 oligomers induced by Gal-3 (A), while an iso-type control antibody had no effect (B).

Next, we tested if Gal-3 blocking antibodies can dissolve $A\beta_{42}$ oligomers induced by Gal-3. As shown in FIGS. 26A and 26B, SIF001 dissolved $A\beta_{42}$ aggregates in a dose-dependent manner, while an iso-type control antibody had no effect.

Figure 27:
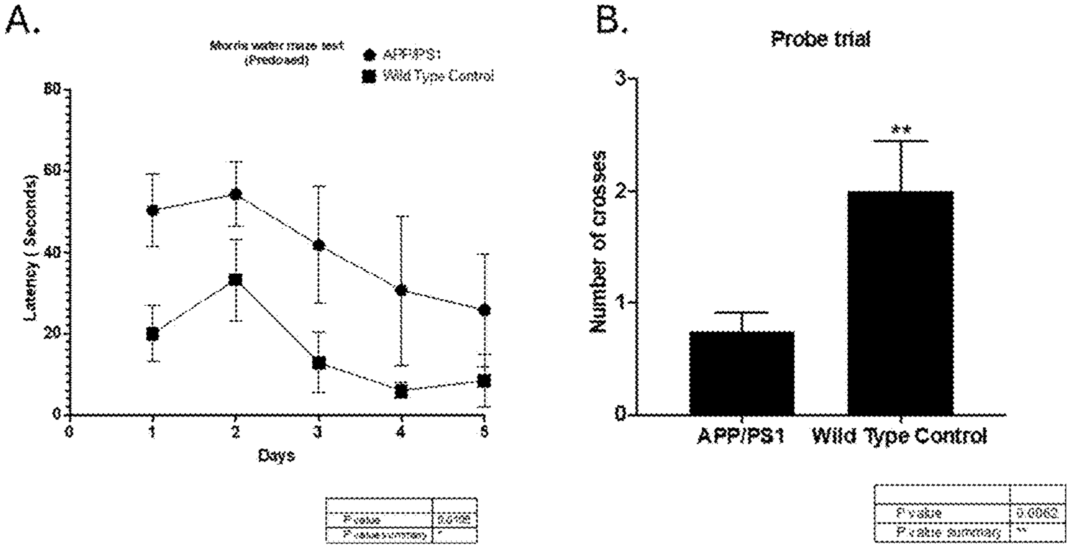
FIG. 27 depicts the cognitive deficit of APP/PS1 mice in terms of latency to reach the platform (A) and number of crosses in the Morris water maze (B) as compared to age matched wild type mice.

We further investigated the hippocampal dependent memory function test in AD transgenic mice model. APP/PS1 mice demonstrated significant deficits in cognition in terms of latency to reach the platform and number of crosses in the Morris water maze as compared to age matched wild type mice, as shown in FIGS. 27A and 27B.

Figure 28:
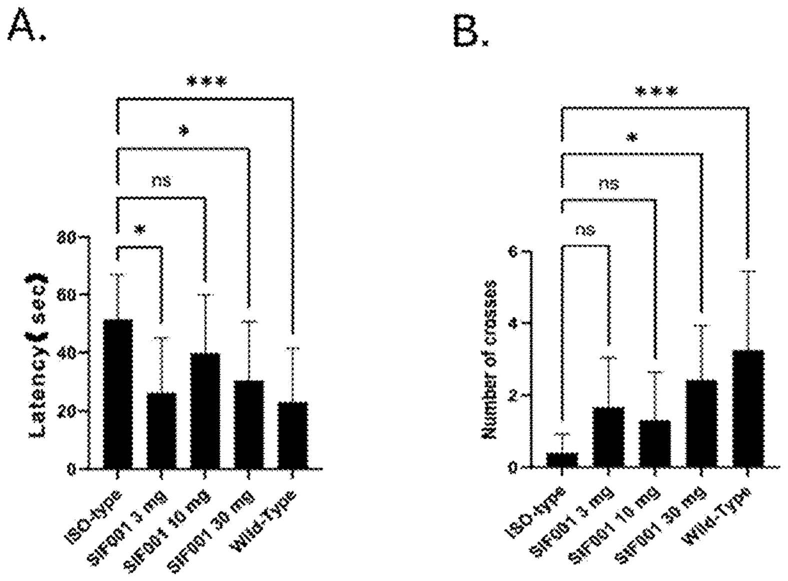
FIG. 28 depicts dose dependent efficacy of SIF001 in Alzheimer's mouse model APP/PS1 on hippocampal dependent spatial memory (Morris water maze training) in terms of latency to reach the platform (A) and number of crosses (B).

To explore the effect of SIF001 Ab (3-30 mg/kg) on spatial memory test, Morris water maze test was conducted. As shown in FIGS. 28A and 28B, mice dosed with 10 and 30 mg/kg significantly decreased latency to reach platform (FIG. 28A) and mice with 30 mg/kg significantly increased the number of crosses of the platform (FIG. 28B), as compared to the isotype control antibody treated mice.

Conclusions

Galectin-3 intrinsically promotes oligomerization of $A\beta_{42}$, Phospho tau and APOE4 but not normal tau. Anti galectin-3 antibody SIF001 dissolved $A\beta_{42}$ aggregates in a dose-dependent manner, while an iso-type control antibody had no effect. In APP/PS1 transgenic mouse model of AD, treatment with mSIF001 of 30 mg/kg was able to show statistically significant improvement in cognitive function in terms of memory as compared to the isotype antibody treated mice.

Example 10. SIF001 Investigator-Initiated Trial (IIT) for Treating Drug-Resistant Epilepsy This example illustrates a pilot study of a monoclonal antibody (SIF001) for the treatment of drug-resistant epilepsy.

The exemplary study is a multicenter, prospective, open-label study to explore the efficacy and safety of the monoclonal antibody SIF001 in the treatment of drug-resistant epilepsy. A total of 6 patients with drug-resistant epilepsy who could not undergo respective surgery were enrolled (3 patients in each center). The effectiveness of the monoclonal antibody SIF001 was evaluated by recording epilepsy diaries and electroencephalogram epileptic discharges, and the safety was evaluated by recording adverse reactions.

SIF001 Product

SIF001 is a monoclonal antibody drug (IgG4) targeting Gal-3. It is a colorless transparent solution stored in a disposable sterile glass bottle for injection, sealed with a rubber stopper and an aluminum flat flip cap. Each bottle contains 10 mL, with a concentration of 20 mg/mL and an optimal storage temperature of 2-8 degrees Celsius.

SIF001 Drug Safety

Monoclonal antibodies based on the same target and the same region have similar safety profiles, so the safety profile of SIF001 should be similar to that of TB006, a similar product that has completed clinical trials. In a Phase 1 single-dose escalation study of healthy volunteers completed in the United States, the monoclonal antibody TB006 showed good tolerability and safety even at a dose of up to 5000 mg. In a Phase 2 clinical trial of TB006 for Alzheimer's disease that has been completed, only 4 drug-related adverse reactions were reported among 63 patients who received the drug, including one dizziness (1/63, 1.59%), one phlebitis (1/63, 1.59%), and two infusion reactions (2/63, 3.17%), all of which were mild, sporadic and self-limiting, and the drug had good safety.

Based on the above conditions, the potential benefits of SIF001 treatment to patients far outweigh the possible risks, so an exploratory pilot study is planned to evaluate the safety and efficacy of this product as an adjunctive treatment for drug-resistant epilepsy. Referring to the dose of TB006, this study uses a 50 mg/kg intravenous injection for two times.

Study Design

1. Overall Design and Determination Basis

The purpose of this trial is to preliminarily verify the safety and efficacy of monoclonal antibody SIF001 in the treatment of drug-resistant epilepsy. This project is an exploratory clinical trial. After enrollment, the subjects need to receive a single intravenous injection of monoclonal antibody SIF001. The trial adopts a multicenter, exploratory pilot design. This study will be conducted in two centers in China, and a total of 6 subjects are planned to be included. After the subjects sign the informed consent form (ICF) approved by the Ethics Committee, they will enter the screening procedure to screen subjects who meet the inclusion criteria and do not meet any of the exclusion criteria, and assign subject numbers in order of enrollment time. After completing all follow-up visits for each case, the next case will be enrolled.

Subjects were treated with intravenous monoclonal antibody SIF001 on the 1st and 15th days (±1 day) after enrollment. On the 28th day after enrollment, the number of SIF001 injections could be increased according to the patient's specific situation. The frequency of subsequent additional treatment was limited to no more than once every 28 days, and continued for 1 year after treatment. The clinical evaluation time nodes include 7 days after the first treatment, 14 days after treatment (±1 day), 21 days after treatment (±1 day), 28 days after treatment (±3 days), and 84 days after treatment (±7 days). If additional treatment is given, the follow-up point should also include 28 days (±3 days) after each subsequent treatment. Laboratory tests, scale evaluations, etc. are performed at the specified nodes to verify the treatment effect and safety.

2. Selection of Subjects

Subjects were selected using the following inclusion criteria:

a) Diagnosed with drug-resistant epilepsy;

b) Aged ≥10 and ≤50 years old, regardless of gender;

c) The subject is considered unable to benefit from respective surgery through preoperative evaluation of epilepsy surgery or the subject refuses the treatment;

d) The subject is not suitable for or refuses implantable vagus nerve stimulation or deep brain stimulation treatment;

e) Epileptic seizures ≥8 times per month, including focal seizures and/or generalized seizures;

f) Not participated in other clinical trials within three months;

g) The subjects and their families have reasonable expectations that the subjects can keep an epileptic seizure diary alone or with the help of their family members;

h) Volunteer to participate in this trial and sign the written informed consent;

i) No severe immune deficiency;

j) Weight≥50 kg, body mass index (BMI) between 18-35.

3. Enrollment Time and Study Duration

This feasibility trial was conducted in a hospital in China, and the enrollment time of the feasibility trial is expected to be 3 months. The expected overall duration of the feasibility study and the reasons for its determination The feasibility trial plan was formulated in 1 month, and the ethical review and approval is expected to take 1-2 months. The enrollment is planned to start in August 2024, and it will take 12-24 months from the start of enrollment to the completion of the trial and data collection. The overall duration of this trial is 15-27 months from the ethics application to the end of the trial.

The subjects are expected to participate in the trial for about 3 months, including screening (−14 to +7 days), informed consent, drug treatment (+1 day, +15 days), 7 days after treatment, 14 days after treatment (±1 day), 21 days after treatment (±1 day), 28 days after treatment (±3 days), and 84 days after treatment (±7 days). If additional treatment is given, the follow-up point should also include 28 days (±3 days) after each subsequent treatment.

4. Evaluation Methods

Based on previous clinical research and treatment practices, this trial requires clinical evaluation of the subjects enrolled at screening (−14~+7 days, 0 day for enrollment), drug treatment day (+1 day, +15 day), 7 days after treatment, 14 days after treatment (±1 day), 21 days after treatment (±1 day), 28 days after treatment (±3 days), and 84 days after treatment (±7 days). If additional treatment is given, the follow-up point should also include 28 days (+3 days) after each subsequent treatment. Laboratory tests, scale evaluations, etc. are performed at specified nodes to verify the treatment effect and safety.

A. Effectiveness Evaluation

Main Evaluation Indicators

The main evaluation indicator set in this trial is the reduction rate of epileptic seizure frequency 28 days after drug treatment compared with the baseline, which is used to evaluate the effectiveness of treating epilepsy.

Evaluation of epilepsy treatment efficacy: The subjects or their family members record the type, number, and duration of epileptic seizures every day. The researchers count the frequency of epileptic seizures on a weekly basis. The treatment is considered effective if the frequency of epileptic seizures in the subjects is reduced by 50% or more compared to the baseline. The treatment is considered "significantly effective" if the frequency of epileptic seizures is reduced by more than 90%. The treatment is considered "effective" if the frequency of epileptic seizures is reduced by 50%-89% compared with before. The treatment is considered "ineffective" if the frequency of epileptic seizures decreased by 49% or less compared with the previous period.

Total effective=significant effect+effective

Effectiveness=(total number of effective subjects/total number of subjects participating in clinical trials)×100%

Inefficiency=(total number of ineffective subjects/total number of subjects participating in clinical trials)×100%

Evaluation time points: screening period, 7 days after treatment, 14 days (±1 day), 21 days (±1 day), 28 days (±3 days), 84 days (±7 days). If additional treatment is given, the follow-up point should also include 28 days (±3 days) after each subsequent treatment.

Secondary Evaluation Indicators

Secondary evaluation indicators include the following three changes.

① Changes in the number of EEG epileptiform discharges relative to the baseline, and compare with the baseline to evaluate the improvement of EEG.

Evaluation method: The number of epileptiform discharges per hour recorded by EEG.

Evaluation time points: screening period, 7 days after treatment, 28 days (±3 days), 84 days (±7 days). If additional treatment is given, the follow-up point should also include 28 days (±3 days) after each subsequent treatment.

② Changes from baseline in the Quality of Life in Epilepsy Scale-31 (QOLIE-31) after treatment.

Evaluation method: The patients were evaluated according to the Quality of Life in Epilepsy Scale-31 (QOLIE-31).

Evaluation time points: screening period, 28 days (±3 days), and 84 days (±7 days) after treatment. If additional treatment is given, the follow-up point should also include 28 days (±3 days) after each subsequent treatment.

③ Changes in the Hamilton Depression Rating Scale and Hamilton Anxiety Rating Scale of epilepsy patients relative to baseline after treatment.

Evaluation method: Evaluation according to the Hamilton Depression Rating Scale and the Hamilton Anxiety Rating Scale.

Evaluation time points: screening period, 28 days (±3 days), and 84 days (±7 days) after treatment. If additional treatment is given, the follow-up point should also include 28 days (±3 days) after each subsequent treatment.

B. Safety Evaluation

Safety evaluation includes the following six criteria.

① Collect and analyze blood biochemistry (alanine aminotransferase, aspartate aminotransferase, creatine kinase, albumin, creatinine, direct bilirubin, glucose, high-density lipoprotein, low-density lipoprotein, total bilirubin, triglycerides, urea nitrogen, calcium ion, potassium ion, sodium ion, uric acid);

② Collect and analyze routine blood test;

④ Collect and analyze glycosylated hemoglobin;

⑤ Collect and analyze urine routine test;

⑥ Collect vital signs (blood pressure, respiration, body temperature, pulse).

Evaluation time points: screening period, 7 days, 28 days (±3 days), and 84 days (±7 days) after treatment. If additional treatment is given, the follow-up point should also include 28 days (±3 days) after each subsequent treatment.

C. Test Process

Test process includes screening period and treatment period.

(1) Screening Period (−14~+7 days)

① Sign the informed consent form;

② Collect medical history, demographic and other information;

③ Vital signs and laboratory tests (blood routine, biochemistry, glycosylated hemoglobin, urine routine, HIV antibody, Gal-3 (tested by Kangxu Biotechnology Co., Ltd.), electrocardiogram);

④ Anti-epileptic drug records;

⑤ Record of epileptic seizure frequency (daily);

⑥ Scales (Hamilton Depression Rating Scale, Hamilton Anxiety Rating Scale, Quality of Life in Epilepsy Scale-31 (QOLIE-31));

⑦ The number of epileptic discharges per hour recorded by EEG.

(2) Treatment Period

Treatment period includes (drug treatment day (+1 day, +15 day), 7 days after treatment, 14 days after treatment (±1 day), 21 days after treatment (±1 day), 28 days after treatment (±3 days), 84 days after treatment (±7 days). If additional treatment is given, the follow-up point should also include 28 days after each subsequent treatment (±3 days)).

① Drug treatment days (+1 day, +15 days): medication process records, vital signs, adverse event records, seizure frequency, anti-epileptic drug records and combined treatments.

② 7 days after treatment: vital signs, adverse event records, seizure frequency, anti-epileptic drug records and concomitant treatment, electroencephalogram, laboratory tests (blood routine, biochemistry, urine routine, electrocardiogram).

③ 14 days after treatment (±1 day): vital signs, adverse event records, seizure frequency, anti-epileptic drug records and concomitant treatments.

④ 21 days after treatment (±1 day): vital signs, adverse event records, seizure frequency, anti-epileptic drug records and concomitant treatments.

⑤ 28 days after treatment (±3 days): vital signs, adverse event records, seizure frequency, anti-epileptic drug records and concomitant treatment, electroencephalogram, laboratory tests (blood routine, biochemistry, urine routine, Gal-3 (tested by Kangxu Biotechnology Co., Ltd.), electrocardiogram), Hamilton Depression Rating Scale, Hamilton Anxiety Rating Scale, Quality of Life Assessment Scale for Epilepsy-31 (QOLIE-31).

⑥ 84 days after treatment (±7 days): vital signs, adverse event records, seizure frequency, anti-epileptic drug records and concomitant treatment, electroencephalogram, laboratory tests (blood routine, biochemistry, glycosylated hemoglobin, urine routine, Gal-3 (tested by Antenruilin (Shanghai) Biotechnology Co., Ltd.), electrocardiogram), Hamilton Depression Rating Scale, Hamilton Anxiety Rating Scale, Quality of Life Assessment Scale for Epilepsy-31 (QOLIE-31).

⑦ If additional treatment is given, the follow-up point should also include 28 days (±3 days) after each subsequent treatment: vital signs, adverse event records, seizure frequency, anti-epileptic drug records and concomitant treatment, electroencephalogram, laboratory tests (blood routine, biochemistry, glycosylated hemoglobin, urine routine, Gal-3 (tested by Kangxu Biotechnology Co., Ltd.), electrocardiogram), Hamilton Depression Rating Scale, Hamilton Anxiety Rating Scale, Quality of Life Assessment Scale for Epilepsy-31 (QOLIE-31).

D. Drug Treatment Specifications

Infusion procedures were performed by epilepsy specialist nurses. Drug storage: 4-degree refrigerator, epilepsy ward. Before administration, the dose was calculated according to the patient's weight (50 mg/kg), and the SIF001 drug (20 mg/mL) was diluted to 500 mL with sterile saline, and the infusion was completed within 1 or 2 hours. The drug was infused on the 1st and 15th days respectively. On the 28th day after enrollment, the number of SIF001 injections can be increased as appropriate according to the patient's specific situation, and the subsequent treatment frequency is limited to no more than 1 time every 28 days, and continues for 1 year after treatment.

E. Statistical Considerations

This trial was an exploratory pilot trial and only included 6 subjects. Therefore, no statistical analysis was performed. Only information such as the subjects' demographic data, medical history, and trial conditions were described.

F. Data Management

This feasibility trial uses a case report form, which is filled out by the researcher or his/her authorized personnel. The case report form for each selected case must be completed.

Study Results

Patient 1

Patient 1 was 10 years and 4 months old when enrolled to the trail. The disease started at the age of 4. The possibility of Rasmussen's encephalitis was considered high, and the family refused surgery. When the patient was enrolled in December 2024, his left muscle strength was grade 4 and the right muscle strength was grade 3. The patient had mixed aphasia, could occasionally answer single words, and had poor intelligence. Seizures occurred once every $10^{-30}$ minutes, and >50 attacks per day. The specific number of attacks could not be counted in detail, with more frequent attacks during sleep, occurring once every 5-10 minutes. The patient had one seizure pattern: looking to the right with head and shaking of right limbs, which lasts for 5-10 seconds and is relieved. The patient appeared poor consciousness, drowsiness, bedridden, and nasogastric feeding.

Figure 29:
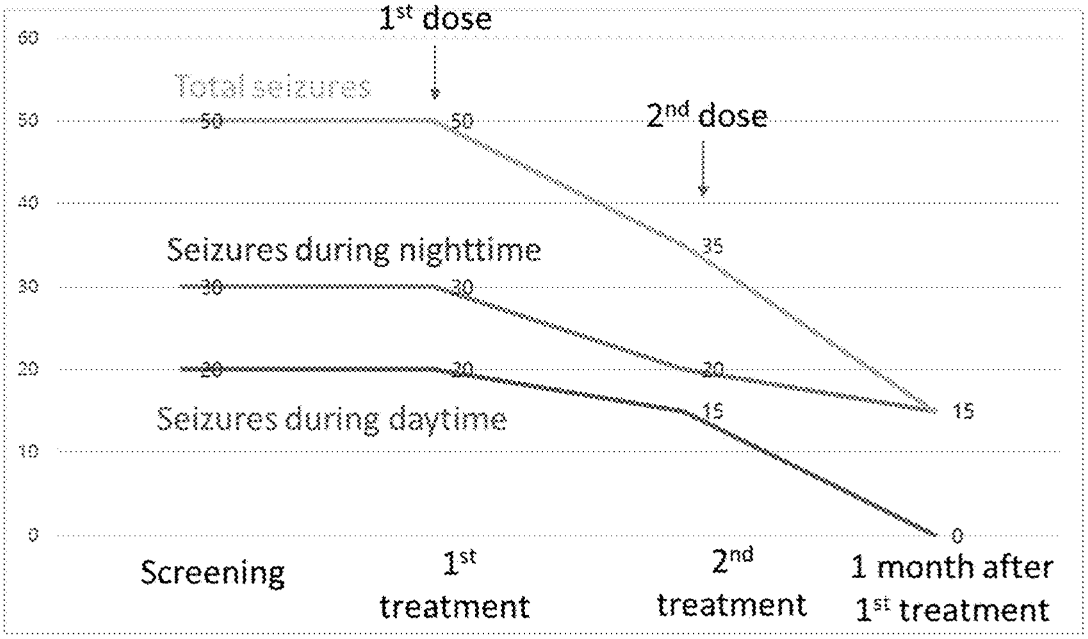
FIG. 29 depicts the efficacy of SIF001 treatment in patient 1 during the epilepsy investigator-initiated trial (IIT).

One month after using the monoclonal antibody SIF001, there were almost no attacks during daytime, and the attacks at night were significantly reduced to no more than 15 attacks during nighttime, as shown in FIG. 29. The patient appeared in good mental condition and conscious. The left muscle strength changed to grade 5 and the right muscle strength up to grade 4. The patient can get out of bed and eat independently.

Patient 2

Patient 2 was 13 years and 2 months old when enrolled to the trail, with an epilepsy history of 7 years since 2017 Sep. 14. Commonly used anti-epileptic drugs are ineffective to the patient. The patient did vagus nerve stimulation (VNS) in 2018. Before treatment, the patient experienced more than 10 attacks per month and in a cognitive state of dementia.

Figure 30:
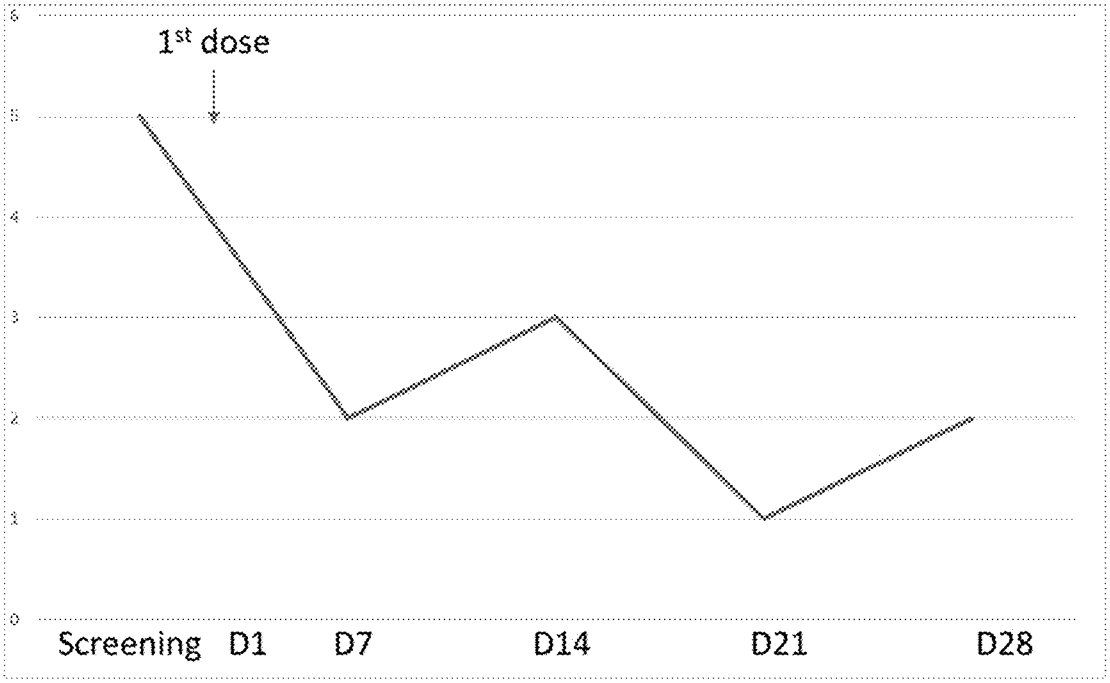
FIG. 30 depicts the efficacy of SIF001 treatment in patient 2 during the epilepsy investigator-initiated trial (IIT).

Four weeks after using the monoclonal antibody SIF001, seizure frequency of the patient reduced from 5 times per week to 2 times per week, as shown in FIG. 30.

Patient 3

Patient 3 was 12 years old when enrolled to the trail, male, episodic limb twitching, consciousness disorder for 7 years. The disease started at the age of 5, with 2 types of attacks: Episodic stupor and Episodic limb twitching, disturbance of consciousness, flexion of the upper limbs, straightening of the lower limbs and shaking. Before treatment, the average number of attacks was 8-10 times a day. Commonly used anti-epileptic drugs are ineffective to the patient. hormone shock, intravenous immunoglobulin (IVIG) treatments and low-temperature plasma (LTP) stimulation had certain effects to the patient. Transcranial magnetic stimulation and electrical stimulation treatments had poor results on the patient. The patient had cognition worse than peers but still can take care of himself. The patient was diagnosed with post-encephalitic epilepsy.

Figure 31:
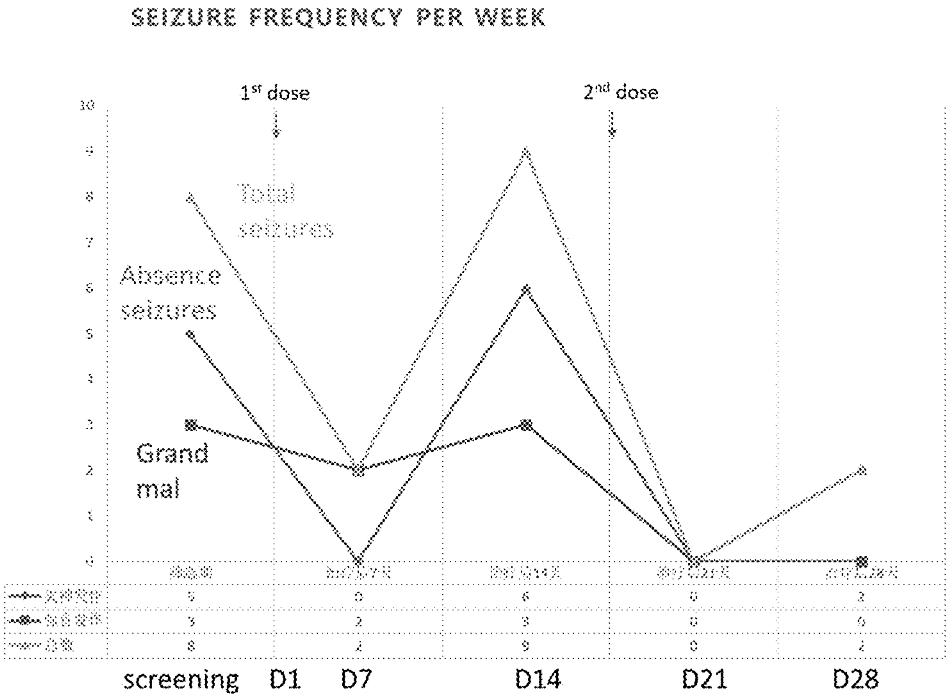
FIG. 31 depicts the efficacy of SIF001 treatment in patient 3 during the epilepsy investigator-initiated trial (IIT).

Four weeks after treating with the monoclonal antibody SIF001 for twice, the grand mal seizure frequency of the patient reduced from 3 times per week to zero; the absence seizure frequency of the patient reduced from 5 times per week to 2 times per week; and the total seizure frequency of the patient reduced from 8 times per week to 2 times per week, as shown in FIG. 31. Caregiver reported that patient's language expression and motor abilities improved significantly after taking the medicine.

Patient 4

Patient 4 was 13 years when enrolled to the trail, male, with episodic loss of consciousness and twitching of limbs for more than 10 years. The disease onset at the age of 3, with 2 seizure patterns: 1. Attack while awake, loss of consciousness, falling to the ground with limb twitching, obvious twitching of the right upper limb, left limb stiffness, and head turning to the right; 2. Attack while sleeping, sitting up, right corner of mouth twitching, left upper limb flexion and stiffness. The patient experienced average of 15-20 attacks per day before treatment. The patient was diagnosed with genetically related epilepsy. Gene testing results indicated that MAN2B2 heterozygous mutation and STK26 hemizygous missense mutation. Commonly used anti-epileptic drugs are ineffective to the patient. Effects of both resection of the epileptic focus in the left central functional area performed in 2022 and VNS implantation in 2024 were not satisfactory. Cognitive impairment was significant, and schooling had been discontinued.

Figure 32:
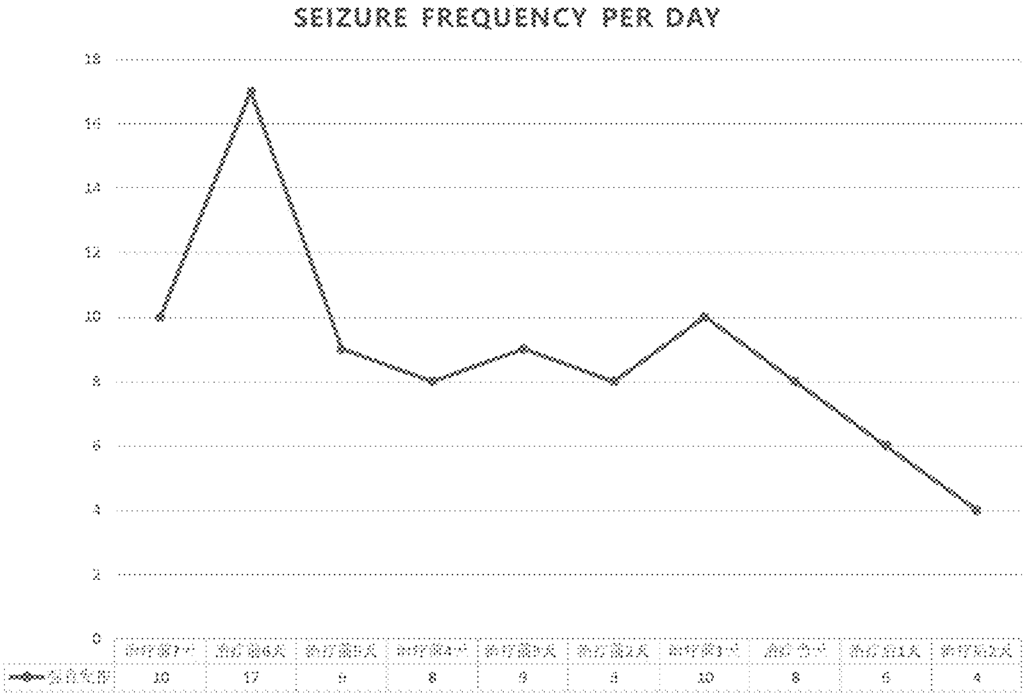
FIG. 32 depicts the efficacy of SIF001 treatment in patient 4 during the epilepsy investigator-initiated trial (IIT).

Two days after using the monoclonal antibody SIF001, seizure frequency of the patient reduced from 8-17 times per day before the treatment to 4 times per day post the treatment, as shown in FIG. 32.

Patient 5

Patient 5 was 30 years old when enrolled to the trail, male, with episodic stupor, limb rigidity and loss of consciousness for 27 years. The disease onset at the age of 3, with 3 seizure patterns: 1. Paroxysmal stupor, lasting for dozens of seconds; 2. Paroxysmal nodding, lasting for 1-2 seconds; 3. Loss of consciousness with limb rigidity, lasting for 1-2 minutes and relieved. The patient experienced average>20 seizures a day before treatment. The patient was diagnosed with Lennox-Gastaut Syndrome (LGS).

Figure 33:
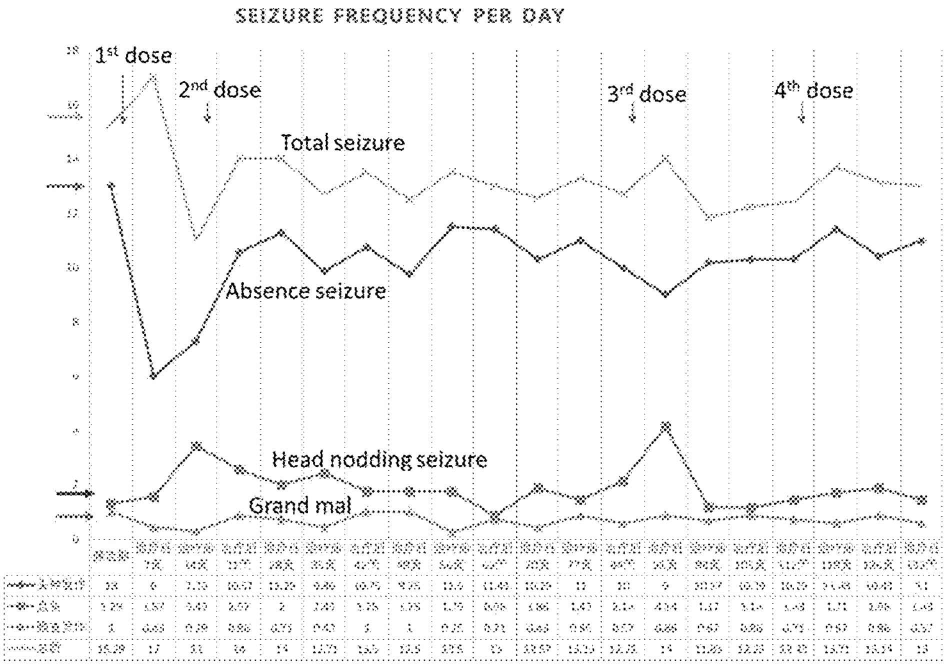
FIG. 33 depicts the efficacy of SIF001 treatment in patient 5 during the epilepsy investigator-initiated trial (IIT), as measured by daily seizure frequency before and after SIF001 treatment.
Figure 34:
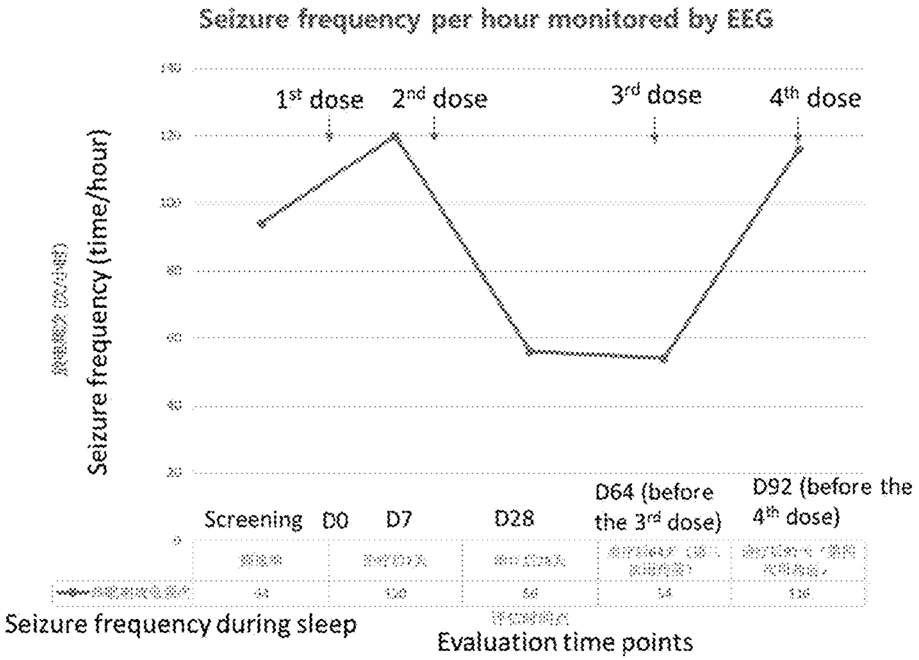
FIG. 34 depicts the efficacy of SIF001 treatment in patient 5 during the epilepsy investigator-initiated trial (IIT), as measured by hourly seizure frequency during sleep through electroencephalogram (EEG) before and after SIF001 treatment.

The patient was administrated with the SIF001 four times. As shown in FIG. 33, 133 days after the first treatment with the monoclonal antibody SIF001, the absence seizure frequency of the patient reduced from 13 times per day before the treatment to 6-11 times per day; and the total seizure frequency of the patient reduced from 15.29 times per day before the treatment to 11-13 times per day post the treatment, as shown in FIG. 33. We also monitored the patient's seizure frequence during sleep through electroencephalogram (EEG). As shown in FIG. 34, the patient's seizure frequence during sleep was reduced from 94 times per hour before the treatment to 54-56 times per hour post the treatment, while some fluctuations were observed.

Example 11. SIF001 Phase I Study in Healthy Subjects and in a Patient Cohort with Epilepsy This example illustrates a Phase 1, double-blind, placebo-controlled, randomized, single and multiple ascending dose escalation study to assess the safety, tolerability, pharmacokinetics and pharmacodynamics of SIF001 in healthy subjects and in a patient cohort with epilepsy.

Study Rationale

SIF001 is an investigational humanized IgG4 (S228P) antibody against galectin-3 (Gal-3), developed for the treatment of neurological disorders such as epilepsy. In order to evaluate the safety, tolerability, and pharmacokinetics of SIF001, a Phase 1, randomized, double-blind, placebo-controlled, single and multiple ascending dose escalation study will be conducted in healthy volunteers.

The single-ascending dose (SAD) stage will be conducted in healthy volunteers to evaluate the dose levels to be further investigated in the multiple-ascending dose (MAD) stage. The MAD stage will then evaluate the safety of 3 doses of SIF001 administered every 2 weeks (Q2W) in healthy volunteers.

Given the unmet medical need of patients with drug-resistant epilepsy, an additional cohort in the MAD stage is planned to enroll patients with epilepsy, who have not responded on prior treatment of antiepileptic drugs (AEDs). This cohort will help assess the safety and pharmacokinetics (PK) of SIF001-001 in the target patient population and generate preliminary efficacy data in a relatively small group of patients before exposing larger groups of patients to SIF001.

A recommended phase 2 dose (RP2D) will then be selected after evaluation of the SAD and MAD stages for further proof-of-concept evaluation of SIF001 in patients with epilepsy.

Study Design

This is a Phase 1, randomized, double-blind, placebo-controlled, single and multiple ascending dose escalation study to evaluate the safety, tolerability, and pharmacokinetics of SIF001 in healthy volunteers and one cohort of patients with epilepsy. The total study duration for each subject will be up to approximately 11 weeks.

This study consists of two stages:

Stage I: Phase 1a Single-Ascending Dose (SAD) Study of SIF001 in Healthy Volunteers Subjects in this study stage will receive a single administration of SIF001 or placebo on Day 1 of the study.

Dose groups will be enrolled sequentially. The starting dose in humans will be 10 mg/kg. The subsequent planned doses are 20 mg/kg, 40 mg/kg and 70 mg/kg. The planned doses for each group following the initial dose group are subject to change (increase or decrease) based on the safety, tolerability and pharmacokinetic (if available) data from the previous groups. In addition, dose groups may be added or removed from the planned design based on emerging data. All doses are infused intravenously over 1 or 2 hours.

Eight subjects will be enrolled into each dose group; 6 subjects in each group will be randomized to active SIF001 treatment and 2 subjects to placebo. A total of approximately 24 subjects will be randomized in this stage, with 18 receiving SIF001 treatment at different dose levels and 6 receiving the placebo.

Within each dose group, a sentinel dosing schedule will be used as follows:

- On Day 1, 2 subjects (1 active SIF001; 1 placebo) will be dosed and observed.
- On Day 3, if safety and tolerability from subjects dosed on Day 1 is satisfactory, the remaining subjects will be dosed and observed. As an additional precaution, the remaining subjects will not all be dosed simultaneously, but be staggered with two subjects being dosed at a time.

Dose escalation decisions will use emerging safety and tolerability data through 7 days after the last subject in the current dose group was dosed (Day 8). Data will be reviewed by a blinded Safety Review Committee (SRC). For dose levels higher than 20 mg/kg, available clinical data will also be presented to the US FDA for review.

The initiation of enrollment at the 40 mg/kg dose level will only be initiated upon the review of the clinical data of the 10 and 20 mg/kg dose levels by the FDA. The Sponsor will submit to the FDA all available safety and tolerability data (e.g., AEs, clinical laboratory tests, vital signs, 12-lead safety electrocardiograms [ECGs], and physical examinations) for all subjects in the 10 mg/kg SAD dose group and all available data through at least 7 days for at least 6 out of 8 subjects in the 20 mg/kg SAD dose group.

Similarly, the initiation of enrollment at the 70 mg/kg dose level will only be initiated upon the review of the clinical data of the 10, 20, and 40 mg/kg dose levels by the FDA. The Sponsor will submit to the FDA all available safety and tolerability data for all subjects in the 10 and 20 mg/kg SAD dose groups and all available data through at least 7 days for at least 6 out of 8 subjects in the 40 mg/kg SAD dose group.

Study assessments will be conducted, and subjects will be dosed as scheduled. Subjects will be admitted to the clinical unit 1 day prior to their scheduled dosing (Day-1). Subjects will fast overnight prior to dosing. Subjects will remain at the clinical unit for at least 2 days following their dosing for safety assessments and pharmacokinetics (PK) sampling. Subjects will be discharged from the clinical unit at the discretion of the principal investigator following completion of the assessments on Day 2 provided there are no safety concerns identified from review of the clinical data. Subjects will return to the clinical unit on pre-specified days outlined in the Schedule of Assessments for safety assessments and PK/pharmacodynamics (PD) sampling for 75 days. If a subject reports any adverse events (AEs), they may be required to return to the clinical unit at the discretion of the principal investigator for additional assessments. All AEs must be followed to adequate resolution.

Stage II: Phase 1b Multiple-Ascending Dose (MAD) Study of SIF001 in Healthy Volunteers, Followed by One Patient Cohort Subjects in this study stage will receive repeated administrations of SIF001 or placebo on Days 1, 15, and 29 of the study.

Stage II enrollment for the first dose group will be initiated at least 15 days after the last subject of Group 2 of Stage I has received their dose of SIF001 and there are no safety concerns identified from review of the clinical data. The other dose groups will also have the same rule applied.

The provisional planned doses are 10 mg/kg, 20 mg/kg, 40 mg/kg and 70 mg/kg. The dose escalation design is identical with Stage I, including sentinel dosing of the first dose and randomization of 6 subjects to SIF001 and 2 subjects to placebo, with the exception that the SRC will convene at least 14 days after the last subject in the dose group has received their last dose of SIF001 (Day 43).

Within each dose group, a sentinel dosing schedule for the first dose administration will be used as follows:

- On Day 1, 2 subjects (1 active SIF001; 1 placebo) will be dosed and observed.
- On Day 3, if safety and tolerability from subjects dosed on Day 1 is satisfactory, the remaining subjects will be dosed and observed. As an additional precaution, the remaining subjects will not all be dosed simultaneously but be staggered with two subjects being dosed at a time.

After all subjects in the highest provisional dose level have completed their second dose (D15) or after a lower dose level is declared as the highest tolerated dose, one patient cohort of patients with epilepsy is planned to be enrolled at the highest tolerated dose. Forty (40) subjects will be randomized 3:2 to receive SIF001 or placebo.

Dose Escalation and Stopping Rules:

Dose escalation decisions will be made based on all available safety and tolerability data (e.g., AEs, clinical laboratory tests, vital signs, 12-lead safety electrocardiograms [ECGs], and physical examinations) through 7 days after all subjects in the current dose group have received their first dose of SIF001 (SAD) and through 14 days after all subjects in the current dose group received their last dose of SIF001 (MAD). Data will be reviewed by a blinded SRC consisting of the Principal Investigator and sponsor representatives including the medical monitor, pharmacokineticist (if PK data is available), and others as deemed necessary.

The following variables (at a minimum) will be taken into account by the SRC at the protocol-specified time points for dose escalation decisions, and when events arise during the course of study treatment. AEs will be graded by the Investigator or qualified designee as noted.

- Number and frequency of AEs characterized as moderate or severe in severity
- Number and frequency of serious adverse events (SAEs)
- Discontinuation due to AEs
- Emergent cardiovascular events, such as corrected QT interval (QTc) increases or vital sign changes
- Liver function enzyme increases Interim PK data from previous cohort(s) will not be needed for a dose escalation decision but may be used to guide the dose escalation decision, as data becomes available. Any PK data will be presented to the SRC in an anonymized format to preserve the blind. A decision will be made by the group to either continue dosing as planned, modify dosing of the next and subsequent groups, or discontinue the study.

Scientific Rationale for Study Design

The two stages of the proposed clinical trial evaluate the single- and multiple-dose safety and tolerability of SIF001 in healthy volunteers. In the SAD (Stage I) and MAD (Stage II) portions of the study, 8 healthy volunteers will be randomized 3:1 to receive active SIF001 treatment or placebo. Within each dose group, a sentinel dosing schedule will be applied to SAD and MAD stages mitigate potential safety risks.

Dose escalation decisions will be based on all available safety and tolerability data through 7 days after at least 6 out of 8 subjects in the current dose group have received their first dose of SIF001. Data will be reviewed by a blinded SRC consisting of the Principal Investigator and sponsor representatives including the medical monitor, pharmacokineticist (if PK data is available), statistician, and others as deemed necessary. A decision will be made by the group to either continue dosing as planned, modify dosing of the next and subsequent groups, or discontinue the study.

Given the unmet medical need of patients with drug-resistant epilepsy, an additional cohort in the MAD stage is planned to enroll patients with epilepsy, who have not responded on prior treatment of AEDs. This cohort will help assess the safety and PK of SIF001-001 in the target patient population and generate preliminary efficacy data in a relatively small group of patients before exposing larger groups of patients to SIF001. Forty (40) patients with epilepsy will be enrolled, randomizing 24 patients to SIF001 and 16 patients to placebo (3:2). Assuming an early dropout rate of approximately 12.5%, 35 patients randomized 3:2 to active or placebo will provide 80% power to detect a difference of 30% in median percent reduction in seizure frequency between an active dosage group and placebo group, at a 2-sided alpha level of 0.05, assuming a standard deviation of 30%.

Upon the determination of an RP2D from the SAD and MAD evaluation, further studies of SIF001 may be conducted at the RP2D in the clinical development of SIF001.

Justification for Dose

Nonclinical toxicology evaluation of SIF001 was conducted in Sprague Dawley rats and beagle dogs. The no observed adverse effect level (NOAEL) from the repeat-dose Good Laboratory Practice-compliant toxicology studies was 200 mg/kg (Q2W×3 doses) in both rats and beagle dogs. The human equivalent dose (HED) of the NOAEL calculated based on body surface area conversion is as follows:

In rats: 200 mg/kg/6.2=32.3 mg/kg

In dogs: 200 mg/kg/1.8=111.1 mg/kg

Assuming beagle dogs as the most appropriate species for calculation of the initial clinical dose, and applying a safety factor of 10, the maximum recommended starting dose (MRSD) is: 111.1 mg/kg (HED)×1/10=11.1 mg/kg. Thus, the starting dose for the proposed Investigational New Drug (IND)-opening study is conservatively set at 10 mg/kg.

The high-dose selection of 200 mg/kg for the pivotal GLP toxicology studies in rats and dogs was partially due to the maximum allowable volume of intravenous fluids that may be administered to healthy adult animals according to Institutional Animal Care and Use Committee (IACUC) guidelines, which is 10.0 ml/kg for both rats and dogs [12]. Because the formulation of the SIF001 drug substance used for the toxicology studies was 20 mg/mL, the maximum feasible dose that could be tested in rats and dogs was 200 mg/kg.

According to ICH S6 (R1) Addendum (May 2012), the high-dose selection should reflect an approximately 10-fold exposure multiple over the maximum exposure to be achieved in the clinic unless there is a justification for using a lower dose (e.g., maximum feasible dose) [13]. Since dose levels above 200 mg/kg could not be tested in rats and dogs, a review of the available clinical data by US FDA will be planned for dose escalations above 20 mg/kg (1/10 of the maximum feasible dose tested in nonclinical studies). The proposed dose levels for the SAD and MAD stages of this trial are 10, 20, 40, and 70 mg/kg.

Population Size

A total of 104 subjects are tentatively planned to be enrolled in the dose escalation study. Stage I ($10^{-70}$ mg/kg): approximately 32 subjects. Stage II ($10^{-70}$ mg/kg): approximately 72 subjects including 32 healthy volunteers and 40 patients with epilepsy Inclusion Criteria Participants are eligible to be included in the study only if they meet the following criteria:

Healthy Volunteers (Stage I and II (Phase 1a and 1b)):

1. Male or female 18 to 55 years of age at the time of signing the informed consent.
2. In good health as determined by the Investigator, based on medical history and screening evaluations.
3. Body weight of ≥50 kg and BMI within the range 18-30 kg/$m^2$ (inclusive)

Patients with Epilepsy (Stage II (Phase 1b)):

4. Male or female 18 to 70 years of age at the time of signing the informed consent.
5. Clinical diagnosis of epilepsy. Subjects having either partial or generalized epilepsy with motor seizures or seizures with clear alteration of awareness are eligible for enrollment.
6. Has a minimum of 4 seizures per 4-week period while taking 1 to 3 anti-seizure medications
7. All medications and epilepsy interventions must be stable for 8 weeks before screening and are expected to remain stable during the study All Subjects:

8. Negative serum pregnancy test at screening and urine pregnancy test on Day −1 before starting study treatment in all pre-menopausal women and women<12 months after the onset of menopause.
9. Female participants of child-bearing potential and male participants must agree to use adequate contraception for the duration of the protocol.
10. Able to sign informed consent and comply with the protocol.

Storage, Preparation, and Administration of Study Drug

The study drug, SIF001 Injection or placebo, is supplied as a 20 mg/mL solution, with 8 mL per vial. The study drug should be stored at 2~8° C.

Subjects will be randomly assigned to receive SIF001 or placebo. Investigators will remain blinded to each subject's assigned study treatment throughout the course of the study. In order to maintain this blind, an unblinded pharmacist will be responsible for the reconstitution and dispensation of the study drug.

SIF001 will be administered based on body weight. The provisional dose levels planned for SAD stage are 10, 20, 40, and 70 mg/kg on Day 1, and the provisional dose levels planned for the MAD stage are 10, 20, 40, and 70 mg/kg on Days 1, 15, and 29.

The test drug for this study is SIF001 and the control drug is placebo. Study drug will be administered as a one to two-hour IV infusion from a diluted saline bag with a total volume of 100, 250, or 500 mL, depending on dose level.

Sample Size

In the SAD and MAD healthy volunteer cohorts, subjects will be recruited sequentially in separate increasing dose groups, with each group randomizing 6 subjects to a specific dose of SIF001 and 2 randomized to placebo (3:1). No formal sample size calculations have been performed for the SAD and MAD healthy volunteer cohorts. The number of subjects is based on feasibility and is considered sufficient to meet the study objectives.

In the MAD patient cohort, 40 patients with epilepsy will be enrolled and dosed, randomizing 24 patients to SIF001 and 16 patients to placebo (3:2). Assuming an early dropout rate of approximately 12.5%, 35 patients randomized 3:2 to active or placebo will provide 80% power to detect a difference of 30% in mean percent reduction in seizure frequency between an active dosage group and placebo group, at a 2-sided alpha level of 0.05, assuming a standard deviation of 30%.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the Applicant reserves the right to challenge the accuracy and pertinence of the cited documents. It will be clearly understood that, although a number of information sources, including scientific journal articles, patent documents, and textbooks, may be referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure and are to be included within the scope of this application.

While particular alternatives of the present disclosure have been disclosed, it is to be understood that various modifications and combinations are possible and are contemplated within the scope of the appended claims. There is no intention, therefore, of limitations to the exact abstract and disclosure herein presented.

Example 12. In Vitro Epitope Binning of Antibodies Binding with Human Galectin-3 (hGal-3)

This example illustrates utilizing competitive binning to determine the anti-Gal-3 antibodies compete to bind to human Gal-3.

Summary

The purpose of this study is to determine the epitope binning of antibodies against human Gal-3. Binning assay was conducted to characterize epitopes of the anti-Gal-3 antibodies using a Carterra LSA instrument. All the antibodies were constructed in hIgG4 backbone. Antibodies as ligands were covalently linked to a HC200M chip. The antigen hGal-3 as the analyte was injected to flow cells to bind to the captured ligands. Competitive binning was programmed to determine if two mAbs can bind simultaneously to the same antigen. The experiment showed 66 antibodies of the dendrogram with a cut height that created 18 well differentiated branches.

Figure 35:
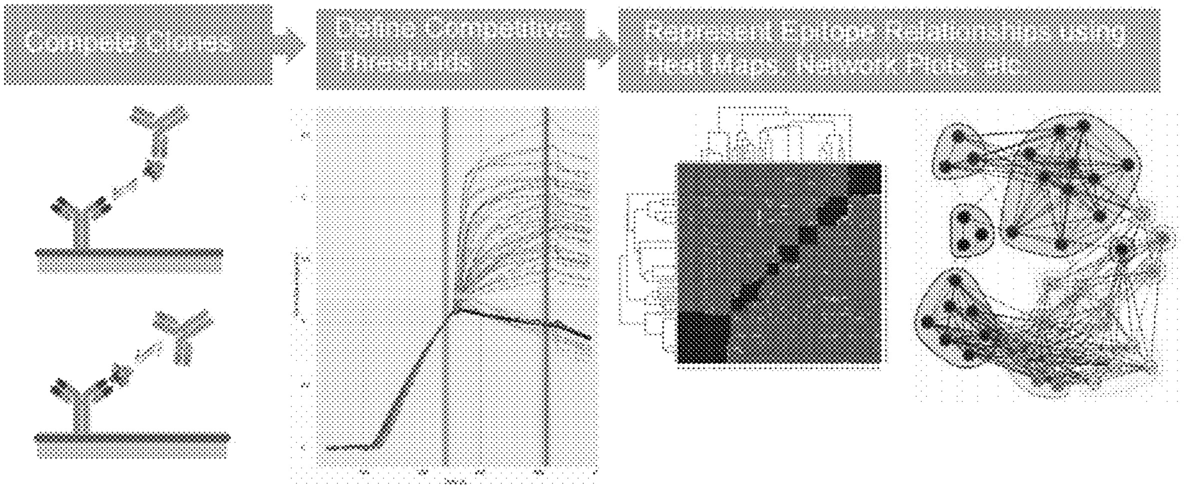
FIG. 35 depicts a schematic drawing of LSA epitope binning workflow.

Carterra LSA is a monoclonal antibody (mAb) characterization platform that combines patented flow printing microfluidics with high throughput surface plasmon resonance (SPR) detection. In this study, Carterra LSA was used to measure the affinity of Gal-3 binding to antibody with surface plasmon resonance (SPR) and epitope binning. The LSA Epitope Binning workflow is illustrated in FIG. 35.

Epitope binning assay procedure. An array of antibodies as ligand were coupled to the chip surface HC200M using the Multichannel PH with the running buffer (25 mM MES buffer). The NHS/EDC activation time and coupling time was set at 5 min and 15 min respectively. The SFC then docked onto the chip, and in each cycle, antigen human Galectin-3 was injected across the entire Ab array, with association time of 5 min, followed by a single antibody as analyte with association time of 5 min. After 1 min dissociation, regeneration buffer (pH 2.0, 10 mM Glycine) was applied for 20 s for three times. The data were analyzed by Caterra Epitope Data Analysis Software.

An overview of the epitope binning results is displayed as follows.

Community clusters. A combined dendrogram with a cut height creating 18 well differentiated branches, which correspond to 18 epitope clusters. The individual community clusters with their exemplary antibodies are listed in Table 10. It is understood that additional antibodies may be classified into one of the community clusters based on results of epitope binning experiments as described above.

TABLE 10

| 18 epitope clusters | | | |
|---|---|---|---|
| Com 1 | 1104SBC1068-033 | Com 9 | 20240903SBC1093-015 |
| Com 2 | 1220SBC1068-186 | | 20240903SBC1093-020 |
| | 1220SBC1068-205 | | 20240903SBC1093-023 |
| | 1220SBC1068-022 | | 20240903SBC1093-030 |
| | 1220SBC1068-058 | | 20240628SBC1080-005 |
| | 1220SBC1068-056 | | 20240903SBC1093-183 |
| | 20241223SBC1205-119 | | 20240903SBC1093-220 |
| | 1104SBC1068-160 | | 20240903SBC1093-230 |
| Com 3 | 20240628SBC1080-009 | | 20240903SBC1093-185 |
| | 20240628SBC1080-002 | | 20240903SBC1093-021 |
| | 1104SBC1068-374 | | 20240903SBC1093-037 |
| | 20240929SBC1205-022 | | 20240903SBC1093-036 |
| | 1104SBC1068-335 | | 20240903SBC1093-099 |
| | 20040628SBC1080-006 | | 20240903SBC1093-025 |
| | 20240628SBC1080-008 | | 20240903SBC1093-182 |
| | 1104SBC1068-378 | | 20240903SBC1093-184 |
| | 1104SBC1068-365 | Com 10 | 20240903SBC1093-033 |
| | ANb1361-G119-5M- | Com 11 | 20240903SBC1093-034 |
| | LP2R2-58-higg4P | Com 12 | 20240903SBC1093-228 |
| | 20240628SBC1080-007 | | 20240903SBC1093-074 |
| Com 4 | 1220SBC1068-035 | | 20240903SBC1093-193 |
| Com 5 | 1220SBC1068-098 | | 20240903SBC1093-044 |
| | 1220SBC1068-210 | | 20240903SBC1093-059 |
| | 1220SBC1068-041 | | 20240903SBC1093-056 |
| | 1220SBC1068-063 | | 20240903SBC1093-057 |
| | 1220SBC1068-274 | | 20240903SBC1093-219 |
| | 1220SBC1068-129 | | 20240903SBC1093-194 |
| | 1220SBC1068-099 | | 20240903SBC1093-035 |
| | 1220SBC1068-164 | Com 13 | 20240903SBC1093-055 |
| | 1220SBC1068-197 | Com 14 | 20240903SBC1093-075 |
| Com 6 | 1220SBC1068-097 | Com 15 | 20241223SBC1205-061 |
| Com 7 | 20240628SBC1080-003 | Com 16 | 20241223SBC1205-063 |
| Com 8 | 20240628SBC1080-004 | Com 17 | 20241223SBC1205-130 |
| Com 18 | 20241223SBC1205-131 | | |

The term "Com" stands for community cluster.

Conclusions

The epitope identification data of the 66 antibodies demonstrate a diverse range of epitopes.

REFERENCES

1. Ahmed, H.; Du, S.-J.; O'Leary, N.; Vasta, G. R. Biochemical and molecular characterization of galectins from zebrafish (*Danio rerio*): Notochord-specific expression of a prototype galectin during early embryogenesis. Glycobiology 2003, 14, 219-232.
2. Nakahara, S.; Raz, A. Regulation of cancer-related gene expression by galectin-3 and the molecular mechanism of its nuclear import pathway. Cancer Metastasis Rev. 2007, 26, 605-610.
3. Mariño, K. V.; Cagnoni, A. J.; Croci, D. O.; Rabinovich, G. A. Targeting galectin-driven regulatory circuits in cancer and fibrosis. Nat. Rev. Drug. Discov. 2023, 22, 295-316.
4. Nakahara, S.; Raz, A. Biological modulation by lectins and their ligands in tumor progression and metastasis. Anticancer. Agents Med. Chem. 2008, 8, 22-36.
5. Vasta, G. R. Roles of galectins in infection. Nat. Rev. Genet. 2009, 7, 424-438.
6. Henderson, N. C.; Mackinnon, A. C.; Farnworth, S. L.; Poirier, F.; Russo, F. P.; Iredale, J. P.; Haslett, C.; Simpson, K. J.; Sethi, T. Galectin-3 regulates myofibroblast activation and hepatic fibrosis. Proc. Natl. Acad. Sci. USA 2006, 103, 5060-5065.
7. Nishi, Y.; Sano, H.; Kawashima, T.; Okada, T.; Kuroda, T.; Kikkawa, K.; Kawashima, S.; Tanabe, M.; Goto, T.; Matsuzawa, Y.; et al. Role of Galectin-3 in Human Pulmonary Fibrosis. Allergol. Int. 2007, 56, 57-65.
8. Juniantito, V.; Izawa, T.; Yamamoto, E.; Murai, F.; Kuwamura, M.; Yamate, J. Heterogeneity of Macrophage Populations and Expression of Galectin-3 in Cutaneous Wound Healing in Rats. J. Comp. Pathol. 2011, 145, 378-389.
9. Henderson, N. C.; Mackinnon, A. C.; Farnworth, S. L.; Kipari, T.; Haslett, C.; Iredale, J. P.; Liu, F.-T.; Hughes, J.; Sethi, T. Galectin-3 Expression and Secretion Links Macrophages to the Promotion of Renal Fibrosis. Am. J. Pathol. 2008, 172, 288-298.
10. Ho, J. E.; Liu, C.; Lyass, A.; Courchesne, P.; Pencina, M. J.; Vasan, R. S.; Larson, M. G.; Levy, D. Galectin-3, a Marker of Cardiac Fibrosis, Predicts Incident Heart Failure in the Community. J. Am. Coll. Cardiol. 2012, 60, 1249-1256.
11. Li, P.; Liu, S.; Lu, M.; Bandyopadhyay, G.; Oh, D.; Imamura, T.; Johnson, A. M. F.; Scars, D.; Shen, Z.; Cui, B.; et al. Hematopoietic Derived Galectin-3 Causes Cellular and Systemic Insulin Resistance. Cell 2016, 167, 973-984.e12.
12. Pejnovic, N. Galectin-3 In Obesity And Type 2 Diabetes. Serb. J. Exp. Clin. Res. 2015, 16, 273-280.
13. Bobronnikova, L. Galectin-3 as a potential biomarker of metabolic disorders and cardiovascular remodeling in patients with hypertension and type 2 diabetes. Vessel Plus
14. Yilmaz, H.; Cakmak, M.; Inan, O.; Darcin, T.; Akcay, A. Increased levels of galectin-3 were associated with prediabetes and diabetes: New risk factor? J. Endocrinol. Investig. 2015, 38, 527-533.
15. Siwicki, M.; Engblom, C.; Pittet, M. J. Gal3 Links Inflammation and Insulin Resistance. Cell Metab. 2016, 24, 655-656.
16. Mensah-Brown, E.; Al Rabesi, Z.; Shahin, A.; Al Shamsi, M.; Arsenijevic, N.; Hsu, D.; Liu, F.-T.; Lukic, M. Targeted disruption of the galectin-3 gene results in decreased susceptibility to multiple low dose streptozotocin-induced diabetes in mice. Clin. Immunol. 2009, 130, 83-88.
17. Elola, M. T.; Wolfenstein-Todel, C.; Troncoso, M. F.; Vasta, G. R.; Rabinovich, G. A. Galectins: Matricellular glycan-binding proteins linking cell adhesion, migration, and survival. Cell. Mol. Life Sci. 2007, 64, 1679-1700.
18. Nakahara, S.; Oka, N.; Raz, A. On the role of galectin-3 in cancer apoptosis. Apoptosis. 2005, 10, 267-275.
19. Dumic, J.; Dabelic, S.; Flögel, M. Galectin-3: An open-ended story. Biochim. Biophys. Acta (BBA) Gen. Subj. 2006, 1760, 616-635.
20. Henderson, N. C.; Sethi, T. The regulation of inflammation by galectin-3. Immunol. Rev. 2009, 230, 160-171.
21. Ahmed, H.; AlSadek, D. M. M. Galectin-3 as a Potential Target to Prevent Cancer Metastasis. Clin. Med. Insights Oncol. 2015, 9, 113-121.
22. Bian, C.-F.; Zhang, Y.; Sun, H.; Li, D.-F.; Wang, D.-C. Structural Basis for Distinct Binding Properties of the Human Galectins to Thomsen-Friedenreich Antigen. PloS ONE 2011, 6, e25007.
23. Liao, D. I.; Kapadia, G.; Ahmed, H.; Vasta, G. R.; Herzberg, O. Structure of S-lectin, a developmentally regulated vertebrate beta-galactoside binding protein. Proc. Natl. Acad. Sci. USA 1994, 91, 1428-1432.
24. Bianchet, M. A.; Ahmed, H.; Vasta, G. R.; Amzel, L. M. A soluble β-galactosyl-binding lectin (galectin) from toad (*Bufo arenarum* Hensel) ovary: Crystallographic studies of two protein-sugar complexes. Proteins. 2000, 40, 378-388.

25. Hirabayashi, J.; Kasai, K. The family of metazoan metal-independent β-galactoside-binding lectins: Structure, function and molecular evolution. Glycobiology. 1993, 3, 297-304.

26. Cooper, D. N.; Barondes, S. H. Evidence for export of a muscle lectin from cytosol to extracellular matrix and for a novel secretory mechanism. J. Cell Biol. 1990, 110, 1681-1691.

27. Cho, M.; Cummings, R. D. Galectin-1, a β-galactoside-binding lectin in Chinese hamster ovary cells, II. Localization and biosynthesis. J. Biol. Chem. 1995, 270, 5207-5212.

28. Barboni, E. A.; Bawumia, S.; Hughes, R. C. Kinetic measurements of binding of galectin 3 to a laminin substratum. Glycoconj. J. 1999, 16, 365-373.

29. Kariya, Y.; Kawamura, C.; Tabci, T.; Gu, J. Bisecting GlcNAc Residues on Laminin-332 Down-regulate Galectin-3-dependent Keratinocyte Motility. J. Biol. Chem. 2010, 285, 3330-3340.

30. Ochieng, J.; Leite-Browning, M. L.; Warfield, P. Regulation of Cellular Adhesion to Extracellular Matrix Proteins by Galectin-3. Biochem. Biophys. Res. Commun. 1998, 246, 788-791.

31. Fukumori, T.; Takenaka, Y.; Yoshii, T.; Kim, H.-R. C.; Hogan, V.; Inohara, H.; Kagawa, S.; Raz, A. CD29 and CD7 mediate galectin-3-induced type II T-cell apoptosis. Cancer Res. 2003, 63, 8302-8311.

32. Feuk-Lagerstedt, E.; Jordan, E. T.; Leffler, H.; Dahlgren, C.; Karlsson, A. Identification of CD66a and CD66b as the major galectin-3 receptor candidates in human neutrophils. J. Immunol. 1999, 163, 5592-5598.

33. Rosenberg, I.; Cherayil, B. J.; Isselbacher, K. J.; Pillai, S. Mac-2-binding glycoproteins. Putative ligands for a cytosolic betagalactoside lectin. J. Biol. Chem. 1991, 266, 18731-18736.

34. Park, J. W.; Voss, P. G.; Grabski, S.; Wang, J. L.; Patterson, R. J. Association of galectin-1 and galectin-3 with Gemin4 in complexes containing the SMN protein. Nucleic Acids Res. 2001, 29, 3595-3602.

35. Liu, L.; Sakai, T.; Sano, N.; Fukui, K. Nucling mediates apoptosis by inhibiting expression of galectin-3 through interference with nuclear factor kappaB signalling. Biochem. J. 2004, 380, 31-41.

36. Yu, F.; Finley, R. L., Jr.; Raz, A.; Kim, H. R. Galectin-3 translocates to the perinuclear membranes and inhibits cytochrome c release from the mitochondria. A role for synexin in galectin-3 translocation. J. Biol. Chem. 2002, 277, 15819-15827.

37. Shimura, T.; Takenaka, Y.; Tsutsumi, S.; Hogan, V.; Kikuchi, A.; Raz, A. Galectin-3, a novel binding partner of beta-catenin. Cancer Res. 2004, 64, 6363-6367.

38. Song, S.; Mazurek, N.; Liu, C.; Sun, Y.; Ding, Q. Q.; Liu, K.; Hung, M. C.; Bresalier, R. S. Galectin-3 mediates nuclear beta-catenin accumulation and Wnt signaling in human colon cancer cells by regulation of glycogen synthase kinase-3beta activity. Cancer Res. 2009, 69, 1343-1349.

39. Hencka M T, Golenbock D T, Latz E. Innate immunity in Alzheimer's disease. Nat Immunol. 2015; 16 (3): 229-36.

40. Cai Z, Hussain M D, Yan L J. Microglia, neuroinflammation, and beta-amyloid protein in Alzheimer's disease. Int J Neurosci. 2014; 124 (5): 307-21.

41. Yang R Y, Rabinovich G A, Liu F T. Galectins: structure, function and therapeutic potential. Expert Rev Mol Med. 2008; 10: e17.

42. Ramírez Hernández E, et al. The therapeutic potential of galectin-1 and galectin-3 in the treatment of neurodegenerative diseases. Expert Rev Neurother. 2020; 20 (5): 439-48.

43. Mendonca H R, et al. Neuroinflammation and oxidative stress act in concert to promote neurodegeneration in the diabetic retina and optic nerve: galectin-3 participation. Neural Regen Res. 2020; 15 (4): 625-35.

44. Dong R, et al. Galectin-3 as a novel biomarker for disease diagnosis and a target for therapy (Review). Int J Mol Med. 2018; 41 (2): 599-614.

45. Shin T. The pleiotropic effects of galectin-3 in neuroinflammation: a review. Acta Histochem. 2013; 115 (5): 407-11.

46. Yoo H I, et al. Neuroanatomical distribution of galectin-3 in the adult rat brain. J Mol Histol. 2017; 48 (2): 133-46.

47. Song L, et al. Annexin A7 and its binding protein galectin-3 influence mouse hepatocellular carcinoma cell line in vitro. Biomed Pharmacother. 2014; 68 (3): 377-84.

48. Li Q, Barres B A. Microglia and macrophages in brain homeostasis and disease. Nat Rev Immunol. 2018; 18 (4): 225-42.

49. Xu L, He D, Bai Y. Microglia-mediated inflammation and neurodegenerative disease. Mol Neurobiol. 2016; 53 (10): 6709-15.

50. Tang Y, Le W. Differential roles of M1 and M2 microglia in neurodegenerative diseases. Mol Neurobiol. 2016; 53 (2): 1181-94.

51. Jeon S B, et al. Galectin-3 exerts cytokine-like regulatory actions through the JAK-STAT pathway. J Immunol. 2010; 185 (11): 7037-46.

52. Rahimian R, Beland L C, Kriz J. Galectin-3: mediator of microglia responses in injured brain. Drug Discov Today. 2018; 23 (2): 375-81.

53. Siew J J, Chern Y. Microglial lectins in health and neurological diseases. Front Mol Neurosci. 2018; 11:158.

54. Rahimian R, et al. Delayed galectin-3-mediated reprogramming of microglia after stroke is protective. Mol Neurobiol. 2019; 56 (9): 6371-85.

55. Yip P K, et al. Galectin-3 released in response to traumatic brain injury acts as an alarmin orchestrating brain immune response and promoting neurodegeneration. Sci Rep. 2017; 7:41689.

56. Itabashi T, et al. Cell- and stage-specific localization of galectin-3, a beta-galactoside-binding lectin, in a mouse model of experimental autoimmune encephalomyelitis. Neurochem Int. 2018; 118:176-84.

57. Ahmed, R.; Anam, K.; Ahmed, H. Development of Galectin-3 Targeting Drugs for Therapeutic Applications in Various Diseases. Int. J. Mol. Sci. 2023, 24, 8116.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. An antibody or a binding fragment thereof that binds to Galectin-3, wherein the antibody comprises:

- a heavy chain variable ($V_H$) region comprising
  - a HCDR1 amino acid sequence of SEQ ID NO: 4, a HCDR2 amino acid sequence of SEQ ID NO: 25, and a HCDR3 amino acid sequence of SEQ ID NO: 46, and
- a light chain variable ($V_L$) region comprising
  - a LCDR1 amino acid sequence of SEQ ID NO: 172, a LCDR2 amino acid sequence of SEQ ID NO: 193, and a LCDR3 amino acid sequence of SEQ ID NO: 214;
- a $V_H$ region comprising a HCDR1 amino acid sequence of SEQ ID NO: 373, a HCDR2 amino acid sequence of SEQ ID NO: 393, and a HCDR3 amino acid sequence of SEQ ID NO: 419, and a $V_L$ region comprising a LCDR1 amino acid sequence of SEQ ID NO: 447, a LCDR2 amino acid sequence of SEQ ID NO: 470, and a LCDR3 amino acid sequence of SEQ ID NO: 484;
- a $V_H$ region comprising a HCDR1 amino acid sequence of SEQ ID NO: 370, a HCDR2 amino acid sequence of SEQ ID NO: 390, and a HCDR3 amino acid sequence of SEQ ID NO: 418, and a $V_L$ region comprising a LCDR1 amino acid sequence of SEQ ID NO: 440, a LCDR2 amino acid sequence of SEQ ID NO: 463, and a LCDR3 amino acid sequence of SEQ ID NO: 481;
- a $V_H$ region comprising a HCDR1 amino acid sequence of SEQ ID NO: 386, a HCDR2 amino acid sequence of SEQ ID NO: 412, and a HCDR3 amino acid sequence of SEQ ID NO: 434, and a $V_L$ region comprising a LCDR1 amino acid sequence of SEQ ID NO: 460, a LCDR2 amino acid sequence of SEQ ID NO: 479, and a LCDR3 amino acid sequence of SEQ ID NO: 502;
- a $V_H$ region comprising a HCDR1 amino acid sequence of SEQ ID NO: 2, a HCDR2 amino acid sequence of SEQ ID NO: 23, and a HCDR3 amino acid sequence of SEQ ID NO: 44, and a $V_L$ region comprising a LCDR1 amino acid sequence of SEQ ID NO: 170, a LCDR2 amino acid sequence of SEQ ID NO: 191, and a LCDR3 amino acid sequence of SEQ ID NO: 212;
- a $V_H$ region comprising a HCDR1 amino acid sequence of SEQ ID NO: 374, a HCDR2 amino acid sequence of SEQ ID NO: 394, and a HCDR3 amino acid sequence of SEQ ID NO: 420, and a $V_L$ region comprising a LCDR1 amino acid sequence of SEQ ID NO: 444, a LCDR2 amino acid sequence of SEQ ID NO: 467, and a LCDR3 amino acid sequence of SEQ ID NO: 485;
- a $V_H$ region comprising a HCDR1 amino acid sequence of SEQ ID NO: 376, a HCDR2 amino acid sequence of SEQ ID NO: 396, and a HCDR3 amino acid sequence of SEQ ID NO: 422, and a $V_L$ region comprising a LCDR1 amino acid sequence of SEQ ID NO: 446, a LCDR2 amino acid sequence of SEQ ID NO: 469, and a LCDR3 amino acid sequence of SEQ ID NO: 487;
- a $V_H$ region comprising a HCDR1 amino acid sequence of SEQ ID NO: 5, a HCDR2 amino acid sequence of SEQ ID NO: 26, and a HCDR3 amino acid sequence of SEQ ID NO: 47, and a $V_L$ region comprising a LCDR1 amino acid sequence of SEQ ID NO: 173, a LCDR2 amino acid sequence of SEQ ID NO: 194, and a LCDR3 amino acid sequence of SEQ ID NO: 215;
- a $V_H$ region comprising a HCDR1 amino acid sequence of SEQ ID NO: 3, a HCDR2 amino acid sequence of SEQ ID NO: 24, and a HCDR3 amino acid sequence of SEQ ID NO: 45, and a $V_L$ region comprising a LCDR1 amino acid sequence of SEQ ID NO: 171, a LCDR2 amino acid sequence of SEQ ID NO: 192, and a LCDR3 amino acid sequence of SEQ ID NO: 213; or
- a $V_H$ region comprising a HCDR1 amino acid sequence of SEQ ID NO: 375, a HCDR2 amino acid sequence of SEQ ID NO: 395, and a HCDR3 amino acid sequence of SEQ ID NO: 421, and a $V_L$ region comprising a LCDR1 amino acid sequence of SEQ ID NO: 445, a LCDR2 amino acid sequence of SEQ ID NO: 468, and a LCDR3 amino acid sequence of SEQ ID NO: 486.

2. The antibody or the binding fragment thereof of claim 1, wherein the antibody comprises:

- a $V_H$ region comprising a HCDR1 amino acid sequence of SEQ ID NO: 4, a HCDR2 amino acid sequence of SEQ ID NO: 25, and a HCDR3 amino acid sequence of SEQ ID NO: 46; and
- a $V_L$ region comprising a LCDR1 amino acid sequence of SEQ ID NO: 172, a LCDR2 amino acid sequence of SEQ ID NO: 193, and a LCDR3 amino acid sequence of SEQ ID NO: 214.

3. The antibody or the binding fragment thereof of claim 1, wherein the antibody comprises:

a $V_H$ region comprising a $V_H$ amino acid sequence with at least 80% identity to SEQ ID NO: 353 and a $V_L$ region comprising a $V_L$ amino acid sequence with at least 80% identity to SEQ ID NO: 354.

4. The antibody or the binding fragment thereof of claim 1, wherein the antibody comprises a $V_H$ region comprising a $V_H$ amino acid sequence with at least 80% identity to SEQ ID NO: 149, and a $V_L$ region comprising a $V_L$ amino acid sequence with at least 70% identity to SEQ ID NO: 317;

a $V_H$ region comprising a $V_H$ amino acid sequence with at least 80% identity to SEQ ID NO: 150, and a $V_L$ region comprising a $V_L$ amino acid sequence with at least 70% identity to SEQ ID NO: 318;

a $V_H$ region comprising a $V_H$ amino acid sequence with at least 80% identity to SEQ ID NO: 151, and a $V_L$ region comprising a $V_L$ amino acid sequence with at least 80% identity to SEQ ID NO: 319; or a $V_H$ region comprising a $V_H$ amino acid sequence with at least 80% identity to SEQ ID NO: 152, and a $V_L$ region comprising a $V_L$ amino acid sequence with at least 80% identity to SEQ ID NO: 320.

5. The antibody or the binding fragment thereof of claim 1, wherein the antibody comprises both the $V_H$ and $V_L$ of an antibody selected from the group consisting of 1104SBC1068-335, 1104SBC1068-365, 1104SBC1068-374, 1104SBC1068-378, SIF-001, and a variant thereof.

6. The antibody of claim 1, wherein the antibody is a humanized, chimeric, or human antibody.

7. A polypeptide comprising a $V_H$ sequence and/or a $V_L$ sequence of the antibody of claim 1.

8. A polynucleotide encoding the polypeptide of claim 7.

9. A cell that comprises the polypeptide of claim 7.

10. An immunoconjugate comprising the antibody of claim 1 and a cytotoxic agent.

11. A pharmaceutical composition comprising the antibody of claim 1 and a pharmaceutically acceptable carrier.

12. A method of treating epilepsy or a related neurological disorder in a subject in need thereof, comprising administering to the subject an effective amount of the pharmaceutical composition of claim 11.

13. The method of claim 12, wherein the effective amount is about 5-100 mg/kg of the antibody or the immunoconjugate per the subject's body weight.

14. The antibody or the binding fragment thereof of claim 3, wherein the antibody comprises the $V_H$ region comprising the $V_H$ amino acid sequence of SEQ ID NO: 353, and the $V_L$ region comprising the $V_L$ amino acid sequence of SEQ ID NO: 354.

15. The antibody or the binding fragment thereof of claim 5, wherein the antibody comprises both the $V_H$ and $V_L$ of SIF-001.

16. The antibody of claim 15, wherein the antibody is SIF-001.

17. The method of claim 13, wherein the effective amount is about 10, 20, 40, 70, 80, 90, or 100 mg/kg of the antibody or the immunoconjugate per the subject's body weight.

18. The method of claim 13, wherein the pharmaceutical composition is administered intravenously or subcutaneously into the subject.

19. The method of claim 13, wherein the pharmaceutical composition is administered more than once.

20. The method of claim 19, wherein each administration is at least 7 days apart or at least 14 days apart.

* * * * *

SEQUENCE LISTING

```
Sequence total quantity: 508
SEQ ID NO: 1            moltype = AA  length = 6
FEATURE                 Location/Qualifiers
source                  1..6
                        mol_type = protein
                        organism = synthetic construct
SEQUENCE: 1
SDYAWN                                                                 6

SEQ ID NO: 2            moltype = AA  length = 5
FEATURE                 Location/Qualifiers
source                  1..5
                        mol_type = protein
                        organism = synthetic construct
SEQUENCE: 2
NYGMN                                                                  5

SEQ ID NO: 3            moltype = AA  length = 5
FEATURE                 Location/Qualifiers
source                  1..5
                        mol_type = protein
                        organism = synthetic construct
SEQUENCE: 3
NYGMN                                                                  5

SEQ ID NO: 4            moltype = AA  length = 5
FEATURE                 Location/Qualifiers
source                  1..5
                        mol_type = protein
                        organism = synthetic construct
SEQUENCE: 4
NYGMN                                                                  5

SEQ ID NO: 5            moltype = AA  length = 5
FEATURE                 Location/Qualifiers
source                  1..5
                        mol_type = protein
                        organism = synthetic construct
SEQUENCE: 5
NYGMN                                                                  5

SEQ ID NO: 6            moltype = AA  length = 5
FEATURE                 Location/Qualifiers
source                  1..5
                        mol_type = protein
                        organism = synthetic construct
SEQUENCE: 6
DYGMA                                                                  5

SEQ ID NO: 7            moltype = AA  length = 5
FEATURE                 Location/Qualifiers
source                  1..5
                        mol_type = protein
                        organism = synthetic construct
SEQUENCE: 7
GYTMN                                                                  5

SEQ ID NO: 8            moltype = AA  length = 5
FEATURE                 Location/Qualifiers
source                  1..5
                        mol_type = protein
                        organism = synthetic construct
SEQUENCE: 8
RFWMS                                                                  5

SEQ ID NO: 9            moltype = AA  length = 5
FEATURE                 Location/Qualifiers
source                  1..5
                        mol_type = protein
                        organism = synthetic construct
SEQUENCE: 9
DYGMA                                                                  5

SEQ ID NO: 10           moltype = AA  length = 5
FEATURE                 Location/Qualifiers
source                  1..5
                        mol_type = protein
                        organism = synthetic construct
```

```
SEQUENCE: 10
DYGMA                                                                5

SEQ ID NO: 11            moltype = AA  length = 5
FEATURE                  Location/Qualifiers
source                   1..5
                         mol_type = protein
                         organism = synthetic construct
SEQUENCE: 11
RFWMS                                                                5

SEQ ID NO: 12            moltype = AA  length = 5
FEATURE                  Location/Qualifiers
source                   1..5
                         mol_type = protein
                         organism = synthetic construct
SEQUENCE: 12
RYWMS                                                                5

SEQ ID NO: 13            moltype = AA  length = 5
FEATURE                  Location/Qualifiers
source                   1..5
                         mol_type = protein
                         organism = synthetic construct
SEQUENCE: 13
RYWMS                                                                5

SEQ ID NO: 14            moltype = AA  length = 5
FEATURE                  Location/Qualifiers
source                   1..5
                         mol_type = protein
                         organism = synthetic construct
SEQUENCE: 14
RYWMT                                                                5

SEQ ID NO: 15            moltype = AA  length = 5
FEATURE                  Location/Qualifiers
source                   1..5
                         mol_type = protein
                         organism = synthetic construct
SEQUENCE: 15
RFWMS                                                                5

SEQ ID NO: 16            moltype = AA  length = 5
FEATURE                  Location/Qualifiers
source                   1..5
                         mol_type = protein
                         organism = synthetic construct
SEQUENCE: 16
RYWMS                                                                5

SEQ ID NO: 17            moltype = AA  length = 5
FEATURE                  Location/Qualifiers
source                   1..5
                         mol_type = protein
                         organism = synthetic construct
SEQUENCE: 17
GYTMN                                                                5

SEQ ID NO: 18            moltype = AA  length = 5
FEATURE                  Location/Qualifiers
source                   1..5
                         mol_type = protein
                         organism = synthetic construct
SEQUENCE: 18
RFWMS                                                                5

SEQ ID NO: 19            moltype = AA  length = 5
FEATURE                  Location/Qualifiers
source                   1..5
                         mol_type = protein
                         organism = synthetic construct
SEQUENCE: 19
RYWMS                                                                5

SEQ ID NO: 20            moltype = AA  length = 5
FEATURE                  Location/Qualifiers
source                   1..5
                         mol_type = protein
```

```
                        organism = synthetic construct
SEQUENCE: 20
RYWMS                                                                  5

SEQ ID NO: 21           moltype = AA  length = 5
FEATURE                 Location/Qualifiers
source                  1..5
                        mol_type = protein
                        organism = synthetic construct
SEQUENCE: 21
DFGMA                                                                  5

SEQ ID NO: 22           moltype = AA  length = 16
FEATURE                 Location/Qualifiers
source                  1..16
                        mol_type = protein
                        organism = synthetic construct
SEQUENCE: 22
YISYSGSTSY NPSLKS                                                      16

SEQ ID NO: 23           moltype = AA  length = 17
FEATURE                 Location/Qualifiers
source                  1..17
                        mol_type = protein
                        organism = synthetic construct
SEQUENCE: 23
WINTYSGEPT YVDDFKG                                                     17

SEQ ID NO: 24           moltype = AA  length = 17
FEATURE                 Location/Qualifiers
source                  1..17
                        mol_type = protein
                        organism = synthetic construct
SEQUENCE: 24
WINTNTGEPT YSEEFKG                                                     17

SEQ ID NO: 25           moltype = AA  length = 17
FEATURE                 Location/Qualifiers
source                  1..17
                        mol_type = protein
                        organism = synthetic construct
SEQUENCE: 25
WINTYTGEPT YADDFKG                                                     17

SEQ ID NO: 26           moltype = AA  length = 17
FEATURE                 Location/Qualifiers
source                  1..17
                        mol_type = protein
                        organism = synthetic construct
SEQUENCE: 26
WINTYTGEPT YADDFKG                                                     17

SEQ ID NO: 27           moltype = AA  length = 17
FEATURE                 Location/Qualifiers
source                  1..17
                        mol_type = protein
                        organism = synthetic construct
SEQUENCE: 27
FISNLAYSVY YADTVTG                                                     17

SEQ ID NO: 28           moltype = AA  length = 17
FEATURE                 Location/Qualifiers
source                  1..17
                        mol_type = protein
                        organism = synthetic construct
SEQUENCE: 28
LISPYSGGTN YNQRFKG                                                     17

SEQ ID NO: 29           moltype = AA  length = 17
FEATURE                 Location/Qualifiers
source                  1..17
                        mol_type = protein
                        organism = synthetic construct
SEQUENCE: 29
EISPDSNTID LTPSLKD                                                     17

SEQ ID NO: 30           moltype = AA  length = 17
FEATURE                 Location/Qualifiers
source                  1..17
```

```
                        mol_type = protein
                        organism = synthetic construct
SEQUENCE: 30
FISNLAYSVY YADTVTG                                                   17

SEQ ID NO: 31           moltype = AA  length = 17
FEATURE                 Location/Qualifiers
source                  1..17
                        mol_type = protein
                        organism = synthetic construct
SEQUENCE: 31
FISNLAYSVY YADTVTG                                                   17

SEQ ID NO: 32           moltype = AA  length = 17
FEATURE                 Location/Qualifiers
source                  1..17
                        mol_type = protein
                        organism = synthetic construct
SEQUENCE: 32
EISPNSSTIH QTPSLKD                                                   17

SEQ ID NO: 33           moltype = AA  length = 17
FEATURE                 Location/Qualifiers
source                  1..17
                        mol_type = protein
                        organism = synthetic construct
SEQUENCE: 33
EINPDSSTID LTPSLKD                                                   17

SEQ ID NO: 34           moltype = AA  length = 17
FEATURE                 Location/Qualifiers
source                  1..17
                        mol_type = protein
                        organism = synthetic construct
SEQUENCE: 34
EISPDSSTID LTPSLKD                                                   17

SEQ ID NO: 35           moltype = AA  length = 17
FEATURE                 Location/Qualifiers
source                  1..17
                        mol_type = protein
                        organism = synthetic construct
SEQUENCE: 35
EINPHSSTIT YTPSLKD                                                   17

SEQ ID NO: 36           moltype = AA  length = 17
FEATURE                 Location/Qualifiers
source                  1..17
                        mol_type = protein
                        organism = synthetic construct
SEQUENCE: 36
EINPDSSTIT YTPSLKD                                                   17

SEQ ID NO: 37           moltype = AA  length = 17
FEATURE                 Location/Qualifiers
source                  1..17
                        mol_type = protein
                        organism = synthetic construct
SEQUENCE: 37
EISPDSSTIN YTASLKD                                                   17

SEQ ID NO: 38           moltype = AA  length = 17
FEATURE                 Location/Qualifiers
source                  1..17
                        mol_type = protein
                        organism = synthetic construct
SEQUENCE: 38
LISPYSGGTN YNQKFKG                                                   17

SEQ ID NO: 39           moltype = AA  length = 17
FEATURE                 Location/Qualifiers
source                  1..17
                        mol_type = protein
                        organism = synthetic construct
SEQUENCE: 39
EISPNSSTIH QTPSLKD                                                   17

SEQ ID NO: 40           moltype = AA  length = 17
FEATURE                 Location/Qualifiers
```

```
source                  1..17
                        mol_type = protein
                        organism = synthetic construct
SEQUENCE: 40
EINPDSSTID LTPSLKD                                               17

SEQ ID NO: 41           moltype = AA  length = 17
FEATURE                 Location/Qualifiers
source                  1..17
                        mol_type = protein
                        organism = synthetic construct
SEQUENCE: 41
EISPDSNTID LTPSLKD                                               17

SEQ ID NO: 42           moltype = AA  length = 17
FEATURE                 Location/Qualifiers
source                  1..17
                        mol_type = protein
                        organism = synthetic construct
SEQUENCE: 42
FISNLAYNIY YSDTVTG                                               17

SEQ ID NO: 43           moltype = AA  length = 14
FEATURE                 Location/Qualifiers
source                  1..14
                        mol_type = protein
                        organism = synthetic construct
SEQUENCE: 43
EGGRGGTEGY YFDY                                                  14

SEQ ID NO: 44           moltype = AA  length = 8
FEATURE                 Location/Qualifiers
source                  1..8
                        mol_type = protein
                        organism = synthetic construct
SEQUENCE: 44
GTVVGFDY                                                         8

SEQ ID NO: 45           moltype = AA  length = 8
FEATURE                 Location/Qualifiers
source                  1..8
                        mol_type = protein
                        organism = synthetic construct
SEQUENCE: 45
SSYYAMDY                                                         8

SEQ ID NO: 46           moltype = AA  length = 5
FEATURE                 Location/Qualifiers
source                  1..5
                        mol_type = protein
                        organism = synthetic construct
SEQUENCE: 46
YAMDY                                                            5

SEQ ID NO: 47           moltype = AA  length = 9
FEATURE                 Location/Qualifiers
source                  1..9
                        mol_type = protein
                        organism = synthetic construct
SEQUENCE: 47
WDDYDGFAY                                                        9

SEQ ID NO: 48           moltype = AA  length = 10
FEATURE                 Location/Qualifiers
source                  1..10
                        mol_type = protein
                        organism = synthetic construct
SEQUENCE: 48
DRGLRESMDY                                                       10

SEQ ID NO: 49           moltype = AA  length = 14
FEATURE                 Location/Qualifiers
source                  1..14
                        mol_type = protein
                        organism = synthetic construct
SEQUENCE: 49
SGFITTGVPT NFDV                                                  14

SEQ ID NO: 50           moltype = AA  length = 6
```

```
FEATURE                 Location/Qualifiers
source                  1..6
                        mol_type = protein
                        organism = synthetic construct
SEQUENCE: 50
PYYGYY                                                          6

SEQ ID NO: 51           moltype = AA  length = 10
FEATURE                 Location/Qualifiers
source                  1..10
                        mol_type = protein
                        organism = synthetic construct
SEQUENCE: 51
DRGLRESMDY                                                      10

SEQ ID NO: 52           moltype = AA  length = 10
FEATURE                 Location/Qualifiers
source                  1..10
                        mol_type = protein
                        organism = synthetic construct
SEQUENCE: 52
DRGLRETMDY                                                      10

SEQ ID NO: 53           moltype = AA  length = 6
FEATURE                 Location/Qualifiers
source                  1..6
                        mol_type = protein
                        organism = synthetic construct
SEQUENCE: 53
PYYGYY                                                          6

SEQ ID NO: 54           moltype = AA  length = 6
FEATURE                 Location/Qualifiers
source                  1..6
                        mol_type = protein
                        organism = synthetic construct
SEQUENCE: 54
PYHGYY                                                          6

SEQ ID NO: 55           moltype = AA  length = 6
FEATURE                 Location/Qualifiers
source                  1..6
                        mol_type = protein
                        organism = synthetic construct
SEQUENCE: 55
PYHGYY                                                          6

SEQ ID NO: 56           moltype = AA  length = 6
FEATURE                 Location/Qualifiers
source                  1..6
                        mol_type = protein
                        organism = synthetic construct
SEQUENCE: 56
PYYGYY                                                          6

SEQ ID NO: 57           moltype = AA  length = 6
FEATURE                 Location/Qualifiers
source                  1..6
                        mol_type = protein
                        organism = synthetic construct
SEQUENCE: 57
PYYGYY                                                          6

SEQ ID NO: 58           moltype = AA  length = 6
FEATURE                 Location/Qualifiers
source                  1..6
                        mol_type = protein
                        organism = synthetic construct
SEQUENCE: 58
PYYGYY                                                          6

SEQ ID NO: 59           moltype = AA  length = 14
FEATURE                 Location/Qualifiers
source                  1..14
                        mol_type = protein
                        organism = synthetic construct
SEQUENCE: 59
SGFITTGVAT NFDV                                                 14
```

```
SEQ ID NO: 60          moltype = AA  length = 6
FEATURE                Location/Qualifiers
source                 1..6
                       mol_type = protein
                       organism = synthetic construct
SEQUENCE: 60
PYYGYY                                                            6

SEQ ID NO: 61          moltype = AA  length = 6
FEATURE                Location/Qualifiers
source                 1..6
                       mol_type = protein
                       organism = synthetic construct
SEQUENCE: 61
PYYGYY                                                            6

SEQ ID NO: 62          moltype = AA  length = 6
FEATURE                Location/Qualifiers
source                 1..6
                       mol_type = protein
                       organism = synthetic construct
SEQUENCE: 62
PYYGYY                                                            6

SEQ ID NO: 63          moltype = AA  length = 10
FEATURE                Location/Qualifiers
source                 1..10
                       mol_type = protein
                       organism = synthetic construct
SEQUENCE: 63
DRGLRETMDY                                                        10

SEQ ID NO: 64          moltype = AA  length = 30
FEATURE                Location/Qualifiers
source                 1..30
                       mol_type = protein
                       organism = synthetic construct
SEQUENCE: 64
DVQLQESGPG LVKPSQSLSL TCTVTGYSIT                                  30

SEQ ID NO: 65          moltype = AA  length = 30
FEATURE                Location/Qualifiers
source                 1..30
                       mol_type = protein
                       organism = synthetic construct
SEQUENCE: 65
QIQLVQSGPE LKKPGETVKI SCKASGYIFT                                  30

SEQ ID NO: 66          moltype = AA  length = 30
FEATURE                Location/Qualifiers
source                 1..30
                       mol_type = protein
                       organism = synthetic construct
SEQUENCE: 66
QIQLVQSGPE LKKPGETVKI SCKASGYTFT                                  30

SEQ ID NO: 67          moltype = AA  length = 30
FEATURE                Location/Qualifiers
source                 1..30
                       mol_type = protein
                       organism = synthetic construct
SEQUENCE: 67
QIQLVQSGPE LKKPGETVKI SCKASGYTFT                                  30

SEQ ID NO: 68          moltype = AA  length = 30
FEATURE                Location/Qualifiers
source                 1..30
                       mol_type = protein
                       organism = synthetic construct
SEQUENCE: 68
QIQLVQSGPE LKKPGETVKI SCKASGYTFT                                  30

SEQ ID NO: 69          moltype = AA  length = 30
FEATURE                Location/Qualifiers
source                 1..30
                       mol_type = protein
                       organism = synthetic construct
SEQUENCE: 69
EVKLVESGGG LVQPGGSRKL SCAASGFTFS                                  30
```

```
SEQ ID NO: 70          moltype = AA  length = 30
FEATURE                Location/Qualifiers
source                 1..30
                       mol_type = protein
                       organism = synthetic construct
SEQUENCE: 70
EVQLQQSGPE LVKPGASMKI SCKASGYAFT                                   30

SEQ ID NO: 71          moltype = AA  length = 30
FEATURE                Location/Qualifiers
source                 1..30
                       mol_type = protein
                       organism = synthetic construct
SEQUENCE: 71
EVKLLESGGG LVQPGGSLKL SCAASGFDFS                                   30

SEQ ID NO: 72          moltype = AA  length = 30
FEATURE                Location/Qualifiers
source                 1..30
                       mol_type = protein
                       organism = synthetic construct
SEQUENCE: 72
EVKLVESGGG LVQPGGSRKL SCAASGFTFS                                   30

SEQ ID NO: 73          moltype = AA  length = 30
FEATURE                Location/Qualifiers
source                 1..30
                       mol_type = protein
                       organism = synthetic construct
SEQUENCE: 73
EVKLVESGGG LVQPGGSRKL SCAASGFTFS                                   30

SEQ ID NO: 74          moltype = AA  length = 30
FEATURE                Location/Qualifiers
source                 1..30
                       mol_type = protein
                       organism = synthetic construct
SEQUENCE: 74
EVNLLESGGG LVQPGGSLKL SCEASGFDFS                                   30

SEQ ID NO: 75          moltype = AA  length = 30
FEATURE                Location/Qualifiers
source                 1..30
                       mol_type = protein
                       organism = synthetic construct
SEQUENCE: 75
EVKLLESGGG LVQPGGSLKL SCAASGFDFS                                   30

SEQ ID NO: 76          moltype = AA  length = 30
FEATURE                Location/Qualifiers
source                 1..30
                       mol_type = protein
                       organism = synthetic construct
SEQUENCE: 76
EVKLLESGGG LVQPGGSLKL SCAASGFDFS                                   30

SEQ ID NO: 77          moltype = AA  length = 30
FEATURE                Location/Qualifiers
source                 1..30
                       mol_type = protein
                       organism = synthetic construct
SEQUENCE: 77
EVKLLESGGG LVQPGGSLKL SCAASGFDFS                                   30

SEQ ID NO: 78          moltype = AA  length = 30
FEATURE                Location/Qualifiers
source                 1..30
                       mol_type = protein
                       organism = synthetic construct
SEQUENCE: 78
EVKLLESGGD LVQPGGSLKL SCAASGFDFS                                   30

SEQ ID NO: 79          moltype = AA  length = 30
FEATURE                Location/Qualifiers
source                 1..30
                       mol_type = protein
                       organism = synthetic construct
SEQUENCE: 79
```

```
EVKLLESGGG LVQPGGSLKL SCAASGFDFS                                 30

SEQ ID NO: 80          moltype = AA  length = 30
FEATURE                Location/Qualifiers
source                 1..30
                       mol_type = protein
                       organism = synthetic construct
SEQUENCE: 80
EVQLQQSGPE LVKPGASMKM SCKASGYSFT                                 30

SEQ ID NO: 81          moltype = AA  length = 30
FEATURE                Location/Qualifiers
source                 1..30
                       mol_type = protein
                       organism = synthetic construct
SEQUENCE: 81
EVNLLESGGG LVQPGGSLKL SCEASGFDFS                                 30

SEQ ID NO: 82          moltype = AA  length = 30
FEATURE                Location/Qualifiers
source                 1..30
                       mol_type = protein
                       organism = synthetic construct
SEQUENCE: 82
EVKLLESGGG LVQPGGSLKL SCAASGFDFS                                 30

SEQ ID NO: 83          moltype = AA  length = 30
FEATURE                Location/Qualifiers
source                 1..30
                       mol_type = protein
                       organism = synthetic construct
SEQUENCE: 83
EVKLLESGGG LVQPGGSLKL SCAASGFDFS                                 30

SEQ ID NO: 84          moltype = AA  length = 30
FEATURE                Location/Qualifiers
source                 1..30
                       mol_type = protein
                       organism = synthetic construct
SEQUENCE: 84
EVKLVESGGG LVQSGGSRKL SCAASGFTFS                                 30

SEQ ID NO: 85          moltype = AA  length = 14
FEATURE                Location/Qualifiers
source                 1..14
                       mol_type = protein
                       organism = synthetic construct
SEQUENCE: 85
WIRQFPGNKL EWMG                                                  14

SEQ ID NO: 86          moltype = AA  length = 14
FEATURE                Location/Qualifiers
source                 1..14
                       mol_type = protein
                       organism = synthetic construct
SEQUENCE: 86
WVKQAPGKGL KWMG                                                  14

SEQ ID NO: 87          moltype = AA  length = 14
FEATURE                Location/Qualifiers
source                 1..14
                       mol_type = protein
                       organism = synthetic construct
SEQUENCE: 87
WVKQAPGKGL KWMG                                                  14

SEQ ID NO: 88          moltype = AA  length = 14
FEATURE                Location/Qualifiers
source                 1..14
                       mol_type = protein
                       organism = synthetic construct
SEQUENCE: 88
WVKQAPGKGL KWMG                                                  14

SEQ ID NO: 89          moltype = AA  length = 14
FEATURE                Location/Qualifiers
source                 1..14
                       mol_type = protein
                       organism = synthetic construct
```

```
SEQUENCE: 89
WVKQAPGKGL KWMG                                                    14

SEQ ID NO: 90          moltype = AA  length = 14
FEATURE                Location/Qualifiers
source                 1..14
                       mol_type = protein
                       organism = synthetic construct
SEQUENCE: 90
WFRQAPGKGP EWVA                                                    14

SEQ ID NO: 91          moltype = AA  length = 14
FEATURE                Location/Qualifiers
source                 1..14
                       mol_type = protein
                       organism = synthetic construct
SEQUENCE: 91
WVKQSHGKNL EWIG                                                    14

SEQ ID NO: 92          moltype = AA  length = 14
FEATURE                Location/Qualifiers
source                 1..14
                       mol_type = protein
                       organism = synthetic construct
SEQUENCE: 92
WVRQAPGKGL EWIG                                                    14

SEQ ID NO: 93          moltype = AA  length = 14
FEATURE                Location/Qualifiers
source                 1..14
                       mol_type = protein
                       organism = synthetic construct
SEQUENCE: 93
WFRQAPGKGP EWVA                                                    14

SEQ ID NO: 94          moltype = AA  length = 14
FEATURE                Location/Qualifiers
source                 1..14
                       mol_type = protein
                       organism = synthetic construct
SEQUENCE: 94
WFRQAPGKGP EWVA                                                    14

SEQ ID NO: 95          moltype = AA  length = 14
FEATURE                Location/Qualifiers
source                 1..14
                       mol_type = protein
                       organism = synthetic construct
SEQUENCE: 95
WVRQTPGEGL EWIG                                                    14

SEQ ID NO: 96          moltype = AA  length = 14
FEATURE                Location/Qualifiers
source                 1..14
                       mol_type = protein
                       organism = synthetic construct
SEQUENCE: 96
WVRQAPGKGL EWIG                                                    14

SEQ ID NO: 97          moltype = AA  length = 14
FEATURE                Location/Qualifiers
source                 1..14
                       mol_type = protein
                       organism = synthetic construct
SEQUENCE: 97
WVRQAPGKGL EWIG                                                    14

SEQ ID NO: 98          moltype = AA  length = 14
FEATURE                Location/Qualifiers
source                 1..14
                       mol_type = protein
                       organism = synthetic construct
SEQUENCE: 98
WVRQAPGKGL EWIG                                                    14

SEQ ID NO: 99          moltype = AA  length = 14
FEATURE                Location/Qualifiers
source                 1..14
                       mol_type = protein
```

```
                        organism = synthetic construct
SEQUENCE: 99
WVRQAPGKGL EWIG                                                  14

SEQ ID NO: 100          moltype = AA  length = 14
FEATURE                 Location/Qualifiers
source                  1..14
                        mol_type = protein
                        organism = synthetic construct
SEQUENCE: 100
WVRQAPGKGL EWIG                                                  14

SEQ ID NO: 101          moltype = AA  length = 14
FEATURE                 Location/Qualifiers
source                  1..14
                        mol_type = protein
                        organism = synthetic construct
SEQUENCE: 101
WVKQSHGKNL EWIG                                                  14

SEQ ID NO: 102          moltype = AA  length = 14
FEATURE                 Location/Qualifiers
source                  1..14
                        mol_type = protein
                        organism = synthetic construct
SEQUENCE: 102
WVRQTPGEGL EWIG                                                  14

SEQ ID NO: 103          moltype = AA  length = 14
FEATURE                 Location/Qualifiers
source                  1..14
                        mol_type = protein
                        organism = synthetic construct
SEQUENCE: 103
WVRQAPGKGL EWIG                                                  14

SEQ ID NO: 104          moltype = AA  length = 14
FEATURE                 Location/Qualifiers
source                  1..14
                        mol_type = protein
                        organism = synthetic construct
SEQUENCE: 104
WVRQAPGKGL EWIG                                                  14

SEQ ID NO: 105          moltype = AA  length = 14
FEATURE                 Location/Qualifiers
source                  1..14
                        mol_type = protein
                        organism = synthetic construct
SEQUENCE: 105
WVRQAPGKGP EWVA                                                  14

SEQ ID NO: 106          moltype = AA  length = 32
FEATURE                 Location/Qualifiers
source                  1..32
                        mol_type = protein
                        organism = synthetic construct
SEQUENCE: 106
RISITRDASK NQFFLQLNSV TTEDTATYYC AR                              32

SEQ ID NO: 107          moltype = AA  length = 32
FEATURE                 Location/Qualifiers
source                  1..32
                        mol_type = protein
                        organism = synthetic construct
SEQUENCE: 107
RFVFSLETSA STAYLQINNL KNEDMATYFC AR                              32

SEQ ID NO: 108          moltype = AA  length = 32
FEATURE                 Location/Qualifiers
source                  1..32
                        mol_type = protein
                        organism = synthetic construct
SEQUENCE: 108
RFAFSLETSA STAYLQINNL KNEDTATYFC GR                              32

SEQ ID NO: 109          moltype = AA  length = 32
FEATURE                 Location/Qualifiers
source                  1..32
```

```
                        mol_type = protein
                        organism = synthetic construct
SEQUENCE: 109
RFAFSLETSA STAYLQINNL KNEDMATYFC AR                                  32

SEQ ID NO: 110          moltype = AA  length = 32
FEATURE                 Location/Qualifiers
source                  1..32
                        mol_type = protein
                        organism = synthetic construct
SEQUENCE: 110
RFAFSLETSA STAYLQINNL KNEDTATYFC AR                                  32

SEQ ID NO: 111          moltype = AA  length = 32
FEATURE                 Location/Qualifiers
source                  1..32
                        mol_type = protein
                        organism = synthetic construct
SEQUENCE: 111
RFTISRENAK NTLFLEMSSL RSEDTAIYYC TR                                  32

SEQ ID NO: 112          moltype = AA  length = 32
FEATURE                 Location/Qualifiers
source                  1..32
                        mol_type = protein
                        organism = synthetic construct
SEQUENCE: 112
KATFTVDKSS STAYMELLSL TSEDSGVYYC AR                                  32

SEQ ID NO: 113          moltype = AA  length = 32
FEATURE                 Location/Qualifiers
source                  1..32
                        mol_type = protein
                        organism = synthetic construct
SEQUENCE: 113
NFIISRDNAK NALFLQMSKV RSEDTALYYC TR                                  32

SEQ ID NO: 114          moltype = AA  length = 32
FEATURE                 Location/Qualifiers
source                  1..32
                        mol_type = protein
                        organism = synthetic construct
SEQUENCE: 114
RFTISRENAK NTLYLEMSSL RSEDTAIYYC TR                                  32

SEQ ID NO: 115          moltype = AA  length = 32
FEATURE                 Location/Qualifiers
source                  1..32
                        mol_type = protein
                        organism = synthetic construct
SEQUENCE: 115
RFTISRENAK NTLYLEMNSL RSEDTAIYYC TR                                  32

SEQ ID NO: 116          moltype = AA  length = 32
FEATURE                 Location/Qualifiers
source                  1..32
                        mol_type = protein
                        organism = synthetic construct
SEQUENCE: 116
RFIISRDNAK NTLFLQMTKV TSDDSALYYC AR                                  32

SEQ ID NO: 117          moltype = AA  length = 32
FEATURE                 Location/Qualifiers
source                  1..32
                        mol_type = protein
                        organism = synthetic construct
SEQUENCE: 117
NFIISRDNAK NALYLQMSKV KSEDTALYYC TR                                  32

SEQ ID NO: 118          moltype = AA  length = 32
FEATURE                 Location/Qualifiers
source                  1..32
                        mol_type = protein
                        organism = synthetic construct
SEQUENCE: 118
NFIISRDNAK NALYLQMSKV KSEDTALYYC TR                                  32

SEQ ID NO: 119          moltype = AA  length = 32
FEATURE                 Location/Qualifiers
```

```
source                  1..32
                        mol_type = protein
                        organism = synthetic construct
SEQUENCE: 119
KFIISRDNAK NTLYLQMSKV SSEDTALYYC AR                             32

SEQ ID NO: 120          moltype = AA  length = 32
FEATURE                 Location/Qualifiers
source                  1..32
                        mol_type = protein
                        organism = synthetic construct
SEQUENCE: 120
KFIISRDNAK SSLYLQMSKV TSEDTALYYC AR                             32

SEQ ID NO: 121          moltype = AA  length = 32
FEATURE                 Location/Qualifiers
source                  1..32
                        mol_type = protein
                        organism = synthetic construct
SEQUENCE: 121
KFNISRDNAK NTLYLQMSKV RSEDTALYYC AR                             32

SEQ ID NO: 122          moltype = AA  length = 32
FEATURE                 Location/Qualifiers
source                  1..32
                        mol_type = protein
                        organism = synthetic construct
SEQUENCE: 122
KATLTVDKSS STAYMEVFSL TSEDSGVYYC AR                             32

SEQ ID NO: 123          moltype = AA  length = 32
FEATURE                 Location/Qualifiers
source                  1..32
                        mol_type = protein
                        organism = synthetic construct
SEQUENCE: 123
KFFISRDNAK STLFLQMTNV TSEDSALYYC AR                             32

SEQ ID NO: 124          moltype = AA  length = 32
FEATURE                 Location/Qualifiers
source                  1..32
                        mol_type = protein
                        organism = synthetic construct
SEQUENCE: 124
NFIISRDNAK NALYLQMSKV RSEDTALYYC TR                             32

SEQ ID NO: 125          moltype = AA  length = 32
FEATURE                 Location/Qualifiers
source                  1..32
                        mol_type = protein
                        organism = synthetic construct
SEQUENCE: 125
NFIISRDNAK NALYLQMSKL RSEDTALYYC TR                             32

SEQ ID NO: 126          moltype = AA  length = 32
FEATURE                 Location/Qualifiers
source                  1..32
                        mol_type = protein
                        organism = synthetic construct
SEQUENCE: 126
RFTISRENAK NTLYLEMSSL RSEDTAVYYC TR                             32

SEQ ID NO: 127          moltype = AA  length = 11
FEATURE                 Location/Qualifiers
source                  1..11
                        mol_type = protein
                        organism = synthetic construct
SEQUENCE: 127
WGQGTTLTVS S                                                    11

SEQ ID NO: 128          moltype = AA  length = 11
FEATURE                 Location/Qualifiers
source                  1..11
                        mol_type = protein
                        organism = synthetic construct
SEQUENCE: 128
WGQGTTLTVS S                                                    11

SEQ ID NO: 129          moltype = AA  length = 11
```

```
FEATURE                 Location/Qualifiers
source                  1..11
                        mol_type = protein
                        organism = synthetic construct
SEQUENCE: 129
WGQGTSVTVS S                                                        11

SEQ ID NO: 130          moltype = AA  length = 11
FEATURE                 Location/Qualifiers
source                  1..11
                        mol_type = protein
                        organism = synthetic construct
SEQUENCE: 130
WGQGTSVTVS S                                                        11

SEQ ID NO: 131          moltype = AA  length = 11
FEATURE                 Location/Qualifiers
source                  1..11
                        mol_type = protein
                        organism = synthetic construct
SEQUENCE: 131
WGQGTLVTVS A                                                        11

SEQ ID NO: 132          moltype = AA  length = 11
FEATURE                 Location/Qualifiers
source                  1..11
                        mol_type = protein
                        organism = synthetic construct
SEQUENCE: 132
WGQGTSVTVS S                                                        11

SEQ ID NO: 133          moltype = AA  length = 11
FEATURE                 Location/Qualifiers
source                  1..11
                        mol_type = protein
                        organism = synthetic construct
SEQUENCE: 133
WGAGTTVTVS S                                                        11

SEQ ID NO: 134          moltype = AA  length = 11
FEATURE                 Location/Qualifiers
source                  1..11
                        mol_type = protein
                        organism = synthetic construct
SEQUENCE: 134
WGQGTLVTVS A                                                        11

SEQ ID NO: 135          moltype = AA  length = 11
FEATURE                 Location/Qualifiers
source                  1..11
                        mol_type = protein
                        organism = synthetic construct
SEQUENCE: 135
WGQGTSVTVS S                                                        11

SEQ ID NO: 136          moltype = AA  length = 11
FEATURE                 Location/Qualifiers
source                  1..11
                        mol_type = protein
                        organism = synthetic construct
SEQUENCE: 136
WGQGTSVTVS S                                                        11

SEQ ID NO: 137          moltype = AA  length = 11
FEATURE                 Location/Qualifiers
source                  1..11
                        mol_type = protein
                        organism = synthetic construct
SEQUENCE: 137
WGHGTLVTVS A                                                        11

SEQ ID NO: 138          moltype = AA  length = 11
FEATURE                 Location/Qualifiers
source                  1..11
                        mol_type = protein
                        organism = synthetic construct
SEQUENCE: 138
WGQGTLVTVS A                                                        11
```

```
SEQ ID NO: 139          moltype = AA  length = 11
FEATURE                 Location/Qualifiers
source                  1..11
                        mol_type = protein
                        organism = synthetic construct
SEQUENCE: 139
WGQGTLVTVS A                                                    11

SEQ ID NO: 140          moltype = AA  length = 11
FEATURE                 Location/Qualifiers
source                  1..11
                        mol_type = protein
                        organism = synthetic construct
SEQUENCE: 140
WGQGTLVTVS A                                                    11

SEQ ID NO: 141          moltype = AA  length = 11
FEATURE                 Location/Qualifiers
source                  1..11
                        mol_type = protein
                        organism = synthetic construct
SEQUENCE: 141
WGQGTLVTVS A                                                    11

SEQ ID NO: 142          moltype = AA  length = 11
FEATURE                 Location/Qualifiers
source                  1..11
                        mol_type = protein
                        organism = synthetic construct
SEQUENCE: 142
WGQGTLVTVS E                                                    11

SEQ ID NO: 143          moltype = AA  length = 11
FEATURE                 Location/Qualifiers
source                  1..11
                        mol_type = protein
                        organism = synthetic construct
SEQUENCE: 143
WGAGTTVTVS S                                                    11

SEQ ID NO: 144          moltype = AA  length = 11
FEATURE                 Location/Qualifiers
source                  1..11
                        mol_type = protein
                        organism = synthetic construct
SEQUENCE: 144
WGHGTLVTVS A                                                    11

SEQ ID NO: 145          moltype = AA  length = 11
FEATURE                 Location/Qualifiers
source                  1..11
                        mol_type = protein
                        organism = synthetic construct
SEQUENCE: 145
WGQGTLVTVS A                                                    11

SEQ ID NO: 146          moltype = AA  length = 11
FEATURE                 Location/Qualifiers
source                  1..11
                        mol_type = protein
                        organism = synthetic construct
SEQUENCE: 146
WGQGTLVTVS A                                                    11

SEQ ID NO: 147          moltype = AA  length = 11
FEATURE                 Location/Qualifiers
source                  1..11
                        mol_type = protein
                        organism = synthetic construct
SEQUENCE: 147
WGQGTSVTVS S                                                    11

SEQ ID NO: 148          moltype = AA  length = 123
FEATURE                 Location/Qualifiers
source                  1..123
                        mol_type = protein
                        organism = synthetic construct
SEQUENCE: 148
DVQLQESGPG LVKPSQSLSL TCTVTGYSIT SDYAWNWIRQ FPGNKLEWMG YISYSGSTSY  60
```

```
NPSLKSRISI TRDASKNQFF LQLNSVTTED TATYYCAREG GRGGTEGYYF DYWGQGTTLT  120
VSS                                                               123

SEQ ID NO: 149         moltype = AA  length = 117
FEATURE                Location/Qualifiers
source                 1..117
                       mol_type = protein
                       organism = synthetic construct
SEQUENCE: 149
QIQLVQSGPE LKKPGETVKI SCKASGYIFT NYGMNWVKQA PGKGLKWMGW INTYSGEPTY  60
VDDFKGRFVF SLETSASTAY LQINNLKNED MATYFCARGT VVGFDYWGQG TTLTVSS     117

SEQ ID NO: 150         moltype = AA  length = 117
FEATURE                Location/Qualifiers
source                 1..117
                       mol_type = protein
                       organism = synthetic construct
SEQUENCE: 150
QIQLVQSGPE LKKPGETVKI SCKASGYTFT NYGMNWVKQA PGKGLKWMGW INTNTGEPTY  60
SEEFKGRFAF SLETSASTAY LQINNLKNED TATYFCGRSS YYAMDYWGQG TSVTVSS     117

SEQ ID NO: 151         moltype = AA  length = 114
FEATURE                Location/Qualifiers
source                 1..114
                       mol_type = protein
                       organism = synthetic construct
SEQUENCE: 151
QIQLVQSGPE LKKPGETVKI SCKASGYTFT NYGMNWVKQA PGKGLKWMGW INTYTGEPTY  60
ADDFKGRFAF SLETSASTAY LQINNLKNED MATYFCARYA MDYWGQGTSV TVSS        114

SEQ ID NO: 152         moltype = AA  length = 118
FEATURE                Location/Qualifiers
source                 1..118
                       mol_type = protein
                       organism = synthetic construct
SEQUENCE: 152
QIQLVQSGPE LKKPGETVKI SCKASGYTFT NYGMNWVKQA PGKGLKWMGW INTYTGEPTY  60
ADDFKGRFAF SLETSASTAY LQINNLKNED TATYFCARWD DYDGFAYWGQ GTLVTVSA    118

SEQ ID NO: 153         moltype = AA  length = 119
FEATURE                Location/Qualifiers
source                 1..119
                       mol_type = protein
                       organism = synthetic construct
SEQUENCE: 153
EVKLVESGGG LVQPGGSRKL SCAASGFTFS DYGMAWFRQA PGKGPEWVAF ISNLAYSVYY  60
ADTVTGRFTI SRENAKNTLF LEMSSLRSED TAIYYCTRDR GLRESMDYWG QGTSVTVSS   119

SEQ ID NO: 154         moltype = AA  length = 123
FEATURE                Location/Qualifiers
source                 1..123
                       mol_type = protein
                       organism = synthetic construct
SEQUENCE: 154
EVQLQQSGPE LVKPGASMKI SCKASGYAFT GYTMNWVKQS HGKNLEWIGL ISPYSGGTNY  60
NQRFKGKATF TVDKSSSTAY MELLSLTSED SGVYYCARSG FITTGVPTNF DVWGAGTTVT  120
VSS                                                               123

SEQ ID NO: 155         moltype = AA  length = 115
FEATURE                Location/Qualifiers
source                 1..115
                       mol_type = protein
                       organism = synthetic construct
SEQUENCE: 155
EVKLLESGGG LVQPGGSLKL SCAASGFDFS RFWMSWVRQA PGKGLEWIGE ISPDSNTIDL  60
TPSLKDNFII SRDNAKNALF LQMSKVRSED TALYYCTRPY YGYYWGQGTL VTVSA       115

SEQ ID NO: 156         moltype = AA  length = 119
FEATURE                Location/Qualifiers
source                 1..119
                       mol_type = protein
                       organism = synthetic construct
SEQUENCE: 156
EVKLVESGGG LVQPGGSRKL SCAASGFTFS DYGMAWFRQA PGKGPEWVAF ISNLAYSVYY  60
ADTVTGRFTI SRENAKNTLY LEMSSLRSED TAIYYCTRDR GLRESMDYWG QGTSVTVSS   119

SEQ ID NO: 157         moltype = AA  length = 119
FEATURE                Location/Qualifiers
source                 1..119
```

```
                         mol_type = protein
                         organism = synthetic construct
SEQUENCE: 157
EVKLVESGGG LVQPGGSRKL SCAASGFTFS DYGMAWFRQA PGKGPEWVAF ISNLAYSVYY  60
ADTVTGRFTI SRENAKNTLY LEMNSLRSED TAIYYCTRDR GLRETMDYWG QGTSVTVSS   119

SEQ ID NO: 158           moltype = AA  length = 115
FEATURE                  Location/Qualifiers
source                   1..115
                         mol_type = protein
                         organism = synthetic construct
SEQUENCE: 158
EVNLLESGGG LVQPGGSLKL SCEASGFDFS RFWMSWVRQT PGEGLEWIGE ISPNSSTIHQ  60
TPSLKDRFII SRDNAKNTLF LQMTKVTSDD SALYYCARPY YGYYWGHGTL VTVSA       115

SEQ ID NO: 159           moltype = AA  length = 115
FEATURE                  Location/Qualifiers
source                   1..115
                         mol_type = protein
                         organism = synthetic construct
SEQUENCE: 159
EVKLLESGGG LVQPGGSLKL SCAASGFDFS RYWMSWVRQA PGKGLEWIGE INPDSSTIDL  60
TPSLKDNFII SRDNAKNALY LQMSKVKSED TALYYCTRPY HGYYWGQGTL VTVSA       115

SEQ ID NO: 160           moltype = AA  length = 115
FEATURE                  Location/Qualifiers
source                   1..115
                         mol_type = protein
                         organism = synthetic construct
SEQUENCE: 160
EVKLLESGGG LVQPGGSLKL SCAASGFDFS RYWMSWVRQA PGKGLEWIGE ISPDSSTIDL  60
TPSLKDNFII SRDNAKNALY LQMSKVKSED TALYYCTRPY HGYYWGQGTL VTVSA       115

SEQ ID NO: 161           moltype = AA  length = 115
FEATURE                  Location/Qualifiers
source                   1..115
                         mol_type = protein
                         organism = synthetic construct
SEQUENCE: 161
EVKLLESGGG LVQPGGSLKL SCAASGFDFS RYWMTWVRQA PGKGLEWIGE INPHSSTITY  60
TPSLKDKFII SRDNAKNTLY LQMSKVSSED TALYYCARPY YGYYWGQGTL VTVSA       115

SEQ ID NO: 162           moltype = AA  length = 115
FEATURE                  Location/Qualifiers
source                   1..115
                         mol_type = protein
                         organism = synthetic construct
SEQUENCE: 162
EVKLLESGGD LVQPGGSLKL SCAASGFDFS RFWMSWVRQA PGKGLEWIGE INPDSSTITY  60
TPSLKDKFII SRDNAKSSLY LQMSKVTSED TALYYCARPY YGYYWGQGTL VTVSA       115

SEQ ID NO: 163           moltype = AA  length = 115
FEATURE                  Location/Qualifiers
source                   1..115
                         mol_type = protein
                         organism = synthetic construct
SEQUENCE: 163
EVKLLESGGG LVQPGGSLKL SCAASGFDFS RYWMSWVRQA PGKGLEWIGE ISPDSSTINY  60
TASLKDKFNI SRDNAKNTLY LQMSKVRSED TALYYCARPY YGYYWGQGTL VTVSE       115

SEQ ID NO: 164           moltype = AA  length = 123
FEATURE                  Location/Qualifiers
source                   1..123
                         mol_type = protein
                         organism = synthetic construct
SEQUENCE: 164
EVQLQQSGPE LVKPGASMKM SCKASGYSFT GYTMNWVKQS HGKNLEWIGL ISPYSGGTNY  60
NQKFKGKATL TVDKSSSTAY MEVFSLTSED SGVYYCARSG FITTGVATNF DVWGAGTTVT  120
VSS                                                                123

SEQ ID NO: 165           moltype = AA  length = 115
FEATURE                  Location/Qualifiers
source                   1..115
                         mol_type = protein
                         organism = synthetic construct
SEQUENCE: 165
EVNLLESGGG LVQPGGSLKL SCEASGFDFS RFWMSWVRQT PGEGLEWIGE ISPNSSTIHQ  60
TPSLKDKFFI SRDNAKSTLF LQMTNVTSED SALYYCARPY YGYYWGHGTL VTVSA       115
```

```
SEQ ID NO: 166         moltype = AA  length = 115
FEATURE                Location/Qualifiers
source                 1..115
                       mol_type = protein
                       organism = synthetic construct
SEQUENCE: 166
EVKLLESGGG LVQPGGSLKL SCAASGFDFS RYWMSWVRQA PGKGLEWIGE INPDSSTIDL  60
TPSLKDNFII SRDNAKNALY LQMSKVRSED TALYYCTRPY YGYYWGQGTL VTVSA       115

SEQ ID NO: 167         moltype = AA  length = 115
FEATURE                Location/Qualifiers
source                 1..115
                       mol_type = protein
                       organism = synthetic construct
SEQUENCE: 167
EVKLLESGGG LVQPGGSLKL SCAASGFDFS RYWMSWVRQA PGKGLEWIGE ISPDSNTIDL  60
TPSLKDNFII SRDNAKNALY LQMSKLRSED TALYYCTRPY YGYYWGQGTL VTVSA       115

SEQ ID NO: 168         moltype = AA  length = 119
FEATURE                Location/Qualifiers
source                 1..119
                       mol_type = protein
                       organism = synthetic construct
SEQUENCE: 168
EVKLVESGGG LVQSGGSRKL SCAASGFTFS DFGMAWVRQA PGKGPEWVAF ISNLAYNIYY  60
SDTVTGRFTI SRENAKNTLY LEMSSLRSED TAVYYCTRDR GLRETMDYWG QGTSVTVSS   119

SEQ ID NO: 169         moltype = AA  length = 15
FEATURE                Location/Qualifiers
source                 1..15
                       mol_type = protein
                       organism = synthetic construct
SEQUENCE: 169
RASESVDSYG NSFMH                                                   15

SEQ ID NO: 170         moltype = AA  length = 16
FEATURE                Location/Qualifiers
source                 1..16
                       mol_type = protein
                       organism = synthetic construct
SEQUENCE: 170
KSSQSLLDSD GKTYLN                                                  16

SEQ ID NO: 171         moltype = AA  length = 16
FEATURE                Location/Qualifiers
source                 1..16
                       mol_type = protein
                       organism = synthetic construct
SEQUENCE: 171
KSSQSLLDSD GKTYLN                                                  16

SEQ ID NO: 172         moltype = AA  length = 14
FEATURE                Location/Qualifiers
source                 1..14
                       mol_type = protein
                       organism = synthetic construct
SEQUENCE: 172
RSSTGAVTTS NYAN                                                    14

SEQ ID NO: 173         moltype = AA  length = 11
FEATURE                Location/Qualifiers
source                 1..11
                       mol_type = protein
                       organism = synthetic construct
SEQUENCE: 173
RASQSISNNL H                                                       11

SEQ ID NO: 174         moltype = AA  length = 16
FEATURE                Location/Qualifiers
source                 1..16
                       mol_type = protein
                       organism = synthetic construct
SEQUENCE: 174
RSSKSLLHNN GNTYLC                                                  16

SEQ ID NO: 175         moltype = AA  length = 11
FEATURE                Location/Qualifiers
source                 1..11
                       mol_type = protein
```

```
                        organism = synthetic construct
SEQUENCE: 175
KASQDVSTAV A                                                  11

SEQ ID NO: 176          moltype = AA  length = 17
FEATURE                 Location/Qualifiers
source                  1..17
                        mol_type = protein
                        organism = synthetic construct
SEQUENCE: 176
RSSQSLFNST NQKNYLT                                            17

SEQ ID NO: 177          moltype = AA  length = 16
FEATURE                 Location/Qualifiers
source                  1..16
                        mol_type = protein
                        organism = synthetic construct
SEQUENCE: 177
GSSKSLLHKN GNTYLC                                             16

SEQ ID NO: 178          moltype = AA  length = 16
FEATURE                 Location/Qualifiers
source                  1..16
                        mol_type = protein
                        organism = synthetic construct
SEQUENCE: 178
RSSKSLLHNN GNTYLC                                             16

SEQ ID NO: 179          moltype = AA  length = 17
FEATURE                 Location/Qualifiers
source                  1..17
                        mol_type = protein
                        organism = synthetic construct
SEQUENCE: 179
KSSQSLLSSI NQKNYLT                                            17

SEQ ID NO: 180          moltype = AA  length = 17
FEATURE                 Location/Qualifiers
source                  1..17
                        mol_type = protein
                        organism = synthetic construct
SEQUENCE: 180
RSSQSLLNST NQKNYLT                                            17

SEQ ID NO: 181          moltype = AA  length = 17
FEATURE                 Location/Qualifiers
source                  1..17
                        mol_type = protein
                        organism = synthetic construct
SEQUENCE: 181
RSSQSLLNST NQKNYLT                                            17

SEQ ID NO: 182          moltype = AA  length = 17
FEATURE                 Location/Qualifiers
source                  1..17
                        mol_type = protein
                        organism = synthetic construct
SEQUENCE: 182
KSSQSLLNSG NQKIYLT                                            17

SEQ ID NO: 183          moltype = AA  length = 17
FEATURE                 Location/Qualifiers
source                  1..17
                        mol_type = protein
                        organism = synthetic construct
SEQUENCE: 183
KSSQSLLNST NQKNYLT                                            17

SEQ ID NO: 184          moltype = AA  length = 17
FEATURE                 Location/Qualifiers
source                  1..17
                        mol_type = protein
                        organism = synthetic construct
SEQUENCE: 184
KSSQSLFNSG NQKNYLT                                            17

SEQ ID NO: 185          moltype = AA  length = 11
FEATURE                 Location/Qualifiers
source                  1..11
```

```
                        mol_type = protein
                        organism = synthetic construct
SEQUENCE: 185
KASQDVSTAV A                                                11

SEQ ID NO: 186          moltype = AA  length = 17
FEATURE                 Location/Qualifiers
source                  1..17
                        mol_type = protein
                        organism = synthetic construct
SEQUENCE: 186
KSSQSLLNSI NQKNYLT                                          17

SEQ ID NO: 187          moltype = AA  length = 17
FEATURE                 Location/Qualifiers
source                  1..17
                        mol_type = protein
                        organism = synthetic construct
SEQUENCE: 187
RSSQSLLNST NQKNYLT                                          17

SEQ ID NO: 188          moltype = AA  length = 17
FEATURE                 Location/Qualifiers
source                  1..17
                        mol_type = protein
                        organism = synthetic construct
SEQUENCE: 188
RSSQSLLNST NQKNYLT                                          17

SEQ ID NO: 189          moltype = AA  length = 16
FEATURE                 Location/Qualifiers
source                  1..16
                        mol_type = protein
                        organism = synthetic construct
SEQUENCE: 189
RSNKSLLHSN GNAYLS                                           16

SEQ ID NO: 190          moltype = AA  length = 7
FEATURE                 Location/Qualifiers
source                  1..7
                        mol_type = protein
                        organism = synthetic construct
SEQUENCE: 190
LASNLES                                                     7

SEQ ID NO: 191          moltype = AA  length = 7
FEATURE                 Location/Qualifiers
source                  1..7
                        mol_type = protein
                        organism = synthetic construct
SEQUENCE: 191
LVSKLDS                                                     7

SEQ ID NO: 192          moltype = AA  length = 7
FEATURE                 Location/Qualifiers
source                  1..7
                        mol_type = protein
                        organism = synthetic construct
SEQUENCE: 192
LVSKLDS                                                     7

SEQ ID NO: 193          moltype = AA  length = 7
FEATURE                 Location/Qualifiers
source                  1..7
                        mol_type = protein
                        organism = synthetic construct
SEQUENCE: 193
GTSNRAP                                                     7

SEQ ID NO: 194          moltype = AA  length = 7
FEATURE                 Location/Qualifiers
source                  1..7
                        mol_type = protein
                        organism = synthetic construct
SEQUENCE: 194
YASQSIS                                                     7

SEQ ID NO: 195          moltype = AA  length = 7
FEATURE                 Location/Qualifiers
```

```
source                  1..7
                        mol_type = protein
                        organism = synthetic construct
SEQUENCE: 195
RMSDLAS                                                                7

SEQ ID NO: 196          moltype = AA  length = 7
FEATURE                 Location/Qualifiers
source                  1..7
                        mol_type = protein
                        organism = synthetic construct
SEQUENCE: 196
SASYRYT                                                                7

SEQ ID NO: 197          moltype = AA  length = 7
FEATURE                 Location/Qualifiers
source                  1..7
                        mol_type = protein
                        organism = synthetic construct
SEQUENCE: 197
WASSRES                                                                7

SEQ ID NO: 198          moltype = AA  length = 7
FEATURE                 Location/Qualifiers
source                  1..7
                        mol_type = protein
                        organism = synthetic construct
SEQUENCE: 198
RMSNLAS                                                                7

SEQ ID NO: 199          moltype = AA  length = 7
FEATURE                 Location/Qualifiers
source                  1..7
                        mol_type = protein
                        organism = synthetic construct
SEQUENCE: 199
RMSNLAS                                                                7

SEQ ID NO: 200          moltype = AA  length = 7
FEATURE                 Location/Qualifiers
source                  1..7
                        mol_type = protein
                        organism = synthetic construct
SEQUENCE: 200
WATSRES                                                                7

SEQ ID NO: 201          moltype = AA  length = 7
FEATURE                 Location/Qualifiers
source                  1..7
                        mol_type = protein
                        organism = synthetic construct
SEQUENCE: 201
WASTRES                                                                7

SEQ ID NO: 202          moltype = AA  length = 7
FEATURE                 Location/Qualifiers
source                  1..7
                        mol_type = protein
                        organism = synthetic construct
SEQUENCE: 202
WASTKES                                                                7

SEQ ID NO: 203          moltype = AA  length = 7
FEATURE                 Location/Qualifiers
source                  1..7
                        mol_type = protein
                        organism = synthetic construct
SEQUENCE: 203
WASIRES                                                                7

SEQ ID NO: 204          moltype = AA  length = 7
FEATURE                 Location/Qualifiers
source                  1..7
                        mol_type = protein
                        organism = synthetic construct
SEQUENCE: 204
WASTRDS                                                                7

SEQ ID NO: 205          moltype = AA  length = 7
```

```
FEATURE                 Location/Qualifiers
source                  1..7
                        mol_type = protein
                        organism = synthetic construct
SEQUENCE: 205
WAYTRES                                                                     7

SEQ ID NO: 206          moltype = AA  length = 7
FEATURE                 Location/Qualifiers
source                  1..7
                        mol_type = protein
                        organism = synthetic construct
SEQUENCE: 206
SASNRYT                                                                     7

SEQ ID NO: 207          moltype = AA  length = 7
FEATURE                 Location/Qualifiers
source                  1..7
                        mol_type = protein
                        organism = synthetic construct
SEQUENCE: 207
WATFRES                                                                     7

SEQ ID NO: 208          moltype = AA  length = 7
FEATURE                 Location/Qualifiers
source                  1..7
                        mol_type = protein
                        organism = synthetic construct
SEQUENCE: 208
WASTRES                                                                     7

SEQ ID NO: 209          moltype = AA  length = 7
FEATURE                 Location/Qualifiers
source                  1..7
                        mol_type = protein
                        organism = synthetic construct
SEQUENCE: 209
WASTRES                                                                     7

SEQ ID NO: 210          moltype = AA  length = 7
FEATURE                 Location/Qualifiers
source                  1..7
                        mol_type = protein
                        organism = synthetic construct
SEQUENCE: 210
RVSDLAS                                                                     7

SEQ ID NO: 211          moltype = AA  length = 9
FEATURE                 Location/Qualifiers
source                  1..9
                        mol_type = protein
                        organism = synthetic construct
SEQUENCE: 211
QQNNEDPLT                                                                   9

SEQ ID NO: 212          moltype = AA  length = 9
FEATURE                 Location/Qualifiers
source                  1..9
                        mol_type = protein
                        organism = synthetic construct
SEQUENCE: 212
WQGTHFPQT                                                                   9

SEQ ID NO: 213          moltype = AA  length = 9
FEATURE                 Location/Qualifiers
source                  1..9
                        mol_type = protein
                        organism = synthetic construct
SEQUENCE: 213
WQATHFPQT                                                                   9

SEQ ID NO: 214          moltype = AA  length = 9
FEATURE                 Location/Qualifiers
source                  1..9
                        mol_type = protein
                        organism = synthetic construct
SEQUENCE: 214
ALWYSTHYV                                                                   9
```

```
SEQ ID NO: 215          moltype = AA  length = 9
FEATURE                 Location/Qualifiers
source                  1..9
                        mol_type = protein
                        organism = synthetic construct
SEQUENCE: 215
QQSNSWPLT                                                  9

SEQ ID NO: 216          moltype = AA  length = 9
FEATURE                 Location/Qualifiers
source                  1..9
                        mol_type = protein
                        organism = synthetic construct
SEQUENCE: 216
MQHLEYPYT                                                  9

SEQ ID NO: 217          moltype = AA  length = 9
FEATURE                 Location/Qualifiers
source                  1..9
                        mol_type = protein
                        organism = synthetic construct
SEQUENCE: 217
QQHYTTPRT                                                  9

SEQ ID NO: 218          moltype = AA  length = 9
FEATURE                 Location/Qualifiers
source                  1..9
                        mol_type = protein
                        organism = synthetic construct
SEQUENCE: 218
QNDYTSPFT                                                  9

SEQ ID NO: 219          moltype = AA  length = 9
FEATURE                 Location/Qualifiers
source                  1..9
                        mol_type = protein
                        organism = synthetic construct
SEQUENCE: 219
MQHLEYPYT                                                  9

SEQ ID NO: 220          moltype = AA  length = 9
FEATURE                 Location/Qualifiers
source                  1..9
                        mol_type = protein
                        organism = synthetic construct
SEQUENCE: 220
MQHLEYPYT                                                  9

SEQ ID NO: 221          moltype = AA  length = 9
FEATURE                 Location/Qualifiers
source                  1..9
                        mol_type = protein
                        organism = synthetic construct
SEQUENCE: 221
HNDYSYPFT                                                  9

SEQ ID NO: 222          moltype = AA  length = 9
FEATURE                 Location/Qualifiers
source                  1..9
                        mol_type = protein
                        organism = synthetic construct
SEQUENCE: 222
QNDYTSPFT                                                  9

SEQ ID NO: 223          moltype = AA  length = 9
FEATURE                 Location/Qualifiers
source                  1..9
                        mol_type = protein
                        organism = synthetic construct
SEQUENCE: 223
QNDYTSPFT                                                  9

SEQ ID NO: 224          moltype = AA  length = 9
FEATURE                 Location/Qualifiers
source                  1..9
                        mol_type = protein
                        organism = synthetic construct
SEQUENCE: 224
QNDYSSPFT                                                  9
```

```
SEQ ID NO: 225          moltype = AA  length = 9
FEATURE                 Location/Qualifiers
source                  1..9
                        mol_type = protein
                        organism = synthetic construct
SEQUENCE: 225
HNDYISPFT                                                                9

SEQ ID NO: 226          moltype = AA  length = 9
FEATURE                 Location/Qualifiers
source                  1..9
                        mol_type = protein
                        organism = synthetic construct
SEQUENCE: 226
HNDYTSPFT                                                                9

SEQ ID NO: 227          moltype = AA  length = 9
FEATURE                 Location/Qualifiers
source                  1..9
                        mol_type = protein
                        organism = synthetic construct
SEQUENCE: 227
QQHYSTPRT                                                                9

SEQ ID NO: 228          moltype = AA  length = 9
FEATURE                 Location/Qualifiers
source                  1..9
                        mol_type = protein
                        organism = synthetic construct
SEQUENCE: 228
HNDYSYPFT                                                                9

SEQ ID NO: 229          moltype = AA  length = 9
FEATURE                 Location/Qualifiers
source                  1..9
                        mol_type = protein
                        organism = synthetic construct
SEQUENCE: 229
QNDYTSPFT                                                                9

SEQ ID NO: 230          moltype = AA  length = 9
FEATURE                 Location/Qualifiers
source                  1..9
                        mol_type = protein
                        organism = synthetic construct
SEQUENCE: 230
QNDYTSPFT                                                                9

SEQ ID NO: 231          moltype = AA  length = 9
FEATURE                 Location/Qualifiers
source                  1..9
                        mol_type = protein
                        organism = synthetic construct
SEQUENCE: 231
MQHLEFPYT                                                                9

SEQ ID NO: 232          moltype = AA  length = 23
FEATURE                 Location/Qualifiers
source                  1..23
                        mol_type = protein
                        organism = synthetic construct
SEQUENCE: 232
NIVLTQSPAS LAVSLGQRAT ISC                                                23

SEQ ID NO: 233          moltype = AA  length = 23
FEATURE                 Location/Qualifiers
source                  1..23
                        mol_type = protein
                        organism = synthetic construct
SEQUENCE: 233
DVVMTQTPLT LSVTIGQPAS ISC                                                23

SEQ ID NO: 234          moltype = AA  length = 23
FEATURE                 Location/Qualifiers
source                  1..23
                        mol_type = protein
                        organism = synthetic construct
SEQUENCE: 234
```

```
DVVMTQTPLT LSVTIGQPAS ISC                                         23

SEQ ID NO: 235          moltype = AA  length = 22
FEATURE                 Location/Qualifiers
source                  1..22
                        mol_type = protein
                        organism = synthetic construct
SEQUENCE: 235
QAVVTQESAL TTSPGGTVIL TC                                          22

SEQ ID NO: 236          moltype = AA  length = 23
FEATURE                 Location/Qualifiers
source                  1..23
                        mol_type = protein
                        organism = synthetic construct
SEQUENCE: 236
DIVLTQSPAT LSVTPGDSVS LSC                                         23

SEQ ID NO: 237          moltype = AA  length = 23
FEATURE                 Location/Qualifiers
source                  1..23
                        mol_type = protein
                        organism = synthetic construct
SEQUENCE: 237
DIVMTQAAPS VPVTPGESVS ISC                                         23

SEQ ID NO: 238          moltype = AA  length = 23
FEATURE                 Location/Qualifiers
source                  1..23
                        mol_type = protein
                        organism = synthetic construct
SEQUENCE: 238
DIVMTQSHKF MSTSVGDGVN ITC                                         23

SEQ ID NO: 239          moltype = AA  length = 23
FEATURE                 Location/Qualifiers
source                  1..23
                        mol_type = protein
                        organism = synthetic construct
SEQUENCE: 239
DIVMTQSPSS LTVTAGEKVT MNC                                         23

SEQ ID NO: 240          moltype = AA  length = 23
FEATURE                 Location/Qualifiers
source                  1..23
                        mol_type = protein
                        organism = synthetic construct
SEQUENCE: 240
DIVMTQAAPS VPVTPGESVS ISC                                         23

SEQ ID NO: 241          moltype = AA  length = 23
FEATURE                 Location/Qualifiers
source                  1..23
                        mol_type = protein
                        organism = synthetic construct
SEQUENCE: 241
DIVMTQAAPS VPVTPGESVS ISC                                         23

SEQ ID NO: 242          moltype = AA  length = 23
FEATURE                 Location/Qualifiers
source                  1..23
                        mol_type = protein
                        organism = synthetic construct
SEQUENCE: 242
DIVMTQSPSS LTVTAGEKVT MSC                                         23

SEQ ID NO: 243          moltype = AA  length = 23
FEATURE                 Location/Qualifiers
source                  1..23
                        mol_type = protein
                        organism = synthetic construct
SEQUENCE: 243
DIVMTQSPSS LTVTAGEKVT MNC                                         23

SEQ ID NO: 244          moltype = AA  length = 23
FEATURE                 Location/Qualifiers
source                  1..23
                        mol_type = protein
                        organism = synthetic construct
```

```
SEQUENCE: 244
DIVMTQSPSS LTVTAGEKVT MNC                                          23

SEQ ID NO: 245          moltype = AA  length = 23
FEATURE                 Location/Qualifiers
source                  1..23
                        mol_type = protein
                        organism = synthetic construct
SEQUENCE: 245
DIVMTQSPSS LTVTAGEKVT MSC                                          23

SEQ ID NO: 246          moltype = AA  length = 23
FEATURE                 Location/Qualifiers
source                  1..23
                        mol_type = protein
                        organism = synthetic construct
SEQUENCE: 246
DIVMTQSPSS LTVTAGKEVT MSC                                          23

SEQ ID NO: 247          moltype = AA  length = 23
FEATURE                 Location/Qualifiers
source                  1..23
                        mol_type = protein
                        organism = synthetic construct
SEQUENCE: 247
DIVMTQSPSS LTVTAGEKVT MSC                                          23

SEQ ID NO: 248          moltype = AA  length = 23
FEATURE                 Location/Qualifiers
source                  1..23
                        mol_type = protein
                        organism = synthetic construct
SEQUENCE: 248
DIVMTQSHKF MSTSVGDRVS ITC                                          23

SEQ ID NO: 249          moltype = AA  length = 23
FEATURE                 Location/Qualifiers
source                  1..23
                        mol_type = protein
                        organism = synthetic construct
SEQUENCE: 249
DIVMTQSPSS LTVTAGEKVT MSC                                          23

SEQ ID NO: 250          moltype = AA  length = 23
FEATURE                 Location/Qualifiers
source                  1..23
                        mol_type = protein
                        organism = synthetic construct
SEQUENCE: 250
DIVMTQSPSS LTVTAGEKVT MNC                                          23

SEQ ID NO: 251          moltype = AA  length = 23
FEATURE                 Location/Qualifiers
source                  1..23
                        mol_type = protein
                        organism = synthetic construct
SEQUENCE: 251
DIVMTQSPSS LTVTAGEKVT MNC                                          23

SEQ ID NO: 252          moltype = AA  length = 23
FEATURE                 Location/Qualifiers
source                  1..23
                        mol_type = protein
                        organism = synthetic construct
SEQUENCE: 252
DIVMTQAAPS VPVTPGESVS ISC                                          23

SEQ ID NO: 253          moltype = AA  length = 15
FEATURE                 Location/Qualifiers
source                  1..15
                        mol_type = protein
                        organism = synthetic construct
SEQUENCE: 253
WYQQKPGQPP KLLIY                                                   15

SEQ ID NO: 254          moltype = AA  length = 15
FEATURE                 Location/Qualifiers
source                  1..15
                        mol_type = protein
```

```
                         organism = synthetic construct
SEQUENCE: 254
WLLQRPGQSP KRLIY                                                          15

SEQ ID NO: 255           moltype = AA  length = 15
FEATURE                  Location/Qualifiers
source                   1..15
                         mol_type = protein
                         organism = synthetic construct
SEQUENCE: 255
WLLQRPGQSP KRLIY                                                          15

SEQ ID NO: 256           moltype = AA  length = 15
FEATURE                  Location/Qualifiers
source                   1..15
                         mol_type = protein
                         organism = synthetic construct
SEQUENCE: 256
WVQEKPDHLF TGLIG                                                          15

SEQ ID NO: 257           moltype = AA  length = 15
FEATURE                  Location/Qualifiers
source                   1..15
                         mol_type = protein
                         organism = synthetic construct
SEQUENCE: 257
WYQQKSHESP RLLIK                                                          15

SEQ ID NO: 258           moltype = AA  length = 15
FEATURE                  Location/Qualifiers
source                   1..15
                         mol_type = protein
                         organism = synthetic construct
SEQUENCE: 258
WFLQRPGQSP QLLIY                                                          15

SEQ ID NO: 259           moltype = AA  length = 15
FEATURE                  Location/Qualifiers
source                   1..15
                         mol_type = protein
                         organism = synthetic construct
SEQUENCE: 259
WYQQKPGQSP RLLIY                                                          15

SEQ ID NO: 260           moltype = AA  length = 15
FEATURE                  Location/Qualifiers
source                   1..15
                         mol_type = protein
                         organism = synthetic construct
SEQUENCE: 260
WYQQKPGQPP KLLIY                                                          15

SEQ ID NO: 261           moltype = AA  length = 15
FEATURE                  Location/Qualifiers
source                   1..15
                         mol_type = protein
                         organism = synthetic construct
SEQUENCE: 261
WFLQRPGQSP QLLIY                                                          15

SEQ ID NO: 262           moltype = AA  length = 15
FEATURE                  Location/Qualifiers
source                   1..15
                         mol_type = protein
                         organism = synthetic construct
SEQUENCE: 262
WFLQRPGQSP QLLIY                                                          15

SEQ ID NO: 263           moltype = AA  length = 15
FEATURE                  Location/Qualifiers
source                   1..15
                         mol_type = protein
                         organism = synthetic construct
SEQUENCE: 263
WYQQKPGQPP KLLIY                                                          15

SEQ ID NO: 264           moltype = AA  length = 15
FEATURE                  Location/Qualifiers
source                   1..15
```

```
                        mol_type = protein
                        organism = synthetic construct
SEQUENCE: 264
WYQQKPGQPP KLLIY                                                15

SEQ ID NO: 265          moltype = AA  length = 15
FEATURE                 Location/Qualifiers
source                  1..15
                        mol_type = protein
                        organism = synthetic construct
SEQUENCE: 265
WYQQKPGQPP KLLIY                                                15

SEQ ID NO: 266          moltype = AA  length = 15
FEATURE                 Location/Qualifiers
source                  1..15
                        mol_type = protein
                        organism = synthetic construct
SEQUENCE: 266
WYQQKPGQPP KLLIY                                                15

SEQ ID NO: 267          moltype = AA  length = 15
FEATURE                 Location/Qualifiers
source                  1..15
                        mol_type = protein
                        organism = synthetic construct
SEQUENCE: 267
WYQQKPGQSP KLLIY                                                15

SEQ ID NO: 268          moltype = AA  length = 15
FEATURE                 Location/Qualifiers
source                  1..15
                        mol_type = protein
                        organism = synthetic construct
SEQUENCE: 268
WYQQKPGQPP KLLIY                                                15

SEQ ID NO: 269          moltype = AA  length = 15
FEATURE                 Location/Qualifiers
source                  1..15
                        mol_type = protein
                        organism = synthetic construct
SEQUENCE: 269
WYQQRPGQSP KLLIY                                                15

SEQ ID NO: 270          moltype = AA  length = 15
FEATURE                 Location/Qualifiers
source                  1..15
                        mol_type = protein
                        organism = synthetic construct
SEQUENCE: 270
WYQQKPGQPP KLLIY                                                15

SEQ ID NO: 271          moltype = AA  length = 15
FEATURE                 Location/Qualifiers
source                  1..15
                        mol_type = protein
                        organism = synthetic construct
SEQUENCE: 271
WYQQRPGQPP KLLIY                                                15

SEQ ID NO: 272          moltype = AA  length = 15
FEATURE                 Location/Qualifiers
source                  1..15
                        mol_type = protein
                        organism = synthetic construct
SEQUENCE: 272
WYQQKPGQPP KLLIY                                                15

SEQ ID NO: 273          moltype = AA  length = 15
FEATURE                 Location/Qualifiers
source                  1..15
                        mol_type = protein
                        organism = synthetic construct
SEQUENCE: 273
WFLQRPGQSP QLLIY                                                15

SEQ ID NO: 274          moltype = AA  length = 32
FEATURE                 Location/Qualifiers
```

```
source                  1..32
                        mol_type = protein
                        organism = synthetic construct
SEQUENCE: 274
GVPARFSGSG SRTDFTLTID PVEADDAATY YC                              32

SEQ ID NO: 275          moltype = AA  length = 32
FEATURE                 Location/Qualifiers
source                  1..32
                        mol_type = protein
                        organism = synthetic construct
SEQUENCE: 275
GVPDRFTGSG SGTDFTLKIS RVEAEDLGVY YC                              32

SEQ ID NO: 276          moltype = AA  length = 32
FEATURE                 Location/Qualifiers
source                  1..32
                        mol_type = protein
                        organism = synthetic construct
SEQUENCE: 276
GVPDRFTGSG SGTDFTLKIS RVEAEDLGVY YC                              32

SEQ ID NO: 277          moltype = AA  length = 32
FEATURE                 Location/Qualifiers
source                  1..32
                        mol_type = protein
                        organism = synthetic construct
SEQUENCE: 277
GVPVRFSGSL IGDKAALTIT GAQTEDDAMY FC                              32

SEQ ID NO: 278          moltype = AA  length = 32
FEATURE                 Location/Qualifiers
source                  1..32
                        mol_type = protein
                        organism = synthetic construct
SEQUENCE: 278
GIPSRFSGSG SGTDFTLSIN SVETEDFGMY FC                              32

SEQ ID NO: 279          moltype = AA  length = 32
FEATURE                 Location/Qualifiers
source                  1..32
                        mol_type = protein
                        organism = synthetic construct
SEQUENCE: 279
GVPDRFSGSG SGTAFTLRIS RVEAEDVGVY YC                              32

SEQ ID NO: 280          moltype = AA  length = 32
FEATURE                 Location/Qualifiers
source                  1..32
                        mol_type = protein
                        organism = synthetic construct
SEQUENCE: 280
GVPDRFTGSG SGTDFTFTIS SMQAEDLAVY YC                              32

SEQ ID NO: 281          moltype = AA  length = 32
FEATURE                 Location/Qualifiers
source                  1..32
                        mol_type = protein
                        organism = synthetic construct
SEQUENCE: 281
GVPDRFTGSG SGTDFTLTIS TVQTEDLAVY YC                              32

SEQ ID NO: 282          moltype = AA  length = 32
FEATURE                 Location/Qualifiers
source                  1..32
                        mol_type = protein
                        organism = synthetic construct
SEQUENCE: 282
GVPDRFSGSG SGTAFTLRIS SVEAEDVGIY YC                              32

SEQ ID NO: 283          moltype = AA  length = 32
FEATURE                 Location/Qualifiers
source                  1..32
                        mol_type = protein
                        organism = synthetic construct
SEQUENCE: 283
GVPDRFSGSG SGTAFTLRIS RVEAEDVGVY YC                              32

SEQ ID NO: 284          moltype = AA  length = 32
```

```
FEATURE                Location/Qualifiers
source                 1..32
                       mol_type = protein
                       organism = synthetic construct
SEQUENCE: 284
GVPDRFTGSG SGTDFTLTIS SLQAEDLAVY YC                              32

SEQ ID NO: 285         moltype = AA  length = 32
FEATURE                Location/Qualifiers
source                 1..32
                       mol_type = protein
                       organism = synthetic construct
SEQUENCE: 285
GVPDRFTGSG SGTDFTLTIN TVQAEDLAIY YC                              32

SEQ ID NO: 286         moltype = AA  length = 32
FEATURE                Location/Qualifiers
source                 1..32
                       mol_type = protein
                       organism = synthetic construct
SEQUENCE: 286
GVPDRFTGSG SGTDFTLTIN TVQAEDLAVY YC                              32

SEQ ID NO: 287         moltype = AA  length = 32
FEATURE                Location/Qualifiers
source                 1..32
                       mol_type = protein
                       organism = synthetic construct
SEQUENCE: 287
GVPDRFTGSG SGTDFTLTIS SVQAEDLAVY YC                              32

SEQ ID NO: 288         moltype = AA  length = 32
FEATURE                Location/Qualifiers
source                 1..32
                       mol_type = protein
                       organism = synthetic construct
SEQUENCE: 288
GVPDRFTGSG SGTDFTLTIS SVQAEDLAIY YC                              32

SEQ ID NO: 289         moltype = AA  length = 32
FEATURE                Location/Qualifiers
source                 1..32
                       mol_type = protein
                       organism = synthetic construct
SEQUENCE: 289
GVPDRFTGSG SGTDFTLTIH GVQAEDLAVY YC                              32

SEQ ID NO: 290         moltype = AA  length = 32
FEATURE                Location/Qualifiers
source                 1..32
                       mol_type = protein
                       organism = synthetic construct
SEQUENCE: 290
GVPDRFTGSG SGTDFTFTIS SMQAEDLAIY YC                              32

SEQ ID NO: 291         moltype = AA  length = 32
FEATURE                Location/Qualifiers
source                 1..32
                       mol_type = protein
                       organism = synthetic construct
SEQUENCE: 291
GVPDRFTGSG SGTDFTLTIS GLQAEDLAVY YC                              32

SEQ ID NO: 292         moltype = AA  length = 32
FEATURE                Location/Qualifiers
source                 1..32
                       mol_type = protein
                       organism = synthetic construct
SEQUENCE: 292
GVPDRFTGSG SGTDFTLTIS TVQAEDLAVY YC                              32

SEQ ID NO: 293         moltype = AA  length = 32
FEATURE                Location/Qualifiers
source                 1..32
                       mol_type = protein
                       organism = synthetic construct
SEQUENCE: 293
GVPDRFTGSG SGSDFTLTIS TVQAEDLAVY YC                              32
```

```
SEQ ID NO: 294          moltype = AA  length = 32
FEATURE                 Location/Qualifiers
source                  1..32
                        mol_type = protein
                        organism = synthetic construct
SEQUENCE: 294
GVPDRFSGSG SGTAFTLRIS RVEAEDVGIY YC                                32

SEQ ID NO: 295          moltype = AA  length = 10
FEATURE                 Location/Qualifiers
source                  1..10
                        mol_type = protein
                        organism = synthetic construct
SEQUENCE: 295
FGAGTKLELK                                                         10

SEQ ID NO: 296          moltype = AA  length = 10
FEATURE                 Location/Qualifiers
source                  1..10
                        mol_type = protein
                        organism = synthetic construct
SEQUENCE: 296
FGGGTKLEIK                                                         10

SEQ ID NO: 297          moltype = AA  length = 10
FEATURE                 Location/Qualifiers
source                  1..10
                        mol_type = protein
                        organism = synthetic construct
SEQUENCE: 297
FGGGTKLEIK                                                         10

SEQ ID NO: 298          moltype = AA  length = 10
FEATURE                 Location/Qualifiers
source                  1..10
                        mol_type = protein
                        organism = synthetic construct
SEQUENCE: 298
FGGGTKVTVL                                                         10

SEQ ID NO: 299          moltype = AA  length = 10
FEATURE                 Location/Qualifiers
source                  1..10
                        mol_type = protein
                        organism = synthetic construct
SEQUENCE: 299
FGAGTKLELK                                                         10

SEQ ID NO: 300          moltype = AA  length = 10
FEATURE                 Location/Qualifiers
source                  1..10
                        mol_type = protein
                        organism = synthetic construct
SEQUENCE: 300
FGGGTKLEIK                                                         10

SEQ ID NO: 301          moltype = AA  length = 10
FEATURE                 Location/Qualifiers
source                  1..10
                        mol_type = protein
                        organism = synthetic construct
SEQUENCE: 301
FGGGTKLEIK                                                         10

SEQ ID NO: 302          moltype = AA  length = 10
FEATURE                 Location/Qualifiers
source                  1..10
                        mol_type = protein
                        organism = synthetic construct
SEQUENCE: 302
FGSGTRLEIK                                                         10

SEQ ID NO: 303          moltype = AA  length = 10
FEATURE                 Location/Qualifiers
source                  1..10
                        mol_type = protein
                        organism = synthetic construct
SEQUENCE: 303
FGGGTKLEIK                                                         10
```

```
SEQ ID NO: 304          moltype = AA  length = 10
FEATURE                 Location/Qualifiers
source                  1..10
                        mol_type = protein
                        organism = synthetic construct
SEQUENCE: 304
FGGGTKLEIK                                                                10

SEQ ID NO: 305          moltype = AA  length = 10
FEATURE                 Location/Qualifiers
source                  1..10
                        mol_type = protein
                        organism = synthetic construct
SEQUENCE: 305
FGSGTRLEIK                                                                10

SEQ ID NO: 306          moltype = AA  length = 10
FEATURE                 Location/Qualifiers
source                  1..10
                        mol_type = protein
                        organism = synthetic construct
SEQUENCE: 306
FGSGTKLEIK                                                                10

SEQ ID NO: 307          moltype = AA  length = 10
FEATURE                 Location/Qualifiers
source                  1..10
                        mol_type = protein
                        organism = synthetic construct
SEQUENCE: 307
FGSGTKLEIK                                                                10

SEQ ID NO: 308          moltype = AA  length = 10
FEATURE                 Location/Qualifiers
source                  1..10
                        mol_type = protein
                        organism = synthetic construct
SEQUENCE: 308
FGSGTKLEIK                                                                10

SEQ ID NO: 309          moltype = AA  length = 10
FEATURE                 Location/Qualifiers
source                  1..10
                        mol_type = protein
                        organism = synthetic construct
SEQUENCE: 309
FGSGTKLEIK                                                                10

SEQ ID NO: 310          moltype = AA  length = 10
FEATURE                 Location/Qualifiers
source                  1..10
                        mol_type = protein
                        organism = synthetic construct
SEQUENCE: 310
FGSGTKLEMK                                                                10

SEQ ID NO: 311          moltype = AA  length = 10
FEATURE                 Location/Qualifiers
source                  1..10
                        mol_type = protein
                        organism = synthetic construct
SEQUENCE: 311
FGGGTKLEIK                                                                10

SEQ ID NO: 312          moltype = AA  length = 10
FEATURE                 Location/Qualifiers
source                  1..10
                        mol_type = protein
                        organism = synthetic construct
SEQUENCE: 312
FGSGTRLEIK                                                                10

SEQ ID NO: 313          moltype = AA  length = 10
FEATURE                 Location/Qualifiers
source                  1..10
                        mol_type = protein
                        organism = synthetic construct
SEQUENCE: 313
```

```
FGSGTKLEIK                                                        10

SEQ ID NO: 314          moltype = AA  length = 10
FEATURE                 Location/Qualifiers
source                  1..10
                        mol_type = protein
                        organism = synthetic construct
SEQUENCE: 314
FGSGTKLEIK                                                        10

SEQ ID NO: 315          moltype = AA  length = 10
FEATURE                 Location/Qualifiers
source                  1..10
                        mol_type = protein
                        organism = synthetic construct
SEQUENCE: 315
FGGGTKLEIK                                                        10

SEQ ID NO: 316          moltype = AA  length = 111
FEATURE                 Location/Qualifiers
source                  1..111
                        mol_type = protein
                        organism = synthetic construct
SEQUENCE: 316
NIVLTQSPAS LAVSLGQRAT ISCRASESVD SYGNSFMHWY QQKPGQPPKL LIYLASNLES  60
GVPARFSGSG SRTDFTLTID PVEADDAATY YCQQNNEDPL TFGAGTKLEL K           111

SEQ ID NO: 317          moltype = AA  length = 112
FEATURE                 Location/Qualifiers
source                  1..112
                        mol_type = protein
                        organism = synthetic construct
SEQUENCE: 317
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP QTFGGGTKLE IK          112

SEQ ID NO: 318          moltype = AA  length = 112
FEATURE                 Location/Qualifiers
source                  1..112
                        mol_type = protein
                        organism = synthetic construct
SEQUENCE: 318
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQATHFP QTFGGGTKLE IK          112

SEQ ID NO: 319          moltype = AA  length = 109
FEATURE                 Location/Qualifiers
source                  1..109
                        mol_type = protein
                        organism = synthetic construct
SEQUENCE: 319
QAVVTQESAL TTSPGGTVIL TCRSSTGAVT TSNYANWVQE KPDHLFTGLI GGTSNRAPGV  60
PVRFSGSLIG DKAALTITGA QTEDDAMYFC ALWYSTHYVF GGGTKVTVL              109

SEQ ID NO: 320          moltype = AA  length = 107
FEATURE                 Location/Qualifiers
source                  1..107
                        mol_type = protein
                        organism = synthetic construct
SEQUENCE: 320
DIVLTQSPAT LSVTPGDSVS LSCRASQSIS NNLHWYQQKS HESPRLLIKY ASQSISGIPS  60
RFSGSGSGTD FTLSINSVET EDFGMYFCQQ SNSWPLTFGA GTKLELK                107

SEQ ID NO: 321          moltype = AA  length = 112
FEATURE                 Location/Qualifiers
source                  1..112
                        mol_type = protein
                        organism = synthetic construct
SEQUENCE: 321
DIVMTQAAPS VPVTPGESVS ISCRSSKSLL HNNGNTYLCW FLQRPGQSPQ LLIYRMSDLA  60
SGVPDRFSGS GSGTAFTLRI SRVEAEDVGV YYCMQHLEYP YTFGGGTKLE IK          112

SEQ ID NO: 322          moltype = AA  length = 107
FEATURE                 Location/Qualifiers
source                  1..107
                        mol_type = protein
                        organism = synthetic construct
SEQUENCE: 322
DIVMTQSHKF MSTSVGDGVN ITCKASQDVS TAVAWYQQKP GQSPRLLIYS ASYRYTGVPD  60
```

```
RFTGSGSGTD FTFTISSMQA EDLAVYYCQQ HYTTPRTFGG GTKLEIK              107

SEQ ID NO: 323          moltype = AA  length = 113
FEATURE                 Location/Qualifiers
source                  1..113
                        mol_type = protein
                        organism = synthetic construct
SEQUENCE: 323
DIVMTQSPSS LTVTAGEKVT MNCRSSQSLF NSTNQKNYLT WYQQKPGQPP KLLIYWASSR  60
ESGVPDRFTG SGSGTDFTLT ISTVQTEDLA VYYCQNDYTS PFTFGSGTRL EIK         113

SEQ ID NO: 324          moltype = AA  length = 112
FEATURE                 Location/Qualifiers
source                  1..112
                        mol_type = protein
                        organism = synthetic construct
SEQUENCE: 324
DIVMTQAAPS VPVTPGESVS ISCGSSKSLL HKNGNTYLCW FLQRPGQSPQ LLIYRMSNLA  60
SGVPDRFSGS GSGTAFTLRI SSVEAEDVGI YYCMQHLEYP YTFGGGTKLE IK          112

SEQ ID NO: 325          moltype = AA  length = 112
FEATURE                 Location/Qualifiers
source                  1..112
                        mol_type = protein
                        organism = synthetic construct
SEQUENCE: 325
DIVMTQAAPS VPVTPGESVS ISCRSSKSLL HNNGNTYLCW FLQRPGQSPQ LLIYRMSNLA  60
SGVPDRFSGS GSGTAFTLRI SRVEAEDVGV YYCMQHLEYP YTFGGGTKLE IK          112

SEQ ID NO: 326          moltype = AA  length = 113
FEATURE                 Location/Qualifiers
source                  1..113
                        mol_type = protein
                        organism = synthetic construct
SEQUENCE: 326
DIVMTQSPSS LTVTAGEKVT MSCKSSQSLL SSINQKNYLT WYQQKPGQPP KLLIYWATSR  60
ESGVPDRFTG SGSGTDFTLT ISSLQAEDLA VYYCHNDYSY PFTFGSGTRL EIK         113

SEQ ID NO: 327          moltype = AA  length = 113
FEATURE                 Location/Qualifiers
source                  1..113
                        mol_type = protein
                        organism = synthetic construct
SEQUENCE: 327
DIVMTQSPSS LTVTAGEKVT MNCRSSQSLL NSTNQKNYLT WYQQKPGQPP KLLIYWASTR  60
ESGVPDRFTG SGSGTDFTLT INTVQAEDLA IYYCQNDYTS PFTFGSGTKL EIK         113

SEQ ID NO: 328          moltype = AA  length = 113
FEATURE                 Location/Qualifiers
source                  1..113
                        mol_type = protein
                        organism = synthetic construct
SEQUENCE: 328
DIVMTQSPSS LTVTAGEKVT MNCRSSQSLL NSTNQKNYLT WYQQKPGQPP KLLIYWASTK  60
ESGVPDRFTG SGSGTDFTLT INTVQAEDLA VYYCQNDYTS PFTFGSGTKL EIK         113

SEQ ID NO: 329          moltype = AA  length = 113
FEATURE                 Location/Qualifiers
source                  1..113
                        mol_type = protein
                        organism = synthetic construct
SEQUENCE: 329
DIVMTQSPSS LTVTAGEKVT MSCKSSQSLL NSGNQKIYLT WYQQKPGQPP KLLIYWASIR  60
ESGVPDRFTG SGSGTDFTLT ISSVQAEDLA VYYCQNDYSS PFTFGSGTKL EIK         113

SEQ ID NO: 330          moltype = AA  length = 113
FEATURE                 Location/Qualifiers
source                  1..113
                        mol_type = protein
                        organism = synthetic construct
SEQUENCE: 330
DIVMTQSPSS LTVTAGKEVT MSCKSSQSLL NSTNQKNYLT WYQQKPGQSP KLLIYWASTR  60
DSGVPDRFTG SGSGTDFTLT ISSVQAEDLA IYYCHNDYIS PFTFGSGTKL EIK         113

SEQ ID NO: 331          moltype = AA  length = 113
FEATURE                 Location/Qualifiers
source                  1..113
                        mol_type = protein
                        organism = synthetic construct
```

```
SEQUENCE: 331
DIVMTQSPSS LTVTAGEKVT MSCKSSQSLF NSGNQKNYLT WYQQKPGQPP KLLIYWAYTR  60
ESGVPDRFTG SGSGTDFTLT IHGVQAEDLA VYYCHNDYTS PFTFGSGTKL EMK         113

SEQ ID NO: 332          moltype = AA  length = 107
FEATURE                 Location/Qualifiers
source                  1..107
                        mol_type = protein
                        organism = synthetic construct
SEQUENCE: 332
DIVMTQSHKF MSTSVGDRVS ITCKASQDVS TAVAWYQQRP GQSPKLLIYS ASNRYTGVPD  60
RFTGSGSGTD FTFTISSMQA EDLAIYYCQQ HYSTPRTFGG GTKLEIK               107

SEQ ID NO: 333          moltype = AA  length = 113
FEATURE                 Location/Qualifiers
source                  1..113
                        mol_type = protein
                        organism = synthetic construct
SEQUENCE: 333
DIVMTQSPSS LTVTAGEKVT MSCKSSQSLL NSINQKNYLT WYQQKPGQPP KLLIYWATFR  60
ESGVPDRFTG SGSGTDFTLT ISGLQAEDLA VYYCHNDYSY PFTFGSGTRL EIK         113

SEQ ID NO: 334          moltype = AA  length = 113
FEATURE                 Location/Qualifiers
source                  1..113
                        mol_type = protein
                        organism = synthetic construct
SEQUENCE: 334
DIVMTQSPSS LTVTAGEKVT MNCRSSQSLL NSTNQKNYLT WYQQRPGQPP KLLIYWASTR  60
ESGVPDRFTG SGSGTDFTLT ISTVQAEDLA VYYCQNDYTS PFTFGSGTKL EIK         113

SEQ ID NO: 335          moltype = AA  length = 113
FEATURE                 Location/Qualifiers
source                  1..113
                        mol_type = protein
                        organism = synthetic construct
SEQUENCE: 335
DIVMTQSPSS LTVTAGEKVT MNCRSSQSLL NSTNQKNYLT WYQQKPGQPP KLLIYWASTR  60
ESGVPDRFTG SGSGSDFTLT ISTVQAEDLA VYYCQNDYTS PFTFGSGTKL EIK         113

SEQ ID NO: 336          moltype = AA  length = 112
FEATURE                 Location/Qualifiers
source                  1..112
                        mol_type = protein
                        organism = synthetic construct
SEQUENCE: 336
DIVMTQAAPS VPVTPGESVS ISCRSNKSLL HSNGNAYLSW FLQRPGQSPQ LLIYRVSDLA  60
SGVPDRFSGS GSGTAFTLRI SRVEAEDVGI YYCMQHLEFP YTFGGGTKLE IK          112

SEQ ID NO: 337          moltype = AA  length = 30
FEATURE                 Location/Qualifiers
source                  1..30
                        mol_type = protein
                        organism = synthetic construct
SEQUENCE: 337
QVQLVQSGSE LKKPGASVKV SCKASGYTFT                                   30

SEQ ID NO: 338          moltype = AA  length = 14
FEATURE                 Location/Qualifiers
source                  1..14
                        mol_type = protein
                        organism = synthetic construct
SEQUENCE: 338
WVRQAPGQGL EWMG                                                    14

SEQ ID NO: 339          moltype = AA  length = 32
FEATURE                 Location/Qualifiers
source                  1..32
                        mol_type = protein
                        organism = synthetic construct
SEQUENCE: 339
RFVFSLDTSV STAYLQISSL KNEDMAVYFC AR                                32

SEQ ID NO: 340          moltype = AA  length = 11
FEATURE                 Location/Qualifiers
source                  1..11
                        mol_type = protein
                        organism = synthetic construct
SEQUENCE: 340
```

```
WGQGTLVTVS S                                                     11

SEQ ID NO: 341          moltype = AA  length = 30
FEATURE                 Location/Qualifiers
source                  1..30
                        mol_type = protein
                        organism = synthetic construct
SEQUENCE: 341
EVQLLESGGG LVQPGGSLRL SCAASGFTFS                                 30

SEQ ID NO: 342          moltype = AA  length = 14
FEATURE                 Location/Qualifiers
source                  1..14
                        mol_type = protein
                        organism = synthetic construct
SEQUENCE: 342
WVRQAPGKGL EWVS                                                  14

SEQ ID NO: 343          moltype = AA  length = 32
FEATURE                 Location/Qualifiers
source                  1..32
                        mol_type = protein
                        organism = synthetic construct
SEQUENCE: 343
RFTISRDNSK NTLYLQMNSL RAEDTAVYYC AK                              32

SEQ ID NO: 344          moltype = AA  length = 11
FEATURE                 Location/Qualifiers
source                  1..11
                        mol_type = protein
                        organism = synthetic construct
SEQUENCE: 344
WGQGTLVTVS S                                                     11

SEQ ID NO: 345          moltype = AA  length = 22
FEATURE                 Location/Qualifiers
source                  1..22
                        mol_type = protein
                        organism = synthetic construct
SEQUENCE: 345
EAVVTQEPSL TVSPGGTVTL TC                                         22

SEQ ID NO: 346          moltype = AA  length = 15
FEATURE                 Location/Qualifiers
source                  1..15
                        mol_type = protein
                        organism = synthetic construct
SEQUENCE: 346
WVQQKPGQAF TGLIG                                                 15

SEQ ID NO: 347          moltype = AA  length = 32
FEATURE                 Location/Qualifiers
source                  1..32
                        mol_type = protein
                        organism = synthetic construct
SEQUENCE: 347
GTPARFSGSL LGDKAALTLL GAQPEDEAEY FC                              32

SEQ ID NO: 348          moltype = AA  length = 10
FEATURE                 Location/Qualifiers
source                  1..10
                        mol_type = protein
                        organism = synthetic construct
SEQUENCE: 348
FGGGTKLTVL                                                       10

SEQ ID NO: 349          moltype = AA  length = 23
FEATURE                 Location/Qualifiers
source                  1..23
                        mol_type = protein
                        organism = synthetic construct
SEQUENCE: 349
DIVMTQSPDS LAVSLGERAT MNC                                        23

SEQ ID NO: 350          moltype = AA  length = 15
FEATURE                 Location/Qualifiers
source                  1..15
                        mol_type = protein
                        organism = synthetic construct
```

```
SEQUENCE: 350
WYQQKPGQPP KLLIY                                                 15

SEQ ID NO: 351          moltype = AA  length = 32
FEATURE                 Location/Qualifiers
source                  1..32
                        mol_type = protein
                        organism = synthetic construct
SEQUENCE: 351
GVPDRFSGSG SGTDFTLTIS SLQAEDVAVY YC                              32

SEQ ID NO: 352          moltype = AA  length = 10
FEATURE                 Location/Qualifiers
source                  1..10
                        mol_type = protein
                        organism = synthetic construct
SEQUENCE: 352
FGQGTRLEIK                                                       10

SEQ ID NO: 353          moltype = AA  length = 114
FEATURE                 Location/Qualifiers
source                  1..114
                        mol_type = protein
                        organism = synthetic construct
SEQUENCE: 353
QVQLVQSGSE LKKPGASVKV SCKASGYTFT NYGMNWVRQA PGQGLEWMGW INTYTGEPTY  60
ADDFKGRFVF SLDTSVSTAY LQISSLKNED MAVYFCARYA MDYWGQGTLV TVSS        114

SEQ ID NO: 354          moltype = AA  length = 109
FEATURE                 Location/Qualifiers
source                  1..109
                        mol_type = protein
                        organism = synthetic construct
SEQUENCE: 354
EAVVTQEPSL TVSPGGTVTL TCRSSTGAVT TSNYANWVQQ KPGQAFTGLI GGTSNRAPGT  60
PARFSGSLLG DKAALTLLGA QPEDEAEYFC ALWYSTHYVF GGGTKLTVL             109

SEQ ID NO: 355          moltype = AA  length = 115
FEATURE                 Location/Qualifiers
source                  1..115
                        mol_type = protein
                        organism = synthetic construct
SEQUENCE: 355
EVQLLESGGG LVQPGGSLRL SCAASGFTFS RFWMSWVRQA PGKGLEWVSE ISPDSNTIDL  60
TPSLKDRFTI SRDNSKNTLY LQMNSLRAED TAVYYCAKPY YGYYWGQGTL VTVSS       115

SEQ ID NO: 356          moltype = AA  length = 113
FEATURE                 Location/Qualifiers
source                  1..113
                        mol_type = protein
                        organism = synthetic construct
SEQUENCE: 356
DIVMTQSPDS LAVSLGERAT MNCRSSQSLF SSTNQKNYLT WYQQKPGQPP KLLIYWASSR  60
ESGVPDRFSG SGSGTDFTLT ISSLQAEDVA VYYCQNDYTS PFTFGQGTRL EIK         113

SEQ ID NO: 357          moltype = AA  length = 5
FEATURE                 Location/Qualifiers
source                  1..5
                        mol_type = protein
                        organism = synthetic construct
VARIANT                 2
                        note = Y can be replaced by W or F
SEQUENCE: 357
NYGMN                                                            5

SEQ ID NO: 358          moltype = AA  length = 17
FEATURE                 Location/Qualifiers
source                  1..17
                        mol_type = protein
                        organism = synthetic construct
VARIANT                 1
                        note = W can be replaced by Y or F
VARIANT                 3
                        note = N can be replaced by Q
SEQUENCE: 358
WINTYTGEPT YADDFKG                                               17

SEQ ID NO: 359          moltype = AA  length = 5
FEATURE                 Location/Qualifiers
```

```
source                  1..5
                        mol_type = protein
                        organism = synthetic construct
SEQUENCE: 359
YAMDY                                                                        5

SEQ ID NO: 360          moltype = AA  length = 14
FEATURE                 Location/Qualifiers
source                  1..14
                        mol_type = protein
                        organism = synthetic construct
VARIANT                 12
                        note = Y can be replaced by W or F
SEQUENCE: 360
RSSTGAVTTS NYAN                                                              14

SEQ ID NO: 361          moltype = AA  length = 7
FEATURE                 Location/Qualifiers
source                  1..7
                        mol_type = protein
                        organism = synthetic construct
SEQUENCE: 361
GTSNRAP                                                                      7

SEQ ID NO: 362          moltype = AA  length = 9
FEATURE                 Location/Qualifiers
source                  1..9
                        mol_type = protein
                        organism = synthetic construct
VARIANT                 3
                        note = Y can be replaced by W or F
VARIANT                 8
                        note = Y can be replaced by W or F
SEQUENCE: 362
ALYYSTHYV                                                                    9

SEQ ID NO: 363          moltype = AA  length = 5
FEATURE                 Location/Qualifiers
source                  1..5
                        mol_type = protein
                        organism = synthetic construct
VARIANT                 3
                        note = Y can be replaced by W or F
SEQUENCE: 363
RFYMS                                                                        5

SEQ ID NO: 364          moltype = AA  length = 17
FEATURE                 Location/Qualifiers
source                  1..17
                        mol_type = protein
                        organism = synthetic construct
VARIANT                 1
                        note = E can be replaced by D
SEQUENCE: 364
EISPDSNTID LTPSLKD                                                           17

SEQ ID NO: 365          moltype = AA  length = 6
FEATURE                 Location/Qualifiers
source                  1..6
                        mol_type = protein
                        organism = synthetic construct
VARIANT                 5
                        note = Y can be replaced by W or F
SEQUENCE: 365
PYYGYY                                                                       6

SEQ ID NO: 366          moltype = AA  length = 17
FEATURE                 Location/Qualifiers
source                  1..17
                        mol_type = protein
                        organism = synthetic construct
VARIANT                 15
                        note = Y can be replaced by W or F
SEQUENCE: 366
RSSQSLFSST NQKNYLT                                                           17

SEQ ID NO: 367          moltype = AA  length = 7
FEATURE                 Location/Qualifiers
source                  1..7
```

```
                        mol_type = protein
                        organism = synthetic construct
SEQUENCE: 367
WASSRES                                                     7

SEQ ID NO: 368          moltype = AA  length = 9
FEATURE                 Location/Qualifiers
source                  1..9
                        mol_type = protein
                        organism = synthetic construct
SEQUENCE: 368
QNDYTSPFT                                                   9

SEQ ID NO: 369          moltype = AA  length = 17
FEATURE                 Location/Qualifiers
source                  1..17
                        mol_type = protein
                        organism = synthetic construct
SEQUENCE: 369
RSSQSLFSST NQKNYLT                                          17

SEQ ID NO: 370          moltype = AA  length = 5
FEATURE                 Location/Qualifiers
source                  1..5
                        mol_type = protein
                        organism = synthetic construct
SEQUENCE: 370
NHHIN                                                       5

SEQ ID NO: 371          moltype = AA  length = 5
FEATURE                 Location/Qualifiers
source                  1..5
                        mol_type = protein
                        organism = synthetic construct
SEQUENCE: 371
NHHIN                                                       5

SEQ ID NO: 372          moltype = AA  length = 5
FEATURE                 Location/Qualifiers
source                  1..5
                        mol_type = protein
                        organism = synthetic construct
SEQUENCE: 372
NNAMT                                                       5

SEQ ID NO: 373          moltype = AA  length = 5
FEATURE                 Location/Qualifiers
source                  1..5
                        mol_type = protein
                        organism = synthetic construct
SEQUENCE: 373
RYGVS                                                       5

SEQ ID NO: 374          moltype = AA  length = 5
FEATURE                 Location/Qualifiers
source                  1..5
                        mol_type = protein
                        organism = synthetic construct
SEQUENCE: 374
YYAMG                                                       5

SEQ ID NO: 375          moltype = AA  length = 5
FEATURE                 Location/Qualifiers
source                  1..5
                        mol_type = protein
                        organism = synthetic construct
SEQUENCE: 375
HYAMG                                                       5

SEQ ID NO: 376          moltype = AA  length = 5
FEATURE                 Location/Qualifiers
source                  1..5
                        mol_type = protein
                        organism = synthetic construct
SEQUENCE: 376
NNHMG                                                       5

SEQ ID NO: 377          moltype = AA  length = 5
FEATURE                 Location/Qualifiers
```

```
source                1..5
                      mol_type = protein
                      organism = synthetic construct
SEQUENCE: 377
SYWMI                                                                    5

SEQ ID NO: 378        moltype = AA  length = 5
FEATURE               Location/Qualifiers
source                1..5
                      mol_type = protein
                      organism = synthetic construct
SEQUENCE: 378
DYAVF                                                                    5

SEQ ID NO: 379        moltype = AA  length = 5
FEATURE               Location/Qualifiers
source                1..5
                      mol_type = protein
                      organism = synthetic construct
SEQUENCE: 379
KYAVN                                                                    5

SEQ ID NO: 380        moltype = AA  length = 5
FEATURE               Location/Qualifiers
source                1..5
                      mol_type = protein
                      organism = synthetic construct
SEQUENCE: 380
NYAVN                                                                    5

SEQ ID NO: 381        moltype = AA  length = 5
FEATURE               Location/Qualifiers
source                1..5
                      mol_type = protein
                      organism = synthetic construct
SEQUENCE: 381
NYAVY                                                                    5

SEQ ID NO: 382        moltype = AA  length = 5
FEATURE               Location/Qualifiers
source                1..5
                      mol_type = protein
                      organism = synthetic construct
SEQUENCE: 382
DYNFQ                                                                    5

SEQ ID NO: 383        moltype = AA  length = 5
FEATURE               Location/Qualifiers
source                1..5
                      mol_type = protein
                      organism = synthetic construct
SEQUENCE: 383
NYYMN                                                                    5

SEQ ID NO: 384        moltype = AA  length = 5
FEATURE               Location/Qualifiers
source                1..5
                      mol_type = protein
                      organism = synthetic construct
SEQUENCE: 384
SYYMN                                                                    5

SEQ ID NO: 385        moltype = AA  length = 5
FEATURE               Location/Qualifiers
source                1..5
                      mol_type = protein
                      organism = synthetic construct
SEQUENCE: 385
RYYMS                                                                    5

SEQ ID NO: 386        moltype = AA  length = 5
FEATURE               Location/Qualifiers
source                1..5
                      mol_type = protein
                      organism = synthetic construct
SEQUENCE: 386
RYVMH                                                                    5

SEQ ID NO: 387        moltype = AA  length = 5
```

```
FEATURE                Location/Qualifiers
source                 1..5
                       mol_type = protein
                       organism = synthetic construct
SEQUENCE: 387
DYIML                                                                  5

SEQ ID NO: 388         moltype = AA  length = 5
FEATURE                Location/Qualifiers
source                 1..5
                       mol_type = protein
                       organism = synthetic construct
SEQUENCE: 388
GYFMN                                                                  5

SEQ ID NO: 389         moltype = AA  length = 5
FEATURE                Location/Qualifiers
source                 1..5
                       mol_type = protein
                       organism = synthetic construct
SEQUENCE: 389
HYSIG                                                                  5

SEQ ID NO: 390         moltype = AA  length = 16
FEATURE                Location/Qualifiers
source                 1..16
                       mol_type = protein
                       organism = synthetic construct
SEQUENCE: 390
IISASGSAYY ANWAKG                                                      16

SEQ ID NO: 391         moltype = AA  length = 16
FEATURE                Location/Qualifiers
source                 1..16
                       mol_type = protein
                       organism = synthetic construct
SEQUENCE: 391
IISNGGSAYY ANWAKG                                                      16

SEQ ID NO: 392         moltype = AA  length = 16
FEATURE                Location/Qualifiers
source                 1..16
                       mol_type = protein
                       organism = synthetic construct
SEQUENCE: 392
YIWRGGETYY ASWAKG                                                      16

SEQ ID NO: 393         moltype = AA  length = 17
FEATURE                Location/Qualifiers
source                 1..17
                       mol_type = protein
                       organism = synthetic construct
SEQUENCE: 393
YIYIGDGSTY YASWVNG                                                     17

SEQ ID NO: 394         moltype = AA  length = 16
FEATURE                Location/Qualifiers
source                 1..16
                       mol_type = protein
                       organism = synthetic construct
SEQUENCE: 394
IIDTNNVTYY ASWAKG                                                      16

SEQ ID NO: 395         moltype = AA  length = 16
FEATURE                Location/Qualifiers
source                 1..16
                       mol_type = protein
                       organism = synthetic construct
SEQUENCE: 395
YITFGGIAYY ANWAKG                                                      16

SEQ ID NO: 396         moltype = AA  length = 18
FEATURE                Location/Qualifiers
source                 1..18
                       mol_type = protein
                       organism = synthetic construct
SEQUENCE: 396
FINGNGVGSA FYANWAKG                                                    18
```

```
SEQ ID NO: 397          moltype = AA  length = 16
FEATURE                 Location/Qualifiers
source                  1..16
                        mol_type = protein
                        organism = synthetic construct
SEQUENCE: 397
GISTIDNTYY ASWAKG                                                   16

SEQ ID NO: 398          moltype = AA  length = 16
FEATURE                 Location/Qualifiers
source                  1..16
                        mol_type = protein
                        organism = synthetic construct
SEQUENCE: 398
GISTIDNTYY ATWAKG                                                   16

SEQ ID NO: 399          moltype = AA  length = 16
FEATURE                 Location/Qualifiers
source                  1..16
                        mol_type = protein
                        organism = synthetic construct
SEQUENCE: 399
GISTIDNTYY STWAKG                                                   16

SEQ ID NO: 400          moltype = AA  length = 16
FEATURE                 Location/Qualifiers
source                  1..16
                        mol_type = protein
                        organism = synthetic construct
SEQUENCE: 400
FISSIGSTYY ASWAKG                                                   16

SEQ ID NO: 401          moltype = AA  length = 16
FEATURE                 Location/Qualifiers
source                  1..16
                        mol_type = protein
                        organism = synthetic construct
SEQUENCE: 401
FISSVGTTFY ASWAKG                                                   16

SEQ ID NO: 402          moltype = AA  length = 16
FEATURE                 Location/Qualifiers
source                  1..16
                        mol_type = protein
                        organism = synthetic construct
SEQUENCE: 402
FISSVGTTFY ATWAKG                                                   16

SEQ ID NO: 403          moltype = AA  length = 16
FEATURE                 Location/Qualifiers
source                  1..16
                        mol_type = protein
                        organism = synthetic construct
SEQUENCE: 403
FIDAVGDTYY ARWAKG                                                   16

SEQ ID NO: 404          moltype = AA  length = 16
FEATURE                 Location/Qualifiers
source                  1..16
                        mol_type = protein
                        organism = synthetic construct
SEQUENCE: 404
FIDAVGNTYY ARWAKG                                                   16

SEQ ID NO: 405          moltype = AA  length = 16
FEATURE                 Location/Qualifiers
source                  1..16
                        mol_type = protein
                        organism = synthetic construct
SEQUENCE: 405
FIDAVGSTYY ARWAKG                                                   16

SEQ ID NO: 406          moltype = AA  length = 16
FEATURE                 Location/Qualifiers
source                  1..16
                        mol_type = protein
                        organism = synthetic construct
SEQUENCE: 406
FISSVGTKFY ASWAKG                                                   16
```

```
SEQ ID NO: 407          moltype = AA  length = 16
FEATURE                 Location/Qualifiers
source                  1..16
                        mol_type = protein
                        organism = synthetic construct
SEQUENCE: 407
FISSVGTTYY APWAKG                                                     16

SEQ ID NO: 408          moltype = AA  length = 16
FEATURE                 Location/Qualifiers
source                  1..16
                        mol_type = protein
                        organism = synthetic construct
SEQUENCE: 408
TIGIGTDTYY ATWAIG                                                     16

SEQ ID NO: 409          moltype = AA  length = 16
FEATURE                 Location/Qualifiers
source                  1..16
                        mol_type = protein
                        organism = synthetic construct
SEQUENCE: 409
FINTGGSAYY ASWAKG                                                     16

SEQ ID NO: 410          moltype = AA  length = 16
FEATURE                 Location/Qualifiers
source                  1..16
                        mol_type = protein
                        organism = synthetic construct
SEQUENCE: 410
FIDTGGSAYF ASWAKG                                                     16

SEQ ID NO: 411          moltype = AA  length = 16
FEATURE                 Location/Qualifiers
source                  1..16
                        mol_type = protein
                        organism = synthetic construct
SEQUENCE: 411
SITTGGKGYY ASWAKG                                                     16

SEQ ID NO: 412          moltype = AA  length = 17
FEATURE                 Location/Qualifiers
source                  1..17
                        mol_type = protein
                        organism = synthetic construct
SEQUENCE: 412
YINPYNHDTK YNEKFKG                                                    17

SEQ ID NO: 413          moltype = AA  length = 17
FEATURE                 Location/Qualifiers
source                  1..17
                        mol_type = protein
                        organism = synthetic construct
SEQUENCE: 413
NINPYYGSTS YNLKFKG                                                    17

SEQ ID NO: 414          moltype = AA  length = 17
FEATURE                 Location/Qualifiers
source                  1..17
                        mol_type = protein
                        organism = synthetic construct
SEQUENCE: 414
WINTYTGEPT YVDDFKG                                                    17

SEQ ID NO: 415          moltype = AA  length = 17
FEATURE                 Location/Qualifiers
source                  1..17
                        mol_type = protein
                        organism = synthetic construct
SEQUENCE: 415
RINHYNGDTF YNQKFKG                                                    17

SEQ ID NO: 416          moltype = AA  length = 17
FEATURE                 Location/Qualifiers
source                  1..17
                        mol_type = protein
                        organism = synthetic construct
SEQUENCE: 416
```

```
WINTYTGEPT YSDDFKG                                                    17

SEQ ID NO: 417          moltype = AA  length = 17
FEATURE                 Location/Qualifiers
source                  1..17
                        mol_type = protein
                        organism = synthetic construct
SEQUENCE: 417
CISTSDGSTY YADSVKG                                                    17

SEQ ID NO: 418          moltype = AA  length = 6
FEATURE                 Location/Qualifiers
source                  1..6
                        mol_type = protein
                        organism = synthetic construct
SEQUENCE: 418
ESWMDL                                                                6

SEQ ID NO: 419          moltype = AA  length = 11
FEATURE                 Location/Qualifiers
source                  1..11
                        mol_type = protein
                        organism = synthetic construct
SEQUENCE: 419
SYLSSGWGVD L                                                          11

SEQ ID NO: 420          moltype = AA  length = 5
FEATURE                 Location/Qualifiers
source                  1..5
                        mol_type = protein
                        organism = synthetic construct
SEQUENCE: 420
GGLDL                                                                 5

SEQ ID NO: 421          moltype = AA  length = 8
FEATURE                 Location/Qualifiers
source                  1..8
                        mol_type = protein
                        organism = synthetic construct
SEQUENCE: 421
YADFAYNL                                                              8

SEQ ID NO: 422          moltype = AA  length = 9
FEATURE                 Location/Qualifiers
source                  1..9
                        mol_type = protein
                        organism = synthetic construct
SEQUENCE: 422
GPGYGCFDL                                                             9

SEQ ID NO: 423          moltype = AA  length = 4
FEATURE                 Location/Qualifiers
source                  1..4
                        mol_type = protein
                        organism = synthetic construct
SEQUENCE: 423
NFDT                                                                  4

SEQ ID NO: 424          moltype = AA  length = 4
FEATURE                 Location/Qualifiers
source                  1..4
                        mol_type = protein
                        organism = synthetic construct
SEQUENCE: 424
NFDI                                                                  4

SEQ ID NO: 425          moltype = AA  length = 5
FEATURE                 Location/Qualifiers
source                  1..5
                        mol_type = protein
                        organism = synthetic construct
SEQUENCE: 425
WNLDI                                                                 5

SEQ ID NO: 426          moltype = AA  length = 5
FEATURE                 Location/Qualifiers
source                  1..5
                        mol_type = protein
                        organism = synthetic construct
```

```
SEQUENCE: 426
WNTDI                                                        5

SEQ ID NO: 427          moltype = AA  length = 5
FEATURE                 Location/Qualifiers
source                  1..5
                        mol_type = protein
                        organism = synthetic construct
SEQUENCE: 427
WNMDI                                                        5

SEQ ID NO: 428          moltype = AA  length = 8
FEATURE                 Location/Qualifiers
source                  1..8
                        mol_type = protein
                        organism = synthetic construct
SEQUENCE: 428
DLYGGDSV                                                     8

SEQ ID NO: 429          moltype = AA  length = 8
FEATURE                 Location/Qualifiers
source                  1..8
                        mol_type = protein
                        organism = synthetic construct
SEQUENCE: 429
DLYGGDSI                                                     8

SEQ ID NO: 430          moltype = AA  length = 8
FEATURE                 Location/Qualifiers
source                  1..8
                        mol_type = protein
                        organism = synthetic construct
SEQUENCE: 430
DLYGGDNI                                                     8

SEQ ID NO: 431          moltype = AA  length = 9
FEATURE                 Location/Qualifiers
source                  1..9
                        mol_type = protein
                        organism = synthetic construct
SEQUENCE: 431
FAVVAGLNI                                                    9

SEQ ID NO: 432          moltype = AA  length = 9
FEATURE                 Location/Qualifiers
source                  1..9
                        mol_type = protein
                        organism = synthetic construct
SEQUENCE: 432
FAVVGGLNI                                                    9

SEQ ID NO: 433          moltype = AA  length = 9
FEATURE                 Location/Qualifiers
source                  1..9
                        mol_type = protein
                        organism = synthetic construct
SEQUENCE: 433
WDYLTDFDI                                                    9

SEQ ID NO: 434          moltype = AA  length = 9
FEATURE                 Location/Qualifiers
source                  1..9
                        mol_type = protein
                        organism = synthetic construct
SEQUENCE: 434
LDGYYAMDY                                                    9

SEQ ID NO: 435          moltype = AA  length = 11
FEATURE                 Location/Qualifiers
source                  1..11
                        mol_type = protein
                        organism = synthetic construct
SEQUENCE: 435
DGNEKYGRFA Y                                                 11

SEQ ID NO: 436          moltype = AA  length = 14
FEATURE                 Location/Qualifiers
source                  1..14
                        mol_type = protein
```

```
                        organism = synthetic construct
SEQUENCE: 436
YGDYYGNSYR GFDY                                                   14

SEQ ID NO: 437          moltype = AA  length = 13
FEATURE                 Location/Qualifiers
source                  1..13
                        mol_type = protein
                        organism = synthetic construct
SEQUENCE: 437
AEIHYDYDDA MDY                                                    13

SEQ ID NO: 438          moltype = AA  length = 14
FEATURE                 Location/Qualifiers
source                  1..14
                        mol_type = protein
                        organism = synthetic construct
SEQUENCE: 438
YGDYYGSSYR GFDY                                                   14

SEQ ID NO: 439          moltype = AA  length = 12
FEATURE                 Location/Qualifiers
source                  1..12
                        mol_type = protein
                        organism = synthetic construct
SEQUENCE: 439
GKGSRCHGDL DA                                                     12

SEQ ID NO: 440          moltype = AA  length = 13
FEATURE                 Location/Qualifiers
source                  1..13
                        mol_type = protein
                        organism = synthetic construct
SEQUENCE: 440
QASQSVGGNN DLA                                                    13

SEQ ID NO: 441          moltype = AA  length = 13
FEATURE                 Location/Qualifiers
source                  1..13
                        mol_type = protein
                        organism = synthetic construct
SEQUENCE: 441
QSSQSVGNNN DLA                                                    13

SEQ ID NO: 442          moltype = AA  length = 12
FEATURE                 Location/Qualifiers
source                  1..12
                        mol_type = protein
                        organism = synthetic construct
SEQUENCE: 442
QSSQRVYNNW LS                                                     12

SEQ ID NO: 443          moltype = AA  length = 11
FEATURE                 Location/Qualifiers
source                  1..11
                        mol_type = protein
                        organism = synthetic construct
SEQUENCE: 443
QASESIDNAL A                                                      11

SEQ ID NO: 444          moltype = AA  length = 13
FEATURE                 Location/Qualifiers
source                  1..13
                        mol_type = protein
                        organism = synthetic construct
SEQUENCE: 444
QSSQSVYNYN WLS                                                    13

SEQ ID NO: 445          moltype = AA  length = 13
FEATURE                 Location/Qualifiers
source                  1..13
                        mol_type = protein
                        organism = synthetic construct
SEQUENCE: 445
QASQSVYSDN RLA                                                    13

SEQ ID NO: 446          moltype = AA  length = 13
FEATURE                 Location/Qualifiers
source                  1..13
```

```
                        mol_type = protein
                        organism = synthetic construct
SEQUENCE: 446
QSSQSVYNNN LLA                                                 13

SEQ ID NO: 447          moltype = AA  length = 11
FEATURE                 Location/Qualifiers
source                  1..11
                        mol_type = protein
                        organism = synthetic construct
SEQUENCE: 447
QANETIGNAL A                                                   11

SEQ ID NO: 448          moltype = AA  length = 13
FEATURE                 Location/Qualifiers
source                  1..13
                        mol_type = protein
                        organism = synthetic construct
SEQUENCE: 448
QSSQSVGSNN RLS                                                 13

SEQ ID NO: 449          moltype = AA  length = 13
FEATURE                 Location/Qualifiers
source                  1..13
                        mol_type = protein
                        organism = synthetic construct
SEQUENCE: 449
QSSHSVGSNN RLS                                                 13

SEQ ID NO: 450          moltype = AA  length = 13
FEATURE                 Location/Qualifiers
source                  1..13
                        mol_type = protein
                        organism = synthetic construct
SEQUENCE: 450
QSSQSVGNNK RLS                                                 13

SEQ ID NO: 451          moltype = AA  length = 13
FEATURE                 Location/Qualifiers
source                  1..13
                        mol_type = protein
                        organism = synthetic construct
SEQUENCE: 451
QSSQTIWDNN WLA                                                 13

SEQ ID NO: 452          moltype = AA  length = 13
FEATURE                 Location/Qualifiers
source                  1..13
                        mol_type = protein
                        organism = synthetic construct
SEQUENCE: 452
QSSQSIWDNN WLA                                                 13

SEQ ID NO: 453          moltype = AA  length = 13
FEATURE                 Location/Qualifiers
source                  1..13
                        mol_type = protein
                        organism = synthetic construct
SEQUENCE: 453
HSSHSIYDNN WLS                                                 13

SEQ ID NO: 454          moltype = AA  length = 13
FEATURE                 Location/Qualifiers
source                  1..13
                        mol_type = protein
                        organism = synthetic construct
SEQUENCE: 454
QSSESVWQNN RLS                                                 13

SEQ ID NO: 455          moltype = AA  length = 13
FEATURE                 Location/Qualifiers
source                  1..13
                        mol_type = protein
                        organism = synthetic construct
SEQUENCE: 455
QASQSVWQNN RLS                                                 13

SEQ ID NO: 456          moltype = AA  length = 13
FEATURE                 Location/Qualifiers
```

```
source                  1..13
                        mol_type = protein
                        organism = synthetic construct
SEQUENCE: 456
QSSQSVYNNN WLS                                                    13

SEQ ID NO: 457          moltype = AA  length = 12
FEATURE                 Location/Qualifiers
source                  1..12
                        mol_type = protein
                        organism = synthetic construct
SEQUENCE: 457
QSSESVYSDW LS                                                     12

SEQ ID NO: 458          moltype = AA  length = 12
FEATURE                 Location/Qualifiers
source                  1..12
                        mol_type = protein
                        organism = synthetic construct
SEQUENCE: 458
QSSQSVYSDW LS                                                     12

SEQ ID NO: 459          moltype = AA  length = 13
FEATURE                 Location/Qualifiers
source                  1..13
                        mol_type = protein
                        organism = synthetic construct
SEQUENCE: 459
QASESVYNNN FLS                                                    13

SEQ ID NO: 460          moltype = AA  length = 11
FEATURE                 Location/Qualifiers
source                  1..11
                        mol_type = protein
                        organism = synthetic construct
SEQUENCE: 460
SASQAISNYL N                                                      11

SEQ ID NO: 461          moltype = AA  length = 17
FEATURE                 Location/Qualifiers
source                  1..17
                        mol_type = protein
                        organism = synthetic construct
SEQUENCE: 461
KSSQSLLYSS NQKNYLA                                                17

SEQ ID NO: 462          moltype = AA  length = 11
FEATURE                 Location/Qualifiers
source                  1..11
                        mol_type = protein
                        organism = synthetic construct
SEQUENCE: 462
KASQDVGTVV A                                                      11

SEQ ID NO: 463          moltype = AA  length = 7
FEATURE                 Location/Qualifiers
source                  1..7
                        mol_type = protein
                        organism = synthetic construct
SEQUENCE: 463
KASNLAS                                                           7

SEQ ID NO: 464          moltype = AA  length = 7
FEATURE                 Location/Qualifiers
source                  1..7
                        mol_type = protein
                        organism = synthetic construct
SEQUENCE: 464
RTSNLAP                                                           7

SEQ ID NO: 465          moltype = AA  length = 7
FEATURE                 Location/Qualifiers
source                  1..7
                        mol_type = protein
                        organism = synthetic construct
SEQUENCE: 465
EASKLAS                                                           7

SEQ ID NO: 466          moltype = AA  length = 7
```

```
FEATURE                Location/Qualifiers
source                 1..7
                       mol_type = protein
                       organism = synthetic construct
SEQUENCE: 466
LASTLVP                                                      7

SEQ ID NO: 467         moltype = AA  length = 7
FEATURE                Location/Qualifiers
source                 1..7
                       mol_type = protein
                       organism = synthetic construct
SEQUENCE: 467
SVSTLAS                                                      7

SEQ ID NO: 468         moltype = AA  length = 7
FEATURE                Location/Qualifiers
source                 1..7
                       mol_type = protein
                       organism = synthetic construct
SEQUENCE: 468
RASTLAS                                                      7

SEQ ID NO: 469         moltype = AA  length = 7
FEATURE                Location/Qualifiers
source                 1..7
                       mol_type = protein
                       organism = synthetic construct
SEQUENCE: 469
STSTLAS                                                      7

SEQ ID NO: 470         moltype = AA  length = 7
FEATURE                Location/Qualifiers
source                 1..7
                       mol_type = protein
                       organism = synthetic construct
SEQUENCE: 470
LASTLAS                                                      7

SEQ ID NO: 471         moltype = AA  length = 7
FEATURE                Location/Qualifiers
source                 1..7
                       mol_type = protein
                       organism = synthetic construct
SEQUENCE: 471
GASNLAS                                                      7

SEQ ID NO: 472         moltype = AA  length = 7
FEATURE                Location/Qualifiers
source                 1..7
                       mol_type = protein
                       organism = synthetic construct
SEQUENCE: 472
GAFNLAS                                                      7

SEQ ID NO: 473         moltype = AA  length = 7
FEATURE                Location/Qualifiers
source                 1..7
                       mol_type = protein
                       organism = synthetic construct
SEQUENCE: 473
LASKLAS                                                      7

SEQ ID NO: 474         moltype = AA  length = 7
FEATURE                Location/Qualifiers
source                 1..7
                       mol_type = protein
                       organism = synthetic construct
SEQUENCE: 474
SASTLAS                                                      7

SEQ ID NO: 475         moltype = AA  length = 7
FEATURE                Location/Qualifiers
source                 1..7
                       mol_type = protein
                       organism = synthetic construct
SEQUENCE: 475
LASKLAT                                                      7
```

```
SEQ ID NO: 476          moltype = AA  length = 7
FEATURE                 Location/Qualifiers
source                  1..7
                        mol_type = protein
                        organism = synthetic construct
SEQUENCE: 476
TASTLAS                                                                     7

SEQ ID NO: 477          moltype = AA  length = 7
FEATURE                 Location/Qualifiers
source                  1..7
                        mol_type = protein
                        organism = synthetic construct
SEQUENCE: 477
QASKLAS                                                                     7

SEQ ID NO: 478          moltype = AA  length = 7
FEATURE                 Location/Qualifiers
source                  1..7
                        mol_type = protein
                        organism = synthetic construct
SEQUENCE: 478
YASTLAS                                                                     7

SEQ ID NO: 479          moltype = AA  length = 7
FEATURE                 Location/Qualifiers
source                  1..7
                        mol_type = protein
                        organism = synthetic construct
SEQUENCE: 479
YTSSLYS                                                                     7

SEQ ID NO: 480          moltype = AA  length = 7
FEATURE                 Location/Qualifiers
source                  1..7
                        mol_type = protein
                        organism = synthetic construct
SEQUENCE: 480
WASTRHT                                                                     7

SEQ ID NO: 481          moltype = AA  length = 10
FEATURE                 Location/Qualifiers
source                  1..10
                        mol_type = protein
                        organism = synthetic construct
SEQUENCE: 481
QGYYPGWIRA                                                                  10

SEQ ID NO: 482          moltype = AA  length = 10
FEATURE                 Location/Qualifiers
source                  1..10
                        mol_type = protein
                        organism = synthetic construct
SEQUENCE: 482
LAYYPDWIRG                                                                  10

SEQ ID NO: 483          moltype = AA  length = 13
FEATURE                 Location/Qualifiers
source                  1..13
                        mol_type = protein
                        organism = synthetic construct
SEQUENCE: 483
LGTYDCSSAD CGA                                                              13

SEQ ID NO: 484          moltype = AA  length = 12
FEATURE                 Location/Qualifiers
source                  1..12
                        mol_type = protein
                        organism = synthetic construct
SEQUENCE: 484
QQGYSISNVD NV                                                               12

SEQ ID NO: 485          moltype = AA  length = 13
FEATURE                 Location/Qualifiers
source                  1..13
                        mol_type = protein
                        organism = synthetic construct
SEQUENCE: 485
LGIYDCVSAD CYG                                                              13
```

```
SEQ ID NO: 486          moltype = AA  length = 11
FEATURE                 Location/Qualifiers
source                  1..11
                        mol_type = protein
                        organism = synthetic construct
SEQUENCE: 486
LGEYSDSGED T                                                     11

SEQ ID NO: 487          moltype = AA  length = 10
FEATURE                 Location/Qualifiers
source                  1..10
                        mol_type = protein
                        organism = synthetic construct
SEQUENCE: 487
QAFYNDDMWV                                                       10

SEQ ID NO: 488          moltype = AA  length = 13
FEATURE                 Location/Qualifiers
source                  1..13
                        mol_type = protein
                        organism = synthetic construct
SEQUENCE: 488
LGSYNCADGD CNA                                                   13

SEQ ID NO: 489          moltype = AA  length = 13
FEATURE                 Location/Qualifiers
source                  1..13
                        mol_type = protein
                        organism = synthetic construct
SEQUENCE: 489
LGSYNCANGD CNA                                                   13

SEQ ID NO: 490          moltype = AA  length = 13
FEATURE                 Location/Qualifiers
source                  1..13
                        mol_type = protein
                        organism = synthetic construct
SEQUENCE: 490
LGSYNCADGD CNT                                                   13

SEQ ID NO: 491          moltype = AA  length = 13
FEATURE                 Location/Qualifiers
source                  1..13
                        mol_type = protein
                        organism = synthetic construct
SEQUENCE: 491
LGSYNCAEGD CNA                                                   13

SEQ ID NO: 492          moltype = AA  length = 10
FEATURE                 Location/Qualifiers
source                  1..10
                        mol_type = protein
                        organism = synthetic construct
SEQUENCE: 492
AGTYSDNIYS                                                       10

SEQ ID NO: 493          moltype = AA  length = 10
FEATURE                 Location/Qualifiers
source                  1..10
                        mol_type = protein
                        organism = synthetic construct
SEQUENCE: 493
AGTYSDNVYT                                                       10

SEQ ID NO: 494          moltype = AA  length = 10
FEATURE                 Location/Qualifiers
source                  1..10
                        mol_type = protein
                        organism = synthetic construct
SEQUENCE: 494
AGTYSYNIYT                                                       10

SEQ ID NO: 495          moltype = AA  length = 10
FEATURE                 Location/Qualifiers
source                  1..10
                        mol_type = protein
                        organism = synthetic construct
SEQUENCE: 495
```

```
AGTYTYNIYT                                                          10

SEQ ID NO: 496          moltype = AA  length = 10
FEATURE                 Location/Qualifiers
source                  1..10
                        mol_type = protein
                        organism = synthetic construct
SEQUENCE: 496
AGTYSDNIYT                                                          10

SEQ ID NO: 497          moltype = AA  length = 12
FEATURE                 Location/Qualifiers
source                  1..12
                        mol_type = protein
                        organism = synthetic construct
SEQUENCE: 497
AGLKAWNDDD DG                                                       12

SEQ ID NO: 498          moltype = AA  length = 12
FEATURE                 Location/Qualifiers
source                  1..12
                        mol_type = protein
                        organism = synthetic construct
SEQUENCE: 498
AGLRAWNDDD DG                                                       12

SEQ ID NO: 499          moltype = AA  length = 10
FEATURE                 Location/Qualifiers
source                  1..10
                        mol_type = protein
                        organism = synthetic construct
SEQUENCE: 499
AGDYSVGIYT                                                          10

SEQ ID NO: 500          moltype = AA  length = 10
FEATURE                 Location/Qualifiers
source                  1..10
                        mol_type = protein
                        organism = synthetic construct
SEQUENCE: 500
AGDYSVGIYA                                                          10

SEQ ID NO: 501          moltype = AA  length = 12
FEATURE                 Location/Qualifiers
source                  1..12
                        mol_type = protein
                        organism = synthetic construct
SEQUENCE: 501
AGVKSDSTDG IA                                                       12

SEQ ID NO: 502          moltype = AA  length = 9
FEATURE                 Location/Qualifiers
source                  1..9
                        mol_type = protein
                        organism = synthetic construct
SEQUENCE: 502
QQYIKLPRT                                                           9

SEQ ID NO: 503          moltype = AA  length = 8
FEATURE                 Location/Qualifiers
source                  1..8
                        mol_type = protein
                        organism = synthetic construct
SEQUENCE: 503
QQYYSYPT                                                            8

SEQ ID NO: 504          moltype = AA  length = 9
FEATURE                 Location/Qualifiers
source                  1..9
                        mol_type = protein
                        organism = synthetic construct
SEQUENCE: 504
QQYSSYPLT                                                           9

SEQ ID NO: 505          moltype = AA  length = 9
FEATURE                 Location/Qualifiers
source                  1..9
                        mol_type = protein
                        organism = synthetic construct
```

-continued

```
SEQUENCE: 505
QQYYNYPLT                                                        9

SEQ ID NO: 506          moltype = AA  length = 9
FEATURE                 Location/Qualifiers
source                  1..9
                        mol_type = protein
                        organism = synthetic construct
SEQUENCE: 506
QQYSRYPLT                                                        9

SEQ ID NO: 507          moltype = AA  length = 9
FEATURE                 Location/Qualifiers
source                  1..9
                        mol_type = protein
                        organism = synthetic construct
SEQUENCE: 507
QQYSSFPLT                                                        9

SEQ ID NO: 508          moltype = AA  length = 29
FEATURE                 Location/Qualifiers
source                  1..29
                        mol_type = protein
                        organism = synthetic construct
SEQUENCE: 508
GAPGAYPGAP APGVYPGPPS GPGAYPSSG                                  29
```